(12) United States Patent
Kenyon et al.

(10) Patent No.: US 11,413,278 B2
(45) Date of Patent: Aug. 16, 2022

(54) COMPOUNDS AND METHODS FOR PROMOTING STRESS RESISTANCE

(71) Applicant: The Regents of the University of California, Oakland, CA (US)

(72) Inventors: Cynthia Kenyon, Nicasio, CA (US); Peichuan Zhang, Berkeley, CA (US); James Cregg, San Francisco, CA (US); Kean-Hooi Ang, San Francisco, CA (US); Michelle Arkin, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 52 days.

(21) Appl. No.: 15/766,797

(22) PCT Filed: Oct. 7, 2016

(86) PCT No.: PCT/US2016/055964
§ 371 (c)(1),
(2) Date: Apr. 6, 2018

(87) PCT Pub. No.: WO2017/062751
PCT Pub. Date: Apr. 13, 2017

(65) Prior Publication Data
US 2018/0289682 A1    Oct. 11, 2018

Related U.S. Application Data

(60) Provisional application No. 62/245,812, filed on Oct. 23, 2015, provisional application No. 62/239,244, filed on Oct. 8, 2015.

(51) Int. Cl.
*A61K 31/443* (2006.01)
*A61P 9/00* (2006.01)
(Continued)

(52) U.S. Cl.
CPC ............ *A61K 31/443* (2013.01); *A61K 31/12* (2013.01); *A61K 31/341* (2013.01);
(Continued)

(58) Field of Classification Search
CPC .... A61P 31/55; A61P 3/10; A61P 9/00; A61P 29/00; A61P 35/00
See application file for complete search history.

(56) References Cited

U.S. PATENT DOCUMENTS

2011/0136246 A1    6/2011   Shibata et al.
2013/0295566 A1   11/2013   Donlon et al.
2014/0328863 A1   11/2014   Longo

FOREIGN PATENT DOCUMENTS

WO    WO-2016/109470 A1    7/2016

OTHER PUBLICATIONS

Gunatilleke, Diverse Inhibitor Chemotypes Targeting Trypanosoma cruzi CYP51, PLoS Neglected Tropical Diseases, 2012, 6(7), pp. 1-16. (Year: 2012).*

(Continued)

*Primary Examiner* — Savitha M Rao
*Assistant Examiner* — Andrew P Lee
(74) *Attorney, Agent, or Firm* — Mintz, Levin, Cohn, Ferris, Glovsky and Popeo, P.C.

(57) ABSTRACT

Disclosed herein, inter alia, are compounds and methods useful for increasing stress resistance.

9 Claims, 9 Drawing Sheets

(51) Int. Cl.

| | | |
|---|---|---|
| *A61P 3/10* | (2006.01) | |
| *A61P 29/00* | (2006.01) | |
| *A61K 31/12* | (2006.01) | |
| *A61K 31/341* | (2006.01) | |
| *A61K 31/404* | (2006.01) | |
| *A61K 31/4184* | (2006.01) | |
| *A61K 31/437* | (2006.01) | |
| *A61K 31/4406* | (2006.01) | |
| *A61K 31/4439* | (2006.01) | |
| *A61K 31/45* | (2006.01) | |
| *A61K 31/519* | (2006.01) | |
| *A61K 31/55* | (2006.01) | |
| *A61K 31/44* | (2006.01) | |
| *A61P 35/00* | (2006.01) | |

(52) U.S. Cl.
CPC ........ *A61K 31/404* (2013.01); *A61K 31/4184* (2013.01); *A61K 31/437* (2013.01); *A61K 31/44* (2013.01); *A61K 31/4406* (2013.01); *A61K 31/4439* (2013.01); *A61K 31/45* (2013.01); *A61K 31/519* (2013.01); *A61K 31/55* (2013.01); *A61P 3/10* (2018.01); *A61P 9/00* (2018.01); *A61P 29/00* (2018.01); *A61P 35/00* (2018.01)

(56) References Cited

OTHER PUBLICATIONS

Danziger, Automated site-directed drug design: a general algorithm for knowledge acquisition about hydrogen-bonding regions at protein surfaces, Proc. R. Soc. Lond., 236, pp. 101-113 (Year: 1989).*
Leclerc, Profiling gene expression of whole cytochrome P450 superfamily in human bronchial and peripheral lung tissues: Differential expression in non-small cell lung cancers, Biochimie, 2010, 92, pp. 292-306 (Year: 2010).*
Courtney, K.D. et al. (May 2012). "The evolving paradigm of second-line hormonal therapy options for castration-resistant prostate cancer," *Curr Opin Oncol* 24(3):272-277.
International Search Report dated Mar. 2, 2017, for PCT Application No. PCT/US2016/055954, filed Oct. 7, 2016, 5 pages.
Litton, J.K. et al. (Feb. 2012, e-published Jan. 14, 2012). "Aromatase inhibitors and breast cancer prevention," *Expert Opin Pharmacother* 13(3):325-331.
Written Opinion dated Mar. 2, 2017, for PCT Application No. PCT/US2016/055954, filed Oct. 7, 2016, 6 pages.

* cited by examiner

COMPOUNDS AND METHODS FOR PROMOTING STRESS RESISTANCE

CROSS-REFERENCES TO RELATED APPLICATIONS

This application is a Section 371 US National Phase of PCT/US2016/055964 filed Oct. 7, 2016, which claims the benefit of U.S. Provisional Application No. 62/239,244 filed Oct. 8, 2015 and U.S. Provisional Application No. 62/245,812 filed Oct. 23, 2015 which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under Grant No. R01 AG044515 awarded by The National Institutes of Health. The government has certain rights in the invention.

BACKGROUND

Increased resistance to environmental stress at the cellular level is often correlated with organismal longevity, as seen for cells from long-lived mutants and wild animal species. Likewise, in many experimental organisms, screens for increased stress resistance have yielded mutants that are long-lived. No compound, to our knowledge, has been shown to extend lifespan, or healthy lifespan, of humans. Only a few small molecules, including resveratrol, metformin and rapamycin, are known to extend lifespan of experimental animals. Provided herein are solutions to these and other problems in the art.

BRIEF SUMMARY OF THE INVENTION

In an aspect is provided a method of increasing resistance to cellular stress in a subject, the method including administering an effective amount of a stress resistance increasing compound, or a pharmaceutically acceptable salt thereof, as described herein (including embodiments) to the subject.

In an aspect is provided a method of increasing lifespan in a subject in need, the method including administering a stress resistance increasing compound, or a pharmaceutically acceptable salt thereof, as described herein (including embodiments) to the subject.

In an aspect is provided a method of treating an age associated disease in a subject in need, the method comprising administering a stress resistance increasing compound, or a pharmaceutically acceptable salt thereof, as described herein (including embodiments) to the subject.

In an aspect is provided a method of inhibiting proliferation of cancer cells, the method including contacting the cell with a stress resistance increasing compound, or a pharmaceutically acceptable salt thereof, as described herein (including embodiments).

In an aspect is provided a method of inhibiting survival of cancer cells, the method including contacting the cell with a stress resistance increasing compound, or a pharmaceutically acceptable salt thereof, as described herein (including embodiments).

In an aspect is provided a method of increasing the level of FOXO3 activity in a cell, the method including contacting the cell with a stress resistance increasing compound, or a pharmaceutically acceptable salt thereof, as described herein (including embodiments).

In an aspect is provided a method of increasing the level of NRF2 activity in a cell, the method including contacting the cell with a stress resistance increasing compound, or a pharmaceutically acceptable salt thereof, as described herein (including embodiments).

In an aspect is provided a method of increasing the level of autophagy in a cell, the method including contacting the cell with a stress resistance increasing compound, or a pharmaceutically acceptable salt thereof, as described herein (including embodiments).

In an aspect is provided a method of reducing the level of mTOR activity in a cell, the method including contacting the cell with a stress resistance increasing compound, or a pharmaceutically acceptable salt thereof, as described herein (including embodiments).

In another aspect is provided a pharmaceutical composition including a pharmaceutically acceptable excipient and a compound, or pharmaceutically acceptable salt thereof, as described herein, including embodiments (e.g. in an aspect, embodiment, example, figure, table, or claim).

In another aspect is provided a method of treating aging in a subject in need of such treatment, the method including administering a compound, or a pharmaceutically acceptable salt thereof, as described herein, including embodiments (e.g. a claim, embodiment, example, table, figure, or claim) to the subject.

In another aspect is provided a compound as described herein for use as a medicament. In embodiments, the medicament may be useful for treating aging in a subject in need of such treatment. In embodiments, the use may include administering a compound, or a pharmaceutically acceptable salt thereof, as described herein, including embodiments (e.g. an aspect, embodiment, example, table, figure, or claim) to the subject.

BRIEF DESCRIPTION OF THE DRAWINGS

(FIG. 6A) wild-type animals, in liquid, with FuDR to block progeny production, 20° C. constant. Control, 21.1±0.5 (mean±SD), n=77/81 (observed/total); Gr-4D-treated, 31.9±1.1 (~51.2% increase), n=41/41, P<0.001 (log-rank test); O13-treated, 28.1±1.1 (~33.2% increase), n=36/36, P<0.001. (FIG. 6B) (fer-15(b26)II rol-6(su1006)II; fem-1(hc17)IV) temperature-sensitive sterile rollers, on plate, without FuDR, 25° C. then room temperature (~22° C.). Control, 18.4±0.4, n=65/80; Gr-4D-treated, 22.5±0.4 (~% increase), n=74/95, P<0.001 (log-rank test); O13-treated, 23.4±0.4 (~% increase), n=72/76, P<0.001. See Table 12 for details.

DETAILED DESCRIPTION

Figure 1:
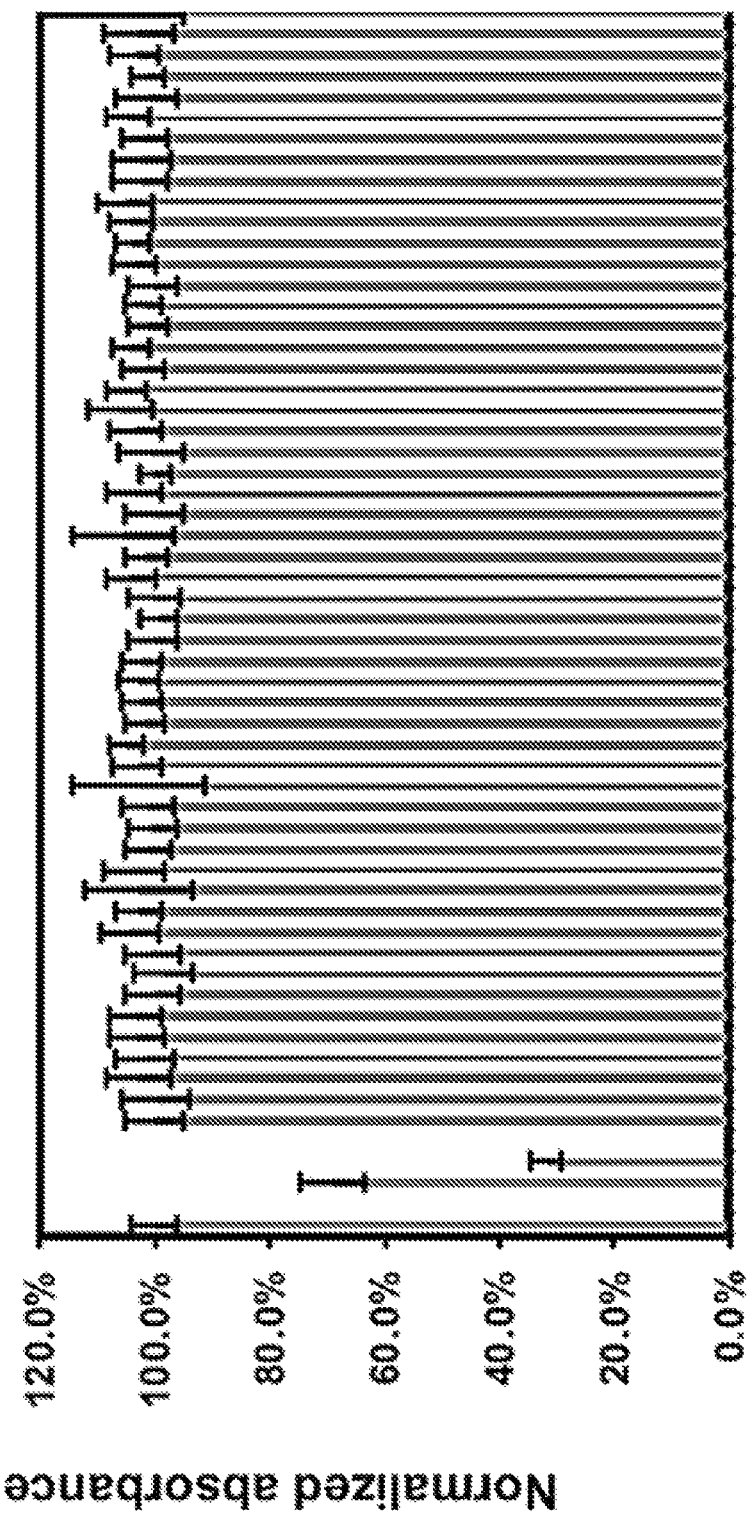
FIG. 1. Small molecules do not quench $H_2O_2$. Amplex Red assay indicated that none of the 54 repurchased molecules quenches $H_2O_2$ (n=4, technical replicates). Catalase (0.02 U and 0.04 U) MP (Biomedicals), as the control, substantially reduced the absorbance. Molecules tested in this assay (as identified on the x axis) are in order left to right: Control, 0.02 U catalase, 0.04 U catalase, Gr-1A, Gr-1B, Gr-1C, Gr-1D, Gr-1E, Gr-1F, Gr-1G, Gr-2A, Gr-2B, Gr-2C, Gr-2E, Gr-3A, Gr-3B, Gr-3C, Gr-4A, Gr-4B, Gr-4C, Gr-4D, Gr-5A, Gr-5B, Gr-5C, Gr-5D, Gr-6A, Gr-6B, Gr-6C, Gr-7A, Gr-7B, Gr-7C, O1, O3, O4, O5, O6, O7, O8, O9, O10, O11, O12, O13, O14, O15, O16, O17, O18, O19, O20, O21, O22, O23, O24, O25, O26, and O27, respectively.

Applicants have screened a library of 104,121 small molecules in a human primary fibroblast cell line and identified 61 that increased oxidative stress resistance. Thirty hits fall into seven structurally related chemical groups, suggesting that they may promote stress resistance by acting on common targets. Three small molecules increased *C. elegans*' stress resistance, and at least twelve extended their lifespan (from ~10% to ~50%). In human cells, some small molecules affect the activities of FOXO3, NRF2, and/or mTOR, proteins whose activation or inhibition can extend lifespan in model organisms. This new strategy as suggested by basic aging research may provide small molecules that extend healthy, youthful lifespan and combat age-related diseases.

A. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched non-cyclic chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH═CH—O—$CH_3$, —Si($CH_3$)$_3$, —$CH_2$—CH═N—$OCH_3$, —CH═CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl", "heteroalkyl", "cycloalkyl", "heterocycloalkyl", "aryl", and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C=(O)NR"NR"'R"", —CN, —NO$_2$, in a number ranging from zero to (2m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C=(O)NR"NR"'R"", —CN, —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R"', and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, therapeutic agents) to a biological system (e.g. in a subject, in a cancer cell, in the extracellular space near a cancer cell).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

The symbol " $\sim$ " denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease.

An "effective amount" is an amount sufficient to accomplish a stated purpose (e.g. achieve the effect for which it is administered, treat a disease, reduce enzyme activity, increase enzyme activity, reduce protein function, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug or prodrug is an amount of a drug or prodrug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "associated" or "associated with" in the context of a substance or substance activity or function associated with a disease (e.g. cancer) means that the disease is caused by (in whole or in part), or a symptom of the disease is caused by (in whole or in part) the substance or substance activity or function. As used herein, what is described as being associated with a disease, if a causative agent, could be a target for treatment of the disease. For example, a disease associated with cellular stress may be treated with an agent (e.g. compound as described herein) effective for increasing resistance to cellular stress.

"Control" or "control experiment" or "standard control" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme.

As defined herein, the term "inhibition", "inhibit", "inhibiting" and the like in reference to a protein-inhibitor (e.g. antagonist) interaction means negatively affecting (e.g. decreasing) the level of activity or function of the protein relative to the level of activity or function of the protein in the absence of the inhibitor. In some embodiments inhibition refers to reduction of a disease or symptoms of disease. Thus, inhibition may include, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g. agonist) interaction means positively affecting (e.g. increasing) the activity or function of the protein relative to the activity or function of the protein in the absence of the activator (e.g. compound described herein). Thus, activation may include, at least in part, partially or totally increasing stimulation, increasing or enabling activation, or activating, sensitizing, or up-regulating signal transduction or enzymatic activity or the amount of a protein decreased in a disease. Activation may include, at least in part, partially or totally increasing stimulation, increasing or enabling activation, or activating, sensitizing, or up-regulating signal transduction or enzymatic activity or the amount of a protein.

The term "modulator" refers to a composition that increases or decreases the level of a target molecule or the function of a target molecule.

"Anti-cancer agent" or "anti-cancer drug" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent approved by the FDA or similar regulatory agency of a country other than the USA, for treating cancer. Examples of anti-cancer agents include, but are not limited to, anti-androgens (e.g., Casodex, Flutamide, MDV3100, or ARN-509), MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002), mTOR inhibitors, antibodies (e.g., rituxan), 5-aza-2'-deoxycytidine, doxorubicin, vincristine, etoposide, gemcitabine, imatinib (Gleevec®), geldanamycin, 17-N-Allylamino-17-Demethoxygeldanamycin (17-AAG), bortezomib, trastuzumab, anastrozole; angiogenesis inhibitors; antiandrogen, antiestrogen; antisense oligonucleotides; apoptosis gene modulators; apoptosis regulators; arginine deaminase; BCR/ABL antagonists; beta lactam derivatives; bFGF inhibitor; bicalutamide; camptothecin derivatives; casein kinase inhibitors (ICOS); clomifene analogues; cytarabine dacliximab; dexamethasone; estrogen agonists; estrogen antagonists; etanidazole; etoposide phosphate; exemestane; fadrozole; finasteride; fludarabine; fluorodaunorunicin hydrochloride; gadolinium texaphyrin; gallium nitrate; gelatinase inhibitors; gemcitabine; glutathione inhibitors; hepsulfam; immunostimulant peptides; insulin-like growth factor-1 receptor inhibitor; interferon agonists; interferons; interleukins; letrozole; leukemia inhibiting factor; leukocyte alpha interferon; leuprolide+estrogen+progesterone; leuprorelin; matrilysin inhibitors; matrix metalloproteinase inhibitors; MIF inhibitor; mifepristone; mismatched double stranded RNA; monoclonal antibody; mycobacterial cell wall extract; nitric oxide modulators; oxaliplatin; panomifene; pentrozole; phosphatase inhibitors; plasminogen activator inhibitor; platinum complex; platinum compounds; prednisone; proteasome inhibitors; protein A-based immune modulator; protein kinase C inhibitor; protein tyrosine phosphatase inhibitors; purine nucleoside phosphorylase inhibitors; ras farnesyl protein transferase inhibitors; ras inhibitors; ras-GAP inhibitor; ribozymes; signal transduction inhibitors; signal transduction modulators; single chain antigen-binding protein; stem cell inhibitor; stem-cell division inhibitors; stromelysin inhibitors; synthetic glycosaminoglycans; tamoxifen methiodide; telomerase inhibitors; thyroid stimulating hormone; translation inhibitors; tyrosine kinase inhibitors; urokinase receptor antagonists; steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, pyrrolo benzodiazepines (e.g. tomaymycin), carboplatin, CC-1065 and CC-1065 analogs including amino-CBIs, nitrogen mustards (such as chlorambucil and melphalan), dolastatin and dolastatin analogs (including auristatins: eg. monomethyl auristatin E), anthracycline antibiotics (such as doxorubicin, daunorubicin, etc.), duocarmycins and duocarmycin analogs, enediynes (such as neocarzinostatin and calicheamicins), leptomycin derivaties, maytansinoids and maytansinoid analogs (e.g. mertansine), methotrexate, mitomycin C, taxoids, vinca alkaloids (such as vinblastine and vincristine), epothilones (e.g. epothilone B), camptothecin and its clinical analogs topotecan and irinotecan, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

"Patient" or "subject in need thereof" or "subject" refers to a living organism suffering from or prone to a disease or condition that can be treated by administration of a compound or pharmaceutical composition or by a method, as provided herein. Non-limiting examples include humans, other mammals, bovines, rats, mice, dogs, monkeys, goat, sheep, cows, deer, and other non-mammalian animals. In some embodiments, a patient is human. In some embodiments, a subject is human.

"Disease" or "condition" refer to a state of being or health status of a patient or subject capable of being treated with a compound, pharmaceutical composition, or method provided herein.

As used herein, the term "cancer" refers to all types of cancer, neoplasm or malignant tumors found in mammals (e.g. humans), including leukemia, carcinomas and sarcomas. Exemplary cancers that may be treated with a compound or method provided herein include cancer of the prostate, thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples may include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

"Nucleic acid" or "oligonucleotide" or "polynucleotide" or grammatical equivalents used herein means at least two nucleotides covalently linked together. The term "nucleic acid" includes single-, double-, or multiple-stranded DNA, RNA and analogs (derivatives) thereof. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. Nucleic acids containing one or more carbocyclic sugars are also included within one definition of nucleic acids.

A particular nucleic acid sequence also encompasses "splice variants." Similarly, a particular protein encoded by a nucleic acid encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

"Polypeptide," "peptide," and "protein" are used herein interchangeably and mean any peptide-linked chain of amino acids, regardless of length or post-translational modification. As noted below, the polypeptides described herein can be, e.g., wild-type proteins, biologically-active fragments of the wild-type proteins, or variants of the wild-type proteins or fragments. Variants, in accordance with the disclosure, can contain amino acid substitutions, deletions, or insertions. The substitutions can be conservative or non-conservative.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation, to increase degradation of a prodrug and release of the drug, detectable agent). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Pharmaceutical compositions provided by the present invention include compositions wherein the active ingredient (e.g. compounds described herein, including embodiments or examples) may be contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., reducing, eliminating, or slowing the progression of disease symptoms (e.g. symptoms of cancer). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating cancer, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for cancer such as radiation or surgery.

The term "EGFR" refers to epidermal growth factor receptor. The term "EGFR" may refer to the nucleotide sequence or protein sequence of human EGRF (e.g., Entrez 1956, UniProt P00533, RefSeq NM_005228, GI:41327737, RefSeq NP_005219, and/or GI:29725609). The term "EGFR" includes both the wild-type form of the nucleotide sequences or proteins as well as any mutants thereof. In some embodiments, "EGFR" is wild-type EGFR. In some embodiments, "EGFR" is one or more mutant forms. The term "EGFR" XYZ refers to a nucleotide sequence or protein of a mutant EGFR wherein the Y numbered amino acid of EGFR that normally has an X amino acid in the wildtype, instead has a Z amino acid in the mutant. In embodiments, an EGFR is the human EGFR. In embodiments, the EGFR has the nucleotide sequence corresponding to reference number GI:41327737. In embodiments, the EGFR has the nucleotide sequence corresponding to RefSeq NM_005228.3. In embodiments, the EGFR has the protein sequence corresponding to RefSeq NP_005219.2. In embodiments, the EGFR has the protein sequence corresponding to GI:29725609.

The term "PIK3CA" or "p110α protein" refers to phosphatidylinositol-4,5-bisphosphate 3-kinase, catalytic subunit alpha. The term "PIK3CA" refers to the nucleotide sequence or protein sequence of human PIK3CA (e.g., Entrez 5290, UniProt P42336, RefSeq NM_006218, GI: 54792081, RefSeq NP_006209, and/or GI:54792082). The term "PIK3CA" includes both the wild-type form of the nucleotide sequences or proteins as well as any mutants thereof. In some embodiments, "PIK3CA" is wild-type PIK3CA. In some embodiments, "PIK3CA" is one or more mutant forms. The term "PIK3CA" XYZ refers to a nucleotide sequence or protein of a mutant PIK3CA wherein the Y numbered amino acid of PIK3CA that normally has an X amino acid in the wildtype, instead has a Z amino acid in the mutant. In embodiments, a PIK3CA is the human PIK3CA. In embodiments, the PIK3CA has the nucleotide sequence corresponding to reference number GI:54792081. In embodiments, the PIK3CA has the nucleotide sequence corresponding to RefSeq NM_006218.2. In embodiments, the PIK3CA has the protein sequence corresponding to RefSeq NP_006209.2. In embodiments, the PIK3CA has the protein sequence corresponding to GI:54792082.

The term "RB1" or "pRb" or "RB" refers to the retinoblastoma protein. The term "RB1" refers to the nucleotide sequence or protein sequence of human RB1 (e.g., Entrez 5925, UniProt P06400, RefSeq NM_000321, GI: 108773786, RefSeq NP_000312, and/or GI: 108773787). The term "RB1" includes both the wild-type form of the nucleotide sequences or proteins as well as any mutants thereof. In some embodiments, "RB1" is wild-type RB1. In some embodiments, "RB1" is one or more mutant forms. The term "RB1" XYZ refers to a nucleotide sequence or protein of a mutant RB1 wherein the Y numbered amino acid of RB1 that normally has an X amino acid in the wildtype, instead has a Z amino acid in the mutant. In embodiments, an RB1 is the human RB1. In embodiments, the RB1 has the nucleotide sequence corresponding to reference number GI:108773786. In embodiments, the RB1 has the nucleotide sequence corresponding to RefSeq NM_000321.2. In embodiments, the RB1 has the protein sequence corresponding to RefSeq NP_000312.2. In embodiments, the RB1 has the protein sequence corresponding to GI:108773787.

The term "TP53" refers to tumor protein p53. The term "TP53" refers to the nucleotide sequence or protein sequence of human RB1 (e.g., Entrez 7157, UniProt P04637, RefSeq NM_000546, GI: 371502114, RefSeq NP_000537, and/or GI:120407068). The term "TP53" includes both the wild-type form of the nucleotide sequences or proteins as well as any mutants thereof. In some embodiments, "TP53" is wild-type TP53. In some embodiments, "TP53" is one or more mutant forms. The term "TP53" XYZ refers to a nucleotide sequence or protein of a mutant TP53 wherein the Y numbered amino acid of TP53 that normally has an X amino acid in the wildtype, instead has a Z amino acid in the mutant. In embodiments, a TP53 is the human TP53. In embodiments, the TP53 has the nucleotide sequence corresponding to reference number GI:371502114. In embodiments, the TP53 has the nucleotide sequence corresponding to RefSeq NM_000546.5. In embodiments, the TP53 has the protein sequence corresponding to RefSeq NP_000537.3. In embodiments, the TP53 has the protein sequence corresponding to GI: 120407068.

The term "NRF2" or "NFE2L2" refers to the protein nuclear factor erythroid 2-related factor 2. The term "NRF2" may refer to the nucleotide sequence or protein sequence of human NRF2 (e.g., Entrez 4780, Uniprot Q16236, RefSeq NM_00001145412, GI: 926657643, RefSeq NP_001138884, and/or GI: 224028257). The term "NRF2" includes both the wild-type form of the nucleotide sequences or proteins as well as any mutants thereof. In some embodiments, "NRF2" is wild-type NRF2. In some embodiments, "NRF2" is one or more mutant forms. The term "NRF2" XYZ refers to a nucleotide sequence or protein of a mutant NRF2 wherein the Y numbered amino acid of NRF2 that normally has an X amino acid in the wildtype, instead has a Z amino acid in the mutant. In embodiments, an NRF2 is the human NRF2. In embodiments, the NRF2 has the nucleotide sequence corresponding to reference number GI:926657643. In embodiments, the NRF2 has the nucleotide sequence corresponding to RefSeq NM_001145412.3. In embodiments, the NRF2 has the protein sequence corresponding to RefSeq NP_001138884.1. In embodiments, the NRF2 has the protein sequence corresponding to GI:224028257.

The term "FOXO3" or "FOXO3a" refers to the protein Forkhead box O3. The term "FOXO3" may refer to the nucleotide sequence or protein sequence of human FOXO3

(e.g., Entrez 2309, Uniprot O43524, RefSeq NM_001455, GI: 146260266, RefSEQ NP_001446, and/or GI: 4503739). The term "FOXO3" includes both the wild-type form of the nucleotide sequences or proteins as well as any mutants thereof. In some embodiments, "FOXO3" is wild-type FOXO3. In some embodiments, "FOXO3" is one or more mutant forms. The term "FOXO3" XYZ refers to a nucleotide sequence or protein of a mutant FOXO3 wherein the Y numbered amino acid of FOXO3 that normally has an X amino acid in the wildtype, instead has a Z amino acid in the mutant. In embodiments, an FOXO3 is the human FOXO3. In embodiments, the FOXO3 has the nucleotide sequence corresponding to reference number GI: 146260266. In embodiments, the FOXO3 has the nucleotide sequence corresponding to RefSeq NM_001455.3. In embodiments, the FOXO3 has the protein sequence corresponding to RefSeq NP_001446.1. In embodiments, the FOXO3 has the protein sequence corresponding to GI: 4503739.

The term "mTOR" refers to the protein "mechanistic target of rapamycin (serine/threonine kinase)" or "mammalian target of rapamycin". The term "mTOR" may refer to the nucleotide sequence or protein sequence of human mTOR (e.g., Entrez 2475, Uniprot P42345, RefSeq NM_004958, or RefSeq NP_004949). The term "mTOR" includes both the wild-type form of the nucleotide sequences or proteins as well as any mutants thereof. In some embodiments, "mTOR" is wild-type mTOR. In some embodiments, "mTOR" is one or more mutant forms. The term "mTOR" XYZ refers to a nucleotide sequence or protein of a mutant mTOR wherein the Y numbered amino acid of mTOR that normally has an X amino acid in the wildtype, instead has a Z amino acid in the mutant. In embodiments, an mTOR is the human mTOR. In embodiments, the mTOR has the nucleotide sequence corresponding to reference number GI:206725550. In embodiments, the mTOR has the nucleotide sequence corresponding to RefSeq NM_004958.3. In embodiments, the mTOR has the protein sequence corresponding to reference number GI:4826730. In embodiments, the mTOR has the protein sequence corresponding to RefSeq NP_004949.1

In embodiments, the mTOR is a mutant mTOR. In embodiments, the mutant mTOR is associated with a disease that is not associated with wildtype mTOR. In embodiments, the mTOR includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to the sequence above.

"Analog" and "analogue" are used interchangeably and are used in accordance with their plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof. Accordingly, an analog is a compound that is similar or comparable in function and appearance but not in structure or origin to a reference compound.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about means the specified value.

As used herein, the term "cellular stress" refers to the decrease in cellular function caused by a stress stimuli (e.g., from an external or internal source) relative to the absence of the stress stimuli. Non-limiting examples of such stimuli ("stressors") are higher and/or lower temperatures than ideal for the proliferation and/or survival of the cell, exposure to oxidizing species, exposure to toxins, radiation, and mechanical damage. Cellular stress encompasses such non-limiting examples as stress due to DNA damage, stress due to RNA damage, stress due to lipid damage, oxidative stress, stress due to mutagens, toxic stress, metabolic stress, and stress due to protein denaturing (e.g., unfolding) and stress due to protein damage (e.g., covalent modification or heavy metal binding). In embodiments cellular stress is associated with a higher level of unfolded proteins compared to the normal level of unfolded proteins under healthy productive conditions (no cellular stress, average cellular stress, baseline cellular stress, or a reduced level of cellular stress). In embodiments, cellular stress is oxidative stress. In embodiments, cellular stress is DNA damage. In embodiments, cellular stress is denatured and/or damaged proteins. In embodiments, cellular stress is associated with exposure to a heavy metal (e.g. cadmium).

As used herein, the term "oxidative stress" is cellular stress caused by oxidative species as the stress stimuli. For example oxidative stress refers to an imbalance between oxidants and antioxidants in favor of the oxidants, leading to a disruption of redox signaling and control and/or cellular damage due to an excess of oxidative species. Non-limiting examples of oxidizing species include superoxide radical, hydroxyl radical, organic hydroperoxide, alkoxy radicals, peroxy radicals, hypochlorous acid, and hydrogen peroxide (Br. J. Exp. Path. (1989) 70, 737-757).

The term "longevity" is used in accordance with its plain ordinary meaning and refers to an increased life span caused by the administration of a stress resistance increasing compound relative to the absence of a stress resistance increasing compound. For example, longevity may refer to a long life or the extension of life expectancy beyond an average life expectancy or beyond a predicted life expectancy. A "longevity agent" is an agent (e.g., composition as described herein) capable of extending the life expectancy of a subject in comparison to the life expectancy of the subject in the absence of the agent (Lamming, D. W., et al. (2012). Science (New York, N.Y.), 335(6076), 1638-1643, McCormick, M. A., et al. (2011). Philosophical Transactions of the Royal Society B: Biological Sciences, 366(1561)). A longevity agent may be capable of inducing one or more anti-aging effects in a subject wherein an aging effect is a condition or symptom of aging normally (e.g., in the absence of the longevity agent) found in a similar subject. Symptoms of aging are well known or may be easily determined by a person having ordinary skill in medicine or the life sciences.

The term "stress resistance increasing compound" as used herein refers to a compound that is capable of improving cell survival, proliferation, and/or growth relative to the absence of the compound when the cell experiences cellular stress. In embodiments, the stress resistance increasing compound increases the longevity and/or increases the lifespan of a cell. In embodiments, the stress resistance increasing compound increases the longevity and/or increases the lifespan of a subject. In embodiments, the stress resistance increasing compound increases the level of FOXO3 activity in a cell. In embodiments, the stress resistance increasing compound increases the level of NRF2 activity in a cell. In embodiments, the stress resistance increasing compound inhibits survival of cancer cells. In embodiments, the stress resistance increasing compound reduces the level of mTOR activity in a cell. In embodiments, the stress resistance increasing compound inhibits PARP activity in a cell. In embodiments, the stress resistance increasing compound inhibits SUMO/sentrin specific peptidase (SENP) activity in a cell. In embodiments, the stress resistance increasing compound increases the level of autophagy activity in a cell. In embodiments, the stress resistance increasing compound mitigates (e.g., reduces) cellular stress.

As used herein, the term "age associated disease" or "aging-associated disease" refers to a disease that occurs more frequently with increasing senescence and/or age. In embodiments, the age associated disease is a cancer, atherosclerosis, neurodegenerative disease, cardiovascular disease, metabolic disease, or inflammatory disease. In embodiments, the neurodegenerative disease is Alzheimer's Disease, Parkinson's Disease, amyotrophic lateral sclerosis, or Huntington's Disease. In embodiments, the metabolic disease is type II diabetes. In embodiments the cancer is lung cancer.

B. Compounds

In embodiments is provided a compound or a pharmaceutically acceptable salt thereof, having the formula:

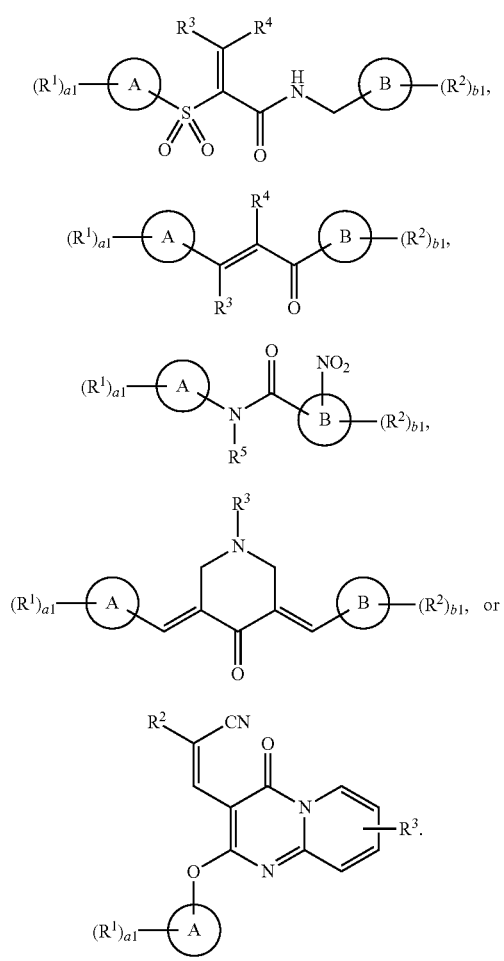

Ring A is aryl or heteroaryl. Ring B is aryl or heteroaryl. $R^1$ is independently a halogen, $—CX^1_3$, $—CN$, $—SO_{n1}R^{10}$, $—SO_{v1}NR^7R^8$, $—NHNH_2$, $—ONR^7R^8$, $—NHC=(O)NHNH_2$, $—NHC=(O)NR^7R^8$, $—N(O)_{m1}$, $—NR^7R^8$, $—C(O)R^9$, $—C(O)—OR^9$, $—C(O)NR^7R^8$, $—OR^{10}$, $—NR^7SO_2R^{10}$, $—NR^7C=(O)R^9$, $—NR^7C(O)—OR^9$, $—NR^7OR^9$, $—OCX^1_3$, $—OCHX^1_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl. $R^2$ is independently a halogen, $—CX^2_3$, $—CN$, $—SO_{n2}R^{14}$, $—SO_{v2}NR^{11}R^{12}$, $—NHNH_2$, $—ONR^{11}R^{12}$, $—NHC=(O)NHNH_2$, $—NHC=(O)NR^{11}R^{12}$, $—N(O)_{m2}$, $—NR^{11}R^{12}$, $—C(O)R^{13}$, $—C(O)—OR^{13}$, $—C(O)NR^{11}R^{12}$, $—OR^{14}$, $—NR^{11}SO_2R^{14}$, $—NR^{11}C=(O)R^{13}$, $—NR^{11}C(O)—OR^{13}$, $—NR^{11}OR^{13}$, $—OCX^2_3$, $—OCHX^2_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl. $R^3$ is independently hydrogen, halogen, $—CX^3_3$, $—CN$, $—OH$, $—NH_2$, $—COOH$, $—CONH_2$, $—NO_2$, $—SH$, $—SO_3H$, $—SO_4H$, $—SO_2NH_2$, $—NHNH_2$, $—ONH_2$, $—NHC=(O)NHNH_2$, $—NHC=(O)NH_2$, $—NHSO_2H$, $—NHC=(O)H$, $—NHC(O)—OH$, $—NHOH$, $—OCX^3_3$, $—OCHX^3_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is independently hydrogen, halogen, $—CX^4_3$, $—CN$, $—OH$, $—NH_2$, $—COOH$, $—CONH_2$, $—NO_2$, $—SH$, $—SO_3H$, $—SO_4H$, $—SO_2NH_2$, $—NHNH_2$, $—ONH_2$, $—NHC=(O)NHNH_2$, $—NHC=(O)NH_2$, $—NHSO_2H$, $—NHC=(O)H$, $—NHC(O)—OH$, $—NHOH$, $—OCX^4_3$, $—OCHX^4_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ is hydrogen, substituted or unsubstituted alkyl, or substituted or unsubstituted heteroalkyl; $R^5$ may optionally be joined to an $R^1$ substituent ortho to the $—N(R^5)—$ to form a substituted or unsubstituted 5 to 6 membered heterocycloalkyl or substituted or unsubstituted 5 to 6 membered heteroaryl. $R^7$, $R^8$, $R^9$, $R^{10}$, $R^{11}$, $R^{12}$, $R^{13}$, and $R^{14}$ are independently hydrogen, halogen, $—CX_3$, $—CN$, $—OH$, $—NH_2$, $—COOH$, $—CONH_2$, $—NO_2$, $—SH$, $—SO_3H$, $—SO_4H$, $—SO_2NH_2$, $—NHNH_2$, $—ONH_2$, $—NHC=(O)NHNH_2$, $—NHC=(O)NH_2$, $—NHSO_2H$, $—NHC=(O)H$, $—NHC(O)—OH$, $—NHOH$, $—OCX_3$, $—OCHX_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl. The symbol a1 is independently an integer from 0 to 7. The symbol b1 is independently an integer from 0 to 7. The symbol m1, m2, v1, and v2 are independently 1 or 2. The symbol n1 and n2 are independently an integer from 0 to 4. The symbol X, $X^1$, $X^2$, $X^3$, and $X^4$ are independently —Cl, —Br, —I, or —F.

In embodiments, Ring A is aryl, or 5 to 6 membered heteroaryl. In embodiments, Ring A is phenyl. In embodiments, Ring A is 5 to 6 membered heteroaryl. In embodiments, Ring A is 5 membered heteroaryl. In embodiments, Ring A is 6 membered heteroaryl. In embodiments, Ring A is pyridyl. In embodiments, Ring A is phenyl. In embodiments, Ring A is furanyl. In embodiments, Ring A is thienyl. In embodiments, Ring A is napthyl. In embodiments, Ring A is indolyl. In embodiments, Ring A is quinolinyl. In embodiments, Ring A is isoquinolinyl. In embodiments, Ring A is biphenyl. In embodiments, Ring A is thiazolyl. In embodiments, Ring A is pyrimidyl. In embodiments, Ring A is quinoxalinyl.

In embodiments, Ring A is substituted or unsubstituted pyrazolyl. In embodiments, Ring A is substituted or unsubstituted imidazolyl. In embodiments, Ring A is substituted or unsubstituted oxazolyl. In embodiments, Ring A is substituted or unsubstituted isoxazolyl. In embodiments, Ring A is substituted or unsubstituted thiazolyl. In embodiments, Ring A is substituted or unsubstituted furanyl. In embodiments, Ring A is substituted or unsubstituted pyrrolyl. In embodiments, Ring A is substituted or unsubstituted thienyl. In embodiments, Ring A is substituted pyrazolyl. In embodiments, Ring A is substituted imidazolyl. In embodiments, Ring A is substituted oxazolyl. In embodiments, Ring A is substituted isoxazolyl. In embodiments, Ring A is substituted thiazolyl. In embodiments, Ring A is substituted furanyl. In embodiments, Ring A is substituted pyrrolyl. In embodiments, Ring A is substituted thienyl. In embodiments, Ring A is unsubstituted pyrazolyl. In embodiments, Ring A is unsubstituted imidazolyl. In embodiments, Ring A is unsubstituted oxazolyl. In embodiments, Ring A is unsubstituted isoxazolyl. In embodiments, Ring A is unsubstituted thiazolyl. In embodiments, Ring A is unsubstituted furanyl. In embodiments, Ring A is unsubstituted pyrrolyl. In embodiments, Ring A is unsubstituted thienyl. In embodiments, Ring A is independently substituted or unsubstituted $C_6$-$C_{10}$ aryl, or substituted or unsubstituted 5 to 10 membered heteroaryl. In embodiments, Ring A is independently substituted or unsubstituted 5 or 10 membered heteroaryl. In embodiments, Ring A is unsubstituted benzimidazolyl. In embodiments, Ring A is pyrazolyl. In embodiments, Ring A is imidazolyl. In embodiments, Ring A is oxazolyl. In embodiments, Ring A is isoxazolyl. In embodiments, Ring A is thiazolyl. In embodiments, Ring A is isothiazolyl. In embodiments, Ring A is furanyl. In embodiments, Ring A is pyrrolyl. In embodiments, Ring A is thienyl. In embodiments, Ring A is independently $C_6$-$C_{10}$ aryl. In embodiments, Ring A is independently 5 to 10 membered heteroaryl. In embodiments, Ring A is benzimidazolyl. It will be understood that when Ring A is bonded to one or more non-hydrogen $R^1$ moieties, then Ring A is substituted. Likewise, it will be understood that when Ring A is not bonded to any $R^1$ moieties, or is bonded to $R^1$ moieties that are all hydrogen moieties, then Ring A is unsubstituted.

In embodiments, Ring B is aryl, or 5 to 6 membered heteroaryl. In embodiments, Ring B is phenyl. In embodiments, Ring B is 5 to 6 membered heteroaryl. In embodiments, Ring B is 5 membered heteroaryl. In embodiments, Ring B is 6 membered heteroaryl. In embodiments, Ring B is pyridyl. In embodiments, Ring B is phenyl. In embodiments, Ring B is furanyl. In embodiments, Ring B is thienyl. In embodiments, Ring B is napthyl. In embodiments, Ring B is indolyl. In embodiments, Ring B is quinolinyl. In embodiments, Ring B is isoquinolinyl. In embodiments, Ring B is biphenyl. In embodiments, Ring B is thiazolyl. In embodiments, Ring B is pyrimidyl. In embodiments, Ring B is quinoxalinyl.

In embodiments, Ring B is substituted or unsubstituted pyrazolyl. In embodiments, Ring B is substituted or unsubstituted imidazolyl. In embodiments, Ring B is substituted or unsubstituted oxazolyl. In embodiments, Ring B is substituted or unsubstituted isoxazolyl. In embodiments, Ring B is substituted or unsubstituted thiazolyl. In embodiments, Ring B is substituted or unsubstituted furanyl. In embodiments, Ring B is substituted or unsubstituted pyrrolyl. In embodiments, Ring B is substituted or unsubstituted thienyl. In embodiments, Ring B is substituted pyrazolyl. In embodiments, Ring B is substituted imidazolyl. In embodiments, Ring B is substituted oxazolyl. In embodiments, Ring B is substituted isoxazolyl. In embodiments, Ring B is substituted thiazolyl. In embodiments, Ring B is substituted furanyl. In embodiments, Ring B is substituted pyrrolyl. In embodiments, Ring B is substituted thienyl. In embodiments, Ring B is unsubstituted pyrazolyl. In embodiments, Ring B is unsubstituted imidazolyl. In embodiments, Ring B is unsubstituted oxazolyl. In embodiments, Ring B is unsubstituted isoxazolyl. In embodiments, Ring B is unsubstituted thiazolyl. In embodiments, Ring B is unsubstituted furanyl. In embodiments, Ring B is unsubstituted pyrrolyl. In embodiments, Ring B is unsubstituted thienyl. In embodiments, Ring B is independently hydrogen, substituted or unsubstituted $C_6$-$C_{10}$ aryl, or substituted or unsubstituted 5 to 10 membered heteroaryl. In embodiments, Ring B is independently substituted or unsubstituted 5 or 10 membered heteroaryl. In embodiments, Ring B is unsubstituted benzimidazolyl. In embodiments, Ring B is pyrazolyl. In embodiments, Ring B is imidazolyl. In embodiments, Ring B is oxazolyl. In embodiments, Ring B is isoxazolyl. In embodiments, Ring B is thiazolyl. In embodiments, Ring B is isothiazolyl. In embodiments, Ring B is furanyl. In embodiments, Ring B is pyrrolyl. In embodiments, Ring B is thienyl. In embodiments, Ring B is independently $C_6$-$C_{10}$ aryl. In embodiments, Ring B is independently 5 to 10 membered heteroaryl. In embodiments, Ring B is benzimidazolyl. It will be understood that when Ring B is bonded to one or more non-hydrogen $R^2$ moieties, then Ring B is substituted. Likewise, it will be understood that when Ring B is not bonded to any $R^2$ moieties, or is bonded to $R^2$ moieties that are all hydrogen moieties, then Ring B is unsubstituted.

In embodiments, $R^1$ is independently a halogen, —$CX^1_3$, —CN, —$SO_{n1}R^{10}$, —$SO_{v1}NR^7R^8$, —$NHNH_2$, —$ONR^7R^8$, —NHC=(O)$NHNH_2$, —NHC=(O)$NR^7R^8$, —$N(O)_{m1}$, —$NR^7R^8$, —$C(O)R^9$, —C(O)—$OR^9$, —$C(O)NR^7R^8$, —$OR^{10}$, —$NR^7SO_2R^{10}$, —$NR^7C$=(O)$R^9$, —$NR^7C(O)$—$OR^9$, —$NR^7OR^9$, —$OCX^1_3$, —$OCHX^1_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^1$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^1$ is independently unsubstituted $C_1$-$C_6$ alkyl. In embodiments, $R^1$ is independently unsubstituted $C_1$-$C_5$ alkyl. In embodiments, $R^1$ is independently unsubstituted $C_1$-$C_4$ alkyl. In embodiments, $R^1$ is independently unsubstituted $C_1$-$C_3$ alkyl. In embodiments, $R^1$ is independently unsubstituted $C_1$-$C_2$ alkyl. In embodiments, $R^1$ is independently unsubstituted $C_2$-$C_6$ alkyl. In embodiments, $R^1$ is independently unsubstituted $C_3$-$C_6$ alkyl. In embodiments, $R^1$ is independently unsubstituted $C_4$-$C_6$ alkyl. In embodiments, $R^1$ is independently substituted $C_1$-$C_6$ alkyl. In embodiments, $R^1$ is independently substituted $C_1$-$C_5$ alkyl. In embodiments, $R^1$ is independently substituted $C_1$-$C_4$ alkyl. In embodiments, $R^1$ is independently substituted $C_1$-$C_3$ alkyl. In embodiments, $R^1$ is independently substituted $C_1$-$C_2$ alkyl. In embodiments, $R^1$ is independently substituted $C_2$-$C_6$ alkyl. In embodiments, $R^1$ is independently substituted $C_3$-$C_6$ alkyl. In embodiments, $R^1$ is independently substituted $C_4$-$C_6$ alkyl. In embodiments, $R^1$ is independently substituted or unsubstituted 2 to 3 membered heteroalkyl. In embodiments, $R^1$ is independently substituted or unsubstituted 2 to 4 membered heteroalkyl. In embodiments, $R^1$ is independently substituted or unsubstituted 2 to 5 membered heteroalkyl. In embodiments, $R^1$ is independently substituted or unsubstituted $C_4$-$C_6$ cycloalkyl. In embodiments, $R^1$ is independently substituted or unsubstituted 4 to 6 membered heterocycloalkyl. In embodiments, $R^1$ is independently substituted or unsubstituted 5 to 6 membered heterocycloalkyl. In embodiments, $R^1$ is independently substituted or unsubstituted 5 membered heteroaryl. In embodiments, $R^1$ is independently substituted or unsubstituted 6 membered heteroaryl. In embodiments, $R^1$ is independently unsubstituted 6 membered heteroaryl. In embodiments, $R^1$ is independently unsubstituted 5 membered heteroaryl. In embodiments, $R^1$ is independently substituted 6 membered heteroaryl. In embodiments, $R^1$ is independently substituted 5 membered heteroaryl. In embodiments, $R^1$ is phenyl.

In embodiments, $R^1$ is independently a halogen, $-CX^1_3$, $-CN$, $-SO_{n1}R^{10}$, $-SO_{v1}NR^7R^8$, $-NHNH_2$, $-ONR^7R^8$, $-NHC=(O)NHNH_2$, $-NHC=(O)NR^7R^8$, $-N(O)_{m1}$, $-NR^7R^8$, $-C(O)R^9$, $-C(O)-OR^9$, $-C(O)NR^7R^8$, $-OR^{10}$, $-NR^7SO_2R^{10}$, $-NR^7C=(O)R^9$, $-NR^7C(O)-OR^9$, $-NR^7OR^9$, $-OCX^1_3$, $-OCHX^1_2$, $R^{20}$-substituted or unsubstituted alkyl, $R^{20}$-substituted or unsubstituted heteroalkyl, $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl; two adjacent $R^1$ substituents may optionally be joined to form a $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl.

In embodiments, $R^1$ is independently a halogen, $-CX^1_3$, $-CN$, $-SO_{n1}R^{10}$, $-SO_{v1}NR^7R^8$, $-NHNH_2$, $-ONR^7R^8$, $-NHC=(O)NHNH_2$, $-NHC=(O)NR^7R^8$, $-N(O)_{m1}$, $-NR^7R^8$, $-C(O)R^9$, $-C(O)-OR^9$, $-C(O)NR^7R^8$, $-OR^{10}$, $-NR^7SO_2R^{10}$, $-NR^7C=(O)R^9$, $-NR^7C(O)-OR^9$, $-NR^7OR^9$, $-OCX^1_3$, $-OCHX^1_2$, $R^{20}$-substituted or unsubstituted $C_1$-$C_6$ alkyl, $R^{20}$-substituted or unsubstituted 2 to 6 membered heteroalkyl, $R^{20}$-substituted or unsubstituted $C_3$-$C_6$ cycloalkyl, $R^{20}$-substituted or unsubstituted 3 to 6 membered heterocycloalkyl, $R^{20}$-substituted or unsubstituted phenyl, or $R^{20}$-substituted or unsubstituted 5 to 6 membered heteroaryl; two adjacent $R^1$ substituents may optionally be joined to form a $R^{20}$-substituted or unsubstituted $C_3$-$C_6$ cycloalkyl, $R^{20}$-substituted or unsubstituted 3 to 6 membered heterocycloalkyl, $R^{20}$-substituted or unsubstituted phenyl, or $R^{20}$-substituted or unsubstituted 5 to 6 membered heteroaryl. In embodiments, $R^1$ is independently $R^{20}$-substituted $C_1$-$C_6$ alkyl. In embodiments, $R^1$ is independently $R^{20}$-substituted $C_1$-$C_5$ alkyl. In embodiments, $R^1$ is independently $R^{20}$-substituted $C_1$-$C_4$ alkyl. In embodiments, $R^1$ is independently $R^{20}$-substituted $C_1$-$C_3$ alkyl. In embodiments, $R^1$ is independently $R^{20}$-substituted $C_1$-$C_2$ alkyl. In embodiments, $R^1$ is independently $R^{20}$-substituted $C_2$-$C_6$ alkyl. In embodiments, $R^1$ is independently $R^{20}$-substituted $C_3$-$C_6$ alkyl. In embodiments, $R^1$ is independently $R^{20}$-substituted $C_4$-$C_6$ alkyl. In embodiments, $R^1$ is independently $R^{20}$-substituted or unsubstituted 2 to 3 membered heteroalkyl. In embodiments, $R^1$ is independently $R^{20}$ substituted or unsubstituted 2 to 4 membered heteroalkyl. In embodiments, $R^1$ is independently $R^{20}$-substituted or unsubstituted 2 to 5 membered heteroalkyl. In embodiments, $R^1$ is independently $R^{20}$-substituted or unsubstituted $C_4$-$C_6$ cycloalkyl. In embodiments, $R^1$ is independently $R^{20}$-substituted or unsubstituted 4 to 6 membered heterocycloalkyl. In embodiments, $R^1$ is independently $R^{20}$-substituted or unsubstituted 5 to 6 membered heterocycloalkyl. In embodiments, $R^1$ is independently substituted or unsubstituted 5 membered heteroaryl. In embodiments, $R^1$ is independently $R^{20}$-substituted or unsubstituted 6 membered heteroaryl. In embodiments, $R^1$ is independently unsubstituted 6 membered heteroaryl. In embodiments, $R^1$ is independently unsubstituted 5 membered heteroaryl. In embodiments, $R^1$ is independently $R^{20}$-substituted 6 membered heteroaryl. In embodiments, $R^1$ is independently $R^{20}$-substituted 5 membered heteroaryl. In embodiments, $R^1$ is independently $R^{20}$-substituted phenyl.

In embodiments, $R^1$ is independently halogen. In embodiments, $R^1$ is independently $-F$. In embodiments, $R^1$ is independently $-Cl$. In embodiments, $R^1$ is independently $-Br$. In embodiments, $R^1$ is independently $-I$. In embodiments, $R^1$ is independently $-CF_3$. In embodiments, $R^1$ is independently $-CH_3$. In embodiments, $R^1$ is $-SO_2NH_2$. In embodiments, $R^1$ is independently $-OH$. In embodiments, $R^1$ is independently $-OCH_3$. In embodiments, $R^1$ is independently a halogen, $-CF_3$, $-SO_2NH_2$, unsubstituted $C_1$-$C_4$ alkyl, or unsubstituted 2 to 4 membered heteroalkyl. In embodiments, $R^1$ is independently unsubstituted $C_2$ alkyl. In embodiments, $R^1$ is independently $-CH_2CH_3$. In embodiments, $R^1$ is independently $-CH_3$ or $-OH$.

In embodiments, $R^2$ is independently a halogen, $-CX^2_3$, $-CN$, $-SO_{n2}R^{14}$, $-SO_{v2}NR^{11}R^{12}$, $-NHNH_2$, $-ONR^{11}R^{12}$, $-NHC=(O)NHNH_2$, $-NHC=(O)NR^{11}R^{12}$, $-N(O)_{m2}$, $-NR^{11}R^{12}$, $-C(O)R^{13}$, $-C(O)OR^{13}$, $-C(O)NR^{11}R^{12}$, $-OR^{14}$, $-NR^{11}SO_2R^{14}$, $-NR^{11}C=(O)R^{13}$, $-NR^{11}C(O)-OR^{13}$, $-NR^{11}OR^{13}$, $-OCX^2_3$, $-OCHX^2_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^2$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^2$ is independently unsubstituted $C_1$-$C_6$ alkyl. In embodiments, $R^2$ is independently unsubstituted $C_1$-$C_5$ alkyl. In embodiments, $R^2$ is independently unsubstituted $C_1$-$C_4$ alkyl. In embodiments, $R^2$ is independently unsubstituted $C_1$-$C_3$ alkyl. In embodiments, $R^2$ is independently unsubstituted $C_1$-$C_2$ alkyl. In embodiments, $R^2$ is independently unsubstituted $C_2$-$C_6$ alkyl. In embodiments, $R^2$ is independently unsubstituted $C_3$-$C_6$ alkyl. In embodiments, $R^2$ is independently unsubstituted $C_4$-$C_6$ alkyl. In embodiments, $R^2$ is independently substituted $C_1$-$C_6$ alkyl. In embodiments, $R^2$ is independently substituted $C_1$-$C_5$ alkyl. In embodiments, $R^2$ is independently substituted $C_1$-$C_4$ alkyl. In embodiments, $R^2$ is independently substituted $C_1$-$C_3$ alkyl. In embodiments, $R^2$ is independently substituted $C_1$-$C_2$ alkyl. In embodiments, $R^2$ is independently substituted $C_2$-$C_6$ alkyl. In embodiments, $R^2$ is substituted $C_3$-$C_6$ alkyl. In embodiments, $R^2$ is independently substituted $C_4$-$C_6$ alkyl. In embodiments, $R^2$ is substituted or unsubstituted 2 to 3 membered heteroalkyl. In embodiments, $R^2$ is independently substituted or unsubstituted 2 to 4 membered heteroalkyl. In embodiments, $R^2$ is independently substituted or unsubstituted 2 to 5 membered heteroalkyl. In embodiments, $R^2$ is independently substituted or unsubstituted $C_4$-$C_6$ cycloalkyl. In embodiments, $R^2$ is independently substituted or unsubstituted 4 to 6 membered heterocycloalkyl. In embodiments, $R^2$ is independently substituted or unsubstituted 5 to 6 membered heterocycloalkyl. In embodiments, $R^2$ is independently substituted or unsubstituted 5 membered heteroaryl. In embodiments, $R^2$ is independently substituted or unsubstituted 6 membered heteroaryl. In embodiments, $R^2$ is independently unsubstituted 6 membered heteroaryl. In embodiments, $R^2$ is independently unsubstituted 5 membered heteroaryl. In embodiments, $R^2$ is independently substituted 6 membered heteroaryl. In embodiments, $R^2$ is independently substituted 5 membered heteroaryl. In embodiments, $R^2$ is independently substituted phenyl. In embodiments, $R^2$ is independently unsubstituted phenyl.

In embodiments, $R^2$ is independently a halogen, —$CX^2_3$, —CN, —$SO_{n2}R^{14}$, —$SO_{v2}NR^{11}R^{12}$, —$NHNH_2$, —$ONR^{11}R^{12}$, —NHC=(O)$NHNH_2$, —NHC=(O)$NR^{11}R^{12}$, —$N(O)_{m2}$, —$NR^{11}R^{12}$, —C(O)$R^{13}$, —C(O)—$OR^{13}$, —C(O)$NR^{11}R^{12}$, —$OR^{14}$, —$NR^{11}SO_2R^{14}$, —$NR^{11}$C=(O)$R^{13}$, —$NR^{11}$C(O)—$OR^{13}$, —$NR^{11}OR^{13}$, —$OCX^2_3$, —$OCHX^2_2$, $R^{23}$-substituted or unsubstituted alkyl, $R^{23}$-substituted or unsubstituted heteroalkyl, $R^{23}$-substituted or unsubstituted cycloalkyl, $R^{23}$-substituted or unsubstituted heterocycloalkyl, $R^{23}$-substituted or unsubstituted aryl, or $R^{23}$-substituted or unsubstituted heteroaryl; two adjacent $R^2$ substituents may optionally be joined to form a $R^{23}$-substituted or unsubstituted cycloalkyl, $R^{23}$-substituted or unsubstituted heterocycloalkyl, $R^{23}$-substituted or unsubstituted aryl, or $R^{23}$-substituted or unsubstituted heteroaryl.

In embodiments, $R^2$ is independently a halogen, —$CX^2_3$, —CN, —$SO_{n2}R^{14}$, —$SO_{v2}NR^{11}R^{12}$, —$NHNH_2$, —$ONR^{11}R^{12}$, —NHC=(O)$NHNH_2$, —NHC=(O)$NR^{11}R^{12}$, —$N(O)_{m2}$, —$NR^{11}R^{12}$, —C(O)$R^{13}$, —C(O)—$OR^{13}$, —C(O)$NR^{11}R^{12}$, —$OR^{14}$, —$NR^{11}SO_2R^{14}$, —$NR^{11}$C=(O)$R^{13}$, —$NR^{11}$C(O)—$OR^{13}$, —$NR^{11}OR^{13}$, —$OCX^2_3$, —$OCHX^2_2$, $R^{23}$-substituted or unsubstituted $C_1$-$C_6$ alkyl, $R^{23}$-substituted or unsubstituted 2 to 6 membered heteroalkyl, $R^{23}$-substituted or unsubstituted $C_3$-$C_6$ cycloalkyl, $R^{23}$-substituted or unsubstituted 3 to 6 membered heterocycloalkyl, $R^{23}$-substituted or unsubstituted phenyl, or $R^{23}$-substituted or unsubstituted 5 to 6 membered heteroaryl; two adjacent $R^2$ substituents may optionally be joined to form a $R^{23}$-substituted or unsubstituted $C_3$-$C_6$ cycloalkyl, $R^{23}$-substituted or unsubstituted 3 to 6 membered heterocycloalkyl, $R^{23}$-substituted or unsubstituted phenyl, or $R^{23}$-substituted or unsubstituted 5 to 6 membered heteroaryl. In embodiments, $R^2$ is independently $R^{23}$-substituted $C_1$-$C_6$ alkyl. In embodiments, $R^2$ is independently $R^{23}$-substituted $C_1$-$C_5$ alkyl. In embodiments, $R^2$ is independently $R^{23}$-substituted $C_1$-$C_4$ alkyl. In embodiments, $R^2$ is independently $R^{23}$-substituted $C_1$-$C_3$ alkyl. In embodiments, $R^2$ is independently $R^{23}$-substituted $C_1$-$C_2$ alkyl. In embodiments, $R^2$ is independently $R^{23}$-substituted $C_2$-$C_6$ alkyl. In embodiments, $R^2$ is independently $R^{23}$-substituted $C_3$-$C_6$ alkyl. In embodiments, $R^2$ is independently $R^{23}$-substituted $C_4$-$C_6$ alkyl. In embodiments, $R^2$ is independently $R^{23}$-substituted or unsubstituted 2 to 3 membered heteroalkyl. In embodiments, $R^2$ is independently $R^{23}$-substituted or unsubstituted 2 to 4 membered heteroalkyl. In embodiments, $R^2$ is independently $R^{23}$-substituted or unsubstituted 2 to 5 membered heteroalkyl. In embodiments, $R^2$ is independently $R^{23}$-substituted or unsubstituted $C_4$-$C_6$ cycloalkyl. In embodiments, $R^2$ is independently $R^{23}$-substituted or unsubstituted 4 to 6 membered heterocycloalkyl. In embodiments, $R^2$ is independently $R^{23}$-substituted or unsubstituted 5 to 6 membered heterocycloalkyl. In embodiments, $R^2$ is independently $R^{23}$-substituted or unsubstituted 5 membered heteroaryl. In embodiments, $R^2$ is independently $R^{23}$-substituted or unsubstituted 6 membered heteroaryl. In embodiments, $R^2$ is independently unsubstituted 6 membered heteroaryl. In embodiments, $R^2$ is independently unsubstituted 5 membered heteroaryl. In embodiments, $R^2$ is independently $R^{23}$-substituted 6 membered heteroaryl. In embodiments, $R^2$ is independently $R^{23}$-substituted 5 membered heteroaryl. In embodiments, $R^2$ is independently $R^{23}$-substituted phenyl.

In embodiments, $R^2$ is independently halogen. In embodiments, $R^2$ is independently —F. In embodiments, $R^2$ is independently —Cl. In embodiments, $R^2$ is independently —Br. In embodiments, $R^2$ is independently —I. In embodiments, $R^2$ is independently —$CF_3$. In embodiments, $R^2$ is independently —$CH_3$. In embodiments, $R^2$ is —$SO_2NH_2$. In embodiments, $R^2$ is independently —OH. In embodiments, $R^2$ is independently —$OCH_3$. In embodiments, $R^2$ is independently a halogen, —$CF_3$, —$SO_2NH_2$, unsubstituted $C_1$-$C_4$ alkyl, or unsubstituted 2 to 4 membered heteroalkyl. In embodiments, $R^2$ is independently unsubstituted $C_2$ alkyl. In embodiments, $R^2$ is independently —$CH_2CH_3$. In embodiments, $R^2$ is independently —$CH_3$ or —OH.

In embodiments, $R^3$ is hydrogen, halogen, —$CX^3_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCX^3_3$, —$OCHX^3_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^3$ is unsubstituted $C_1$-$C_6$ alkyl. In embodiments, $R^3$ is unsubstituted $C_1$-$C_5$ alkyl. In embodiments, $R^3$ is unsubstituted $C_1$-$C_4$ alkyl. In embodiments, $R^3$ is unsubstituted $C_1$-$C_3$ alkyl. In embodiments, $R^3$ is unsubstituted $C_1$-$C_2$ alkyl. In embodiments, $R^3$ is unsubstituted $C_2$-$C_6$ alkyl. In embodiments, $R^3$ is unsubstituted $C_3$-$C_6$ alkyl. In embodiments, $R^3$ is unsubstituted $C_4$-$C_6$ alkyl. In embodiments, $R^3$ is substituted $C_1$-$C_6$ alkyl. In embodiments, $R^3$ is substituted $C_1$-$C_5$ alkyl. In embodiments, $R^3$ is substituted $C_1$-$C_4$ alkyl. In embodiments, $R^3$ is substituted $C_1$-$C_3$ alkyl. In embodiments, $R^3$ is substituted $C_1$-$C_2$ alkyl. In embodiments, $R^3$ is substituted $C_2$-$C_6$ alkyl. In embodiments, $R^3$ is substituted $C_3$-$C_6$ alkyl. In embodiments, $R^3$ is substituted $C_4$-$C_6$ alkyl. In embodiments, $R^3$ is substituted or unsubstituted 2 to 3 membered heteroalkyl. In embodiments, $R^3$ is substituted or unsubstituted 2 to 4 membered heteroalkyl. In embodiments, $R^3$ is substituted or unsubstituted 2 to 5 membered heteroalkyl. In embodiments, $R^3$ is substituted or unsubstituted $C_4$-$C_6$ cycloalkyl. In embodiments, $R^3$ is substituted or unsubstituted 4 to 6 membered heterocycloalkyl. In embodiments, $R^3$ is substituted or unsubstituted 5 to 6 membered heterocycloalkyl. In embodiments, $R^3$ is independently substituted or unsubstituted 5 membered heteroaryl. In embodiments, $R^3$ is independently substituted or unsubstituted 6 membered heteroaryl. In embodiments, $R^3$ is unsubstituted 6 membered heteroaryl. In embodiments, $R^3$ is unsubstituted 5 membered heteroaryl. In embodiments, $R^3$ is independently substituted 6 membered heteroaryl. In embodiments, $R^3$ is independently substituted 5 membered heteroaryl. In embodiments, $R^3$ is independently substituted phenyl. In embodiments, $R^3$ is independently unsubstituted phenyl.

In embodiments, $R^3$ is independently hydrogen, halogen, $-CX^{33}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^3_3$, $-OCHX^3_2$, $R^{26}$-substituted or unsubstituted alkyl, $R^{26}$-substituted or unsubstituted heteroalkyl, $R^{26}$-substituted or unsubstituted cycloalkyl, $R^{26}$-substituted or unsubstituted heterocycloalkyl, $R^{26}$-substituted or unsubstituted aryl, or $R^{26}$-substituted or unsubstituted heteroaryl.

In embodiments, $R^3$ is independently hydrogen, halogen, $-CX^{33}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^3_3$, $-OCHX^3_2$, $R^{26}$-substituted or unsubstituted $C_1$-$C_6$ alkyl, $R^{26}$-substituted or unsubstituted 2 to 6 membered heteroalkyl, $R^{26}$-substituted or unsubstituted $C_3$-$C_6$ cycloalkyl, $R^{26}$-substituted or unsubstituted 3 to 6 membered heterocycloalkyl, $R^{26}$-substituted or unsubstituted phenyl, or $R^{26}$-substituted or unsubstituted 5 to 6 membered heteroaryl. In embodiments, $R^3$ is $R^{26}$-substituted $C_1$-$C_6$ alkyl. In embodiments, $R^3$ is $R^{26}$-substituted $C_1$-$C_5$ alkyl. In embodiments, $R^3$ is $R^{26}$-substituted $C_1$-$C_4$ alkyl. In embodiments, $R^3$ is $R^{26}$-substituted $C_1$-$C_3$ alkyl. In embodiments, $R^3$ is $R^{26}$-substituted $C_1$-$C_2$ alkyl. In embodiments, $R^3$ is $R^{26}$-substituted $C_2$-$C_6$ alkyl. In embodiments, $R^3$ is substituted $C_3$-$C_6$ alkyl. In embodiments, $R^3$ is $R^{26}$-substituted $C_4$-$C_6$ alkyl. In embodiments, $R^3$ is $R^{26}$-substituted or unsubstituted 2 to 3 membered heteroalkyl. In embodiments, $R^3$ is $R^{26}$-Substituted or unsubstituted 2 to 4 membered heteroalkyl. In embodiments, $R^3$ is $R^{26}$-substituted or unsubstituted 2 to 5 membered heteroalkyl. In embodiments, $R^3$ is $R^{26}$-substituted or unsubstituted $C_4$-$C_6$ cycloalkyl. In embodiments, $R^3$ is $R^{26}$-substituted or unsubstituted 4 to 6 membered heterocycloalkyl. In embodiments, $R^3$ is $R^{26}$ substituted or unsubstituted 5 to 6 membered heterocycloalkyl. In embodiments, $R^3$ is $R^{26}$-substituted or unsubstituted 5 membered heteroaryl. In embodiments, $R^3$ is $R^{26}$-substituted or unsubstituted 6 membered heteroaryl. In embodiments, $R^3$ is $R^{26}$-substituted 6 membered heteroaryl. In embodiments, $R^3$ is $R^{26}$-substituted 5 membered heteroaryl. In embodiments, $R^3$ is independently $R^{26}$-substituted phenyl.

In embodiments, $R^3$ is hydrogen, $-CH_2CH_2CH_3$, or $-CH_3$. In embodiments, $R^3$ is hydrogen. In embodiments, $R^3$ is $-CH_2CH_2CH_3$. In embodiments, $R^3$ is $-CH_3$. In embodiments, $R^3$ is independently substituted or unsubstituted furanyl. In embodiments, $R^3$ is independently $R^{26}$-substituted or unsubstituted furanyl. In embodiments, $R^3$ is independently halogen. In embodiments, $R^3$ is independently $-F$. In embodiments, $R^3$ is independently $-Cl$. In embodiments, $R^3$ is independently $-Br$. In embodiments, $R^3$ is independently $-I$. In embodiments, $R^3$ is independently $-CF_3$. In embodiments, $R^3$ is $-SO_2NH_2$. In embodiments, $R^3$ is independently $-OH$. In embodiments, $R^3$ is independently $-OCH_3$.

In embodiments, $R^4$ is independently hydrogen, halogen, $-CX^4_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^4_3$, $-OCHX^4_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^4$ is unsubstituted $C_1$-$C_6$ alkyl. In embodiments, $R^4$ is unsubstituted $C_1$-$C_5$ alkyl. In embodiments, $R^4$ is unsubstituted $C_1$-$C_4$ alkyl. In embodiments, $R^4$ is unsubstituted $C_1$-$C_3$ alkyl. In embodiments, $R^4$ is unsubstituted $C_1$-$C_2$ alkyl. In embodiments, $R^4$ is unsubstituted $C_2$-$C_6$ alkyl. In embodiments, $R^4$ is unsubstituted $C_3$-$C_6$ alkyl. In embodiments, $R^4$ is unsubstituted $C_4$-$C_6$ alkyl. In embodiments, $R^4$ is substituted $C_1$-$C_6$ alkyl. In embodiments, $R^4$ is substituted $C_1$-$C_5$ alkyl. In embodiments, $R^4$ is substituted $C_1$-$C_4$ alkyl. In embodiments, $R^4$ is substituted $C_1$-$C_3$ alkyl. In embodiments, $R^4$ is substituted $C_1$-$C_2$ alkyl. In embodiments, $R^4$ is substituted $C_2$-$C_6$ alkyl. In embodiments, $R^4$ is substituted $C_3$-$C_6$ alkyl. In embodiments, $R^4$ is substituted $C_4$-$C_6$ alkyl. In embodiments, $R^4$ is substituted or unsubstituted 2 to 3 membered heteroalkyl. In embodiments, $R^4$ is substituted or unsubstituted 2 to 4 membered heteroalkyl. In embodiments, $R^4$ is substituted or unsubstituted 2 to 5 membered heteroalkyl. In embodiments, $R^4$ is substituted or unsubstituted $C_4$-$C_6$ cycloalkyl. In embodiments, $R^4$ is substituted or unsubstituted 4 to 6 membered heterocycloalkyl. In embodiments, $R^4$ is substituted or unsubstituted 5 to 6 membered heterocycloalkyl. In embodiments, $R^4$ is independently substituted or unsubstituted 5 membered heteroaryl. In embodiments, $R^4$ is independently substituted or unsubstituted 6 membered heteroaryl. In embodiments, $R^4$ is unsubstituted 6 membered heteroaryl. In embodiments, $R^4$ is unsubstituted 5 membered heteroaryl. In embodiments, $R^4$ is independently substituted 6 membered heteroaryl. In embodiments, $R^4$ is independently substituted 5 membered heteroaryl. In embodiments, $R^4$ is independently substituted phenyl. In embodiments, $R^4$ is independently unsubstituted phenyl.

In embodiments, $R^4$ is independently hydrogen, halogen, $-CX^4_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^4_3$, $-OCHX^4_2$, $R^{29}$-substituted or unsubstituted alkyl, $R^{29}$-substituted or unsubstituted heteroalkyl, $R^{29}$-substituted or unsubstituted cycloalkyl, $R^{29}$-substituted or unsubstituted heterocycloalkyl, $R^{29}$-substituted or unsubstituted aryl, or $R^{29}$-substituted or unsubstituted heteroaryl.

In embodiments, $R^4$ is independently hydrogen, halogen, $-CX^4_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^4_3$, $-OCHX^4_2$, $R^{29}$-substituted or unsubstituted $C_1$-$C_6$ alkyl, $R^{29}$-substituted or unsubstituted 2 to 6 membered heteroalkyl, $R^{29}$-substituted or unsubstituted $C_3$-$C_6$ cycloalkyl, $R^{29}$-substituted or unsubstituted 3 to 6 membered heterocycloalkyl, $R^{29}$-substituted or unsubstituted phenyl, or $R^{29}$-substituted or unsubstituted 5 to 6 membered heteroaryl. In embodiments, $R^4$ is $R^{29}$-substituted $C_1$-$C_6$ alkyl. In embodiments, $R^4$ is $R^{29}$-substituted $C_1$-$C_5$ alkyl. In embodiments, $R^4$ is $R^{29}$-substituted $C_1$-$C_4$ alkyl. In embodiments, $R^4$ is $R^{29}$-substituted $C_1$-$C_3$ alkyl. In embodiments, $R^4$ is $R^{29}$-substituted $C_1$-$C_2$ alkyl. In embodiments, $R^4$ is $R^{29}$-substituted $C_2$-$C_6$ alkyl. In embodiments, $R^4$ is $R^{29}$-substituted $C_3$-$C_6$ alkyl. In embodiments, $R^4$ is $R^{29}$-substituted $C_4$-$C_6$ alkyl. In embodiments, $R^4$ is $R^{29}$-substituted or unsubstituted 2 to 3 membered heteroalkyl. In embodiments, $R^4$ is $R^{29}$-substituted or unsubstituted 2 to 4 membered heteroalkyl. In embodiments, $R^4$ is $R^{29}$-substituted or unsubstituted 2 to 5 membered heteroalkyl. In embodiments, $R^4$ is $R^{29}$-substituted or unsubstituted $C_4$-$C_6$ cycloalkyl. In embodiments, $R^4$ is $R^{29}$-substituted or unsubstituted 4 to 6 membered heterocycloalkyl. In embodiments, $R^4$ is $R^{29}$ substituted or unsubstituted 5 to 6 membered heterocycloalkyl. In embodiments, $R^4$ is $R^{29}$ substituted or unsubstituted 5 membered heteroaryl. In embodiments, $R^4$ is $R^{29}$-substituted or unsubstituted 6 membered heteroaryl. In embodiments, $R^4$ is $R^{29}$-substituted 6 membered heteroaryl. In embodiments, $R^4$ is $R^{29}$-substituted 5 membered heteroaryl. In embodiments, $R^4$ is independently $R^{29}$-substituted phenyl.

In embodiments, $R^4$ is independently hydrogen, substituted or unsubstituted $C_6$-$C_{10}$ aryl, or substituted or unsubstituted 5 to 10 membered heteroaryl. In embodiments, $R^4$ is independently substituted or unsubstituted 5 to 10 membered heteroaryl. In embodiments, $R^4$ is independently $R^{29}$-substituted or unsubstituted benzimidazolyl. In embodiments, $R^4$ is independently hydrogen or substituted or unsubstituted $C_7$-$C_{10}$ aryl. In embodiments, $R^4$ is independently hydrogen or substituted or unsubstituted $C_8$-$C_{10}$ aryl. In embodiments, $R^4$ is independently hydrogen or substituted or unsubstituted $C_9$-$C_{10}$ aryl. In embodiments, $R^4$ is substituted or unsubstituted 6 to 10 membered heteroaryl. In embodiments, $R^4$ is substituted or unsubstituted 7 to 10 membered heteroaryl. In embodiments, $R^4$ is substituted or unsubstituted 8 to 10 membered heteroaryl. In embodiments, $R^4$ is substituted or unsubstituted 9 to 10 membered heteroaryl.

In embodiments, $R^4$ is independently hydrogen or $R^{29}$-substituted or unsubstituted $C_7$-$C_{10}$ aryl. In embodiments, $R^4$ is independently hydrogen or $R^{29}$-substituted or unsubstituted $C_8$-$C_{10}$ aryl. In embodiments, $R^4$ is independently hydrogen or $R^{29}$-substituted or unsubstituted $C_9$-$C_{10}$ aryl. In embodiments, $R^4$ is $R^{29}$-substituted or unsubstituted 6 to 10 membered heteroaryl. In embodiments, $R^4$ is $R^{29}$-substituted or unsubstituted 7 to 10 membered heteroaryl. In embodiments, $R^4$ is $R^{29}$-substituted or unsubstituted 8 to 10 membered heteroaryl. In embodiments, $R^4$ is $R^{29}$-substituted or unsubstituted 9 to 10 membered heteroaryl.

In embodiments, $R^4$ is independently $R^{29}$-substituted or unsubstituted furanyl. In embodiments, $R^4$ is hydrogen. In embodiments, $R^4$ is independently $R^{29}$-substituted phenoxy. In embodiments, $R^4$ is independently $R^{29}$-substituted phenyl. In embodiments, $R^4$ is phenoxybenzyl. In embodiments, $R^4$ is independently halogen. In embodiments, $R^4$ is independently —F. In embodiments, $R^4$ is independently —Cl. In embodiments, $R^4$ is independently —Br. In embodiments, $R^4$ is independently —I. In embodiments, $R^4$ is independently —$CF_3$. In embodiments, $R^4$ is independently —$CH_3$. In embodiments, $R^4$ is —$SO_2NH_2$. In embodiments, $R^4$ is independently —OH. In embodiments, $R^4$ is independently —$OCH_3$.

In embodiments, $R^4$ is substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^4$ is hydrogen, substituted or unsubstituted $C_1$-$C_4$ alkyl, substituted or unsubstituted $C_3$-$C_5$ cycloalkyl, substituted or unsubstituted 3 to 5 membered heterocycloalkyl, or substituted or unsubstituted 5 membered heteroaryl. In embodiments, $R^4$ is hydrogen, substituted or unsubstituted pyrazolyl, substituted or unsubstituted imidazolyl, substituted or unsubstituted oxazolyl, substituted or unsubstituted isoxazolyl, substituted or unsubstituted thiazolyl, substituted or unsubstituted furanyl, substituted or unsubstituted pyrrolyl, or substituted or unsubstituted thienyl. In embodiments, $R^4$ is unsubstituted pyrazolyl, unsubstituted imidazolyl, unsubstituted oxazolyl, unsubstituted isoxazolyl, unsubstituted thiazolyl, unsubstituted furanyl, unsubstituted pyrrolyl, or unsubstituted thienyl. In embodiments, $R^4$ is —$OCH_3$. In embodiments, $R^4$ is —Br. In embodiments, $R^4$ is —Cl.

In embodiments, $R^4$ is substituted or unsubstituted pyrazolyl. In embodiments, $R^4$ is substituted or unsubstituted imidazolyl. In embodiments, $R^4$ is substituted or unsubstituted oxazolyl. In embodiments, $R^4$ is substituted or unsubstituted isoxazolyl. In embodiments, $R^4$ is substituted or unsubstituted thiazolyl. In embodiments, $R^4$ is substituted or unsubstituted furanyl. In embodiments, $R^4$ is substituted or unsubstituted pyrrolyl. In embodiments, $R^4$ is substituted or unsubstituted thienyl. In embodiments, $R^4$ is substituted pyrazolyl. In embodiments, $R^4$ is substituted imidazolyl. In embodiments, $R^4$ is substituted oxazolyl. In embodiments, $R^4$ is substituted isoxazolyl. In embodiments, $R^4$ is substituted thiazolyl. In embodiments, $R^4$ is substituted furanyl. In embodiments, $R^4$ is substituted pyrrolyl. In embodiments, $R^4$ is substituted thienyl. In embodiments, $R^4$ is unsubstituted pyrazolyl. In embodiments, $R^4$ is unsubstituted imidazolyl. In embodiments, $R^4$ is unsubstituted oxazolyl. In embodiments, $R^4$ is unsubstituted isoxazolyl. In embodiments, $R^4$ is unsubstituted thiazolyl. In embodiments, $R^4$ is unsubstituted furanyl. In embodiments, $R^4$ is unsubstituted pyrrolyl. In embodiments, $R^4$ is unsubstituted thienyl. In embodiments, $R^4$ is independently hydrogen, substituted or unsubstituted $C_6$-$C_{10}$ aryl, or substituted or unsubstituted 5 to 10 membered heteroaryl. In embodiments, $R^4$ is independently substituted or unsubstituted 5 or 10 membered heteroaryl. In embodiments, $R^4$ is unsubstituted benzimidazolyl.

In embodiments, $R^5$ is hydrogen, substituted or unsubstituted $C_1$-$C_6$ alkyl, or substituted or unsubstituted 2 to 6 membered heteroalkyl. In embodiments, $R^5$ is unsubstituted $C_1$-$C_6$ alkyl. In embodiments, $R^5$ is unsubstituted $C_1$-$C_5$ alkyl. In embodiments, $R^5$ is unsubstituted $C_1$-$C_4$ alkyl. In embodiments, $R^5$ is unsubstituted $C_1$-$C_3$ alkyl. In embodiments, $R^5$ is unsubstituted $C_1$-$C_2$ alkyl. In embodiments, $R^5$ is unsubstituted $C_2$-$C_6$ alkyl. In embodiments, $R^5$ is unsubstituted $C_3$-$C_6$ alkyl. In embodiments, $R^5$ is unsubstituted $C_4$-$C_6$ alkyl. In embodiments, $R^5$ is substituted $C_1$-$C_6$ alkyl. In embodiments, $R^5$ is substituted $C_1$-$C_5$ alkyl. In embodiments, $R^5$ is substituted $C_1$-$C_4$ alkyl. In embodiments, $R^5$ is substituted $C_1$-$C_3$ alkyl. In embodiments, $R^5$ is substituted $C_1$-$C_2$ alkyl. In embodiments, $R^5$ is substituted $C_2$-$C_6$ alkyl. In embodiments, $R^5$ is substituted $C_3$-$C_6$ alkyl. In embodiments, $R^5$ is substituted $C_4$-$C_6$ alkyl. In embodiments, $R^5$ is substituted 3 to 6 membered heteroalkyl. In embodiments, $R^5$ is unsubstituted 3 to 6 membered heteroalkyl. In embodiments, $R^5$ is substituted 4 to 6 membered heteroalkyl. In embodiments, $R^5$ is unsubstituted 4 to 6 membered heteroalkyl. In embodiments, $R^5$ is hydrogen.

In embodiments, $R^5$ is hydrogen, $R^{32}$-substituted or unsubstituted $C_1$-$C_6$ alkyl, or $R^{32}$ substituted or unsubstituted 2 to 6 membered heteroalkyl. In embodiments, $R^5$ is $R^{32}$-substituted $C_1$-$C_6$ alkyl. In embodiments, $R^5$ is $R^{32}$-substituted $C_1$-$C_5$ alkyl. In embodiments, $R^5$ is $R^{32}$-substituted $C_1$-$C_4$ alkyl. In embodiments, $R^5$ is $R^{32}$-substituted $C_1$-$C_3$ alkyl. In embodiments, $R^5$ is $R^{32}$-substituted $C_1$-$C_2$ alkyl. In embodiments, $R^5$ is $R^{32}$-substituted $C_2$-$C_6$ alkyl. In embodiments, $R^5$ is $R^{32}$-substituted $C_3$-$C_6$ alkyl. In embodiments, $R^5$ is $R^{32}$-substituted $C_4$-$C_6$ alkyl. In embodiments, $R^5$ is $R^{32}$-substituted 3 to 6 membered heteroalkyl. In embodiments, $R^5$ is $R^{32}$-substituted 4 to 6 membered heteroalkyl.

In embodiments, $R^5$ may optionally be joined to an $R^1$ substituent ortho to the —N($R^5$)— to form an unsubstituted 5 membered heterocycloalkyl or unsubstituted 5 membered heteroaryl. In embodiments, $R^5$ is hydrogen or $R^5$ may optionally be joined to an $R^1$ substituent ortho to the —N($R^5$)— to form an unsubstituted 6 membered heterocycloalkyl or unsubstituted 6 membered heteroaryl. In embodiments, $R^5$ is hydrogen.

In embodiments, $R^7$ is independently hydrogen, halogen, —$CX_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX_3$, —$OCHX_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^7$ is independently unsubstituted $C_1$-$C_6$ alkyl. In embodiments, $R^7$ is independently unsubstituted $C_1$-$C_5$ alkyl. In embodiments, $R^7$ is independently unsubstituted $C_1$-$C_4$ alkyl. In embodiments, $R^7$ is independently unsubstituted $C_1$-$C_3$ alkyl. In embodiments, $R^7$ is independently unsubstituted $C_1$-$C_2$ alkyl. In embodiments, $R^7$ is independently unsubstituted $C_2$-$C_6$ alkyl. In embodiments, $R^7$ is independently unsubstituted $C_3$-$C_6$ alkyl. In embodiments, $R^7$ is independently unsubstituted $C_4$-$C_6$ alkyl. In embodiments, $R^7$ is independently substituted $C_1$-$C_6$ alkyl. In embodiments, $R^7$ is independently substituted $C_1$-$C_5$ alkyl. In embodiments, $R^7$ is independently substituted $C_1$-$C_4$ alkyl. In embodiments, $R^7$ is independently substituted $C_1$-$C_3$ alkyl. In embodiments, $R^7$ is independently substituted $C_1$-$C_2$ alkyl. In embodiments, $R^7$ is independently substituted $C_2$-$C_6$ alkyl. In embodiments, $R^7$ is independently substituted $C_3$-$C_6$ alkyl. In embodiments, $R^7$ is independently substituted $C_4$-$C_6$ alkyl. In embodiments, $R^7$ is independently substituted or unsubstituted 2 to 3 membered heteroalkyl. In embodiments, $R^7$ is independently substituted or unsubstituted 2 to 4 membered heteroalkyl. In embodiments, $R^7$ is independently substituted or unsubstituted 2 to 5 membered heteroalkyl. In embodiments, $R^7$ is independently substituted or unsubstituted $C_4$-$C_6$ cycloalkyl. In embodiments, $R^7$ is independently substituted or unsubstituted 4 to 6 membered heterocycloalkyl. In embodiments, $R^7$ is independently substituted or unsubstituted 5 to 6 membered heterocycloalkyl. In embodiments, $R^7$ is independently substituted or unsubstituted 5 membered heteroaryl. In embodiments, $R^7$ is independently substituted or unsubstituted 6 membered heteroaryl. In embodiments, $R^7$ is independently unsubstituted 6 membered heteroaryl. In embodiments, $R^7$ is independently unsubstituted 5 membered heteroaryl. In embodiments, $R^7$ is independently substituted 6 membered heteroaryl. In embodiments, $R^7$ is independently substituted 5 membered heteroaryl. In embodiments, $R^7$ is independently substituted phenyl. In embodiments, $R^7$ is independently unsubstituted phenyl. In embodiments, $R^7$ is independently hydrogen, —$CX_3$, —CN, —COOH, —$CONH_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^7$ is independently hydrogen, —$CX_3$, —COOH, —$CONH_2$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^7$ is independently hydrogen. In embodiments, $R^7$ is independently unsubstituted methyl.

In embodiments, $R^7$ is independently hydrogen, halogen, —$CX_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX_3$, —$OCHX_2$, $R^{35}$-substituted or unsubstituted alkyl, $R^{35}$-substituted or unsubstituted heteroalkyl, $R^{35}$-substituted or unsubstituted cycloalkyl, $R^{35}$-substituted or unsubstituted heterocycloalkyl, $R^{35}$-substituted or unsubstituted aryl, or $R^{35}$-substituted or unsubstituted heteroaryl.

In embodiments, $R^7$ is independently hydrogen, halogen, —$CX_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX_3$, —$OCHX_2$, $R^{35}$-substituted or unsubstituted $C_1$-$C_6$ alkyl, $R^{35}$-substituted or unsubstituted 2 to 6 membered heteroalkyl, $R^{35}$-substituted or unsubstituted $C_3$-$C_6$ cycloalkyl, $R^{35}$-substituted or unsubstituted 3 to 6 membered heterocycloalkyl, $R^{35}$-substituted or unsubstituted phenyl, or $R^{35}$-substituted or unsubstituted 5 to 6 membered heteroaryl. In embodiments, $R^7$ is independently $R^{35}$-substituted $C_1$-$C_6$ alkyl. In embodiments, $R^7$ is independently $R^{35}$-substituted $C_1$-$C_5$ alkyl. In embodiments, $R^7$ is independently $R^{35}$-substituted $C_1$-$C_4$ alkyl. In embodiments, $R^7$ is independently $R^{35}$-substituted $C_1$-$C_3$ alkyl. In embodiments, $R^7$ is independently $R^{35}$-substituted $C_1$-$C_2$ alkyl. In embodiments, $R^7$ is independently $R^{35}$-substituted $C_2$-$C_6$ alkyl. In embodiments, $R^7$ is independently $R^{35}$-substituted $C_3$-$C_6$ alkyl. In embodiments, $R^7$ is independently $R^{35}$-substituted $C_4$-$C_6$ alkyl. In embodiments, $R^7$ is independently $R^{35}$-substituted or unsubstituted 2 to 3 membered heteroalkyl. In embodiments, $R^7$ is independently $R^{35}$-substituted or unsubstituted 2 to 4 membered heteroalkyl. In embodiments, $R^7$ is independently $R^{35}$-substituted or unsubstituted 2 to 5 membered heteroalkyl. In embodiments, $R^7$ is independently $R^{35}$-substituted or unsubstituted $C_4$-$C_6$ cycloalkyl. In embodiments, $R^7$ is independently $R^{35}$-substituted or unsubstituted 4 to 6 membered heterocycloalkyl. In embodiments, $R^7$ is independently $R^{35}$-substituted or unsubstituted 5 to 6 membered heterocycloalkyl. In embodiments, $R^7$ is independently $R^{35}$-substituted or unsubstituted 5 membered heteroaryl. In embodiments, $R^7$ is independently $R^{35}$-substituted or unsubstituted 6 membered heteroaryl. In embodiments, $R^7$ is independently $R^{35}$-substituted 6 membered heteroaryl. In embodiments, $R^7$ is independently $R^{35}$-substituted 5 membered heteroaryl. In embodiments, $R^7$ is independently $R^{35}$-substituted phenyl.

In embodiments, $R^8$ is independently hydrogen, halogen, —$CX_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —NHSO$_2$H, —NHC=(O)H, —NHC(O)—OH, —NHOH, —OCX$_3$, —OCHX$_2$, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl. In embodiments, R$^8$ is independently unsubstituted C$_1$-C$_6$ alkyl. In embodiments, R$^8$ is independently unsubstituted C$_1$-C$_5$ alkyl. In embodiments, R$^8$ is independently unsubstituted C$_1$-C$_4$ alkyl. In embodiments, R$^8$ is independently unsubstituted C$_1$-C$_3$ alkyl. In embodiments, R$^8$ is independently unsubstituted C$_1$-C$_2$ alkyl. In embodiments, R$^8$ is independently unsubstituted C$_2$-C$_6$ alkyl. In embodiments, R$^8$ is independently unsubstituted C$_3$-C$_6$ alkyl. In embodiments, R$^8$ is independently unsubstituted C$_4$-C$_6$ alkyl. In embodiments, R$^8$ is independently substituted C$_1$-C$_6$ alkyl. In embodiments, R$^8$ is independently substituted C$_1$-C$_5$ alkyl. In embodiments, R$^8$ is independently substituted C$_1$-C$_4$ alkyl. In embodiments, R$^8$ is independently substituted C$_1$-C$_3$ alkyl. In embodiments, R$^8$ is independently substituted C$_1$-C$_2$ alkyl. In embodiments, R$^8$ is independently substituted C$_2$-C$_6$ alkyl. In embodiments, R$^8$ is independently substituted C$_3$-C$_6$ alkyl. In embodiments, R$^8$ is independently substituted C$_4$-C$_6$ alkyl. In embodiments, R$^8$ is independently substituted or unsubstituted 2 to 3 membered heteroalkyl. In embodiments, R$^8$ is independently substituted or unsubstituted 2 to 4 membered heteroalkyl. In embodiments, R$^8$ is independently substituted or unsubstituted 2 to 5 membered heteroalkyl. In embodiments, R$^8$ is independently substituted or unsubstituted C$_4$-C$_6$ cycloalkyl. In embodiments, R$^8$ is independently substituted or unsubstituted 4 to 6 membered heterocycloalkyl. In embodiments, R$^8$ is independently substituted or unsubstituted 5 to 6 membered heterocycloalkyl. In embodiments, R$^8$ is independently substituted or unsubstituted 5 membered heteroaryl. In embodiments, R$^8$ is independently substituted or unsubstituted 6 membered heteroaryl. In embodiments, R$^8$ is independently unsubstituted 6 membered heteroaryl. In embodiments, R$^8$ is independently unsubstituted 5 membered heteroaryl. In embodiments, R$^8$ is independently substituted 6 membered heteroaryl. In embodiments, R$^8$ is independently substituted 5 membered heteroaryl. In embodiments, R$^8$ is independently substituted phenyl. In embodiments, R$^8$ is independently unsubstituted phenyl. In embodiments, R$^8$ is independently hydrogen, —CX$_3$, —CN, —COOH, —CONH$_2$, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl. In embodiments, R$^8$ is independently hydrogen, —CX$_3$, —COOH, —CONH$_2$, unsubstituted C$_1$-C$_6$ alkyl, unsubstituted 2 to 6 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl. In embodiments, R$^8$ is independently hydrogen. In embodiments, R$^8$ is independently unsubstituted methyl.

In embodiments, R$^8$ is independently hydrogen, halogen, —CX$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$_3$, —OCHX$_2$, R$^{36}$-substituted or unsubstituted alkyl, R$^{36}$-substituted or unsubstituted heteroalkyl, R$^{36}$-substituted or unsubstituted cycloalkyl, R$^{36}$-substituted or unsubstituted heterocycloalkyl, R$^{36}$-substituted or unsubstituted aryl, or R$^{36}$-substituted or unsubstituted heteroaryl.

In embodiments, R$^8$ is independently hydrogen, halogen, —CX$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$_3$, —OCHX$_2$, R$^{36}$-substituted or unsubstituted C$_1$-C$_6$ alkyl, R$^{36}$-substituted or unsubstituted 2 to 6 membered heteroalkyl, R$^{36}$-substituted or unsubstituted C$_3$-C$_6$ cycloalkyl, R$^{36}$-substituted or unsubstituted 3 to 6 membered heterocycloalkyl, R$^{36}$-substituted or unsubstituted phenyl, or R$^{36}$-substituted or unsubstituted 5 to 6 membered heteroaryl. In embodiments, R$^8$ is independently R$^{36}$-substituted C$_1$-C$_6$ alkyl. In embodiments, R$^8$ is independently R$^{36}$-substituted C$_1$-C$_5$ alkyl. In embodiments, R$^8$ is independently R$^{36}$-substituted C$_1$-C$_4$ alkyl. In embodiments, R$^8$ is independently R$^{36}$-substituted C$_1$-C$_3$ alkyl. In embodiments, R$^8$ is independently R$^{36}$-substituted C$_1$-C$_2$ alkyl. In embodiments, R$^8$ is independently R$^{36}$-substituted C$_2$-C$_6$ alkyl. In embodiments, R$^8$ is independently R$^{36}$-substituted C$_3$-C$_6$ alkyl. In embodiments, R$^8$ is independently R$^{36}$-substituted C$_4$-C$_6$ alkyl. In embodiments, R$^8$ is independently R$^{36}$-substituted or unsubstituted 2 to 3 membered heteroalkyl. In embodiments, R$^8$ is independently R$^{36}$-substituted or unsubstituted 2 to 4 membered heteroalkyl. In embodiments, R$^8$ is independently R$^{36}$-substituted or unsubstituted 2 to 5 membered heteroalkyl. In embodiments, R$^8$ is independently R$^{36}$-substituted or unsubstituted C$_4$-C$_6$ cycloalkyl. In embodiments, R$^8$ is independently R$^{36}$-substituted or unsubstituted 4 to 6 membered heterocycloalkyl. In embodiments, R$^8$ is independently R$^{36}$-substituted or unsubstituted 5 to 6 membered heterocycloalkyl. In embodiments, R$^8$ is independently R$^{36}$-substituted or unsubstituted 5 membered heteroaryl. In embodiments, R$^8$ is independently R$^{36}$-substituted or unsubstituted 6 membered heteroaryl. In embodiments, R$^8$ is independently R$^{36}$-substituted 6 membered heteroaryl. In embodiments, R$^8$ is independently R$^{36}$-substituted 5 membered heteroaryl. In embodiments, R$^8$ is independently R$^{36}$-substituted phenyl.

In embodiments, R$^9$ is independently hydrogen, halogen, —CX$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$_3$, —OCHX$_2$, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered. In embodiments, R$^9$ is independently unsubstituted C$_1$-C$_6$ alkyl. In embodiments, R$^9$ is independently unsubstituted C$_1$-C$_5$ alkyl. In embodiments, R$^9$ is independently unsubstituted C$_1$-C$_4$ alkyl. In embodiments, R$^9$ is independently unsubstituted C$_1$-C$_3$ alkyl. In embodiments, R$^9$ is independently unsubstituted C$_1$-C$_2$ alkyl. In embodiments, R$^9$ is independently unsubstituted C$_2$-C$_6$ alkyl. In embodiments, R$^9$ is independently unsubstituted C$_3$-C$_6$ alkyl. In embodiments, R$^9$ is independently unsubstituted C$_4$-C$_6$ alkyl. In embodiments, R$^9$ is independently substituted C$_1$-C$_6$ alkyl. In embodiments, R$^9$ is independently substituted C$_1$-C$_5$ alkyl. In embodiments, R$^9$ is independently substituted C$_1$-C$_4$ alkyl. In embodiments, R$^9$ is independently substituted C$_1$-C$_3$ alkyl. In embodiments, R$^9$ is independently substituted C$_1$-C$_2$ alkyl. In embodiments, R$^9$ is independently substituted C$_2$-C$_6$ alkyl. In embodiments, R$^9$ is independently substituted C$_3$-C$_6$ alkyl.

In embodiments, $R^9$ is independently substituted $C_4$-$C_6$ alkyl. In embodiments, $R^9$ is independently substituted or unsubstituted 2 to 3 membered heteroalkyl. In embodiments, $R^9$ is independently substituted or unsubstituted 2 to 4 membered heteroalkyl. In embodiments, $R^9$ is independently substituted or unsubstituted 2 to 5 membered heteroalkyl. In embodiments, $R^9$ is independently substituted or unsubstituted $C_4$-$C_6$ cycloalkyl. In embodiments, $R^9$ is independently substituted or unsubstituted 4 to 6 membered heterocycloalkyl. In embodiments, $R^9$ is independently substituted or unsubstituted 5 to 6 membered heterocycloalkyl. In embodiments, $R^9$ is independently substituted or unsubstituted 5 membered heteroaryl. In embodiments, $R^9$ is independently substituted or unsubstituted 6 membered heteroaryl. In embodiments, $R^9$ is independently unsubstituted 6 membered heteroaryl. In embodiments, $R^9$ is independently unsubstituted 5 membered heteroaryl. In embodiments, $R^9$ is independently substituted 6 membered heteroaryl. In embodiments, $R^9$ is independently substituted 5 membered heteroaryl. In embodiments, $R^9$ is independently substituted phenyl. In embodiments, $R^9$ is independently unsubstituted phenyl. In embodiments, $R^9$ is independently hydrogen, —$CX_3$, —CN, —COOH, —$CONH_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^9$ is independently hydrogen, —$CX_3$, —COOH, —$CONH_2$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^9$ is independently hydrogen. In embodiments, $R^9$ is independently unsubstituted methyl.

In embodiments, $R^9$ is independently hydrogen, halogen, —$CX_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX_3$, —$OCHX_2$, $R^{37}$-substituted or unsubstituted alkyl, $R^{37}$-substituted or unsubstituted heteroalkyl, $R^{37}$-substituted or unsubstituted cycloalkyl, $R^{37}$-substituted or unsubstituted heterocycloalkyl, $R^{37}$-substituted or unsubstituted aryl, or $R^{37}$-substituted or unsubstituted heteroaryl.

In embodiments, $R^9$ is independently hydrogen, halogen, —$CX_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX_3$, —$OCHX_2$, $R^{37}$-substituted or unsubstituted $C_1$-$C_6$ alkyl, $R^{37}$-substituted or unsubstituted 2 to 6 membered heteroalkyl, $R^{37}$-substituted or unsubstituted $C_3$-$C_6$ cycloalkyl, $R^{37}$-substituted or unsubstituted 3 to 6 membered heterocycloalkyl, $R^{37}$-substituted or unsubstituted phenyl, or $R^{37}$-substituted or unsubstituted 5 to 6 membered heteroaryl. In embodiments, $R^9$ is independently $R^{37}$-substituted $C_1$-$C_6$ alkyl. In embodiments, $R^9$ is independently $R^{37}$-substituted $C_1$-$C_5$ alkyl. In embodiments, $R^9$ is independently $R^{37}$-substituted $C_1$-$C_4$ alkyl. In embodiments, $R^9$ is independently $R^{37}$-substituted $C_1$-$C_3$ alkyl. In embodiments, $R^9$ is independently $R^{37}$-substituted $C_1$-$C_2$ alkyl. In embodiments, $R^9$ is independently $R^{37}$-substituted $C_2$-$C_6$ alkyl. In embodiments, $R^9$ is independently $R^{37}$-substituted $C_3$-$C_6$ alkyl. In embodiments, $R^9$ is independently $R^{37}$-substituted $C_4$-$C_6$ alkyl. In embodiments, $R^9$ is independently $R^{37}$-substituted or unsubstituted 2 to 3 membered heteroalkyl. In embodiments, $R^9$ is independently $R^{37}$-substituted or unsubstituted 2 to 4 membered heteroalkyl. In embodiments, $R^9$ is independently $R^{37}$-substituted or unsubstituted 2 to 5 membered heteroalkyl. In embodiments, $R^9$ is independently $R^{37}$-substituted or unsubstituted $C_4$-$C_6$ cycloalkyl. In embodiments, $R^9$ is independently $R^{37}$-substituted or unsubstituted 4 to 6 membered heterocycloalkyl. In embodiments, $R^9$ is independently $R^{37}$-substituted or unsubstituted 5 to 6 membered heterocycloalkyl. In embodiments, $R^9$ is independently $R^{37}$-substituted or unsubstituted 5 membered heteroaryl. In embodiments, $R^9$ is independently $R^{37}$-substituted or unsubstituted 6 membered heteroaryl. In embodiments, $R^9$ is independently $R^{37}$-substituted 6 membered heteroaryl. In embodiments, $R^9$ is independently $R^{37}$-substituted 5 membered heteroaryl. In embodiments, $R^9$ is independently $R^{37}$-substituted phenyl.

In embodiments, $R^{10}$ is independently hydrogen, halogen, —$CX_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX_3$, —$OCHX_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{10}$ is independently unsubstituted $C_1$-$C_6$ alkyl. In embodiments, $R^{10}$ is independently unsubstituted $C_1$-$C_5$ alkyl. In embodiments, $R^{10}$ is independently unsubstituted $C_1$-$C_4$ alkyl. In embodiments, $R^{10}$ is independently unsubstituted $C_1$-$C_3$ alkyl. In embodiments, $R^{10}$ is independently unsubstituted $C_1$-$C_2$ alkyl. In embodiments, $R^{10}$ is independently unsubstituted $C_2$-$C_6$ alkyl. In embodiments, $R^{10}$ is independently unsubstituted $C_3$-$C_6$ alkyl. In embodiments, $R^{10}$ is independently unsubstituted $C_4$-$C_6$ alkyl. In embodiments, $R^{10}$ is independently substituted $C_1$-$C_6$ alkyl. In embodiments, $R^{10}$ is independently substituted $C_1$-$C_5$ alkyl. In embodiments, $R^{10}$ is independently substituted $C_1$-$C_4$ alkyl. In embodiments, $R^{10}$ is independently substituted $C_1$-$C_3$ alkyl. In embodiments, $R^{10}$ is independently substituted $C_1$-$C_2$ alkyl. In embodiments, $R^{10}$ is independently substituted $C_2$-$C_6$ alkyl. In embodiments, $R^{10}$ is independently substituted $C_3$-$C_6$ alkyl. In embodiments, $R^{10}$ is independently substituted $C_4$-$C_6$ alkyl. In embodiments, $R^{10}$ is independently substituted or unsubstituted 2 to 3 membered heteroalkyl. In embodiments, $R^{10}$ is independently substituted or unsubstituted 2 to 4 membered heteroalkyl. In embodiments, $R^{10}$ is independently substituted or unsubstituted 2 to 5 membered heteroalkyl. In embodiments, $R^{10}$ is independently substituted or unsubstituted $C_4$-$C_6$ cycloalkyl. In embodiments, $R^{10}$ is independently substituted or unsubstituted 4 to 6 membered heterocycloalkyl. In embodiments, $R^{10}$ is independently substituted or unsubstituted 5 to 6 membered heterocycloalkyl. In embodiments, $R^{10}$ is independently substituted or unsubstituted 5 membered heteroaryl. In embodiments, $R^{10}$ is independently substituted or unsubstituted 6 membered heteroaryl. In embodiments, $R^{10}$ is independently unsubstituted 6 membered heteroaryl. In embodiments, $R^{10}$ is independently unsubstituted 5 membered heteroaryl. In embodiments, $R^{10}$ is independently substituted 6 membered heteroaryl. In embodiments, $R^{10}$ is independently substituted 5 membered heteroaryl. In embodiments, $R^{10}$ is independently substituted phenyl. In embodiments, $R^{10}$ is independently unsubstituted phenyl. In embodiments, $R^{10}$ is independently hydrogen, —$CX_3$, —CN, —COOH, —$CONH_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{10}$ is independently hydrogen, —$CX_3$, —COOH, —$CONH_2$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{10}$ is independently hydrogen. In embodiments, $R^{10}$ is independently unsubstituted methyl.

In embodiments, $R^{10}$ is independently hydrogen, halogen, —$CX_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX_3$, —$OCHX_2$, $R^{38}$-substituted or unsubstituted alkyl, $R^{38}$-substituted or unsubstituted heteroalkyl, $R^{38}$-substituted or unsubstituted cycloalkyl, $R^{38}$-substituted or unsubstituted heterocycloalkyl, $R^{38}$-substituted or unsubstituted aryl, or $R^{38}$-substituted or unsubstituted heteroaryl.

In embodiments, $R^{10}$ is independently hydrogen, halogen, —$CX_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX_3$, —$OCHX_2$, $R^{38}$-substituted or unsubstituted $C_1$-$C_6$ alkyl, $R^{38}$-substituted or unsubstituted 2 to 6 membered heteroalkyl, $R^{38}$-substituted or unsubstituted $C_3$-$C_6$ cycloalkyl, $R^{38}$-substituted or unsubstituted 3 to 6 membered heterocycloalkyl, $R^{38}$-substituted or unsubstituted phenyl, or $R^{38}$-substituted or unsubstituted 5 to 6 membered heteroaryl. In embodiments, $R^{10}$ is independently $R^{38}$-substituted $C_1$-$C_6$ alkyl. In embodiments, $R^{10}$ is independently $R^{38}$-substituted $C_1$-$C_5$ alkyl. In embodiments, $R^{10}$ is independently $R^{38}$-substituted $C_1$-$C_4$ alkyl. In embodiments, $R^{10}$ is independently $R^{38}$-substituted $C_1$-$C_3$ alkyl. In embodiments, $R^{10}$ is independently $R^{38}$-substituted $C_1$-$C_2$ alkyl. In embodiments, $R^{10}$ is independently $R^{38}$-substituted $C_2$-$C_6$ alkyl. In embodiments, $R^{10}$ is independently $R^{38}$-substituted $C_3$-$C_6$ alkyl. In embodiments, $R^{10}$ is independently $R^{38}$-substituted $C_4$-$C_6$ alkyl. In embodiments, $R^{10}$ is independently $R^{38}$-substituted or unsubstituted 2 to 3 membered heteroalkyl. In embodiments, $R^{10}$ is independently $R^{38}$-substituted or unsubstituted 2 to 4 membered heteroalkyl. In embodiments, $R^{10}$ is independently $R^{38}$-substituted or unsubstituted 2 to 5 membered heteroalkyl. In embodiments, $R^{10}$ is independently $R^{38}$-substituted or unsubstituted $C_4$-$C_6$ cycloalkyl. In embodiments, $R^{10}$ is independently $R^{38}$-substituted or unsubstituted 4 to 6 membered heterocycloalkyl. In embodiments, $R^{10}$ is independently $R^{38}$-substituted or unsubstituted 5 to 6 membered heterocycloalkyl. In embodiments, $R^{10}$ is independently $R^{38}$-substituted or unsubstituted 5 membered heteroaryl. In embodiments, $R^{10}$ is independently $R^{38}$-substituted or unsubstituted 6 membered heteroaryl. In embodiments, $R^{10}$ is independently $R^{38}$-substituted 6 membered heteroaryl. In embodiments, $R^{10}$ is independently $R^{38}$-substituted 5 membered heteroaryl. In embodiments, $R^{10}$ is independently $R^{38}$-substituted phenyl.

In embodiments, $R^{11}$ is independently hydrogen, halogen, —$CX_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX_3$, —$OCHX_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{11}$ is independently unsubstituted $C_1$-$C_6$ alkyl. In embodiments, $R^{11}$ is independently unsubstituted $C_1$-$C_5$ alkyl. In embodiments, $R^{11}$ is independently unsubstituted $C_1$-$C_4$ alkyl. In embodiments, $R^{11}$ is independently unsubstituted $C_1$-$C_3$ alkyl. In embodiments, $R^{11}$ is independently unsubstituted $C_1$-$C_2$ alkyl. In embodiments, $R^{11}$ is independently unsubstituted $C_2$-$C_6$ alkyl. In embodiments, $R^{11}$ is independently unsubstituted $C_3$-$C_6$ alkyl. In embodiments, $R^{11}$ is independently unsubstituted $C_4$-$C_6$ alkyl. In embodiments, $R^{11}$ is independently substituted $C_1$-$C_6$ alkyl. In embodiments, $R^{11}$ is independently substituted $C_1$-$C_5$ alkyl. In embodiments, $R^{11}$ is independently substituted $C_1$-$C_4$ alkyl. In embodiments, $R^{11}$ is independently substituted $C_1$-$C_3$ alkyl. In embodiments, $R^{11}$ is independently substituted $C_1$-$C_2$ alkyl. In embodiments, $R^{11}$ is independently substituted $C_2$-$C_6$ alkyl. In embodiments, $R^{11}$ is independently substituted $C_3$-$C_6$ alkyl. In embodiments, $R^{11}$ is independently substituted $C_4$-$C_6$ alkyl. In embodiments, $R^{11}$ is independently substituted or unsubstituted 2 to 3 membered heteroalkyl. In embodiments, $R^{11}$ is independently substituted or unsubstituted 2 to 4 membered heteroalkyl. In embodiments, $R^1$ is independently substituted or unsubstituted 2 to 5 membered heteroalkyl. In embodiments, $R^{11}$ is independently substituted or unsubstituted $C_4$-$C_6$ cycloalkyl. In embodiments, $R^1$ is independently substituted or unsubstituted 4 to 6 membered heterocycloalkyl. In embodiments, $R^1$ is independently substituted or unsubstituted 5 to 6 membered heterocycloalkyl. In embodiments, $R^{11}$ is independently substituted or unsubstituted 5 membered heteroaryl. In embodiments, $R^{11}$ is independently substituted or unsubstituted 6 membered heteroaryl. In embodiments, $R^{11}$ is independently unsubstituted 6 membered heteroaryl. In embodiments, $R^{11}$ is independently unsubstituted 5 membered heteroaryl. In embodiments, $R^{11}$ is independently substituted 6 membered heteroaryl. In embodiments, $R^{11}$ is independently substituted 5 membered heteroaryl. In embodiments, $R^{11}$ is independently substituted phenyl. In embodiments, $R^{11}$ is independently unsubstituted phenyl. In embodiments, $R^{11}$ is independently hydrogen, —$CX_3$, —CN, —COOH, —$CONH_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{11}$ is independently hydrogen, —$CX_3$, —COOH, —$CONH_2$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{11}$ is independently hydrogen. In embodiments, $R^{11}$ is independently unsubstituted methyl.

In embodiments, $R^{11}$ is independently hydrogen, halogen, —$CX_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX_3$, —$OCHX_2$, $R^{39}$-substituted or unsubstituted alkyl, $R^{39}$-substituted or unsubstituted heteroalkyl, $R^{39}$-substituted or unsubstituted cycloalkyl, $R^{39}$-substituted or unsubstituted heterocycloalkyl, $R^{39}$-substituted or unsubstituted aryl, or $R^{39}$-substituted or unsubstituted heteroaryl.

In embodiments, $R^{11}$ is independently hydrogen, halogen, —$CX_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX_3$, —$OCHX_2$, $R^{39}$-substituted or unsubstituted $C_1$-$C_6$ alkyl, $R^{39}$-substituted or unsubstituted 2 to 6 membered heteroalkyl, $R^{39}$-substituted or unsubstituted $C_3$-$C_6$ cycloalkyl, $R^{39}$-substituted or unsubstituted 3 to 6 membered heterocycloalkyl, $R^{39}$-substituted or unsubstituted phenyl, or $R^{39}$-substituted or unsubstituted 5 to 6 membered heteroaryl. In embodiments, $R^{11}$ is independently $R^{39}$-substituted $C_1$-$C_6$ alkyl. In embodiments, $R^{11}$ is independently $R^{39}$-substituted $C_1$-$C_5$ alkyl. In embodiments, $R^{11}$ is independently $R^{39}$-substituted $C_1$-$C_4$ alkyl. In embodiments, $R^{11}$ is independently $R^{39}$-substituted $C_1$-$C_3$ alkyl. In embodiments, $R^{11}$ is independently $R^{39}$-substituted $C_1$-$C_2$ alkyl. In embodiments, $R^{11}$ is independently $R^{39}$-substituted $C_2$-$C_6$ alkyl. In embodiments, $R^{11}$ is independently $R^{39}$-substituted $C_3$-$C_6$ alkyl. In embodiments, $R^{11}$ is independently $R^{39}$-substituted $C_4$-$C_6$ alkyl. In embodiments, $R^{11}$ is independently $R^{39}$-substituted or unsubstituted 2 to 3 membered heteroalkyl. In embodiments, $R^{11}$ is independently $R^{39}$-substituted or unsubstituted 2 to 4 membered heteroalkyl. In embodiments, $R^{11}$ is independently $R^{39}$-substituted or unsubstituted 2 to 5 membered heteroalkyl. In embodiments, $R^{11}$ is independently $R^{39}$-substituted or unsubstituted $C_4$-$C_6$ cycloalkyl. In embodiments, $R^{11}$ is independently $R^{39}$-substituted or unsubstituted 4 to 6 membered heterocycloalkyl. In embodiments, $R^{11}$ is independently $R^{39}$-substituted or unsubstituted 5 to 6 membered heterocycloalkyl. In embodiments, $R^{11}$ is independently $R^{39}$-substituted or unsubstituted 5 membered heteroaryl. In embodiments, $R^{11}$ is independently $R^{39}$-substituted or unsubstituted 6 membered heteroaryl. In embodiments, $R^{11}$ is independently $R^{39}$-substituted 6 membered heteroaryl. In embodiments, $R^{11}$ is independently $R^{39}$-substituted 5 membered heteroaryl. In embodiments, $R^{11}$ is independently $R^{39}$-substituted phenyl.

In embodiments, $R^{12}$ is independently hydrogen, halogen, —$CX_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX_3$, —$OCHX_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{12}$ is independently unsubstituted $C_1$-$C_6$ alkyl. In embodiments, $R^{12}$ is independently unsubstituted $C_1$-$C_5$ alkyl. In embodiments, $R^{12}$ is independently unsubstituted $C_1$-$C_4$ alkyl. In embodiments, $R^{12}$ is independently unsubstituted $C_1$-$C_3$ alkyl. In embodiments, $R^{12}$ is independently unsubstituted $C_1$-$C_2$ alkyl. In embodiments, $R^{12}$ is independently unsubstituted $C_2$-$C_6$ alkyl. In embodiments, $R^{12}$ is independently unsubstituted $C_3$-$C_6$ alkyl. In embodiments, $R^{12}$ is independently unsubstituted $C_4$-$C_6$ alkyl. In embodiments, $R^{12}$ is independently substituted $C_1$-$C_6$ alkyl. In embodiments, $R^{12}$ is independently substituted $C_1$-$C_5$ alkyl. In embodiments, $R^{12}$ is independently substituted $C_1$-$C_4$ alkyl. In embodiments, $R^{12}$ is independently substituted $C_1$-$C_3$ alkyl. In embodiments, $R^{12}$ is independently substituted $C_1$-$C_2$ alkyl. In embodiments, $R^{12}$ is independently substituted $C_2$-$C_6$ alkyl. In embodiments, $R^{12}$ is independently substituted $C_3$-$C_6$ alkyl. In embodiments, $R^{12}$ is independently substituted $C_4$-$C_6$ alkyl. In embodiments, $R^{12}$ is independently substituted or unsubstituted 2 to 3 membered heteroalkyl. In embodiments, $R^{12}$ is independently substituted or unsubstituted 2 to 4 membered heteroalkyl. In embodiments, $R^{12}$ is independently substituted or unsubstituted 2 to 5 membered heteroalkyl. In embodiments, $R^{12}$ is independently substituted or unsubstituted $C_4$-$C_6$ cycloalkyl. In embodiments, $R^{12}$ is independently substituted or unsubstituted 4 to 6 membered heterocycloalkyl. In embodiments, $R^{12}$ is independently substituted or unsubstituted 5 to 6 membered heterocycloalkyl. In embodiments, $R^{12}$ is independently substituted or unsubstituted 5 membered heteroaryl. In embodiments, $R^{12}$ is independently substituted or unsubstituted 6 membered heteroaryl. In embodiments, $R^{12}$ is independently unsubstituted 6 membered heteroaryl. In embodiments, $R^{12}$ is independently unsubstituted 5 membered heteroaryl. In embodiments, $R^{12}$ is independently substituted 6 membered heteroaryl. In embodiments, $R^{12}$ is independently substituted 5 membered heteroaryl. In embodiments, $R^{12}$ is independently substituted phenyl. In embodiments, $R^{12}$ is independently unsubstituted phenyl. In embodiments, $R^{12}$ is independently hydrogen, —$CX_3$, —CN, —COOH, —$CONH_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{12}$ is independently hydrogen, —$CX_3$, —COOH, —$CONH_2$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{12}$ is independently hydrogen. In embodiments, $R^{12}$ is independently unsubstituted methyl.

In embodiments, $R^{12}$ is independently hydrogen, halogen, —$CX_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX_3$, —$OCHX_2$, $R^{40}$-substituted or unsubstituted alkyl, $R^{40}$-substituted or unsubstituted heteroalkyl, $R^{40}$-substituted or unsubstituted cycloalkyl, $R^{40}$-substituted or unsubstituted heterocycloalkyl, $R^{40}$-substituted or unsubstituted aryl, or $R^{40}$-substituted or unsubstituted heteroaryl.

In embodiments, $R^{12}$ is independently hydrogen, halogen, oxo, —$CH_3$, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, $R^{40}$-substituted or unsubstituted $C_1$-$C_6$ alkyl, $R^{40}$-substituted or unsubstituted 2 to 6 membered heteroalkyl, $R^{40}$-substituted or unsubstituted $C_3$-$C_6$ cycloalkyl, $R^{40}$-substituted or unsubstituted 3 to 6 membered heterocycloalkyl, $R^{40}$-substituted or unsubstituted phenyl, or $R^{40}$-substituted or unsubstituted 5 to 6 membered heteroaryl. In embodiments, $R^{12}$ is independently $R^{40}$-substituted $C_1$-$C_6$ alkyl. In embodiments, $R^{12}$ is independently $R^{40}$-substituted $C_1$-$C_5$ alkyl. In embodiments, $R^{12}$ is independently $R^{40}$-substituted $C_1$-$C_4$ alkyl. In embodiments, $R^{12}$ is independently $R^{40}$-substituted $C_1$-$C_3$ alkyl. In embodiments, $R^{12}$ is independently $R^{40}$-substituted $C_1$-$C_2$ alkyl. In embodiments, $R^{12}$ is independently $R^{40}$-substituted $C_2$-$C_6$ alkyl. In embodiments, $R^{12}$ is independently $R^{40}$-substituted $C_3$-$C_6$ alkyl. In embodiments, $R^{12}$ is independently $R^{40}$-substituted $C_4$-$C_6$ alkyl. In embodiments, $R^{12}$ is independently $R^{40}$-substituted or unsubstituted 2 to 3 membered heteroalkyl. In embodiments, $R^{12}$ is independently $R^{40}$-substituted or unsubstituted 2 to 4 membered heteroalkyl. In embodiments, $R^{12}$ is independently $R^{40}$-substituted or unsubstituted 2 to 5 membered heteroalkyl. In embodiments, $R^{12}$ is independently $R^{40}$-substituted or unsubstituted $C_4$-$C_6$ cycloalkyl. In embodiments, $R^{12}$ is independently $R^{40}$-substituted or unsubstituted 4 to 6 membered heterocycloalkyl. In embodiments, $R^{12}$ is independently $R^{40}$-substituted or unsubstituted 5 to 6 membered heterocycloalkyl. In embodiments, $R^{12}$ is independently $R^{40}$-substituted or unsubstituted 5 membered heteroaryl. In embodiments, $R^{12}$ is independently $R^{40}$-substituted or unsubstituted 6 membered heteroaryl. In embodiments, $R^{12}$ is independently $R^{40}$-substituted 6 membered heteroaryl. In embodiments, $R^{12}$ is independently $R^{40}$-substituted 5 membered heteroaryl. In embodiments, $R^{12}$ is independently $R^{40}$-substituted phenyl.

In embodiments, $R^{13}$ is independently hydrogen, halogen, $-CX_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX_3$, $-OCHX_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{13}$ is independently unsubstituted $C_1$-$C_6$ alkyl. In embodiments, $R^{13}$ is independently unsubstituted $C_1$-$C_5$ alkyl. In embodiments, $R^{13}$ is independently unsubstituted $C_1$-$C_4$ alkyl. In embodiments, $R^{13}$ is independently unsubstituted $C_1$-$C_3$ alkyl. In embodiments, $R^{13}$ is independently unsubstituted $C_1$-$C_2$ alkyl. In embodiments, $R^{13}$ is independently unsubstituted $C_2$-$C_6$ alkyl. In embodiments, $R^{13}$ is independently unsubstituted $C_3$-$C_6$ alkyl. In embodiments, $R^{13}$ is independently unsubstituted $C_4$-$C_6$ alkyl. In embodiments, $R^{13}$ is independently substituted $C_1$-$C_6$ alkyl. In embodiments, $R^{13}$ is independently substituted $C_1$-$C_5$ alkyl. In embodiments, $R^{13}$ is independently substituted $C_1$-$C_4$ alkyl. In embodiments, $R^{13}$ is independently substituted $C_1$-$C_3$ alkyl. In embodiments, $R^{13}$ is independently substituted $C_1$-$C_2$ alkyl. In embodiments, $R^{13}$ is independently substituted $C_2$-$C_6$ alkyl. In embodiments, $R^{13}$ is independently substituted $C_3$-$C_6$ alkyl. In embodiments, $R^{13}$ is independently substituted $C_4$-$C_6$ alkyl. In embodiments, $R^{13}$ is independently substituted or unsubstituted 2 to 3 membered heteroalkyl. In embodiments, $R^{13}$ is independently substituted or unsubstituted 2 to 4 membered heteroalkyl. In embodiments, $R^{13}$ is independently substituted or unsubstituted 2 to 5 membered heteroalkyl. In embodiments, $R^{13}$ is independently substituted or unsubstituted $C_4$-$C_6$ cycloalkyl. In embodiments, $R^{13}$ is independently substituted or unsubstituted 4 to 6 membered heterocycloalkyl. In embodiments, $R^{13}$ is independently substituted or unsubstituted 5 to 6 membered heterocycloalkyl. In embodiments, $R^{13}$ is independently substituted or unsubstituted 5 membered heteroaryl. In embodiments, $R^{13}$ is independently substituted or unsubstituted 6 membered heteroaryl. In embodiments, $R^{13}$ is independently unsubstituted 6 membered heteroaryl. In embodiments, $R^{13}$ is independently unsubstituted 5 membered heteroaryl. In embodiments, $R^{13}$ is independently substituted 6 membered heteroaryl. In embodiments, $R^{13}$ is independently substituted 5 membered heteroaryl. In embodiments, $R^{13}$ is independently substituted phenyl. In embodiments, $R^{13}$ is independently unsubstituted phenyl. In embodiments, $R^{13}$ is independently hydrogen, $-CX_3$, $-CN$, $-COOH$, $-CONH_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{13}$ is independently hydrogen, $-CX_3$, $-COOH$, $-CONH_2$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{13}$ is independently hydrogen. In embodiments, $R^{13}$ is independently unsubstituted methyl.

In embodiments, $R^{13}$ is independently hydrogen, halogen, $-CX_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX_3$, $-OCHX_2$, $R^{41}$-substituted or unsubstituted alkyl, $R^{41}$-substituted or unsubstituted heteroalkyl, $R^{41}$-substituted or unsubstituted cycloalkyl, $R^{41}$-substituted or unsubstituted heterocycloalkyl, $R^{41}$-substituted or unsubstituted aryl, or $R^{41}$-substituted or unsubstituted heteroaryl.

In embodiments, $R^{13}$ is independently hydrogen, halogen, $-CX_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX_3$, $-OCHX_2$, $R^{41}$-substituted or unsubstituted $C_1$-$C_6$ alkyl, $R^{41}$-substituted or unsubstituted 2 to 6 membered heteroalkyl, $R^{41}$-substituted or unsubstituted $C_3$-$C_6$ cycloalkyl, $R^{41}$-substituted or unsubstituted 3 to 6 membered heterocycloalkyl, $R^{41}$-substituted or unsubstituted phenyl, or $R^{41}$-substituted or unsubstituted 5 to 6 membered heteroaryl. In embodiments, $R^{13}$ is independently $R^{41}$-substituted $C_1$-$C_6$ alkyl. In embodiments, $R^{13}$ is independently $R^{41}$-substituted $C_1$-$C_5$ alkyl. In embodiments, $R^{13}$ is independently $R^{41}$-substituted $C_1$-$C_4$ alkyl. In embodiments, $R^{13}$ is independently $R^{41}$-substituted $C_1$-$C_3$ alkyl. In embodiments, $R^{13}$ is independently $R^{41}$-substituted $C_1$-$C_2$ alkyl. In embodiments, $R^{13}$ is independently $R^{41}$-substituted $C_2$-$C_6$ alkyl. In embodiments, $R^{13}$ is independently $R^{41}$-substituted $C_3$-$C_6$ alkyl. In embodiments, $R^{13}$ is independently $R^{41}$-substituted $C_4$-$C_6$ alkyl. In embodiments, $R^{13}$ is independently $R^{41}$-substituted or unsubstituted 2 to 3 membered heteroalkyl. In embodiments, $R^{13}$ is independently $R^{41}$ substituted or unsubstituted 2 to 4 membered heteroalkyl. In embodiments, $R^{13}$ is independently $R^{41}$-substituted or unsubstituted 2 to 5 membered heteroalkyl. In embodiments, $R^{13}$ is independently $R^{41}$-substituted or unsubstituted $C_4$-$C_6$ cycloalkyl. In embodiments, $R^{13}$ is independently $R^{41}$-substituted or unsubstituted 4 to 6 membered heterocycloalkyl. In embodiments, $R^{13}$ is independently $R^{41}$-substituted or unsubstituted 5 to 6 membered heterocycloalkyl. In embodiments, $R^{13}$ is independently $R^{41}$-substituted or unsubstituted 5 membered heteroaryl. In embodiments, $R^{13}$ is independently $R^{41}$-substituted or unsubstituted 6 membered heteroaryl. In embodiments, $R^{13}$ is independently $R^{41}$-substituted 6 membered heteroaryl. In embodiments, $R^{13}$ is independently $R^{41}$-substituted 5 membered heteroaryl. In embodiments, $R^{13}$ is independently $R^{41}$-substituted phenyl.

In embodiments, $R^{14}$ is independently hydrogen, halogen, $-CX_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX_3$, $-OCHX_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{14}$ is independently unsubstituted $C_1$-$C_6$ alkyl. In embodiments, $R^{14}$ is independently unsubstituted $C_1$-$C_5$ alkyl. In embodiments, $R^{14}$ is independently unsubstituted $C_1$-$C_4$ alkyl. In embodiments, $R^{14}$ is independently unsubstituted $C_1$-$C_3$ alkyl. In embodiments, $R^{14}$ is independently unsubstituted $C_1$-$C_2$ alkyl. In embodiments, $R^{14}$ is independently unsubstituted $C_2$-$C_6$ alkyl. In embodiments, $R^{14}$ is independently unsubstituted $C_3$-$C_6$ alkyl. In embodiments, $R^{14}$ is independently unsubstituted $C_4$-$C_6$ alkyl. In embodiments, $R^{14}$ is independently substituted $C_1$-$C_6$ alkyl. In embodiments, $R^{14}$ is independently substituted $C_1$-$C_5$ alkyl. In embodiments, $R^{14}$ is independently substituted $C_1$-$C_4$ alkyl. In embodiments, $R^{14}$ is independently substituted $C_1$-$C_3$ alkyl. In embodiments, $R^{14}$ is independently substituted $C_1$-$C_2$ alkyl. In embodiments, $R^{14}$ is independently substituted $C_2$-$C_6$ alkyl. In embodiments, $R^{14}$ is independently substituted $C_3$-$C_6$ alkyl. In embodiments, $R^{14}$ is independently substituted $C_4$-$C_6$ alkyl. In embodiments, $R^{14}$ is independently substituted or unsubstituted 2 to 3 membered heteroalkyl. In embodiments, $R^{14}$ is independently substituted or unsubstituted 2 to 4 membered heteroalkyl. In embodiments, $R^{14}$ is independently substituted or unsubstituted 2 to 5 membered heteroalkyl. In embodiments, $R^{14}$ is independently substituted or unsubstituted $C_4$-$C_6$ cycloalkyl. In embodiments, $R^{14}$ is independently substituted or unsubstituted 4 to 6 membered heterocycloalkyl. In embodiments, $R^{14}$ is independently substituted or unsubstituted 5 to 6 membered heterocycloalkyl. In embodiments, $R^{14}$ is independently substituted or unsubstituted 5 membered heteroaryl. In embodiments, $R^{14}$ is independently substituted or unsubstituted 6 membered heteroaryl. In embodiments, $R^{14}$ is independently unsubstituted 6 membered heteroaryl. In embodiments, $R^{14}$ is independently unsubstituted 5 membered heteroaryl. In embodiments, $R^{14}$ is independently substituted 6 membered heteroaryl. In embodiments, $R^{14}$ is independently substituted 5 membered heteroaryl. In embodiments, $R^{14}$ is independently substituted phenyl. In embodiments, $R^{14}$ is independently unsubstituted phenyl. In embodiments, $R^{14}$ is independently hydrogen, —$CX_3$, —CN, —COOH, —$CONH_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{14}$ is independently hydrogen, —$CX_3$, —COOH, —$CONH_2$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{14}$ is independently hydrogen. In embodiments, $R^{14}$ is independently unsubstituted methyl.

In embodiments, $R^{14}$ is independently hydrogen, halogen, —$CX_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX_3$, —$OCHX_2$, $R^{42}$-substituted or unsubstituted alkyl, $R^{42}$-substituted or unsubstituted heteroalkyl, $R^{42}$-substituted or unsubstituted cycloalkyl, $R^{42}$-substituted or unsubstituted heterocycloalkyl, $R^{42}$-substituted or unsubstituted aryl, or $R^{42}$-substituted or unsubstituted heteroaryl.

In embodiments, $R^{14}$ is independently hydrogen, halogen, —$CX_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX_3$, —$OCHX_2$, $R^{42}$-substituted or unsubstituted $C_1$-$C_6$ alkyl, $R^{42}$-substituted or unsubstituted 2 to 6 membered heteroalkyl, $R^{42}$-substituted or unsubstituted $C_3$-$C_6$ cycloalkyl, $R^{42}$-substituted or unsubstituted 3 to 6 membered heterocycloalkyl, $R^{42}$-substituted or unsubstituted phenyl, or $R^{42}$-substituted or unsubstituted 5 to 6 membered heteroaryl. In embodiments, $R^{14}$ is independently $R^{42}$-substituted $C_1$-$C_6$ alkyl. In embodiments, $R^{14}$ is independently $R^{42}$-substituted $C_1$-$C_5$ alkyl. In embodiments, $R^{14}$ is independently $R^{42}$-substituted $C_1$-$C_4$ alkyl. In embodiments, $R^{14}$ is independently $R^{42}$-substituted $C_1$-$C_3$ alkyl. In embodiments, $R^{14}$ is independently $R^{42}$-substituted $C_1$-$C_2$ alkyl. In embodiments, $R^{14}$ is independently $R^{42}$-substituted $C_2$-$C_6$ alkyl. In embodiments, $R^{14}$ is independently $R^{42}$-substituted $C_3$-$C_6$ alkyl. In embodiments, $R^{14}$ is independently $R^{42}$-substituted $C_4$-$C_6$ alkyl. In embodiments, $R^{14}$ is independently $R^{42}$-substituted or unsubstituted 2 to 3 membered heteroalkyl. In embodiments, $R^{14}$ is independently $R^{42}$ substituted or unsubstituted 2 to 4 membered heteroalkyl. In embodiments, $R^{14}$ is independently $R^{42}$-substituted or unsubstituted 2 to 5 membered heteroalkyl. In embodiments, $R^{14}$ is independently $R^{42}$-substituted or unsubstituted $C_4$-$C_6$ cycloalkyl. In embodiments, $R^{14}$ is independently $R^{42}$-substituted or unsubstituted 4 to 6 membered heterocycloalkyl. In embodiments, $R^{14}$ is independently $R^{42}$-substituted or unsubstituted 5 to 6 membered heterocycloalkyl. In embodiments, $R^{14}$ is independently $R^{42}$-substituted or unsubstituted 5 membered heteroaryl. In embodiments, $R^{14}$ is independently $R^{42}$-substituted or unsubstituted 6 membered heteroaryl. In embodiments, $R^{14}$ is independently $R^{42}$-substituted 6 membered heteroaryl. In embodiments, $R^{14}$ is independently $R^{42}$-substituted 5 membered heteroaryl. In embodiments, $R^{14}$ is independently $R^{42}$-substituted phenyl.

In embodiments, $R^7$ and $R^8$ substituents bonded to the same nitrogen atom may optionally be joined to form a substituted or unsubstituted 3 to 6 membered heterocycloalkyl or substituted or unsubstituted 5 or 6 membered heteroaryl.

In embodiments, $R^{11}$ and $R^{12}$ substituents bonded to the same nitrogen atom may optionally be joined to form a substituted or unsubstituted 3 to 6 membered heterocycloalkyl or substituted or unsubstituted 5 or 6 membered heteroaryl.

$R^{20}$ is independently halogen, oxo, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^{20}$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{20}$ is independently unsubstituted $C_1$-$C_6$ alkyl. In embodiments, $R^{20}$ is independently unsubstituted $C_1$-$C_5$ alkyl. In embodiments, $R^{20}$ is independently unsubstituted $C_1$-$C_4$ alkyl. In embodiments, $R^{20}$ is independently unsubstituted $C_1$-$C_3$ alkyl. In embodiments, $R^{20}$ is independently unsubstituted $C_1$-$C_2$ alkyl. In embodiments, $R^{20}$ is independently unsubstituted $C_2$-$C_6$ alkyl. In embodiments, $R^{20}$ is independently unsubstituted $C_3$-$C_6$ alkyl. In embodiments, $R^{20}$ is independently unsubstituted $C_4$-$C_6$ alkyl. In embodiments, $R^{20}$ is independently substituted $C_1$-$C_6$ alkyl. In embodiments, $R^{20}$ is independently substituted $C_1$-$C_5$ alkyl. In embodiments, $R^{20}$ is independently substituted $C_1$-$C_4$ alkyl. In embodiments, $R^{20}$ is independently substituted $C_1$-$C_3$ alkyl. In embodiments, $R^{20}$ is independently substituted $C_1$-$C_2$ alkyl. In embodiments, $R^{20}$ is independently substituted $C_2$-$C_6$ alkyl. In embodiments, $R^{20}$ is independently substituted $C_3$-$C_6$ alkyl. In embodiments, $R^{20}$ is independently substituted $C_4$-$C_6$ alkyl. In embodiments, $R^{20}$ is independently substituted or unsubstituted 2 to 3 membered heteroalkyl. In embodiments, $R^{20}$ is independently substituted or unsubstituted 2 to 4 membered heteroalkyl. In embodiments, $R^{20}$ is independently substituted or unsubstituted 2 to 5 membered heteroalkyl. In embodiments, $R^{20}$ is independently substituted or unsubstituted $C_4$-$C_6$ cycloalkyl. In embodiments, $R^{20}$ is independently substituted or unsubstituted 4 to 6 membered heterocycloalkyl. In embodiments, $R^{20}$ is independently substituted or unsubstituted 5 to 6 membered heterocycloalkyl. In embodiments, $R^{20}$ is independently substituted or unsubstituted 5 membered heteroaryl. In embodiments, $R^{20}$ is independently substituted or unsubstituted 6 membered heteroaryl. In embodiments, $R^{20}$ is independently unsubstituted 6 membered heteroaryl. In embodiments, $R^{20}$ is independently unsubstituted 5 membered heteroaryl. In embodiments, $R^{20}$ is independently substituted 6 membered heteroaryl. In embodiments, $R^{20}$ is independently substituted 5 membered heteroaryl. In embodiments, $R^{20}$ is independently substituted phenyl. In embodiments, $R^{20}$ is independently unsubstituted phenyl.

In embodiments, $R^{20}$ is independently halogen, oxo, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl; two adjacent $R^{20}$ substituents may optionally be joined to form a $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl.

In embodiments, $R^{20}$ is independently halogen, oxo, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, $R^{21}$-substituted or unsubstituted $C_1$-$C_6$ alkyl, $R^{21}$-substituted or unsubstituted 2 to 6 membered heteroalkyl, $R^{21}$-substituted or unsubstituted $C_3$-$C_6$ cycloalkyl, $R^{21}$-substituted or unsubstituted 3 to 6 membered heterocycloalkyl, $R^{21}$-substituted or unsubstituted phenyl, or $R^{21}$-substituted or unsubstituted 5 to 6 membered heteroaryl; two adjacent $R^{20}$ substituents may optionally be joined to form a $R^{21}$-substituted or unsubstituted $C_3$-$C_6$ cycloalkyl, substituted or unsubstituted 3 to 6 membered heterocycloalkyl, $R^{21}$-substituted or unsubstituted phenyl, or $R^{21}$-substituted or unsubstituted 5 to 6 membered heteroaryl. In embodiments, $R^{20}$ is independently $R^{21}$-substituted $C_1$-$C_6$ alkyl. In embodiments, $R^{20}$ is independently $R^{21}$-substituted $C_1$-$C_5$ alkyl. In embodiments, $R^{20}$ is independently $R^{21}$-substituted $C_1$-$C_4$ alkyl. In embodiments, $R^{20}$ is independently $R^{21}$-substituted $C_1$-$C_3$ alkyl. In embodiments, $R^{20}$ is independently $R^{21}$-substituted $C_1$-$C_2$ alkyl. In embodiments, $R^{20}$ is independently $R^{21}$-substituted $C_2$-$C_6$ alkyl. In embodiments, $R^{20}$ is independently $R^{21}$-substituted $C_3$-$C_6$ alkyl. In embodiments, $R^{20}$ is independently $R^{21}$-substituted $C_4$-$C_6$ alkyl. In embodiments, $R^{20}$ is independently $R^{21}$-substituted or unsubstituted 2 to 3 membered heteroalkyl. In embodiments, $R^{20}$ is independently $R^{21}$-substituted or unsubstituted 2 to 4 membered heteroalkyl. In embodiments, $R^{20}$ is independently $R^{21}$-substituted or unsubstituted 2 to 5 membered heteroalkyl. In embodiments, $R^{20}$ is independently $R^{21}$-substituted or unsubstituted $C_4$-$C_6$ cycloalkyl. In embodiments, $R^{20}$ is independently $R^{21}$-substituted or unsubstituted 4 to 6 membered heterocycloalkyl. In embodiments, $R^{20}$ is independently $R^{21}$-substituted or unsubstituted 5 to 6 membered heterocycloalkyl. In embodiments, $R^{20}$ is independently $R^{21}$-substituted or unsubstituted 5 membered heteroaryl. In embodiments, $R^{20}$ is independently $R^{21}$-substituted or unsubstituted 6 membered heteroaryl. In embodiments, $R^{20}$ is independently $R^{21}$-substituted 6 membered heteroaryl. In embodiments, $R^{20}$ is independently $R^{21}$-substituted 5 membered heteroaryl. In embodiments, $R^{20}$ is independently $R^{21}$-substituted phenyl.

$R^{21}$ is independently halogen, oxo, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^{21}$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{21}$ is independently unsubstituted $C_1$-$C_6$ alkyl. In embodiments, $R^{21}$ is independently unsubstituted $C_1$-$C_5$ alkyl. In embodiments, $R^{21}$ is independently unsubstituted $C_1$-$C_4$ alkyl. In embodiments, $R^{21}$ is independently unsubstituted $C_1$-$C_3$ alkyl. In embodiments, $R^{21}$ is independently unsubstituted $C_1$-$C_2$ alkyl. In embodiments, $R^{21}$ is independently unsubstituted $C_2$-$C_6$ alkyl. In embodiments, $R^{21}$ is independently unsubstituted $C_3$-$C_6$ alkyl. In embodiments, $R^{21}$ is independently unsubstituted $C_4$-$C_6$ alkyl. In embodiments, $R^{21}$ is independently substituted $C_1$-$C_6$ alkyl. In embodiments, $R^{21}$ is independently substituted $C_1$-$C_5$ alkyl. In embodiments, $R^{21}$ is independently substituted $C_1$-$C_4$ alkyl. In embodiments, $R^{21}$ is independently substituted $C_1$-$C_3$ alkyl. In embodiments, $R^{20}$ is independently substituted $C_1$-$C_2$ alkyl. In embodiments, $R^{21}$ is independently substituted $C_2$-$C_6$ alkyl. In embodiments, $R^{21}$ is independently substituted $C_3$-$C_6$ alkyl. In embodiments, $R^{21}$ is independently substituted $C_4$-$C_6$ alkyl. In embodiments, $R^{21}$ is independently substituted or unsubstituted 2 to 3 membered heteroalkyl. In embodiments, $R^{21}$ is independently substituted or unsubstituted 2 to 4 membered heteroalkyl. In embodiments, $R^{21}$ is independently substituted or unsubstituted 2 to 5 membered heteroalkyl. In embodiments, $R^{21}$ is independently substituted or unsubstituted $C_4$-$C_6$ cycloalkyl. In embodiments, $R^{21}$ is independently substituted or unsubstituted 4 to 6 membered heterocycloalkyl. In embodiments, $R^{21}$ is independently substituted or unsubstituted 5 to 6 membered heterocycloalkyl. In embodiments, $R^{21}$ is independently substituted or unsubstituted 5 membered heteroaryl. In embodiments, $R^{21}$ is independently substituted or unsubstituted 6 membered heteroaryl. In embodiments, $R^{21}$ is independently unsubstituted 6 membered heteroaryl. In embodiments, $R^{21}$ is independently unsubstituted 5 membered heteroaryl. In embodiments, $R^{21}$ is independently substituted 6 membered heteroaryl. In embodiments, $R^{21}$ is independently substituted 5 membered heteroaryl. In embodiments, $R^{21}$ is independently substituted phenyl. In embodiments, $R^{21}$ is independently unsubstituted phenyl.

In embodiments, $R^{21}$ is independently halogen, oxo, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, $R^{22}$-substituted or unsubstituted alkyl, $R^{22}$-substituted or unsubstituted heteroalkyl, $R^{22}$-substituted or unsubstituted cycloalkyl, $R^{22}$-substituted or unsubstituted heterocycloalkyl, $R^{22}$-substituted or unsubstituted aryl, or $R^{22}$-substituted or unsubstituted heteroaryl; two adjacent $R^{21}$ substituents may optionally be joined to form a $R^{22}$-substituted or unsubstituted cycloalkyl, $R^{22}$-substituted or unsubstituted heterocycloalkyl, $R^{22}$-substituted or unsubstituted aryl, or $R^{22}$-substituted or unsubstituted heteroaryl.

In embodiments, $R^{21}$ is independently halogen, oxo, —$CH_3$, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, $R^{22}$-substituted or unsubstituted $C_1$-$C_6$ alkyl, $R^{22}$-substituted or unsubstituted 2 to 6 membered heteroalkyl, $R^{22}$-substituted or unsubstituted $C_3$-$C_6$ cycloalkyl, $R^{22}$-substituted or unsubstituted 3 to 6 membered heterocycloalkyl, $R^{22}$-substituted or unsubstituted phenyl, or $R^{22}$-substituted or unsubstituted 5 to 6 membered heteroaryl; two adjacent $R^{21}$ substituents may optionally be joined to form a $R^{22}$-substituted or unsubstituted $C_3$-$C_6$ cycloalkyl, substituted or unsubstituted 3 to 6 membered heterocycloalkyl, $R^{22}$-substituted or unsubstituted phenyl, or $R^{22}$-substituted or unsubstituted 5 to 6 membered heteroaryl. In embodiments, $R^{21}$ is independently $R^{22}$-substituted $C_1$-$C_6$ alkyl. In embodiments, $R^{21}$ is independently $R^{22}$-substituted $C_1$-$C_5$ alkyl. In embodiments, $R^{21}$ is independently $R^{22}$-substituted $C_1$-$C_4$ alkyl. In embodiments, $R^{21}$ is independently $R^{22}$-substituted $C_1$-$C_3$ alkyl. In embodiments, $R^{21}$ is independently $R^{22}$-substituted $C_1$-$C_2$ alkyl. In embodiments, $R^{21}$ is independently $R^{22}$-substituted $C_2$-$C_6$ alkyl. In embodiments, $R^{21}$ is independently $R^{22}$-substituted $C_3$-$C_6$ alkyl. In embodiments, $R^{21}$ is independently $R^{22}$-substituted $C_4$-$C_6$ alkyl. In embodiments, $R^{21}$ is independently $R^{22}$-substituted or unsubstituted 2 to 3 membered heteroalkyl. In embodiments, $R^{21}$ is independently $R^{22}$-substituted or unsubstituted 2 to 4 membered heteroalkyl. In embodiments, $R^{21}$ is independently $R^{22}$-substituted or unsubstituted 2 to 5 membered heteroalkyl. In embodiments, $R^{21}$ is independently $R^{22}$-substituted or unsubstituted $C_4$-$C_6$ cycloalkyl. In embodiments, $R^{21}$ is independently $R^{22}$-substituted or unsubstituted 4 to 6 membered heterocycloalkyl. In embodiments, $R^{21}$ is independently $R^{22}$-substituted or unsubstituted 5 to 6 membered heterocycloalkyl. In embodiments, $R^{21}$ is independently $R^{22}$-substituted or unsubstituted 5 membered heteroaryl. In embodiments, $R^{21}$ is independently $R^{22}$-substituted or unsubstituted 6 membered heteroaryl. In embodiments, $R^{21}$ is independently $R^{22}$-substituted 6 membered heteroaryl. In embodiments, $R^{21}$ is independently $R^{22}$-substituted 5 membered heteroaryl. In embodiments, $R^{21}$ is independently $R^{22}$-substituted phenyl.

$R^{23}$ is independently halogen, oxo, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^{23}$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{23}$ is independently unsubstituted $C_1$-$C_6$ alkyl. In embodiments, $R^{23}$ is independently unsubstituted $C_1$-$C_5$ alkyl. In embodiments, $R^{23}$ is independently unsubstituted $C_1$-$C_4$ alkyl. In embodiments, $R^{23}$ is independently unsubstituted $C_1$-$C_3$ alkyl. In embodiments, $R^{23}$ is independently unsubstituted $C_1$-$C_2$ alkyl. In embodiments, $R^{23}$ is independently unsubstituted $C_2$-$C_6$ alkyl. In embodiments, $R^{23}$ is independently unsubstituted $C_3$-$C_6$ alkyl. In embodiments, $R^{23}$ is independently unsubstituted $C_4$-$C_6$ alkyl. In embodiments, $R^{23}$ is independently substituted $C_1$-$C_6$ alkyl. In embodiments, $R^{23}$ is independently substituted $C_1$-$C_5$ alkyl. In embodiments, $R^{23}$ is independently substituted $C_1$-$C_4$ alkyl. In embodiments, $R^{23}$ is independently substituted $C_1$-$C_3$ alkyl. In embodiments, $R^{23}$ is independently substituted $C_1$-$C_2$ alkyl. In embodiments, $R^{23}$ is independently substituted $C_2$-$C_6$ alkyl. In embodiments, $R^{23}$ is independently substituted $C_3$-$C_6$ alkyl. In embodiments, $R^{23}$ is independently substituted $C_4$-$C_6$ alkyl. In embodiments, $R^{23}$ is independently substituted or unsubstituted 2 to 3 membered heteroalkyl. In embodiments, $R^{23}$ is independently substituted or unsubstituted 2 to 4 membered heteroalkyl. In embodiments, $R^{23}$ is independently substituted or unsubstituted 2 to 5 membered heteroalkyl. In embodiments, $R^{23}$ is independently substituted or unsubstituted $C_4$-$C_6$ cycloalkyl. In embodiments, $R^{23}$ is independently substituted or unsubstituted 4 to 6 membered heterocycloalkyl. In embodiments, $R^{23}$ is independently substituted or unsubstituted 5 to 6 membered heterocycloalkyl. In embodiments, $R^{23}$ is independently substituted or unsubstituted 5 membered heteroaryl. In embodiments, $R^{23}$ is independently substituted or unsubstituted 6 membered heteroaryl. In embodiments, $R^{23}$ is independently unsubstituted 6 membered heteroaryl. In embodiments, $R^{23}$ is independently unsubstituted 5 membered heteroaryl. In embodiments, $R^{23}$ is independently substituted 6 membered heteroaryl. In embodiments, $R^{23}$ is independently substituted 5 membered heteroaryl. In embodiments, $R^{23}$ is independently substituted phenyl. In embodiments, $R^{23}$ is independently unsubstituted phenyl.

In embodiments, $R^{23}$ is independently halogen, oxo, $-CF_3$, $-CCl_3$, $-CN$, $-S(O)CH_3$, $-OH$, $-NH_2$, $-COOH$, $-CONH_2$, $-NO_2$, $-C(O)CH_3$, $-CH_2CH_3$, $-CH_2CH_2OH$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCH_3$, $-OCF_3$, $-OCHF_2$, $R^{24}$-substituted or unsubstituted alkyl, $R^{24}$-substituted or unsubstituted heteroalkyl, $R^{24}$-substituted or unsubstituted cycloalkyl, $R^{24}$-substituted or unsubstituted heterocycloalkyl, $R^{24}$-substituted or unsubstituted aryl, or $R^{24}$-substituted or unsubstituted heteroaryl; two adjacent $R^{23}$ substituents may optionally be joined to form a $R^{24}$-substituted or unsubstituted cycloalkyl, $R^{24}$-substituted or unsubstituted heterocycloalkyl, $R^{24}$-substituted or unsubstituted aryl, or $R^{24}$-substituted or unsubstituted heteroaryl.

In embodiments, $R^{23}$ is independently halogen, oxo, $-CF_3$, $-CCl_3$, $-CN$, $-S(O)CH_3$, $-OH$, $-NH_2$, $-COOH$, $-CONH_2$, $-NO_2$, $-C(O)CH_3$, $-CH_2CH_3$, $-CH_2CH_2OH$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCH_3$, $-OCF_3$, $-OCHF_2$, $R^{24}$-substituted or unsubstituted $C_1$-$C_6$ alkyl, $R^{24}$-substituted or unsubstituted 2 to 6 membered heteroalkyl, $R^{24}$-substituted or unsubstituted $C_3$-$C_6$ cycloalkyl, $R^{24}$-substituted or unsubstituted 3 to 6 membered heterocycloalkyl, $R^{24}$-substituted or unsubstituted phenyl, or $R^{24}$-substituted or unsubstituted 5 to 6 membered heteroaryl; two adjacent $R^{23}$ substituents may optionally be joined to form a $R^{24}$-substituted or unsubstituted $C_3$-$C_6$ cycloalkyl, substituted or unsubstituted 3 to 6 membered heterocycloalkyl, $R^{24}$-substituted or unsubstituted phenyl, or $R^{24}$-substituted or unsubstituted 5 to 6 membered heteroaryl. In embodiments, $R^{23}$ is independently $R^{24}$-substituted $C_1$-$C_6$ alkyl. In embodiments, $R^{23}$ is independently $R^{24}$-substituted $C_1$-$C_5$ alkyl. In embodiments, $R^{23}$ is independently $R^{24}$-substituted $C_1$-$C_4$ alkyl. In embodiments, $R^{23}$ is independently $R^{24}$-substituted $C_1$-$C_3$ alkyl. In embodiments, $R^{23}$ is independently $R^{24}$-substituted $C_1$-$C_2$ alkyl. In embodiments, $R^{23}$ is independently $R^{24}$-substituted $C_2$-$C_6$ alkyl. In embodiments, $R^{23}$ is independently $R^{24}$-substituted $C_3$-$C_6$ alkyl. In embodiments, $R^{23}$ is independently $R^{24}$-substituted $C_4$-$C_6$ alkyl. In embodiments, $R^{23}$ is independently $R^{24}$-substituted or unsubstituted 2 to 3 membered heteroalkyl. In embodiments, $R^{23}$ is independently $R^{24}$-substituted or unsubstituted 2 to 4 membered heteroalkyl. In embodiments, $R^{23}$ is independently $R^{24}$-substituted or unsubstituted 2 to 5 membered heteroalkyl. In embodiments, $R^{23}$ is independently $R^{24}$-substituted or unsubstituted $C_4$-$C_6$ cycloalkyl. In embodiments, $R^{23}$ is independently $R^{24}$-substituted or unsubstituted 4 to 6 membered heterocycloalkyl. In embodiments, $R^{23}$ is independently $R^{24}$-substituted or unsubstituted 5 to 6 membered heterocycloalkyl. In embodiments, $R^{23}$ is independently $R^{24}$-substituted or unsubstituted 5 membered heteroaryl. In embodiments, $R^{23}$ is independently $R^{24}$-substituted or unsubstituted 6 membered heteroaryl. In embodiments, $R^{23}$ is independently $R^{24}$-substituted 6 membered heteroaryl. In embodiments, $R^{23}$ is independently $R^{24}$-substituted 5 membered heteroaryl. In embodiments, $R^{23}$ is independently $R^{24}$-substituted phenyl.

$R^{24}$ is independently halogen, oxo, $-CF_3$, $-CCl_3$, $-CN$, $-S(O)CH_3$, $-OH$, $-NH_2$, $-COOH$, $-CONH_2$, $-NO_2$, $-C(O)CH_3$, $-CH_2CH_3$, $-CH_2CH_2OH$, $-SH$, $-SO_3H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCH_3$, $-OCF_3$, $-OCHF_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^{24}$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{24}$ is independently unsubstituted $C_1$-$C_6$ alkyl. In embodiments, $R^{24}$ is independently unsubstituted $C_1$-$C_5$ alkyl. In embodiments, $R^{24}$ is independently unsubstituted $C_1$-$C_4$ alkyl. In embodiments, $R^{24}$ is independently unsubstituted $C_1$-$C_3$ alkyl. In embodiments, $R^{24}$ is independently unsubstituted $C_1$-$C_2$ alkyl. In embodiments, $R^{24}$ is independently unsubstituted $C_2$-$C_6$ alkyl. In embodiments, $R^{24}$ is independently unsubstituted $C_3$-$C_6$ alkyl. In embodiments, $R^{24}$ is independently unsubstituted $C_4$-$C_6$ alkyl. In embodiments, $R^{24}$ is independently substituted $C_1$-$C_6$ alkyl. In embodiments, $R^{24}$ is independently substituted $C_1$-$C_5$ alkyl. In embodiments, $R^{24}$ is independently substituted $C_1$-$C_4$ alkyl. In embodiments, $R^{24}$ is independently substituted $C_1$-$C_3$ alkyl. In embodiments, $R^{23}$ is independently substituted $C_1$-$C_2$ alkyl. In embodiments, $R^{24}$ is independently substituted $C_2$-$C_6$ alkyl. In embodiments, $R^{24}$ is independently substituted $C_3$-$C_6$ alkyl. In embodiments, $R^{24}$ is independently substituted $C_4$-$C_6$ alkyl. In embodiments, $R^{24}$ is independently substituted or unsubstituted 2 to 3 membered heteroalkyl. In embodiments, $R^{24}$ is independently substituted or unsubstituted 2 to 4 membered heteroalkyl. In embodiments, $R^{24}$ is independently substituted or unsubstituted 2 to 5 membered heteroalkyl. In embodiments, $R^{24}$ is independently substituted or unsubstituted $C_4$-$C_6$ cycloalkyl. In embodiments, $R^{24}$ is independently substituted or unsubstituted 4 to 6 membered heterocycloalkyl. In embodiments, $R^{24}$ is independently substituted or unsubstituted 5 to 6 membered heterocycloalkyl. In embodiments, $R^{24}$ is independently substituted or unsubstituted 5 membered heteroaryl. In embodiments, $R^{24}$ is independently substituted or unsubstituted 6 membered heteroaryl. In embodiments, $R^{24}$ is independently unsubstituted 6 membered heteroaryl. In embodiments, $R^{24}$ is independently unsubstituted 5 membered heteroaryl. In embodiments, $R^{24}$ is independently substituted 6 membered heteroaryl. In embodiments, $R^{24}$ is independently substituted 5 membered heteroaryl. In embodiments, $R^{24}$ is independently substituted phenyl. In embodiments, $R^{24}$ is independently unsubstituted phenyl.

In embodiments, $R^{24}$ is independently halogen, oxo, $-CF_3$, $-CCl_3$, $-CN$, $-S(O)CH_3$, $-OH$, $-NH_2$, $-COOH$, $-CONH_2$, $-NO_2$, $-C(O)CH_3$, $-CH_2CH_3$, $-CH_2CH_2OH$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCH_3$, $-OCF_3$, $-OCHF_2$, $R^{25}$-substituted or unsubstituted alkyl, $R^{25}$-substituted or unsubstituted heteroalkyl, $R^{25}$-substituted or unsubstituted cycloalkyl, $R^{25}$-substituted or unsubstituted heterocycloalkyl, $R^{25}$-substituted or unsubstituted aryl, or $R^{25}$-substituted or unsubstituted heteroaryl; two adjacent $R^{24}$ substituents may optionally be joined to form a $R^{25}$-substituted or unsubstituted cycloalkyl, $R^{25}$-substituted or unsubstituted heterocycloalkyl, $R^{25}$-substituted or unsubstituted aryl, or $R^{25}$-substituted or unsubstituted heteroaryl.

In embodiments, $R^{24}$ is independently halogen, oxo, $-CF_3$, $-CCl_3$, $-CN$, $-S(O)CH_3$, $-OH$, $-NH_2$, —COOH, —CONH₂, —NO₂, —C(O)CH₃, —CH₂CH₃, —CH₂CH₂OH, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)OH, —NHOH, —OCH₃, —OCF₃, —OCHF₂, R$^{25}$-substituted or unsubstituted C₁-C₆ alkyl, R$^{25}$-substituted or unsubstituted 2 to 6 membered heteroalkyl, R$^{25}$-substituted or unsubstituted C₃-C₆ cycloalkyl, R$^{25}$-substituted or unsubstituted 3 to 6 membered heterocycloalkyl, R$^{25}$-substituted or unsubstituted phenyl, or R$^{25}$-substituted or unsubstituted 5 to 6 membered heteroaryl; two adjacent R$^{24}$ substituents may optionally be joined to form a R$^{25}$-substituted or unsubstituted C₃-C₆ cycloalkyl, substituted or unsubstituted 3 to 6 membered heterocycloalkyl, R$^{25}$-substituted or unsubstituted phenyl, or R$^{25}$-substituted or unsubstituted 5 to 6 membered heteroaryl. In embodiments, R$^{24}$ is independently R$^{25}$-substituted C₁-C₆ alkyl. In embodiments, R$^{24}$ is independently R$^{25}$-substituted C₁-C₅ alkyl. In embodiments, R$^{24}$ is independently R$^{25}$-substituted C₁-C₄ alkyl. In embodiments, R$^{24}$ is independently R$^{25}$-substituted C₁-C₃ alkyl. In embodiments, R$^{24}$ is independently R$^{25}$-substituted C₁-C₂ alkyl. In embodiments, R$^{24}$ is independently R$^{25}$-substituted C₂-C₆ alkyl. In embodiments, R$^{24}$ is independently R$^{25}$-substituted C₃-C₆ alkyl. In embodiments, R$^{24}$ is independently R$^{25}$-substituted C₄-C₆ alkyl. In embodiments, R$^{24}$ is independently R$^{25}$-substituted or unsubstituted 2 to 3 membered heteroalkyl. In embodiments, R$^{24}$ is independently R$^{25}$-substituted or unsubstituted 2 to 4 membered heteroalkyl. In embodiments, R$^{24}$ is independently R$^{25}$-substituted or unsubstituted 2 to 5 membered heteroalkyl. In embodiments, R$^{24}$ is independently R$^{25}$-substituted or unsubstituted C₄-C₆ cycloalkyl. In embodiments, R$^{24}$ is independently R$^{25}$-substituted or unsubstituted 4 to 6 membered heterocycloalkyl. In embodiments, R$^{24}$ is independently R$^{25}$-substituted or unsubstituted 5 to 6 membered heterocycloalkyl. In embodiments, R$^{24}$ is independently R$^{25}$-substituted or unsubstituted 5 membered heteroaryl. In embodiments, R$^{24}$ is independently R$^{25}$-substituted or unsubstituted 6 membered heteroaryl. In embodiments, R$^{24}$ is independently R$^{25}$-substituted 6 membered heteroaryl. In embodiments, R$^{24}$ is independently R$^{25}$-substituted 5 membered heteroaryl. In embodiments, R$^{24}$ is independently R$^{25}$-substituted phenyl.

R$^{26}$ is independently halogen, oxo, —CF₃, —CCl₃, —CN, —S(O)CH₃, —OH, —NH₂, —COOH, —CONH₂, —NO₂, —C(O)CH₃, —CH₂CH₃, —CH₂CH₂OH, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)OH, —NHOH, —OCH₃, —OCF₃, —OCHF₂, substituted or unsubstituted C₁-C₆ alkyl, substituted or unsubstituted 2 to 6 membered heteroalkyl, substituted or unsubstituted C₃-C₆ cycloalkyl, substituted or unsubstituted 3 to 6 membered heterocycloalkyl, substituted or unsubstituted phenyl, or substituted or unsubstituted 5 to 6 membered heteroaryl; two adjacent R$^{26}$ substituents may optionally be joined to form a substituted or unsubstituted C₃-C₆ cycloalkyl, substituted or unsubstituted 3 to 6 membered heterocycloalkyl, substituted or unsubstituted phenyl, or substituted or unsubstituted 5 to 6 membered heteroaryl. In embodiments, R$^{26}$ is independently unsubstituted C₁-C₆ alkyl. In embodiments, R$^{26}$ is independently unsubstituted C₁-C₅ alkyl. In embodiments, R$^{26}$ is independently unsubstituted C₁-C₄ alkyl. In embodiments, R$^{26}$ is independently unsubstituted C₁-C₃ alkyl. In embodiments, R$^{26}$ is independently unsubstituted C₁-C₂ alkyl. In embodiments, R$^{26}$ is independently unsubstituted C₂-C₆ alkyl. In embodiments, R$^{26}$ is independently unsubstituted C₃-C₆ alkyl. In embodiments, R$^{26}$ is independently unsubstituted C₄-C₆ alkyl. In embodiments, R$^{26}$ is independently substituted C₁-C₆ alkyl. In embodiments, R$^{26}$ is independently substituted C₁-C₅ alkyl. In embodiments, R$^{26}$ is independently substituted C₁-C₄ alkyl. In embodiments, R$^{26}$ is independently substituted C₁-C₃ alkyl. In embodiments, R$^{26}$ is independently substituted C₁-C₂ alkyl. In embodiments, R$^{26}$ is independently substituted C₂-C₆ alkyl. In embodiments, R$^{26}$ is independently substituted C₃-C₆ alkyl. In embodiments, R$^{26}$ is independently substituted C₄-C₆ alkyl. In embodiments, R$^{26}$ is independently substituted or unsubstituted 2 to 3 membered heteroalkyl. In embodiments, R$^{26}$ is independently substituted or unsubstituted 2 to 4 membered heteroalkyl. In embodiments, R$^{26}$ is independently substituted or unsubstituted 2 to 5 membered heteroalkyl. In embodiments, R$^{26}$ is independently substituted or unsubstituted C₄-C₆ cycloalkyl. In embodiments, R$^{26}$ is independently substituted or unsubstituted 4 to 6 membered heterocycloalkyl. In embodiments, R$^{26}$ is independently substituted or unsubstituted 5 to 6 membered heterocycloalkyl. In embodiments, R$^{26}$ is independently substituted or unsubstituted 5 membered heteroaryl. In embodiments, R$^{26}$ is independently substituted or unsubstituted 6 membered heteroaryl. In embodiments, R$^{26}$ is independently unsubstituted 6 membered heteroaryl. In embodiments, R$^{26}$ is independently unsubstituted 5 membered heteroaryl. In embodiments, R$^{26}$ is independently substituted 6 membered heteroaryl. In embodiments, R$^{26}$ is independently substituted 5 membered heteroaryl. In embodiments, R$^{26}$ is independently substituted phenyl. In embodiments, R$^{26}$ is independently unsubstituted phenyl.

In embodiments, R$^{26}$ is independently halogen, oxo, —CF₃, —CCl₃, —CN, —S(O)CH₃, —OH, —NH₂, —COOH, —CONH₂, —NO₂, —C(O)CH₃, —CH₂CH₃, —CH₂CH₂OH, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)OH, —NHOH, —OCH₃, —OCF₃, —OCHF₂, R$^{27}$-substituted or unsubstituted alkyl, R$^{27}$-substituted or unsubstituted heteroalkyl, R$^{27}$-substituted or unsubstituted cycloalkyl, R$^{27}$-substituted or unsubstituted heterocycloalkyl, R$^{27}$-substituted or unsubstituted aryl, or R$^{27}$-substituted or unsubstituted heteroaryl; two adjacent R$^{26}$ substituents may optionally be joined to form a R$^{27}$-substituted or unsubstituted cycloalkyl, R$^{27}$-substituted or unsubstituted heterocycloalkyl, R$^{27}$-substituted or unsubstituted aryl, or R$^{27}$-substituted or unsubstituted heteroaryl.

In embodiments, R$^{26}$ is independently halogen, oxo, —CF₃, —CCl₃, —CN, —S(O)CH₃, —OH, —NH₂, —COOH, —CONH₂, —NO₂, —C(O)CH₃, —CH₂CH₃, —CH₂CH₂OH, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)OH, —NHOH, —OCH₃, —OCF₃, —OCHF₂, R$^{27}$-substituted or unsubstituted C₁-C₆ alkyl, R$^{27}$-substituted or unsubstituted 2 to 6 membered heteroalkyl, R$^{27}$-substituted or unsubstituted C₃-C₆ cycloalkyl, R$^{27}$-substituted or unsubstituted 3 to 6 membered heterocycloalkyl, R$^{27}$-substituted or unsubstituted phenyl, or R$^{27}$-substituted or unsubstituted 5 to 6 membered heteroaryl; two adjacent R$^{26}$ substituents may optionally be joined to form a R$^{27}$-substituted or unsubstituted C₃-C₆ cycloalkyl, substituted or unsubstituted 3 to 6 membered heterocycloalkyl, R$^{27}$-substituted or unsubstituted phenyl, or R$^{27}$-substituted or unsubstituted 5 to 6 membered heteroaryl. In embodiments, R$^{26}$ is independently R$^{27}$-substituted C₁-C₆ alkyl. In embodiments, R$^{26}$ is independently R$^{27}$-substituted C₁-C₅ alkyl. In embodiments, R$^{26}$ is independently $R^{27}$-substituted $C_1$-$C_4$ alkyl. In embodiments, $R^{26}$ is independently $R^{27}$-substituted $C_1$-$C_3$ alkyl. In embodiments, $R^{26}$ is independently $R^{27}$-substituted $C_1$-$C_2$ alkyl. In embodiments, $R^{26}$ is independently $R^{27}$-substituted $C_2$-$C_6$ alkyl. In embodiments, $R^{26}$ is independently $R^{27}$-substituted $C_3$-$C_6$ alkyl. In embodiments, $R^{26}$ is independently $R^{27}$-substituted $C_4$-$C_6$ alkyl. In embodiments, $R^{26}$ is independently $R^{27}$-substituted or unsubstituted 2 to 3 membered heteroalkyl. In embodiments, $R^{26}$ is independently $R^{27}$-substituted or unsubstituted 2 to 4 membered heteroalkyl. In embodiments, $R^{26}$ is independently $R^{27}$-substituted or unsubstituted 2 to 5 membered heteroalkyl. In embodiments, $R^{26}$ is independently $R^{27}$-substituted or unsubstituted $C_4$-$C_6$ cycloalkyl. In embodiments, $R^{26}$ is independently $R^{27}$-substituted or unsubstituted 4 to 6 membered heterocycloalkyl. In embodiments, $R^{26}$ is independently $R^{27}$-substituted or unsubstituted 5 to 6 membered heterocycloalkyl. In embodiments, $R^{26}$ is independently $R^{27}$-substituted or unsubstituted 5 membered heteroaryl. In embodiments, $R^{26}$ is independently $R^{27}$-substituted or unsubstituted 6 membered heteroaryl. In embodiments, $R^{26}$ is independently $R^{27}$-substituted 6 membered heteroaryl. In embodiments, $R^{26}$ is independently $R^{27}$-substituted 5 membered heteroaryl. In embodiments, $R^{26}$ is independently $R^{27}$-substituted phenyl.

$R^{27}$ is independently halogen, oxo, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^{27}$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{27}$ is independently unsubstituted $C_1$-$C_6$ alkyl. In embodiments, $R^{27}$ is independently unsubstituted $C_1$-$C_5$ alkyl. In embodiments, $R^{27}$ is independently unsubstituted $C_1$-$C_4$ alkyl. In embodiments, $R^{27}$ is independently unsubstituted $C_1$-$C_3$ alkyl. In embodiments, $R^{27}$ is independently unsubstituted $C_1$-$C_2$ alkyl. In embodiments, $R^{27}$ is independently unsubstituted $C_2$-$C_6$ alkyl. In embodiments, $R^{27}$ is independently unsubstituted $C_3$-$C_6$ alkyl. In embodiments, $R^{27}$ is independently unsubstituted $C_4$-$C_6$ alkyl. In embodiments, $R^{27}$ is independently substituted $C_1$-$C_6$ alkyl. In embodiments, $R^{27}$ is independently substituted $C_1$-$C_5$ alkyl. In embodiments, $R^{27}$ is independently substituted $C_1$-$C_4$ alkyl. In embodiments, $R^{27}$ is independently substituted $C_1$-$C_3$ alkyl. In embodiments, $R^{26}$ is independently substituted $C_1$-$C_2$ alkyl. In embodiments, $R^{27}$ is independently substituted $C_2$-$C_6$ alkyl. In embodiments, $R^{27}$ is independently substituted $C_3$-$C_6$ alkyl. In embodiments, $R^{27}$ is independently substituted $C_4$-$C_6$ alkyl. In embodiments, $R^{27}$ is independently substituted or unsubstituted 2 to 3 membered heteroalkyl. In embodiments, $R^{27}$ is independently substituted or unsubstituted 2 to 4 membered heteroalkyl. In embodiments, $R^{27}$ is independently substituted or unsubstituted 2 to 5 membered heteroalkyl. In embodiments, $R^{27}$ is independently substituted or unsubstituted $C_4$-$C_6$ cycloalkyl. In embodiments, $R^{27}$ is independently substituted or unsubstituted 4 to 6 membered heterocycloalkyl. In embodiments, $R^{27}$ is independently substituted or unsubstituted 5 to 6 membered heterocycloalkyl. In embodiments, $R^{27}$ is independently substituted or unsubstituted 5 membered heteroaryl. In embodiments, $R^{27}$ is independently substituted or unsubstituted 6 membered heteroaryl. In embodiments, $R^{27}$ is independently unsubstituted 6 membered heteroaryl. In embodiments, $R^{27}$ is independently unsubstituted 5 membered heteroaryl. In embodiments, $R^{27}$ is independently substituted 6 membered heteroaryl. In embodiments, $R^{27}$ is independently substituted 5 membered heteroaryl. In embodiments, $R^{27}$ is independently substituted phenyl. In embodiments, $R^{27}$ is independently unsubstituted phenyl.

In embodiments, $R^{27}$ is independently halogen, oxo, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, $R^{28}$-substituted or unsubstituted alkyl, $R^{28}$-substituted or unsubstituted heteroalkyl, $R^{28}$-substituted or unsubstituted cycloalkyl, $R^{28}$-substituted or unsubstituted heterocycloalkyl, $R^{28}$-substituted or unsubstituted aryl, or $R^{28}$-substituted or unsubstituted heteroaryl; two adjacent $R^{27}$ substituents may optionally be joined to form a $R^{28}$-substituted or unsubstituted cycloalkyl, $R^{28}$-substituted or unsubstituted heterocycloalkyl, $R^{28}$-substituted or unsubstituted aryl, or $R^{28}$-substituted or unsubstituted heteroaryl.

In embodiments, $R^{27}$ is independently halogen, oxo, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, $R^{28}$-substituted or unsubstituted $C_1$-$C_6$ alkyl, $R^{28}$-substituted or unsubstituted 2 to 6 membered heteroalkyl, $R^{28}$-substituted or unsubstituted $C_3$-$C_6$ cycloalkyl, $R^{28}$-substituted or unsubstituted 3 to 6 membered heterocycloalkyl, $R^{28}$-substituted or unsubstituted phenyl, or $R^{28}$-substituted or unsubstituted 5 to 6 membered heteroaryl; two adjacent $R^{27}$ substituents may optionally be joined to form a $R^{28}$-substituted or unsubstituted $C_3$-$C_6$ cycloalkyl, substituted or unsubstituted 3 to 6 membered heterocycloalkyl, $R^{28}$-substituted or unsubstituted phenyl, or $R^{28}$-substituted or unsubstituted 5 to 6 membered heteroaryl. In embodiments, $R^{27}$ is independently $R^{28}$-substituted $C_1$-$C_6$ alkyl. In embodiments, $R^{27}$ is independently $R^{28}$-substituted $C_1$-$C_5$ alkyl. In embodiments, $R^{27}$ is independently $R^{28}$-substituted $C_1$-$C_4$ alkyl. In embodiments, $R^{27}$ is independently $R^{28}$-substituted $C_1$-$C_3$ alkyl. In embodiments, $R^{27}$ is independently $R^{28}$-substituted $C_1$-$C_2$ alkyl. In embodiments, $R^{27}$ is independently $R^{28}$-substituted $C_2$-$C_6$ alkyl. In embodiments, $R^{27}$ is independently $R^{28}$-substituted $C_3$-$C_6$ alkyl. In embodiments, $R^{27}$ is independently $R^{28}$-substituted $C_4$-$C_6$ alkyl. In embodiments, $R^{27}$ is independently $R^{28}$-substituted or unsubstituted 2 to 3 membered heteroalkyl. In embodiments, $R^{27}$ is independently $R^{28}$-substituted or unsubstituted 2 to 4 membered heteroalkyl. In embodiments, $R^{27}$ is independently $R^{28}$-substituted or unsubstituted 2 to 5 membered heteroalkyl. In embodiments, $R^{27}$ is independently $R^{28}$-substituted or unsubstituted $C_4$-$C_6$ cycloalkyl. In embodiments, $R^{27}$ is independently $R^{28}$-substituted or unsubstituted 4 to 6 membered heterocycloalkyl. In embodiments, $R^{27}$ is independently $R^{28}$-substituted or unsubstituted 5 to 6 membered heterocycloalkyl. In embodiments, $R^{27}$ is independently $R^{28}$-substituted or unsubstituted 5 membered heteroaryl. In embodiments, $R^{27}$ is independently $R^{28}$-substituted or unsubstituted 6 membered heteroaryl. In embodiments, $R^{27}$ is independently $R^{28}$-substituted 6 membered heteroaryl. In embodiments, $R^{27}$ is independently $R^{28}$-substituted 5 membered heteroaryl. In embodiments, $R^{27}$ is independently $R^{28}$-substituted phenyl.

$R^{29}$ is independently halogen, oxo, —$CF_3$, —$CCl_3$, —CN, —$S(O)CH_3$, —OH, —$NH_2$, —COOH, —$CONH_2$, —$NO_2$, —$C(O)CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^{29}$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{29}$ is independently unsubstituted $C_1$-$C_6$ alkyl. In embodiments, $R^{29}$ is independently unsubstituted $C_1$-$C_5$ alkyl. In embodiments, $R^{29}$ is independently unsubstituted $C_1$-$C_4$ alkyl. In embodiments, $R^{29}$ is independently unsubstituted $C_1$-$C_3$ alkyl. In embodiments, $R^{29}$ is independently unsubstituted $C_1$-$C_2$ alkyl. In embodiments, $R^{29}$ is independently unsubstituted $C_2$-$C_6$ alkyl. In embodiments, $R^{29}$ is independently unsubstituted $C_3$-$C_6$ alkyl. In embodiments, $R^{29}$ is independently unsubstituted $C_4$-$C_6$ alkyl. In embodiments, $R^{29}$ is independently substituted $C_1$-$C_6$ alkyl. In embodiments, $R^{29}$ is independently substituted $C_1$-$C_5$ alkyl. In embodiments, $R^{29}$ is independently substituted $C_1$-$C_4$ alkyl. In embodiments, $R^{29}$ is independently substituted $C_1$-$C_3$ alkyl. In embodiments, $R^{29}$ is independently substituted $C_1$-$C_2$ alkyl. In embodiments, $R^{29}$ is independently substituted $C_2$-$C_6$ alkyl. In embodiments, $R^{29}$ is independently substituted $C_3$-$C_6$ alkyl. In embodiments, $R^{29}$ is independently substituted $C_4$-$C_6$ alkyl. In embodiments, $R^{29}$ is independently substituted or unsubstituted 2 to 3 membered heteroalkyl. In embodiments, $R^{29}$ is independently substituted or unsubstituted 2 to 4 membered heteroalkyl. In embodiments, $R^{29}$ is independently substituted or unsubstituted 2 to 5 membered heteroalkyl. In embodiments, $R^{29}$ is independently substituted or unsubstituted $C_4$-$C_6$ cycloalkyl. In embodiments, $R^{29}$ is independently substituted or unsubstituted 4 to 6 membered heterocycloalkyl. In embodiments, $R^{29}$ is independently substituted or unsubstituted 5 to 6 membered heterocycloalkyl. In embodiments, $R^{29}$ is independently substituted or unsubstituted 5 membered heteroaryl. In embodiments, $R^{29}$ is independently substituted or unsubstituted 6 membered heteroaryl. In embodiments, $R^{29}$ is independently unsubstituted 6 membered heteroaryl. In embodiments, $R^{29}$ is independently unsubstituted 5 membered heteroaryl. In embodiments, $R^{29}$ is independently substituted 6 membered heteroaryl. In embodiments, $R^{29}$ is independently substituted 5 membered heteroaryl. In embodiments, $R^{29}$ is independently substituted phenyl. In embodiments, $R^{29}$ is independently unsubstituted phenyl.

In embodiments, $R^{29}$ is independently halogen, oxo, —$CF_3$, —$CCl_3$, —CN, —$S(O)CH_3$, —OH, —$NH_2$, —COOH, —$CONH_2$, —$NO_2$, —$C(O)CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, $R^{30}$-substituted or unsubstituted alkyl, $R^{30}$-substituted or unsubstituted heteroalkyl, $R^{30}$-substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl; two adjacent $R^{29}$ substituents may optionally be joined to form a $R^{30}$-substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl.

In embodiments, $R^{29}$ is independently halogen, oxo, —$CF_3$, —$CCl_3$, —CN, —$S(O)CH_3$, —OH, —$NH_2$, —COOH, —$CONH_2$, —$NO_2$, —$C(O)CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, $R^{30}$-substituted or unsubstituted $C_1$-$C_6$ alkyl, $R^{30}$-substituted or unsubstituted 2 to 6 membered heteroalkyl, $R^{30}$-substituted or unsubstituted $C_3$-$C_6$ cycloalkyl, $R^{30}$-substituted or unsubstituted 3 to 6 membered heterocycloalkyl, $R^{30}$-substituted or unsubstituted phenyl, or $R^{30}$-substituted or unsubstituted 5 to 6 membered heteroaryl; two adjacent $R^{29}$ substituents may optionally be joined to form a $R^{30}$ substituted or unsubstituted $C_3$-$C_6$ cycloalkyl, substituted or unsubstituted 3 to 6 membered heterocycloalkyl, $R^{30}$-substituted or unsubstituted phenyl, or $R^{30}$-substituted or unsubstituted 5 to 6 membered heteroaryl. In embodiments, $R^{29}$ is independently $R^{30}$-substituted $C_1$-$C_6$ alkyl. In embodiments, $R^{29}$ is independently $R^{30}$-substituted $C_1$-$C_5$ alkyl. In embodiments, $R^{29}$ is independently $R^{30}$-substituted $C_1$-$C_4$ alkyl. In embodiments, $R^{29}$ is independently $R^{30}$-substituted $C_1$-$C_3$ alkyl. In embodiments, $R^{29}$ is independently $R^{30}$-substituted $C_1$-$C_2$ alkyl. In embodiments, $R^{29}$ is independently $R^{30}$-substituted $C_2$-$C_6$ alkyl. In embodiments, $R^{29}$ is independently $R^{30}$-substituted $C_3$-$C_6$ alkyl. In embodiments, $R^{29}$ is independently $R^{30}$-substituted $C_4$-$C_6$ alkyl. In embodiments, $R^{29}$ is independently $R^{30}$-substituted or unsubstituted 2 to 3 membered heteroalkyl. In embodiments, $R^{29}$ is independently $R^{30}$-substituted or unsubstituted 2 to 4 membered heteroalkyl. In embodiments, $R^{29}$ is independently $R^{30}$-substituted or unsubstituted 2 to 5 membered heteroalkyl. In embodiments, $R^{29}$ is independently $R^{30}$-substituted or unsubstituted $C_4$-$C_6$ cycloalkyl. In embodiments, $R^{29}$ is independently $R^{30}$-substituted or unsubstituted 4 to 6 membered heterocycloalkyl. In embodiments, $R^{29}$ is independently $R^{30}$-substituted or unsubstituted 5 to 6 membered heterocycloalkyl. In embodiments, $R^{29}$ is independently $R^{30}$-substituted or unsubstituted 5 membered heteroaryl. In embodiments, $R^{29}$ is independently $R^{30}$-substituted or unsubstituted 6 membered heteroaryl. In embodiments, $R^{29}$ is independently $R^{30}$-substituted 6 membered heteroaryl. In embodiments, $R^{29}$ is independently $R^{30}$-substituted 5 membered heteroaryl. In embodiments, $R^{29}$ is independently $R^{30}$-substituted phenyl.

$R^{30}$ is independently halogen, oxo, —$CF_3$, —$CCl_3$, —CN, —$S(O)CH_3$, —OH, —$NH_2$, —COOH, —$CONH_2$, —$NO_2$, —$C(O)CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^{30}$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{30}$ is independently unsubstituted $C_1$-$C_6$ alkyl. In embodiments, $R^{30}$ is independently unsubstituted $C_1$-$C_5$ alkyl. In embodiments, $R^{30}$ is independently unsubstituted $C_1$-$C_4$ alkyl. In embodiments, $R^{30}$ is independently unsubstituted $C_1$-$C_3$ alkyl. In embodiments, $R^{30}$ is independently unsubstituted $C_1$-$C_2$ alkyl. In embodiments, $R^{30}$ is independently unsubstituted $C_2$-$C_6$ alkyl. In embodiments, $R^{30}$ is independently unsubstituted $C_3$-$C_6$ alkyl. In embodiments, $R^{30}$ is independently unsubstituted $C_4$-$C_6$ alkyl. In embodiments, $R^{30}$ is independently substituted $C_1$-$C_6$ alkyl. In embodiments, $R^{30}$ is independently substituted $C_1$-$C_5$ alkyl. In embodiments, $R^{30}$ is independently substituted $C_1$-$C_4$ alkyl. In embodiments, $R^{30}$ is independently substituted $C_1$-$C_3$ alkyl. In embodiments, $R^{30}$ is independently substituted $C_1$-$C_2$ alkyl. In embodiments, $R^{30}$ is independently substituted $C_2$-$C_6$ alkyl. In embodiments, $R^{30}$ is independently substituted $C_3$-$C_6$ alkyl. In embodiments, $R^{30}$ is independently substituted $C_4$-$C_6$ alkyl. In embodiments, $R^{30}$ is independently substituted or unsubstituted 2 to 3 membered heteroalkyl. In embodiments, $R^{30}$ is independently substituted or unsubstituted 2 to 4 membered heteroalkyl. In embodiments, $R^{30}$ is independently substituted or unsubstituted 2 to 5 membered heteroalkyl. In embodiments, $R^{30}$ is independently substituted or unsubstituted $C_4$-$C_6$ cycloalkyl. In embodiments, $R^{30}$ is independently substituted or unsubstituted 4 to 6 membered heterocycloalkyl. In embodiments, $R^{30}$ is independently substituted or unsubstituted 5 to 6 membered heterocycloalkyl. In embodiments, $R^{30}$ is independently substituted or unsubstituted 5 membered heteroaryl. In embodiments, $R^{30}$ is independently substituted or unsubstituted 6 membered heteroaryl. In embodiments, $R^{30}$ is independently unsubstituted 6 membered heteroaryl. In embodiments, $R^{30}$ is independently unsubstituted 5 membered heteroaryl. In embodiments, $R^{30}$ is independently substituted 6 membered heteroaryl. In embodiments, $R^{30}$ is independently substituted 5 membered heteroaryl. In embodiments, $R^{30}$ is independently substituted phenyl. In embodiments, $R^{30}$ is independently unsubstituted phenyl.

In embodiments, $R^{30}$ is independently halogen, oxo, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, $R^{31}$-substituted or unsubstituted alkyl, $R^{31}$-substituted or unsubstituted heteroalkyl, $R^{31}$-substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl; two adjacent $R^{30}$ substituents may optionally be joined to form a $R^{31}$-substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl.

In embodiments, $R^{30}$ is independently halogen, oxo, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, $R^{31}$-substituted or unsubstituted $C_1$-$C_6$ alkyl, $R^{31}$-substituted or unsubstituted 2 to 6 membered heteroalkyl, $R^{31}$-substituted or unsubstituted $C_3$-$C_6$ cycloalkyl, $R^{31}$-substituted or unsubstituted 3 to 6 membered heterocycloalkyl, $R^{31}$-substituted or unsubstituted phenyl, or $R^{31}$-substituted or unsubstituted 5 to 6 membered heteroaryl; two adjacent $R^{30}$ substituents may optionally be joined to form a $R^{31}$ substituted or unsubstituted $C_3$-$C_6$ cycloalkyl, substituted or unsubstituted 3 to 6 membered heterocycloalkyl, $R^{31}$-substituted or unsubstituted phenyl, or $R^{31}$-substituted or unsubstituted 5 to 6 membered heteroaryl. In embodiments, $R^{30}$ is independently $R^{31}$-substituted $C_1$-$C_6$ alkyl. In embodiments, $R^{30}$ is independently $R^{31}$-substituted $C_1$-$C_5$ alkyl. In embodiments, $R^{30}$ is independently $R^{31}$-substituted $C_1$-$C_4$ alkyl. In embodiments, $R^{30}$ is independently $R^{31}$-substituted $C_1$-$C_3$ alkyl. In embodiments, $R^{30}$ is independently $R^{31}$-substituted $C_1$-$C_2$ alkyl. In embodiments, $R^{30}$ is independently $R^{31}$-substituted $C_2$-$C_6$ alkyl. In embodiments, $R^{30}$ is independently $R^{31}$-substituted $C_3$-$C_6$ alkyl. In embodiments, $R^{30}$ is independently $R^{31}$-substituted $C_4$-$C_6$ alkyl. In embodiments, $R^{30}$ is independently $R^{31}$-substituted or unsubstituted 2 to 3 membered heteroalkyl. In embodiments, $R^{30}$ is independently $R^{31}$-substituted or unsubstituted 2 to 4 membered heteroalkyl. In embodiments, $R^{30}$ is independently $R^{31}$-substituted or unsubstituted 2 to 5 membered heteroalkyl. In embodiments, $R^{30}$ is independently $R^{31}$-substituted or unsubstituted $C_4$-$C_6$ cycloalkyl. In embodiments, $R^{30}$ is independently $R^{31}$-substituted or unsubstituted 4 to 6 membered heterocycloalkyl. In embodiments, $R^{30}$ is independently $R^{31}$-substituted or unsubstituted 5 to 6 membered heterocycloalkyl. In embodiments, $R^{30}$ is independently $R^{31}$-substituted or unsubstituted 5 membered heteroaryl. In embodiments, $R^{30}$ is independently $R^{31}$-substituted or unsubstituted 6 membered heteroaryl. In embodiments, $R^{30}$ is independently $R^{31}$-substituted 6 membered heteroaryl. In embodiments, $R^{30}$ is independently $R^{31}$-substituted 5 membered heteroaryl.

$R^{32}$ is independently halogen, oxo, —$CF_3$, —$CCl_3$, —CN, —S(O)$CH_3$, —OH, —$NH_2$, —COOH, —$CONH_2$, —$NO_2$, —C(O)$CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^{32}$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{32}$ is independently unsubstituted $C_1$-$C_6$ alkyl. In embodiments, $R^{32}$ is independently unsubstituted $C_1$-$C_5$ alkyl. In embodiments, $R^{32}$ is independently unsubstituted $C_1$-$C_4$ alkyl. In embodiments, $R^{32}$ is independently unsubstituted $C_1$-$C_3$ alkyl. In embodiments, $R^{32}$ is independently unsubstituted $C_1$-$C_2$ alkyl. In embodiments, $R^{32}$ is independently unsubstituted $C_2$-$C_6$ alkyl. In embodiments, $R^{32}$ is independently unsubstituted $C_3$-$C_6$ alkyl. In embodiments, $R^{32}$ is independently unsubstituted $C_4$-$C_6$ alkyl. In embodiments, $R^{32}$ is independently substituted $C_1$-$C_6$ alkyl. In embodiments, $R^{32}$ is independently substituted $C_1$-$C_5$ alkyl. In embodiments, $R^{32}$ is independently substituted $C_1$-$C_4$ alkyl. In embodiments, $R^{32}$ is independently substituted $C_1$-$C_3$ alkyl. In embodiments, $R^{32}$ is independently substituted $C_1$-$C_2$ alkyl. In embodiments, $R^{32}$ is independently substituted $C_2$-$C_6$ alkyl. In embodiments, $R^{32}$ is independently substituted $C_3$-$C_6$ alkyl. In embodiments, $R^{32}$ is independently substituted $C_4$-$C_6$ alkyl. In embodiments, $R^{32}$ is independently substituted or unsubstituted 2 to 3 membered heteroalkyl. In embodiments, $R^{32}$ is independently substituted or unsubstituted 2 to 4 membered heteroalkyl. In embodiments, $R^{32}$ is independently substituted or unsubstituted 2 to 5 membered heteroalkyl. In embodiments, $R^{32}$ is independently substituted or unsubstituted $C_4$-$C_6$ cycloalkyl. In embodiments, $R^{32}$ is independently substituted or unsubstituted 4 to 6 membered heterocycloalkyl. In embodiments, $R^{32}$ is independently substituted or unsubstituted 5 to 6 membered heterocycloalkyl. In embodiments, $R^{32}$ is independently substituted or unsubstituted 5 membered heteroaryl. In embodiments, $R^{32}$ is independently substituted or unsubstituted 6 membered heteroaryl. In embodiments, $R^{32}$ is independently unsubstituted 6 membered heteroaryl. In embodiments, $R^{32}$ is independently unsubstituted 5 membered heteroaryl. In embodiments, $R^{32}$ is independently substituted 6 membered heteroaryl. In embodiments, $R^{32}$ is independently substituted 5 membered heteroaryl. In embodiments, $R^{32}$ is independently substituted phenyl. In embodiments, $R^{32}$ is independently unsubstituted phenyl.

In embodiments, $R^{32}$ is independently halogen, oxo, —$CF_3$, —$CCl_3$, —CN, —$S(O)CH_3$, —OH, —$NH_2$, —COOH, —$CONH_2$, —$NO_2$, —$C(O)CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, $R^{33}$-substituted or unsubstituted alkyl, $R^{33}$-substituted or unsubstituted heteroalkyl, $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl; two adjacent $R^{32}$ substituents may optionally be joined to form a $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl.

In embodiments, $R^{32}$ is independently halogen, oxo, —$CF_3$, —$CCl_3$, —CN, —$S(O)CH_3$, —OH, —$NH_2$, —COOH, —$CONH_2$, —$NO_2$, —$C(O)CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, $R^{33}$-substituted or unsubstituted $C_1$-$C_6$ alkyl, $R^{33}$-substituted or unsubstituted 2 to 6 membered heteroalkyl, $R^{33}$-substituted or unsubstituted $C_3$-$C_6$ cycloalkyl, $R^{33}$-substituted or unsubstituted 3 to 6 membered heterocycloalkyl, $R^{33}$-substituted or unsubstituted phenyl, or $R^{33}$-substituted or unsubstituted 5 to 6 membered heteroaryl; two adjacent $R^{32}$ substituents may optionally be joined to form a $R^{33}$-substituted or unsubstituted $C_3$-$C_6$ cycloalkyl, substituted or unsubstituted 3 to 6 membered heterocycloalkyl, $R^{33}$-substituted or unsubstituted phenyl, or $R^{33}$-substituted or unsubstituted 5 to 6 membered heteroaryl. In embodiments, $R^{32}$ is independently $R^{33}$-substituted $C_1$-$C_6$ alkyl. In embodiments, $R^{32}$ is independently $R^{33}$-substituted $C_1$-$C_5$ alkyl. In embodiments, $R^{32}$ is independently $R^{33}$-substituted $C_1$-$C_4$ alkyl. In embodiments, $R^{32}$ is independently $R^{33}$-substituted $C_1$-$C_3$ alkyl. In embodiments, $R^{32}$ is independently $R^{33}$-substituted $C_1$-$C_2$ alkyl. In embodiments, $R^{32}$ is independently $R^{33}$-substituted $C_2$-$C_6$ alkyl. In embodiments, $R^{32}$ is independently $R^{33}$-substituted $C_3$-$C_6$ alkyl. In embodiments, $R^{32}$ is independently $R^{33}$-substituted $C_4$-$C_6$ alkyl. In embodiments, $R^{32}$ is independently $R^{33}$-substituted or unsubstituted 2 to 3 membered heteroalkyl. In embodiments, $R^{32}$ is independently $R^{33}$-substituted or unsubstituted 2 to 4 membered heteroalkyl. In embodiments, $R^{32}$ is independently $R^{33}$-substituted or unsubstituted 2 to 5 membered heteroalkyl. In embodiments, $R^{32}$ is independently $R^{33}$-substituted or unsubstituted $C_4$-$C_6$ cycloalkyl. In embodiments, $R^{32}$ is independently $R^{33}$-substituted or unsubstituted 4 to 6 membered heterocycloalkyl. In embodiments, $R^{32}$ is independently $R^{33}$-substituted or unsubstituted 5 to 6 membered heterocycloalkyl. In embodiments, $R^{32}$ is independently $R^{33}$-substituted or unsubstituted 5 membered heteroaryl. In embodiments, $R^{32}$ is independently $R^{33}$-substituted or unsubstituted 6 membered heteroaryl. In embodiments, $R^{32}$ is independently $R^{33}$-substituted 6 membered heteroaryl. In embodiments, $R^{32}$ is independently $R^{33}$-substituted 5 membered heteroaryl. In embodiments, $R^{32}$ is independently $R^{33}$-substituted phenyl.

$R^{33}$ is independently halogen, oxo, —$CF_3$, —$CCl_3$, —CN, —$S(O)CH_3$, —OH, —$NH_2$, —COOH, —$CONH_2$, —$NO_2$, —$C(O)CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^{33}$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{33}$ is independently unsubstituted $C_1$-$C_6$ alkyl. In embodiments, $R^{33}$ is independently unsubstituted $C_1$-$C_5$ alkyl. In embodiments, $R^{33}$ is independently unsubstituted $C_1$-$C_4$ alkyl. In embodiments, $R^{33}$ is independently unsubstituted $C_1$-$C_3$ alkyl. In embodiments, $R^{33}$ is independently unsubstituted $C_1$-$C_2$ alkyl. In embodiments, $R^{33}$ is independently unsubstituted $C_2$-$C_6$ alkyl. In embodiments, $R^{33}$ is independently unsubstituted $C_3$-$C_6$ alkyl. In embodiments, $R^{33}$ is independently unsubstituted $C_4$-$C_6$ alkyl. In embodiments, $R^{33}$ is independently substituted $C_1$-$C_6$ alkyl. In embodiments, $R^{33}$ is independently substituted $C_1$-$C_5$ alkyl. In embodiments, $R^{33}$ is independently substituted $C_1$-$C_4$ alkyl. In embodiments, $R^{33}$ is independently substituted $C_1$-$C_3$ alkyl. In embodiments, $R^{33}$ is independently substituted $C_1$-$C_2$ alkyl. In embodiments, $R^{33}$ is independently substituted $C_2$-$C_6$ alkyl. In embodiments, $R^{33}$ is independently substituted $C_3$-$C_6$ alkyl. In embodiments, $R^{33}$ is independently substituted $C_4$-$C_6$ alkyl. In embodiments, $R^{33}$ is independently substituted or unsubstituted 2 to 3 membered heteroalkyl. In embodiments, $R^{33}$ is independently substituted or unsubstituted 2 to 4 membered heteroalkyl. In embodiments, $R^{33}$ is independently substituted or unsubstituted 2 to 5 membered heteroalkyl. In embodiments, $R^{33}$ is independently substituted or unsubstituted $C_4$-$C_6$ cycloalkyl. In embodiments, $R^{33}$ is independently substituted or unsubstituted 4 to 6 membered heterocycloalkyl. In embodiments, $R^{33}$ is independently substituted or unsubstituted 5 to 6 membered heterocycloalkyl. In embodiments, $R^{33}$ is independently substituted or unsubstituted 5 membered heteroaryl. In embodiments, $R^{33}$ is independently substituted or unsubstituted 6 membered heteroaryl. In embodiments, $R^{33}$ is independently unsubstituted 6 membered heteroaryl. In embodiments, $R^{33}$ is independently unsubstituted 5 membered heteroaryl. In embodiments, $R^{33}$ is independently substituted 6 membered heteroaryl. In embodiments, $R^{33}$ is independently substituted 5 membered heteroaryl. In embodiments, $R^{33}$ is independently substituted phenyl. In embodiments, $R^{33}$ is independently unsubstituted phenyl.

In embodiments, $R^{33}$ is independently halogen, oxo, —$CF_3$, —$CCl_3$, —CN, —$S(O)CH_3$, —OH, —$NH_2$, —COOH, —$CONH_2$, —$NO_2$, —$C(O)CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, $R^{34}$-substituted or unsubstituted alkyl, $R^{34}$-substituted or unsubstituted heteroalkyl, $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl; two adjacent $R^{33}$ substituents may optionally be joined to form a $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl.

In embodiments, $R^{33}$ is independently halogen, oxo, —$CF_3$, —$CCl_3$, —CN, —$S(O)CH_3$, —OH, —$NH_2$, —COOH, —$CONH_2$, —$NO_2$, —$C(O)CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, $R^{34}$-substituted or unsubstituted $C_1$-$C_6$ alkyl, $R^{34}$-substituted or unsubstituted 2 to 6 membered heteroalkyl, $R^{34}$-substituted or unsubstituted $C_3$-$C_6$ cycloalkyl, $R^{34}$-substituted or unsubstituted 3 to 6 membered heterocycloalkyl, $R^{34}$-substituted or unsubstituted phenyl, or $R^{34}$-substituted or unsubstituted 5 to 6 membered heteroaryl; two adjacent $R^{33}$ substituents may optionally be joined to form a $R^{34}$-substituted or unsubstituted $C_3$-$C_6$ cycloalkyl, substituted or unsubstituted 3 to 6 membered heterocycloalkyl, $R^{34}$-substituted or unsubstituted phenyl, or $R^{34}$-substituted or unsubstituted 5 to 6 membered heteroaryl. In embodiments, $R^{33}$ is independently $R^{34}$-substituted $C_1$-$C_6$ alkyl. In embodiments, $R^{33}$ is independently $R^{34}$-substituted $C_1$-$C_5$ alkyl. In embodiments, $R^{33}$ is independently $R^{34}$-substituted $C_1$-$C_4$ alkyl. In embodiments, $R^{33}$ is independently $R^{34}$-substituted $C_1$-$C_3$ alkyl. In embodiments, $R^{33}$ is independently $R^{34}$-substituted $C_1$-$C_2$ alkyl. In embodiments, $R^{33}$ is independently $R^{34}$-substituted $C_2$-$C_6$ alkyl. In embodiments, $R^{33}$ is independently $R^{34}$-substituted $C_3$-$C_6$ alkyl. In embodiments, $R^{33}$ is independently $R^{34}$-substituted $C_4$-$C_6$ alkyl. In embodiments, $R^{33}$ is independently $R^{34}$-substituted or unsubstituted 2 to 3 membered heteroalkyl. In embodiments, $R^{33}$ is independently $R^{34}$-substituted or unsubstituted 2 to 4 membered heteroalkyl. In embodiments, $R^{33}$ is independently $R^{34}$-substituted or unsubstituted 2 to 5 membered heteroalkyl. In embodiments, $R^{33}$ is independently $R^{34}$-substituted or unsubstituted $C_4$-$C_6$ cycloalkyl. In embodiments, $R^{33}$ is independently $R^{34}$-substituted or unsubstituted 4 to 6 membered heterocycloalkyl. In embodiments, $R^{33}$ is independently $R^{34}$-substituted or unsubstituted 5 to 6 membered heterocycloalkyl. In embodiments, $R^{33}$ is independently $R^{34}$-substituted or unsubstituted 5 membered heteroaryl. In embodiments, $R^{33}$ is independently $R^{34}$-substituted or unsubstituted 6 membered heteroaryl. In embodiments, $R^{33}$ is independently $R^{34}$-substituted 6 membered heteroaryl. In embodiments, $R^{33}$ is independently $R^{34}$-substituted 5 membered heteroaryl. In embodiments, $R^{33}$ is independently $R^{34}$-substituted phenyl.

Each $R^{22}$, $R^{25}$, $R^{28}$, $R^{31}$, $R^{34}$, $R^{35}$, $R^{36}$, $R^{37}$, $R^{38}$, $R^{39}$, $R^{40}$, $R^{41}$, and $R^{42}$ is independently halogen, oxo, —$CH_3$, —$CX_3$, —$CHX_2$, —$CH_2X$, —$CF_3$, —$CCl_3$, —CN, —$S(O)CH_3$, —OH, —$NH_2$, —COOH, —$CONH_2$, —$NO_2$, —$C(O)CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, —$OCH_2F$, —$OCX_3$, —$OCHX_2$, —$OCH_2X$, —$SCX_3$, —$SCHX_2$, —$SCH_2X$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{22}$ is independently hydrogen, unsubstituted $C_1$-$C_6$ alkyl, unsubstituted 2 to 6 membered heteroalkyl. In embodiments, $R^{22}$ is independently unsubstituted 3 to 6 membered heteroalkyl. In embodiments, $R^{22}$ is independently unsubstituted 4 to 6 membered heteroalkyl. In embodiments, each $R^{22}$, $R^{25}$, $R^{28}$, $R^{31}$, $R^{34}$, $R^{35}$, $R^{36}$, $R^{37}$, $R^{38}$, $R^{39}$, $R^{40}$, $R^{41}$, and $R^{42}$ is independently halogen, oxo, —$CH_3$, —$CF_3$, —$CCl_3$, —CN, —$S(O)CH_3$, —OH, —$NH_2$, —COOH, —$CONH_2$, —$NO_2$, —$C(O)CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{22}$, $R^{25}$, $R^{28}$, $R^{31}$, $R^{34}$, $R^{35}$, $R^{36}$, $R^{37}$, $R^{38}$, $R^{39}$, $R^{40}$, $R^{41}$, and $R^{42}$ are independently halogen, oxo, —$CH_3$, —$CX_3$, —$CHX_2$, —$CH_2X$, —$CF_3$, —$CCl_3$, —CN, —$S(O)CH_3$, —OH, —$NH_2$, —COOH, —$CONH_2$, —$NO_2$, —$C(O)CH_3$, —$CH_2CH_3$, —$CH_2CH_2OH$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, —$OCH_2F$, —$OCX_3$, —$OCHX_2$, —$OCH_2X$, —$SCX_3$, —$SCHX_2$, —$SCH_2X$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{22}$, $R^{25}$, $R^{28}$, $R^{31}$, $R^{34}$, $R^{35}$, $R^{36}$, $R^{37}$, $R^{38}$, $R^{39}$, $R^{40}$, $R^{41}$, and $R^{42}$ are independently unsubstituted methyl. In embodiments, $R^{22}$, $R^{25}$, $R^{28}$, $R^{31}$, $R^{34}$, $R^{35}$, $R^{36}$, $R^{37}$, $R^{38}$, $R^{39}$, $R^{40}$, $R^{41}$, and $R^{42}$ are independently halogen.

In embodiments, a1 is independently an integer from 0 to 7. In embodiments, a1 is independently an integer from 0 to 6. In embodiments, a1 is independently an integer from 0 to 5. In embodiments, a1 is independently an integer from 0 to 4. In embodiments, a1 is independently an integer from 0 to 3. In embodiments, a1 is independently an integer from 0 to 2. In embodiments, a1 is independently an integer from 0 to 1. In embodiments, a1 is 7. In embodiments, a1 is 6. In embodiments, a1 is 5. In embodiments, a1 is 4. In embodiments, a1 is 3. In embodiments, a1 is 2. In embodiments, a1 is 1. In embodiments, a1 is 0. In embodiments, b1 is independently an integer from 0 to 7. In embodiments, b1 is independently an integer from 0 to 6. In embodiments, b1 is independently an integer from 0 to 5. In embodiments, b1 is independently an integer from 0 to 4. In embodiments, b1 is independently an integer from 0 to 3. In embodiments, b1 is independently an integer from 0 to 2. In embodiments, b1 is independently an integer from 0 to 1. In embodiments, b1 is 7. In embodiments, b1 is 6. In embodiments, b1 is 5. In embodiments, b1 is 4. In embodiments, b1 is 3. In embodiments, b1 is 2. In embodiments, b1 is 1. In embodiments, b1 is 0. In embodiments, m1 is independently an integer from 0 to 2. In embodiments, m1 is independently an integer from 0 to 1. In embodiments, m1 is 0. In embodiments, m1 is 1. In embodiments, m1 is 2. In embodiments, m2 is independently an integer from 0 to 2. In embodiments, m2 is independently an integer from 0 to 1. In embodiments, m2 is 0. In embodiments, m2 is 1. In embodiments, m2 is 2. In embodiments, v1 is independently an integer from 0 to 2. In embodiments, v1 is independently an integer from 0 to 1. In embodiments, v1 is 0. In embodiments, v1 is 1. In embodiments, v1 is 2. In embodiments, v2 is independently an integer from 0 to 2. In embodiments, v2 is independently an integer from 0 to 1. In embodiments, v2 is 0. In embodiments, v2 is 1. In embodiments, v2 is 2. In embodiments, n1 is independently an integer from 0 to 4. In embodiments, n1 is independently an integer from 0 to 3. In embodiments, n1 is independently an integer from 0 to 2. In embodiments, n1 is independently an integer from 0 to 1. In embodiments, n1 is 4. In embodiments, n1 is 3. In embodiments, n1 is 2. In embodiments, n1 is 1. In embodiments, n1 is 0. In embodiments, n2 is independently an integer from 0 to 4. In embodiments, n2 is independently an integer from 0 to 3. In embodiments, n2 is independently an integer from 0 to 2. In embodiments, n2 is independently an integer from 0 to 1. In embodiments, n2 is 4. In embodiments, n2 is 3. In embodiments, n2 is 2. In embodiments, n2 is 1. In embodiments, n2 is 0.

In embodiments, X, $X^1$, $X^2$, $X^3$, and $X^4$ are independently —Cl, —Br, —I, or —F. In embodiments, X is —F. In embodiments, X is —Cl. In embodiments, X is —Br. In embodiments, X is —I. In embodiments, $X^1$ is —F. In embodiments, $X^1$ is —Cl. In embodiments, $X^1$ is —Br. In embodiments, $X^1$ is —I. In embodiments, $X^2$ is —F. In embodiments, $X^2$ is —Cl. In embodiments, $X^2$ is —Br. In embodiments, $X^2$ is —I. In embodiments, $X^3$ is —F. In embodiments, $X^3$ is —Cl. In embodiments, $X^3$ is —Br. In embodiments, $X^3$ is —I. In embodiments, $X^4$ is —F. In embodiments, $X^4$ is —Cl. In embodiments, $X^4$ is —Br. In embodiments, $X^4$ is —I.

In an embodiment, the compound has the formula (I) and Ring A, Ring B, $R^1$, $R^2$, $R^3$, $R^4$, a1, b1, $X^1$ and $X^2$ are as described herein.

In embodiments, Ring A is phenyl. In embodiments, Ring B is 5 or 6 membered heteroaryl. In embodiments, Ring B is pyridyl. In embodiments, $R^1$ is independently a halogen, —$CX^1_3$, —CN, —$SO_{n1}R^{10}$, —$SO_{v1}NR^7R^8$, —$NHNH_2$, —$ONR^7R^8$, —NHC=(O)$NHNH_2$, —NHC=(O)$NR^7R^8$, —N(O)$_{m1}$, —$NR^7R^8$, —C(O)$R^9$, —C(O)—$OR^9$, —C(O)$NR^7R^8$, —$OR^{10}$, —$NR^7SO_2R^{10}$, —$NR^7C$=(O)$R^9$, —$NR^7C(O)$—$OR^9$, —$NR^7OR^9$, —$OCX^1_3$, —$OCHX^1_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^1$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^2$ is independently a halogen, —$CX^2_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^2_3$, —$OCHX^2_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^2$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^3$ is independently hydrogen, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^4$ is independently hydrogen, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, a1 is independently an integer from 0 to 5. In embodiments, b1 is independently an integer from 0 to 4. In embodiments, $X^1$ and $X^2$ are independently —Cl, —Br, —I, or —F.

In an embodiment, the compound has the formula:

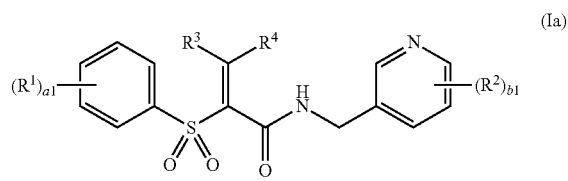

(Ia)

and $R^1$, $R^2$, $R^3$, $R^4$, a1, b1, $X^1$ and $X^2$ are as described herein.

In embodiments, $R^3$ is independently hydrogen, substituted or unsubstituted phenyl, or substituted or unsubstituted 5 to 6 membered heteroaryl. In embodiments, $R^3$ is independently substituted or unsubstituted 5 to 6 membered heteroaryl. In embodiments, $R^3$ is independently substituted or unsubstituted furanyl. In embodiments, $R^3$ is independently $R^{26}$-substituted or unsubstituted furanyl and $R^{26}$ is halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{26}$ is phenyl substituted with halogen. In embodiments, $R^4$ is independently hydrogen, substituted or unsubstituted phenyl, or substituted or unsubstituted 5 to 6 membered heteroaryl. In embodiments, $R^4$ is independently substituted or unsubstituted phenyl. In embodiments, $R^4$ is independently $R^{29}$-substituted or unsubstituted furanyl and $R^{29}$ is halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, phenoxy, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

In an embodiment, the compound has the formula:

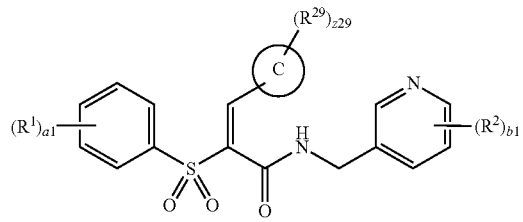

(Ia)

and $R^1$, $R^2$, $R^3$, $R^4$, $R^{29}$, a1, b1, $X^1$ and $X^2$ are as described herein. Ring C is a $R^{29}$-substituted or unsubstituted heterocycloalkyl, $R^{29}$-substituted or unsubstituted aryl, or $R^{29}$-substituted or unsubstituted heteroaryl. In embodiments, Ring C is $R^{29}$-substituted or unsubstituted cycloalkyl, $R^{29}$-substituted or unsubstituted heterocycloalkyl, $R^{29}$-substituted or unsubstituted aryl, or $R^{29}$-substituted or unsubstituted heteroaryl. The symbol z29 is an integer from 0 to 7. In embodiments, z29 is 1.

In embodiments, $R^4$ is independently $R^{29}$-substituted or unsubstituted furanyl and $R^{29}$ is halogen-substituted or unsubstituted phenyl, or halogen-substituted substituted or unsubstituted 5 to 6 membered heteroaryl. In embodiments, $R^4$ is

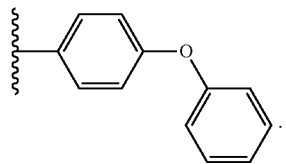 [SMILES: *c1ccc(Oc2ccccc2)cc1]

In embodiments, $R^4$ is independently substituted or unsubstituted phenyl. In embodiments, $R^4$ is independently $R^{29}$-substituted or unsubstituted phenyl and $R^{29}$ is halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, phenoxy, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{29}$ is halogen. In embodiments, $R^{29}$ is —Cl. In embodiments, $R^{29}$ is —Br. In embodiments, $R^{29}$ is

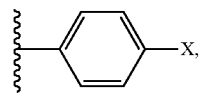

where X is a halogen. In embodiments, $R^{29}$ is

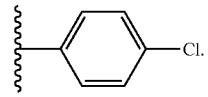

In embodiments, $R^3$ is independently $R^{26}$-substituted or unsubstituted furanyl and $R^{26}$ is halogen-substituted or unsubstituted phenyl, or halogen-substituted or unsubstituted 5 to 6 membered heteroaryl. In embodiments, $R^3$ is

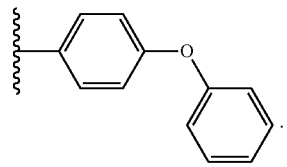

It will be understood that when Ring C is bonded to one or more non-hydrogen $R^{29}$ moieties, then Ring C is substituted. Likewise, it will be understood that when Ring C is not bonded to any $R^{29}$ moieties, or is bonded to $R^{29}$ moieties that are all hydrogen moieties, then Ring C is unsubstituted.

In embodiments, $R^3$ is independently substituted or unsubstituted phenyl. In embodiments, $R^3$ is independently $R^{26}$-substituted or unsubstituted phenyl and $R^{26}$ is halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, phenoxy, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{26}$ is halogen. In embodiments, $R^{26}$ is —Cl. In embodiments, $R^{26}$ is —Br. In embodiments, $R^{26}$ is

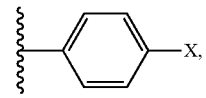

where X is a halogen. In embodiments, $R^{26}$ is

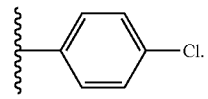 [SMILES: *c1ccc(Cl)cc1]

In embodiments, the compound is Gr-7a, Gr-7b, Gr-7c, or an analogue, prodrug, or derivative thereof (of any one of the compounds). In embodiments, the compound is Gr-7a or an analogue, prodrug, or derivative thereof. In embodiments, the compound is Gr-7b or an analogue, prodrug, or derivative thereof. In embodiments, the compound is Gr-7c or an analogue, prodrug, or derivative thereof.

In embodiments, the compound is not Gr-7a, Gr-7b, Gr-7c or an analogue, prodrug, or derivative thereof (of any one of the compounds). In embodiments, the compound is not Gr-7a or an analogue, prodrug, or derivative thereof. In embodiments, the compound is not Gr-7b or an analogue, prodrug, or derivative thereof. In embodiments, the compound is not Gr-7c or an analogue, prodrug, or derivative thereof.

In embodiments, the compound is Gr-7a, Gr-7b, or Gr-7c. In embodiments, the compound is Gr-7a. In embodiments, the compound is Gr-7b. In embodiments, the compound is Gr-7c.

In embodiments, the compound is not Gr-7a, Gr-7b, or Gr-7c. In embodiments, the compound is not Gr-7a. In embodiments, the compound is not Gr-7b. In embodiments, the compound is not Gr-7c.

In an embodiment, the compound has the formula:

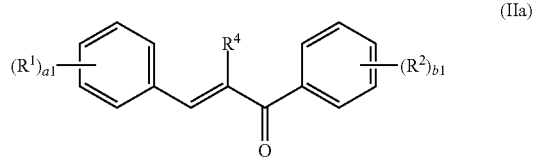

(IIa)

and $R^1$, $R^2$, $R^4$, a1, b1 are as described herein.

In embodiments, $R^1$ is independently a halogen, $-CX^1_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^1_3$, $-OCHX^1_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^1$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^2$ is independently a halogen, $-CX^2_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^2_3$, $-OCHX^2_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^2$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^4$ is independently hydrogen, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl. In embodiments, a1 is independently an integer from 0 to 5. In embodiments, b1 is independently an integer from 0 to 5. In embodiments, $X^1$ and $X^2$ are independently $-Cl$, $-Br$, $-I$, or $-F$. In embodiments, $R^4$ is independently hydrogen, substituted or unsubstituted $C_6$-$C_{10}$ aryl, or substituted or unsubstituted 5 to 10 membered heteroaryl. In embodiments, $R^4$ is independently substituted or unsubstituted 5 or 10 membered heteroaryl. In embodiments, $R^4$ is independently $R^{29}$-substituted or unsubstituted benzimidazolyl and $R^{29}$ is halogen, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, phenoxy, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^4$ is independently unsubstituted benzimidazolyl.

In an embodiment, the compound has the formula:

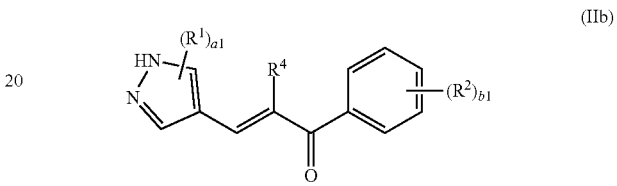

(IIb)

and $R^1$, $R^2$, $R^4$, a1, b1 are as described herein.

In embodiments, $R^1$ is independently a halogen, $-CX^1_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^1_3$, $-OCHX^1_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^1$ substituents may optionally be joined to form a substituted or unsubstituted 5 to 6 membered heterocycloalkyl or substituted or unsubstituted 5 to 6 membered heteroaryl. In embodiments, $R^2$ is independently a halogen, $-CX^2_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^2_3$, $-OCHX^2_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^2$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^4$ is independently hydrogen, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl. In embodiments, a1 is independently an integer from 0 to 5. In embodiments, b1 is independently an integer from 0 to 5. In embodiments, $X^1$ and $X^2$ are independently $-Cl$, $-Br$, $-I$, or $-F$. In embodiments, $R^4$ is hydrogen. In embodiments, wherein $R^1$ is independently a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

In an embodiment, the compound has the formula:

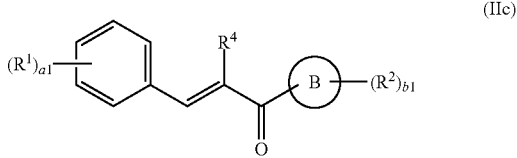

(IIc)

and $R^1$, $R^2$, $R^4$, a1, b1 are as described herein.

In embodiments, Ring B is a pyridyl. In embodiments, $R^1$ is independently a halogen, —$CX^1_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCX^1_3$, —$OCHX^1_2$, substituted or unsubstituted $C_1$-$C_3$ alkyl, or substituted or unsubstituted 2 to 3 membered heteroalkyl. In embodiments, $R^2$ is independently a halogen, —$CX^2_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^2_3$, —$OCHX^2_2$, substituted or unsubstituted $C_1$-$C_3$ alkyl, or substituted or unsubstituted 2 to 3 membered heteroalkyl. In embodiments, $R^4$ is independently hydrogen. In embodiments, a1 is independently an integer from 0 to 5. In embodiments, b1 is independently an integer from 0 to 5. In embodiments, $X^1$ and $X^2$ are independently —Cl, —Br, —I, or —F. In embodiments, $R^1$ is independently a halogen. In embodiments, $R^2$ is independently an —OH, unsubstituted $C_1$-$C_3$ alkyl, or unsubstituted 2 to 3 membered heteroalkyl.

In embodiments, $R^4$ is substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^4$ is substituted or unsubstituted $C_1$-$C_6$ alkyl or substituted or unsubstituted 2 to 6 membered heteroalkyl. In embodiments, $R^2$ is independently a halogen, —$CX^2_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCX^2_3$, —$OCHX^2_2$, or substituted or unsubstituted $C_1$-$C_6$ alkyl. In embodiments, $R^2$ is independently substituted or unsubstituted $C_1$-$C_6$ alkyl. In embodiments, $R^2$ is independently unsubstituted $C_1$-$C_6$ alkyl. In embodiments, $R^2$ is independently unsubstituted $C_1$-$C_2$ alkyl. In embodiments, $R^2$ is independently unsubstituted methyl. In embodiments, $R^2$ is independently —OH. In embodiments, $R^1$ is independently a halogen.

In embodiments, the compound is Gr-4a, Gr-4b, Gr-4c, Gr-4d, Gr-6b, O18 or an analogue, prodrug, or derivative thereof (of any one of the compounds). In embodiments, the compound is Gr-4a or an analogue, prodrug, or derivative thereof. In embodiments, the compound is Gr-4b or an analogue, prodrug, or derivative thereof. In embodiments, the compound is Gr-4c or an analogue, prodrug, or derivative thereof. In embodiments, the compound is Gr-4d or an analogue, prodrug, or derivative thereof. In embodiments, the compound is Gr-6b or an analogue, prodrug, or derivative thereof. In embodiments, the compound is O18 or an analogue, prodrug, or derivative thereof.

In embodiments, the compound is not Gr-4a, Gr-4b, Gr-4c, Gr-4d, Gr-6b, O18 or an analogue, prodrug, or derivative thereof (of any one of the compounds). In embodiments, the compound is not Gr-4a or an analogue, prodrug, or derivative thereof. In embodiments, the compound is not Gr-4b or an analogue, prodrug, or derivative thereof. In embodiments, the compound is not Gr-4c or an analogue, prodrug, or derivative thereof. In embodiments, the compound is not Gr-4d or an analogue, prodrug, or derivative thereof. In embodiments, the compound is not Gr-6b or an analogue, prodrug, or derivative thereof. In embodiments, the compound is not O18 or an analogue, prodrug, or derivative thereof.

In embodiments, the compound is Gr-4a, Gr-4b, Gr-4c, Gr-4d, Gr-6b, or O18. In embodiments, the compound is Gr-4a. In embodiments, the compound is Gr-4b. In embodiments, the compound is Gr-4c. In embodiments, the compound is Gr-4d. In embodiments, the compound is Gr-6b. In embodiments, the compound is O18.

In embodiments, the compound is not Gr-4a, Gr-4b, Gr-4c, Gr-4d, Gr-6b, or O18. In embodiments, the compound is not Gr-4a. In embodiments, the compound is not Gr-4b. In embodiments, the compound is not Gr-4c. In embodiments, the compound is not Gr-4d. In embodiments, the compound is not Gr-6b. In embodiments, the compound is not O18.

In an embodiment, the compound has the formula:

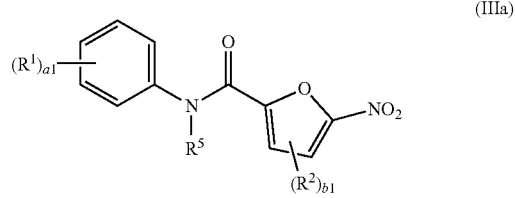

(IIIa)

and $R^1$, $R^2$, $R^5$, a1, b1 are as described herein.

In embodiments, $R^1$ is independently a halogen, —$CX^1_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^1_3$, —$OCHX_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^1$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 or 6 membered heteroaryl. In embodiments, $R^2$ is independently a halogen, —$CX^2_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^2_3$, —$OCHX^2_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^5$ is hydrogen or $R^5$ may optionally be joined to an $R^1$ substituent ortho to the —N(R$^5$)— to form an unsubstituted 5 membered heterocycloalkyl or unsubstituted 5 membered heteroaryl. In embodiments, a1 is independently an integer from 0 to 5. In embodiments, b1 is independently an integer from 0 to 2. In embodiments, X$^1$ and X$^2$ are independently —Cl, —Br, —I, or —F.

In embodiments, R$^1$ is —SO$_2$NH$_2$. In embodiments, R$^1$ is —CF$_3$. In embodiments, R$^1$ is —Cl. In embodiments, R$^1$ is substituted or unsubstituted C$_1$-C$_6$ alkyl. In embodiments, R$^1$ is unsubstituted C$_1$-C$_6$ alkyl. In embodiments, R$^1$ is unsubstituted C$_1$-C$_2$ alkyl. In embodiments, R$^1$ is unsubstituted methyl. In embodiments, a1 is 1. In embodiments, a1 is 2. In embodiments, R$^1$ is halogen. In embodiments, R$^1$ is unsubstituted ethyl.

In embodiments, the compound is Gr-1a, Gr-1b, Gr-1c, Gr-1d, Gr-1e, Gr-1f, Gr-1g, O13 or an analogue, prodrug, or derivative thereof (of any one of the compounds). In embodiments, the compound is G1a or an analogue, prodrug, or derivative thereof. In embodiments, the compound is Gr-1b or an analogue, prodrug, or derivative thereof. In embodiments, the compound is Gr-1c or an analogue, prodrug, or derivative thereof. In embodiments, the compound is Gr-1d or an analogue, prodrug, or derivative thereof. In embodiments, the compound is Gr-1e or an analogue, prodrug, or derivative thereof. In embodiments, the compound is Gr-1f or an analogue, prodrug, or derivative thereof. In embodiments, the compound is Gr-1g or an analogue, prodrug, or derivative thereof. In embodiments, the compound is O13 or an analogue, prodrug, or derivative thereof.

In embodiments, the compound is not Gr-1a, Gr-1b, Gr-1c, Gr-1d, Gr-1e, Gr-1f, Gr-1g, O13 or an analogue, prodrug, or derivative thereof (of any one of the compounds). In embodiments, the compound is not G1a or an analogue, prodrug, or derivative thereof. In embodiments, the compound is not Gr-1b or an analogue, prodrug, or derivative thereof. In embodiments, the compound is not Gr-1c or an analogue, prodrug, or derivative thereof. In embodiments, the compound is not Gr-1d or an analogue, prodrug, or derivative thereof. In embodiments, the compound is not Gr-1e or an analogue, prodrug, or derivative thereof. In embodiments, the compound is not Gr-1f or an analogue, prodrug, or derivative thereof. In embodiments, the compound is not Gr-1g or an analogue, prodrug, or derivative thereof. In embodiments, the compound is not O13 or an analogue, prodrug, or derivative thereof.

In embodiments, the compound is Gr-1a, Gr-1b, Gr-1c, Gr-1d, Gr-1e, Gr-1f, Gr-1g, or O13. In embodiments, the compound is G1a. In embodiments, the compound is Gr-1b. In embodiments, the compound is Gr-1c. In embodiments, the compound is Gr-1d. In embodiments, the compound is Gr-1e. In embodiments, the compound is Gr-1f. In embodiments, the compound is Gr-1g. In embodiments, the compound is O13.

In embodiments, the compound is not Gr-1a, Gr-1b, Gr-1c, Gr-1d, Gr-1e, Gr-1f, Gr-1g, or O13. In embodiments, the compound is not G1a. In embodiments, the compound is not Gr-1b. In embodiments, the compound is not Gr-1c. In embodiments, the compound is not Gr-1d. In embodiments, the compound is not Gr-1e. In embodiments, the compound is not Gr-1f. In embodiments, the compound is not Gr-1g. In embodiments, the compound is not O13.

In an embodiment, the compound has the formula:

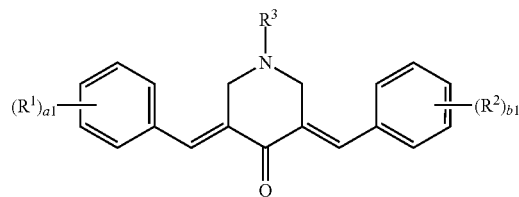

(IVa)

and R$^1$, R$^2$, R$^3$, a1, and b1 are as described herein.

In embodiments, R$^1$ is independently a halogen, —CX$^1_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^1_3$, —OCHX$^1_2$, substituted or unsubstituted C$_1$-C$_6$ alkyl, or substituted or unsubstituted 2 to 6 membered heteroalkyl. In embodiments, R$^2$ is independently a halogen, —CX$^2_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^2_3$, —OCHX$^2_2$, substituted or unsubstituted C$_1$-C$_6$ alkyl, or substituted or unsubstituted 2 to 6 membered heteroalkyl. In embodiments, R$^3$ is independently unsubstituted C$_1$-C$_6$ alkyl or unsubstituted 2 to 6 membered heteroalkyl. In embodiments, a1 is independently an integer from 0 to 5. In embodiments, b1 is independently an integer from 0 to 5. In embodiments, X$^1$ and X$^2$ are independently —Cl, —Br, —I, or —F.

In embodiments, the compound has the formula:

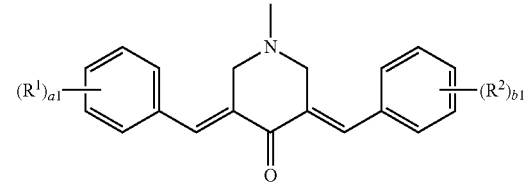

wherein and R$^1$ and R$^2$ are —O(unsubstituted C$_1$-C$_6$ alkyl) and a1, and b1 are as described herein. In embodiments, R$^1$ and R$^2$ are —OCH$_3$.

In embodiments, R$^3$ is independently unsubstituted C$_1$-C$_6$ alkyl. In embodiments, R$^3$ is independently unsubstituted C$_1$-C$_4$ alkyl. In embodiments, R$^3$ is independently unsubstituted C$_1$-C$_3$ alkyl. In embodiments, R$^3$ is independently unsubstituted methyl. In embodiments, R$^3$ is independently unsubstituted ethyl. In embodiments, R$^3$ is independently unsubstituted propyl.

In embodiments, the compound is O15, O23 or an analogue, prodrug, or derivative thereof (of any one of the compounds). In embodiments, the compound is O15 or an analogue, prodrug, or derivative thereof. In embodiments, the compound is O23 or an analogue, prodrug, or derivative thereof.

In embodiments, the compound is not O15, O23 or an analogue, prodrug, or derivative thereof (of any one of the compounds). In embodiments, the compound is not O15 or an analogue, prodrug, or derivative thereof. In embodiments, the compound is not O23 or an analogue, prodrug, or derivative thereof.

In embodiments, the compound is O15 or O23. In embodiments, the compound is O15. In embodiments, the compound is O23.

In embodiments, the compound is not O15 or O23. In embodiments, the compound is not O15. In embodiments, the compound is not O23.

In an embodiment, the compound has the formula:

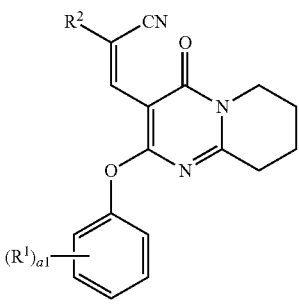

(Va)

and $R^1$, $R^2$, and a1 are as described herein. In embodiments, $R^1$ is independently a halogen, $-CX^1_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^1_3$, $-OCHX^1_2$, substituted or unsubstituted $C_1$-$C_6$ alkyl, or substituted or unsubstituted 2 to 6 membered heteroalkyl. In embodiments, $R^2$ is independently $-SO_2R^{14}$, $-C(O)NR^{11}R^{12}$, or substituted or unsubstituted 2 to 6 membered heteroalkyl. In embodiments, $R^{11}$, $R^{12}$, and $R^{14}$ are independently hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, a1 is independently an integer from 0 to 5.

In embodiments, $R^2$ is independently $-SO_2R^{14}$, $-C(O)NR^{11}R^{12}$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{12}$ is substituted or unsubstituted $C_3$-$C_6$ cycloalkyl. In embodiments, $R^{12}$ is substituted or unsubstituted $C_6$ cycloalkyl. In embodiments, $R^{12}$ is unsubstituted $C_6$ cycloalkyl. In embodiments, $R^{11}$ is hydrogen and $R^{12}$ is substituted or unsubstituted $C_3$-$C_6$ cycloalkyl. In embodiments, $R^{11}$ is hydrogen and $R^{12}$ is substituted or unsubstituted $C_6$ cycloalkyl. In embodiments, $R^{11}$ is hydrogen and $R^{12}$ is unsubstituted $C_6$ cycloalkyl. In embodiments, $R^{12}$ is unsubstituted $C_1$-$C_6$ alkyl. In embodiments, $R^{12}$ is or unsubstituted methyl. In embodiments, $R^{12}$ is $R^{40}$-substituted $C_1$-$C_6$ alkyl and $R^{40}$ is substituted or unsubstituted 5 to 6 membered heteroaryl. In embodiments, $R^{12}$ is $R^{40}$-substituted $C_1$-$C_2$ alkyl and $R^{40}$ is unsubstituted 5 to 6 membered heteroaryl.

In embodiments, $R^{12}$ is substituted or unsubstituted phenyl, or substituted or unsubstituted 5 to 6 membered heteroaryl. In embodiments, $R^{12}$ is substituted phenyl, or substituted 5 to 6 membered heteroaryl. In embodiments, $R^{12}$ is unsubstituted phenyl, or unsubstituted 5 to 6 membered heteroaryl. In embodiments, $R^{12}$ is substituted or unsubstituted phenyl. In embodiments, $R^{12}$ is unsubstituted phenyl.

In embodiments, $R^{12}$ is substituted or unsubstituted 5 to 6 membered heteroaryl. In embodiments, $R^{12}$ is unsubstituted 5 to 6 membered heteroaryl.

In embodiments, $R^{11}$ is hydrogen and $R^{12}$ is

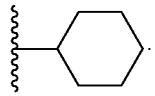

In embodiments, $R^{11}$ is hydrogen and $R^{12}$ is

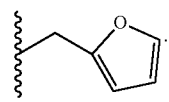 [SMILES: *Cc1ccco1]

In embodiments, $R^{11}$ is hydrogen and $R^{12}$ is

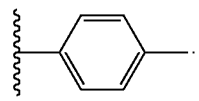

In embodiments, $R^{14}$ is substituted or unsubstituted phenyl, or substituted or unsubstituted 5 to 6 membered heteroaryl. In embodiments, $R^{14}$ is substituted phenyl, or substituted 5 to 6 membered heteroaryl. In embodiments, $R^{14}$ is unsubstituted phenyl, or unsubstituted 5 to 6 membered heteroaryl. In embodiments, $R^{14}$ is substituted or unsubstituted phenyl. In embodiments, $R^{14}$ is unsubstituted phenyl. In embodiments, $R^{12}$ is substituted or unsubstituted 5 to 6 membered heteroaryl. In embodiments, $R^{14}$ is unsubstituted 5 to 6 membered heteroaryl.

In embodiments, $R^{14}$ is

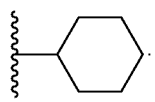

In embodiments, $R^{14}$ is

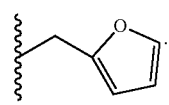

In embodiments, $R^{14}$ is

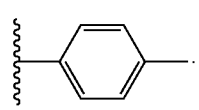

In embodiments, $R^1$ and $R^2$ are independently $-Br$, $-Cl$, $-OCH_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, substituted or unsubstituted $C_1$-$C_6$ alkyl, substituted or unsubstituted 2 to 6 membered heteroalkyl.

In embodiments, the stress resistance increasing compound has the formula:
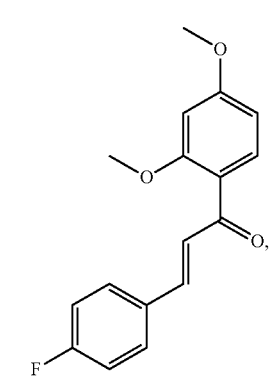
(Gr-4a)
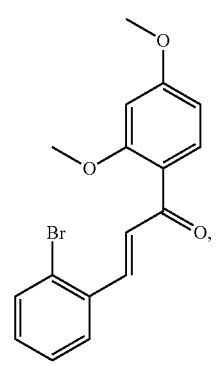
(Gr-4b)
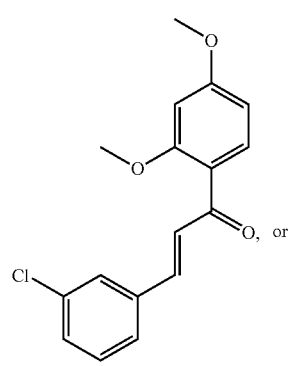
(Gr-4c)
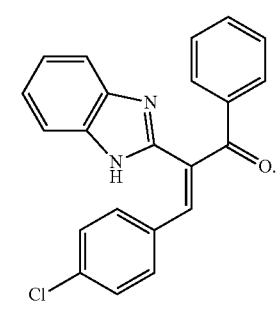
(Gr-4d)
In embodiments, the stress resistance increasing compound has the formula:
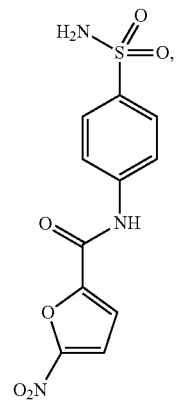
(Gr-Ia)
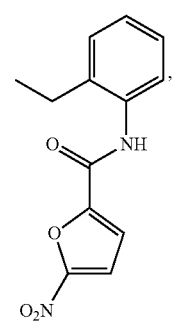
(Gr-Ic)
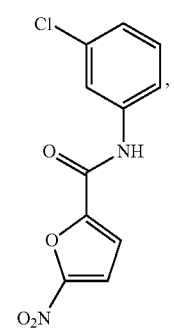
(Gr-Id)
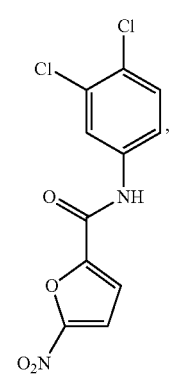
(Gr-Ig)

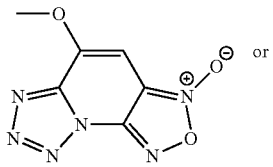
(O11)

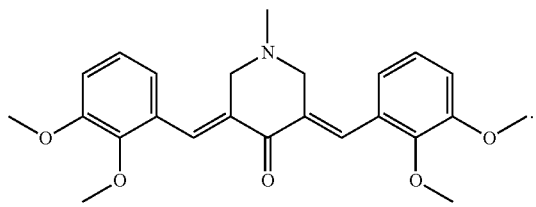
(O23)

In embodiments, the stress resistance increasing compound is

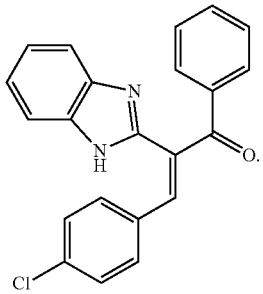 [SMILES: O=C(/C(=C/c1ccc(Cl)cc1)c1nc2ccccc2[nH]1)c1ccccc1]

In embodiments, the compound is Gr-5a, Gr-5b, Gr-5c, Gr-5d or an analogue, prodrug, or derivative thereof (of any one of the compounds). In embodiments, the compound is Gr-5a or an analogue, prodrug, or derivative thereof. In embodiments, the compound is Gr-5b or an analogue, prodrug, or derivative thereof. In embodiments, the compound is Gr-5c or an analogue, prodrug, or derivative thereof. In embodiments, the compound is Gr-5d or an analogue, prodrug, or derivative thereof.

In embodiments, the compound is not Gr-5a, Gr-5b, Gr-5c, Gr-5d or an analogue, prodrug, or derivative thereof (of any one of the compounds). In embodiments, the compound is not Gr-5a or an analogue, prodrug, or derivative thereof. In embodiments, the compound is not Gr-5b or an analogue, prodrug, or derivative thereof. In embodiments, the compound is not Gr-5c or an analogue, prodrug, or derivative thereof. In embodiments, the compound is not Gr-5d or an analogue, prodrug, or derivative thereof.

In embodiments, the compound is Gr-5a, Gr-5b, Gr-5c, or Gr-5d. In embodiments, the compound is Gr-5a. In embodiments, the compound is Gr-5b. In embodiments, the compound is Gr-5c. In embodiments, the compound is Gr-5d.

In embodiments, the compound is not Gr-5a, Gr-5b, Gr-5c, or Gr-5d. In embodiments, the compound is not Gr-5a. In embodiments, the compound is not Gr-5b. In embodiments, the compound is not Gr-5c. In embodiments, the compound is not Gr-5d.

In embodiments, the compound is O11, O20, O6 or an analogue, prodrug, or derivative thereof (of any one of the compounds). In embodiments, the compound is O11 or an analogue, prodrug, or derivative thereof. In embodiments, the compound is O20 or an analogue, prodrug, or derivative thereof. In embodiments, the compound is O6 or an analogue, prodrug, or derivative thereof.

In embodiments, the compound is not O11, O20, O6 or an analogue, prodrug, or derivative thereof (of any one of the compounds). In embodiments, the compound is not O11 or an analogue, prodrug, or derivative thereof. In embodiments, the compound is not O20 or an analogue, prodrug, or derivative thereof. In embodiments, the compound is not O6 or an analogue, prodrug, or derivative thereof.

In embodiments, the compound is O11, O20, or O6. In embodiments, the compound is O11. In embodiments, the compound is O20. In embodiments, the compound is O6.

In embodiments, the compound is not O11, O20, or O6. In embodiments, the compound is not O11. In embodiments, the compound is not O20. In embodiments, the compound is not O6.

In embodiments, the compound (e.g., stress resistance increasing compound) is Gr-3a, Gr-3b, Gr-3c, Gr-6c, O6, O11, O12, O14, O17, or O20. In embodiments, the compound (e.g., stress resistance increasing compound) is Gr-3a. In embodiments, the compound (e.g., stress resistance increasing compound) is Gr-3b. In embodiments, the compound (e.g., stress resistance increasing compound) is Gr-3c. In embodiments, the compound (e.g., stress resistance increasing compound) is Gr-6c. In embodiments, the compound (e.g., stress resistance increasing compound) is O6. In embodiments, the compound (e.g., stress resistance increasing compound) is O11. In embodiments, the compound (e.g., stress resistance increasing compound) is O12. In embodiments, the compound (e.g., stress resistance increasing compound) is O14. In embodiments, the compound (e.g., stress resistance increasing compound) is O17. In embodiments, the compound (e.g., stress resistance increasing compound) is O20.

In embodiments, the compound (e.g., compound capable of increasing lifespan) is Gr-1e, Gr-3a, Gr-3b, Gr-3c, Gr-6c, Gr-7a, O12, O13, O14, O17 and O23. In embodiments, the compound (e.g., compound capable of increasing lifespan) is Gr-1e. In embodiments, the compound (e.g., compound capable of increasing lifespan) is Gr-3a. In embodiments, the compound (e.g., compound capable of increasing lifespan) is Gr-3b. In embodiments, the compound (e.g., compound capable of increasing lifespan) is Gr-3c. In embodiments, the compound (e.g., compound capable of increasing lifespan) is Gr-6c. In embodiments, the compound (e.g., compound capable of increasing lifespan) is Gr-7a. In embodiments, the compound (e.g., compound capable of increasing lifespan) is O12. In embodiments, the compound (e.g., compound capable of increasing lifespan) is O13. In embodiments, the compound (e.g., compound capable of increasing lifespan) is O14. In embodiments, the compound (e.g., compound capable of increasing lifespan) is O17. In embodiments, the compound (e.g., compound capable of increasing lifespan) is O23.

In embodiments, the compound (e.g., stress resistance increasing compound) is Gr-3a, Gr-3b, Gr-3c, Gr-6c, O6, O11, O12, O14, O17, or O20 or an analogue, prodrug, or derivative thereof (of any one of the compounds). In embodiments, the compound (e.g., stress resistance increasing compound) is Gr-3a or an analogue, prodrug, or derivative thereof. In embodiments, the compound (e.g., stress resistance increasing compound) is Gr-3b or an analogue, prodrug, or derivative thereof. In embodiments, the compound (e.g., stress resistance increasing compound) is Gr-3c or an analogue, prodrug, or derivative thereof. In embodiments, the compound (e.g., stress resistance increasing compound) is Gr-6c or an analogue, prodrug, or derivative thereof. In embodiments, the compound (e.g., stress resistance increasing compound) is O6 or an analogue, prodrug, or derivative thereof. In embodiments, the compound (e.g., stress resistance increasing compound) is O11 or an analogue, prodrug, or derivative thereof. In embodiments, the compound (e.g., stress resistance increasing compound) is O12 or an analogue, prodrug, or derivative thereof. In embodiments, the compound (e.g., stress resistance increasing compound) is O14 or an analogue, prodrug, or derivative thereof. In embodiments, the compound (e.g., stress resistance increasing compound) is O17 or an analogue, prodrug, or derivative thereof. In embodiments, the compound (e.g., stress resistance increasing compound) is O20 or an analogue, prodrug, or derivative thereof.

In embodiments, the compound (e.g., compound capable of increasing lifespan) is Gr-1e, Gr-3a, Gr-3b, Gr-3c, Gr-6c, Gr-7a, O12, O13, O14, O17 and O23 or an analogue, prodrug, or derivative thereof (of any one of the compounds). In embodiments, the compound (e.g., compound capable of increasing lifespan) is Gr-1e or an analogue, prodrug, or derivative thereof. In embodiments, the compound (e.g., compound capable of increasing lifespan) is Gr-3a or an analogue, prodrug, or derivative thereof. In embodiments, the compound (e.g., compound capable of increasing lifespan) is Gr-3b or an analogue, prodrug, or derivative thereof. In embodiments, the compound (e.g., compound capable of increasing lifespan) is Gr-3c or an analogue, prodrug, or derivative thereof. In embodiments, the compound (e.g., compound capable of increasing lifespan) is Gr-6c or an analogue, prodrug, or derivative thereof. In embodiments, the compound (e.g., compound capable of increasing lifespan) is Gr-7a or an analogue, prodrug, or derivative thereof. In embodiments, the compound (e.g., compound capable of increasing lifespan) is O12 or an analogue, prodrug, or derivative thereof. In embodiments, the compound (e.g., compound capable of increasing lifespan) is O13 or an analogue, prodrug, or derivative thereof. In embodiments, the compound (e.g., compound capable of increasing lifespan) is O14 or an analogue, prodrug, or derivative thereof. In embodiments, the compound (e.g., compound capable of increasing lifespan) is O17 or an analogue, prodrug, or derivative thereof. In embodiments, the compound (e.g., compound capable of increasing lifespan) is O23 or an analogue, prodrug, or derivative thereof.

In embodiments, the compound is Gr-1A, Gr-1B, Gr-1C, Gr-1D, Gr-1E, Gr-1F, Gr-1G, Gr-2A, Gr-2B, Gr-2C, Gr-2D, Gr-2E, Gr-3A, Gr-3B, Gr-3C, Gr-3D, Gr-4A, Gr-4B, Gr-4C, Gr-4D, Gr-5A, Gr-5B, Gr-5C, Gr-5D, Gr-6A, Gr-6B, Gr-6C, Gr-7A, Gr-7B, Gr-7C, O1, O2, O3, O4, O5, O6, O7, O8, O9, O10, O11, O12, O13, O14, O15, O16, O17, O18, O19, O20, O21, O22, O23, O24, O25, O26, O27, O28, O29, O30, O31; or an analogue, prodrug, or derivative of any of the compounds.

In embodiments, the compound is Gr-1A. In embodiments, the compound is Gr-1B. In embodiments, the compound is Gr-1C. In embodiments, the compound is Gr-1D. In embodiments, the compound is Gr-1E. In embodiments, the compound is Gr-1F. In embodiments, the compound is Gr-1G. In embodiments, the compound is Gr-2A. In embodiments, the compound is Gr-2B. In embodiments, the compound is Gr-2C. In embodiments, the compound is Gr-2D. In embodiments, the compound is Gr-2E. In embodiments, the compound is Gr-3A. In embodiments, the compound is Gr-3B. In embodiments, the compound is Gr-3C. In embodiments, the compound is Gr-3D. In embodiments, the compound is Gr-4A. In embodiments, the compound is Gr-4B. In embodiments, the compound is Gr-4C. In embodiments, the compound is Gr-4D. In embodiments, the compound is Gr-5A. In embodiments, the compound is Gr-5B. In embodiments, the compound is Gr-5C. In embodiments, the compound is Gr-5D. In embodiments, the compound is Gr-6A. In embodiments, the compound is Gr-6B. In embodiments, the compound is Gr-6C. In embodiments, the compound is Gr-7A. In embodiments, the compound is Gr-7B. In embodiments, the compound is Gr-7C. In embodiments, the compound is O1. In embodiments, the compound is O2. In embodiments, the compound is O3. In embodiments, the compound is O4. In embodiments, the compound is O5. In embodiments, the compound is O6. In embodiments, the compound is O7. In embodiments, the compound is O8. In embodiments, the compound is O9. In embodiments, the compound is O10. In embodiments, the compound is O11. In embodiments, the compound is O12. In embodiments, the compound is O13. In embodiments, the compound is O14. In embodiments, the compound is O15. In embodiments, the compound is O16. In embodiments, the compound is O17. In embodiments, the compound is O18. In embodiments, the compound is O19. In embodiments, the compound is O20. In embodiments, the compound is O21. In embodiments, the compound is O22. In embodiments, the compound is O23. In embodiments, the compound is O24. In embodiments, the compound is O25. In embodiments, the compound is O26. In embodiments, the compound is O27. In embodiments, the compound is O28. In embodiments, the compound is O29. In embodiments, the compound is O30. In embodiments, the compound is O31.

In embodiments, the compound is Gr-1A, Gr-1B, Gr-1C, Gr-1D, Gr-1E, Gr-1F, Gr-1G, Gr-2A, Gr-2B, Gr-2C, Gr-2D, Gr-2E, Gr-3A, Gr-3B, Gr-3C, Gr-3D, Gr-4A, Gr-4B, Gr-4C, Gr-4D, Gr-5A, Gr-5B, Gr-5C, Gr-5D, Gr-6A, Gr-6B, Gr-6C, Gr-7A, Gr-7B, Gr-7C, O1, O2, O3, O4, O5, O6, O7, O8, O9, O10, O11, O12, O13, O14, O15, O16, O17, O18, O19, O20, O21, O22, O23, O24, O25, O26, O27, O28, O29, O30, or O31.

In embodiments, the stress resistance increasing compound is Gr-1A, Gr-1B, Gr-1C, Gr-1D, Gr-1E, Gr-1F, Gr-1G, Gr-2A, Gr-2B, Gr-2C, Gr-2D, Gr-2E, Gr-3A, Gr-3B, Gr-3C, Gr-3D, Gr-4A, Gr-4B, Gr-4C, Gr-4D, Gr-5A, Gr-5B, Gr-5C, Gr-5D, Gr-6A, Gr-6B, Gr-6C, Gr-7A, Gr-7B, Gr-7C, O1, O2, O3, O4, O5, O6, O7, O8, O9, O10, O11, O12, O13, O14, O15, O16, O17, O18, O19, O20, O21, O22, O23, O24, O25, O26, O27, O28, O29, O30, O31, or an analogue, prodrug, or derivative of any of the compounds.

In embodiments, the stress resistance increasing compound is Gr-1A. In embodiments, the stress resistance increasing compound is Gr-1B. In embodiments, the stress resistance increasing compound is Gr-1C. In embodiments, the stress resistance increasing compound is Gr-1D. In embodiments, the stress resistance increasing compound is Gr-1E. In embodiments, the stress resistance increasing compound is Gr-1F. In embodiments, the stress resistance increasing compound is Gr-1G. In embodiments, the stress resistance increasing compound is Gr-2A. In embodiments, the stress resistance increasing compound is Gr-2B. In embodiments, the stress resistance increasing compound is Gr-2C. In embodiments, the stress resistance increasing compound is Gr-2D. In embodiments, the stress resistance increasing compound is Gr-2E. In embodiments, the stress resistance increasing compound is Gr-3A. In embodiments, the stress resistance increasing compound is Gr-3B. In embodiments, the stress resistance increasing compound is Gr-3C. In embodiments, the stress resistance increasing compound is Gr-3D. In embodiments, the stress resistance increasing compound is Gr-4A. In embodiments, the stress resistance increasing compound is Gr-4B. In embodiments, the stress resistance increasing compound is Gr-4C. In embodiments, the stress resistance increasing compound is Gr-4D. In embodiments, the stress resistance increasing compound is Gr-5A. In embodiments, the stress resistance increasing compound is Gr-5B. In embodiments, the stress resistance increasing compound is Gr-5C. In embodiments, the stress resistance increasing compound is Gr-5D. In embodiments, the stress resistance increasing compound is Gr-6A. In embodiments, the stress resistance increasing compound is Gr-6B. In embodiments, the stress resistance increasing compound is Gr-6C. In embodiments, the stress resistance increasing compound is Gr-7A. In embodiments, the stress resistance increasing compound is Gr-7B. In embodiments, the stress resistance increasing compound is Gr-7C. In embodiments, the stress resistance increasing compound is O1. In embodiments, the stress resistance increasing compound is O2. In embodiments, the stress resistance increasing compound is O3. In embodiments, the stress resistance increasing compound is O4. In embodiments, the stress resistance increasing compound is O5. In embodiments, the stress resistance increasing compound is O6. In embodiments, the stress resistance increasing compound is O7. In embodiments, the stress resistance increasing compound is O8. In embodiments, the stress resistance increasing compound is O9. In embodiments, the stress resistance increasing compound is O10. In embodiments, the stress resistance increasing compound is O11. In embodiments, the stress resistance increasing compound is O12. In embodiments, the stress resistance increasing compound is O13. In embodiments, the stress resistance increasing compound is O14. In embodiments, the stress resistance increasing compound is O15. In embodiments, the stress resistance increasing compound is O16. In embodiments, the stress resistance increasing compound is O17. In embodiments, the stress resistance increasing compound is O18. In embodiments, the stress resistance increasing compound is O19. In embodiments, the stress resistance increasing compound is O20. In embodiments, the stress resistance increasing compound is O21. In embodiments, the stress resistance increasing compound is O22. In embodiments, the stress resistance increasing compound is O23. In embodiments, the stress resistance increasing compound is O24. In embodiments, the stress resistance increasing compound is O25. In embodiments, the stress resistance increasing compound is O26. In embodiments, the stress resistance increasing compound is O27. In embodiments, the stress resistance increasing compound is O28. In embodiments, the stress resistance increasing compound is O29. In embodiments, the stress resistance increasing compound is O30. In embodiments, the stress resistance increasing compound is O31.

In embodiments, the compound is not Gr-1A, Gr-1B, Gr-1C, Gr-1D, Gr-1E, Gr-1F, Gr-1G, Gr-2A, Gr-2B, Gr-2C, Gr-2D, Gr-2E, Gr-3A, Gr-3B, Gr-3C, Gr-3D, Gr-4A, Gr-4B, Gr-4C, Gr-4D, Gr-5A, Gr-5B, Gr-5C, Gr-5D, Gr-6A, Gr-6B, Gr-6C, Gr-7A, Gr-7B, Gr-7C, O1, O2, O3, O4, O5, O6, O7, O8, O9, O10, O11, O12, O13, O14, O15, O16, O17, O18, O19, O20, O21, O22, O23, O24, O25, O26, O27, O28, O29, O30, O31; or an analogue, prodrug, or derivative of any of the compounds.

In embodiments, the compound is not Gr-1A. In embodiments, the compound is not Gr-1B. In embodiments, the compound is not Gr-1C. In embodiments, the compound is not Gr-1D. In embodiments, the compound is not Gr-1E. In embodiments, the compound is not Gr-1F. In embodiments, the compound is not Gr-1G. In embodiments, the compound is not Gr-2A. In embodiments, the compound is not Gr-2B. In embodiments, the compound is not Gr-2C. In embodiments, the compound is not Gr-2D. In embodiments, the compound is not Gr-2E. In embodiments, the compound is not Gr-3A. In embodiments, the compound is not Gr-3B. In embodiments, the compound is not Gr-3C. In embodiments, the compound is not Gr-3D. In embodiments, the compound is not Gr-4A. In embodiments, the compound is not Gr-4B. In embodiments, the compound is not Gr-4C. In embodiments, the compound is not Gr-4D. In embodiments, the compound is not Gr-5A. In embodiments, the compound is not Gr-5B. In embodiments, the compound is not Gr-5C. In embodiments, the compound is not Gr-5D. In embodiments, the compound is not Gr-6A. In embodiments, the compound is not Gr-6B. In embodiments, the compound is not Gr-6C. In embodiments, the compound is not Gr-7A. In embodiments, the compound is not Gr-7B. In embodiments, the compound is not Gr-7C. In embodiments, the compound is not O1. In embodiments, the compound is not O2. In embodiments, the compound is not O3. In embodiments, the compound is not O4. In embodiments, the compound is not O5. In embodiments, the compound is not O6. In embodiments, the compound is not O7. In embodiments, the compound is not O8. In embodiments, the compound is not O9. In embodiments, the compound is not O10. In embodiments, the compound is not O11. In embodiments, the compound is not O12. In embodiments, the compound is not O13. In embodiments, the compound is not O14. In embodiments, the compound is not O15. In embodiments, the compound is not O16. In embodiments, the compound is not O17. In embodiments, the compound is not O18. In embodiments, the compound is not O19. In embodiments, the compound is not O20. In embodiments, the compound is not O21. In embodiments, the compound is not O22. In embodiments, the compound is not O23. In embodiments, the compound is not O24. In embodiments, the compound is not O25. In embodiments, the compound is not O26. In embodiments, the compound is not O27. In embodiments, the compound is not O28. In embodiments, the compound is not O29. In embodiments, the compound is not O30. In embodiments, the compound is not O31.

In embodiments, the compound is not Gr-1A, Gr-1B, Gr-1C, Gr-1D, Gr-1E, Gr-1F, Gr-1G, Gr-2A, Gr-2B, Gr-2C, Gr-2D, Gr-2E, Gr-3A, Gr-3B, Gr-3C, Gr-3D, Gr-4A, Gr-4B, Gr-4C, Gr-4D, Gr-5A, Gr-5B, Gr-5C, Gr-5D, Gr-6A, Gr-6B, Gr-6C, Gr-7A, Gr-7B, Gr-7C, O1, O2, O3, O4, O5, O6, O7, O8, O9, O10, O11, O12, O13, O14, O15, O16, O17, O18, O19, O20, O21, O22, O23, O24, O25, O26, O27, O28, O29, O30, or O31.

In embodiments, the stress resistance increasing compound is not Gr-1A, Gr-1B, Gr-1C, Gr-1D, Gr-1E, Gr-1F, Gr-1G, Gr-2A, Gr-2B, Gr-2C, Gr-2D, Gr-2E, Gr-3A, Gr-3B, Gr-3C, Gr-3D, Gr-4A, Gr-4B, Gr-4C, Gr-4D, Gr-5A, Gr-5B, Gr-5C, Gr-5D, Gr-6A, Gr-6B, Gr-6C, Gr-7A, Gr-7B, Gr-7C, O1, O2, O3, O4, O5, O6, O7, O8, O9, O10, O11, O12, O13, O14, O15, O16, O17, O18, O19, O20, O21, O22, O23, O24, O25, O26, O27, O28, O29, O30, O31 or an analogue, prodrug, or derivative of any one of the compounds. In embodiments, the stress resistance increasing compound is not Gr-1A, Gr-1B, Gr-1C, Gr-1D, Gr-1E, Gr-1F, Gr-1G, Gr-2A, Gr-2B, Gr-2C, Gr-2D, Gr-2E, Gr-3A, Gr-3B, Gr-3C, Gr-3D, Gr-4A, Gr-4B, Gr-4C, Gr-4D, Gr-5A, Gr-5B, Gr-5C, Gr-5D, Gr-6A, Gr-6B, Gr-6C, Gr-7A, Gr-7B, Gr-7C, O1, O2, O3, O4, O5, O6, O7, O8, O9, O10, O11, O12, O13, O14, O15, O16, O17, O18, O19, O20, O21, O22, O23, O24, O25, O26, O27, O28, O29, O30, or O31.

In embodiments, the stress resistance increasing compound is not Gr-1A. In embodiments, the stress resistance increasing compound is not Gr-1B. In embodiments, the stress resistance increasing compound is not Gr-1C. In embodiments, the stress resistance increasing compound is not Gr-1D. In embodiments, the stress resistance increasing compound is not Gr-1E. In embodiments, the stress resistance increasing compound is not Gr-1F. In embodiments, the stress resistance increasing compound is not Gr-1G. In embodiments, the stress resistance increasing compound is not Gr-2A. In embodiments, the stress resistance increasing compound is not Gr-2B. In embodiments, the stress resistance increasing compound is not Gr-2C. In embodiments, the stress resistance increasing compound is not Gr-2D. In embodiments, the stress resistance increasing compound is not Gr-2E. In embodiments, the stress resistance increasing compound is not Gr-3A. In embodiments, the stress resistance increasing compound is not Gr-3B. In embodiments, the stress resistance increasing compound is not Gr-3C. In embodiments, the stress resistance increasing compound is not Gr-3D. In embodiments, the stress resistance increasing compound is not Gr-4A. In embodiments, the stress resistance increasing compound is not Gr-4B. In embodiments, the stress resistance increasing compound is not Gr-4C. In embodiments, the stress resistance increasing compound is not Gr-4D. In embodiments, the stress resistance increasing compound is not Gr-5A. In embodiments, the stress resistance increasing compound is not Gr-5B. In embodiments, the stress resistance increasing compound is not Gr-5C. In embodiments, the stress resistance increasing compound is not Gr-5D. In embodiments, the stress resistance increasing compound is not Gr-6A. In embodiments, the stress resistance increasing compound is not Gr-6B. In embodiments, the stress resistance increasing compound is not Gr-6C. In embodiments, the stress resistance increasing compound is not Gr-7A. In embodiments, the stress resistance increasing compound is not Gr-7B. In embodiments, the stress resistance increasing compound is not Gr-7C. In embodiments, the stress resistance increasing compound is not O1. In embodiments, the stress resistance increasing compound is not O2. In embodiments, the stress resistance increasing compound is not O3. In embodiments, the stress resistance increasing compound is not O4. In embodiments, the stress resistance increasing compound is not O5. In embodiments, the stress resistance increasing compound is not O6. In embodiments, the stress resistance increasing compound is not O7. In embodiments, the stress resistance increasing compound is not O8. In embodiments, the stress resistance increasing compound is not O9. In embodiments, the stress resistance increasing compound is not O10. In embodiments, the stress resistance increasing compound is not O11. In embodiments, the stress resistance increasing compound is not O12. In embodiments, the stress resistance increasing compound is not O13. In embodiments, the stress resistance increasing compound is not O14. In embodiments, the stress resistance increasing compound is not O15. In embodiments, the stress resistance increasing compound is not O16. In embodiments, the stress resistance increasing compound is not O17. In embodiments, the stress resistance increasing compound is not O18. In embodiments, the stress resistance increasing compound is not O19. In embodiments, the stress resistance increasing compound is not O20. In embodiments, the stress resistance increasing compound is not O21. In embodiments, the stress resistance increasing compound is not O22. In embodiments, the stress resistance increasing compound is not O23. In embodiments, the stress resistance increasing compound is not O24. In embodiments, the stress resistance increasing compound is not O25. In embodiments, the stress resistance increasing compound is not O26. In embodiments, the stress resistance increasing compound is not O27. In embodiments, the stress resistance increasing compound is not O28. In embodiments, the stress resistance increasing compound is not O29. In embodiments, the stress resistance increasing compound is not O30. In embodiments, the stress resistance increasing compound is not O31.

It is understood that the compound may be a stress resistance increasing compound as described herein. It is understood that the compound may not be a stress resistance increasing compound as described herein. In embodiments, the compound is a compound described herein, including in an aspect, embodiment, example, table, figure, or claim.

C. Pharmaceutical Compositions

In an aspect is provided a pharmaceutical composition including a pharmaceutically acceptable excipient and a compound, or pharmaceutically acceptable salt thereof, as described herein, including embodiments (e.g. in an aspect, embodiment, example, figure, table, or claim).

In embodiments of the pharmaceutical compositions, the compound, or pharmaceutically acceptable salt thereof, is included in a therapeutically effective amount. In embodiments of the pharmaceutical compositions, the compound is included in a drug-eluting stent.

In embodiments of the pharmaceutical compositions, the pharmaceutical composition includes a second agent (e.g. therapeutic agent). In embodiments of the pharmaceutical compositions, the pharmaceutical composition includes a second agent (e.g. therapeutic agent) in a therapeutically effective amount. In embodiments, the second agent is an anti-cancer agent. In embodiments, the second agent is an anti-autoimmune disease agent. In embodiments, the second agent is an anti-inflammatory disease agent. In embodiments, the second agent is an anti-neurodegenerative disease agent. In embodiments, the second agent is an anti-metabolic disease agent. In embodiments, the second agent is an anti-cardiovascular disease agent. In embodiments, the second agent is an anti-aging agent. In embodiments, the second agent is a longevity agent. In embodiments, the second agent is resveratrol, a derivative, an analog, or a prodrug thereof. In embodiments, the second agent is metformin, a derivative, an analog, or a prodrug thereof. In embodiments, the second agent is rapamycin, a derivative, an analog, or a prodrug thereof. In embodiments, the compound is a compound described herein, including in an aspect, embodiment, example, table, figure, or claim.

D. Methods of Treatment

In an aspect is provided a method of treating a disease including administering an effective amount of a compound as described herein. In an aspect is provided a compound as described herein for use as a medicament (e.g., for treatment of a disease). In an aspect is provided a compound as describe herein for use in the treatment of a disease (e.g., including administering an effective amount of a compound as described herein).

In an aspect is provided a method of treating a disease including administering an effective amount of a stress resistance increasing compound (e.g. a compound described herein). In an aspect is provided a stress resistance increasing compound (e.g. a compound described herein) for use as a medicament (e.g., for treatment of a disease). In an aspect is provided a stress resistance increasing compound (e.g. a compound described herein) for use in the treatment of a disease (e.g., including administering an effective amount of a stress resistance increasing compound (e.g. a compound described herein)).

In embodiments, the disease is a disease described herein and the compound is a compound described herein. In embodiments, the compound is a compound described herein, including in an aspect, embodiment, example, table, figure, or claim.

In embodiments, the disease is cancer. In embodiments, the disease is an autoimmune disease. In embodiments, the disease is an inflammatory disease. In embodiments, the disease is a neurodegenerative disease. In embodiments, the disease is a metabolic disease. In embodiments, the disease is an inflammatory disease. In embodiments, the disease is a cardiovascular disease. In embodiments, the disease is Cancer (e.g., carcinomas, sarcomas, adenocarcinomas, lymphomas, leukemias, solid cancers, lymphoid cancers; cancer of the kidney, breast, lung, bladder, colon, ovarian, prostate, pancreas, stomach, brain, head and neck, skin, uterine, esophagus, liver; testicular cancer, glioma, hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), multiple myeloma, or breast cancer (e.g., triple negative breast cancer)), Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, Wegener's granulomatosis (i.e., Granulomatosis with Polyangiitis (GPA), traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, atopic dermatitis, Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, Tabes dorsalis, diabetes (e.g., type I or type II), obesity, metabolic syndrome, a mitochondrial disease (e.g., dysfunction of mitochondria or aberrant mitochondrial function), fungal infection, transplant rejection, or a cardiovascular disease (e.g., congestive heart failure; arrhythmogenic syndromes (e.g., paroxysomal tachycardia, delayed after depolarizations, ventricular tachycardia, sudden tachycardia, exercise-induced arrhythmias, long QT syndromes, or bidirectional tachycardia); thromboembolic disorders (e.g., arterial cardiovascular thromboembolic disorders, venous cardiovascular thromboembolic disorders, or thromboembolic disorders in the chambers of the heart); atherosclerosis; restenosis; peripheral arterial disease; coronary bypass grafting surgery; carotid artery disease; arteritis; myocarditis; cardiovascular inflammation; vascular inflammation; coronary heart disease (CHD); unstable angina (UA); unstable refractory angina; stable angina (SA); chronic stable angina; acute coronary syndrome (ACS); myocardial infarction (first or recurrent); acute myocardial infarction (AMI); myocardial infarction; non-Q wave myocardial infarction; non-STE myocardial infarction; coronary artery disease; ischemic heart disease; cardiac ischemia; ischemia; ischemic sudden death; transient ischemic attack; stroke; peripheral occlusive arterial disease; venous thrombosis; deep vein thrombosis; thrombophlebitis; arterial embolism; coronary arterial thrombosis; cerebral arterial thrombosis, cerebral embolism; kidney embolism; pulmonary embolism; thrombosis (e.g., associated with prosthetic valves or other implants, indwelling catheters, stents, cardiopulmonary bypass, hemodialysis); thrombosis (e.g., associated with atherosclerosis, surgery, prolonged immobilization, arterial fibrillation, congenital thrombophilia, cancer, diabetes, hormones, or pregnancy); or cardiac arrhythmias (e.g., supraventricular arrhythmias, atrial arrhythmias, atrial flutter, or atrial fibrillation). In embodiments, the disease is a polycystic disease. In embodiments, the disease is polycystic kidney disease. In embodiments, the disease is stenosis. In embodiments, the disease is restenosis. In embodiments, the disease is neointimal proliferation. In embodiments, the disease is neointimal hyperplasia.

In another aspect is provided a compound as described herein for use as a medicament. In embodiments, the medicament may be useful for treating aging in a subject in need of such treatment. In embodiments, the use may include administering a compound, or a pharmaceutically acceptable salt thereof, as described herein, including embodiments (e.g. an aspect, embodiment, example, table, figure, or claim) to the subject.

In another aspect is provided a compound for use in the treatment of aging in a subject in need of such treatment. In embodiments, the use may include administering a compound, or a pharmaceutically acceptable salt thereof, as described herein, including embodiments (e.g. an aspect, embodiment, example, table, figure, or claim) to the subject.

In another aspect is provided a method of treating aging in a subject in need of such treatment, the method including administering a compound, or a pharmaceutically acceptable salt thereof, as described herein, including embodiments (e.g. a claim, embodiment, example, table, figure, or claim) to the subject.

In another aspect is provided a method of extending lifespan or inducing longevity in a subject in need of such treatment, the method including administering a compound, or a pharmaceutically acceptable salt thereof, as described herein, including embodiments (e.g. a claim, embodiment, example, table, figure, or claim) to the subject. In embodiments, the lifespan is increased 1 day. In embodiments, the lifespan is increased 2 days. In embodiments, the lifespan is increased 3 days. In embodiments, the lifespan is increased 5 days. In embodiments, the lifespan is increased 7 days. In embodiments, the lifespan is increased 1 month. In embodiments, the lifespan is increased 2 months. In embodiments, the lifespan is increased 6 months. In embodiments, the lifespan is increased 12 months. In embodiments, the lifespan is increased 2 years. In embodiments, the lifespan is increased 5 years. In embodiments, the lifespan is increased from about 1 week to about 10 years. In embodiments, the lifespan is increased an average of 1 day. In embodiments, the lifespan is increased an average of 2 days. In embodiments, the lifespan is increased an average of 3 days. In embodiments, the lifespan is increased an average of 5 days. In embodiments, the lifespan is increased an average of 7 days. In embodiments, the lifespan is increased an average of 1 month. In embodiments, the lifespan is increased an average of 2 months. In embodiments, the lifespan is increased an average of 6 months. In embodiments, the lifespan is increased an average of 12 months. In embodiments, the lifespan is increased an average of 2 years. In embodiments, the lifespan is increased an average of 5 years. In embodiments, the lifespan is increased an average of from about 1 week to about 10 years. In embodiments, the lifespan is increased an average of at least 1 day. In embodiments, the lifespan is increased an average of at least 2 days. In embodiments, the lifespan is increased an average of at least 3 days. In embodiments, the lifespan is increased an average of at least 5 days. In embodiments, the lifespan is increased an average of at least 7 days. In embodiments, the lifespan is increased an average of at least 1 month. In embodiments, the lifespan is increased an average of at least 2 months. In embodiments, the lifespan is increased an average of at least 6 months. In embodiments, the lifespan is increased an average of at least 12 months. In embodiments, the lifespan is increased an average of at least 2 years. In embodiments, the lifespan is increased an average of at least 5 years. In embodiments, the lifespan is increased an average of at least from about 1 week to about 10 years. In embodiments, the lifespan extension is measured as a comparison to control (e.g., in the absence of the compound).

In another aspect is provided a compound as described herein for use as a medicament. In embodiments, the medicament may be useful for extending life span or inducing longevity in a subject in need of such treatment. In embodiments, the use may include administering a compound, or a pharmaceutically acceptable salt thereof, as described herein, including embodiments (e.g. an aspect, embodiment, example, table, figure, or claim) to the subject.

In an aspect is provided a method of increasing resistance to cellular stress in a subject, the method including administering an effective amount of a compound, or a pharmaceutically acceptable salt thereof, as described herein (including embodiments) to the subject.

In embodiments, the cellular stress is oxidative stress. In embodiments, the cellular stress is associated with DNA damage. In embodiments, the cellular stress is associated with exposure to a heavy metal.

In an aspect is provided a method of increasing lifespan in a subject in need, the method including administering a compound, or a pharmaceutically acceptable salt thereof (e.g., a stress resistance increasing compound or a compound described herein) to the subject.

In an aspect is provided a method of treating an age associated disease in a subject in need, the method comprising administering a compound, or a pharmaceutically acceptable salt thereof (e.g., a stress resistance increasing compound or a compound described herein) to the subject.

In embodiments, the age associated disease is a cancer, neurodegenerative disease, cardiovascular disease, metabolic disease, or inflammatory disease. In embodiments, the neurodegenerative disease is Alzheimer's Disease, Parkinson's Disease, amyotrophic lateral sclerosis, or Huntington's Disease. In embodiments, the metabolic disease is type II diabetes. In embodiments the cancer is lung cancer. In embodiments, the cancer is non-small cell lung cancer. In embodiments, the cancer is adenosquamous carcinoma.

In an aspect is provided a method of inhibiting proliferation of cancer cells, the method including contacting the cell with a compound, or a pharmaceutically acceptable salt thereof (e.g., a stress resistance increasing compound or a compound described herein).

In an aspect is provided a method of inhibiting survival of cancer cells, the method including contacting the cell with a compound, or a pharmaceutically acceptable salt thereof (e.g., a stress resistance increasing compound or a compound described herein).

In embodiments, the cancer cells are EGFR positive, PIK3CA positive, RB1 negative, and TP53 negative. In embodiments, the cancer cells are EGFR positive. In embodiments, the cancer cells are PIK3CA positive. In embodiments, the cancer cells are RB1 negative. In embodiments, the cancer cells are TP53 negative.

In an aspect is provided a method of increasing the level of FOXO3 activity in a cell, the method including contacting the cell with a compound, or a pharmaceutically acceptable salt thereof (e.g., a stress resistance increasing compound or a compound described herein). In embodiments, the method increases the level of FOXO3 activity in a cell, relative to the absence of the compound, or a pharmaceutically acceptable salt thereof (e.g., a stress resistance increasing compound or a compound described herein).

In an aspect is provided a method of increasing the level of NRF2 activity in a cell, the method including contacting the cell with a compound, or a pharmaceutically acceptable salt thereof (e.g., a stress resistance increasing compound or a compound described herein). In embodiments, the method increases the level of NRF-2 activity in a cell, relative to the absence of the compound, or a pharmaceutically acceptable salt thereof (e.g., a stress resistance increasing compound or a compound described herein).

In an aspect is provided a method of decreasing the level of NF-κB activity in a cell, the method including contacting the cell with a compound, or a pharmaceutically acceptable salt thereof (e.g., a stress resistance increasing compound or a compound described herein). In embodiments, the method increases the level of NF-κB activity in a cell, relative to the absence of the compound, or a pharmaceutically acceptable salt thereof (e.g., a stress resistance increasing compound or a compound described herein).

In an aspect is provided a method of increasing the level of autophagy in a cell, the method including contacting the cell with a compound, or a pharmaceutically acceptable salt thereof (e.g., a stress resistance increasing compound or a compound described herein). In embodiments, the method increases the level of autophagy in a cell, relative to the absence of the compound, or a pharmaceutically acceptable salt thereof (e.g., a stress resistance increasing compound or a compound described herein).

In an aspect is provided a method of increasing the level of mTOR activity in a cell, the method including contacting the cell with a compound, or a pharmaceutically acceptable salt thereof (e.g., a stress resistance increasing compound or a compound described herein). In an aspect is provided a method of decreasing the level of mTOR activity in a cell, the method including contacting the cell with a compound, or a pharmaceutically acceptable salt thereof (e.g., a stress resistance increasing compound or a compound described herein). In embodiments, the method increases the level of mTOR activity in a cell, relative to the absence of the compound, or a pharmaceutically acceptable salt thereof (e.g., a stress resistance increasing compound or a compound described herein). In embodiments, the method decreases the level of mTOR activity in a cell, relative to the absence of the compound, or a pharmaceutically acceptable salt thereof (e.g., a stress resistance increasing compound or a compound described herein).

In embodiments, the method of increasing the level of FOXO3 activity in a cell includes contacting the cell with the compound Gr-7a, Gr-7c, O23 or an analogue, prodrug, or derivative thereof (of any one of the compounds). In embodiments, the method of increasing the level of FOXO3 activity in a cell includes contacting the cell with the compound Gr-7a or an analogue, prodrug, or derivative thereof. In embodiments, the method of increasing the level of FOXO3 activity in a cell includes contacting the cell with the compound Gr-7c or an analogue, prodrug, or derivative thereof. In embodiments, the method of increasing the level of FOXO3 activity in a cell includes contacting the cell with the compound O23 or an analogue, prodrug, or derivative thereof.

In embodiments, the method increases the level of FOXO3 activity in a cell relative to the absence of the compound Gr-7a or an analogue, prodrug, or derivative thereof. In embodiments, the method increases the level of FOXO3 activity in a cell relative to the absence of the compound Gr-7c or an analogue, prodrug, or derivative thereof. In embodiments, the method increases the level of FOXO3 activity in a cell relative to the absence of the compound O23 or an analogue, prodrug, or derivative thereof.

In embodiments, the method of increasing the level of NRF2 activity in a cell includes contacting the cell with the compound Gr-5a, Gr-5b, Gr-5d, Gr-6b, Gr-7c, O6, O13, O15, O18, O20 or an analogue, prodrug, or derivative thereof (of any one of the compounds). In embodiments, the method of increasing the level of NRF2 activity in a cell includes contacting the cell with the compound Gr-5a or an analogue, prodrug, or derivative thereof. In embodiments, the method of increasing the level of NRF2 activity in a cell includes contacting the cell with the compound Gr-5b or an analogue, prodrug, or derivative thereof. In embodiments, the method of increasing the level of NRF2 activity in a cell includes contacting the cell with the compound Gr-5d or an analogue, prodrug, or derivative thereof. In embodiments, the method of increasing the level of NRF2 activity in a cell includes contacting the cell with the compound Gr-6b. In embodiments, the method of increasing the level of NRF2 activity in a cell includes contacting the cell with the compound Gr-7c or an analogue, prodrug, or derivative thereof. In embodiments, the method of increasing the level of NRF2 activity in a cell includes contacting the cell with the compound O6 or an analogue, prodrug, or derivative thereof. In embodiments, the method of increasing the level of NRF2 activity in a cell includes contacting the cell with the compound O13 or an analogue, prodrug, or derivative thereof. In embodiments, the method of increasing the level of NRF2 activity in a cell includes contacting the cell with the compound O15 or an analogue, prodrug, or derivative thereof. In embodiments, the method of increasing the level of NRF2 activity in a cell includes contacting the cell with the compound O18 or an analogue, prodrug, or derivative thereof. In embodiments, the method of increasing the level of NRF2 activity in a cell includes contacting the cell with the compound O20 or an analogue, prodrug, or derivative thereof.

In embodiments, the method increases the level of NRF2 activity in a cell relative to the absence of the compound Gr-5a, Gr-5b, Gr-5d, Gr-6b, Gr-7c, O6, O13, O15, O18, O20 or an analogue, prodrug, or derivative thereof (of any one of the compounds). In embodiments, the method increases the level of NRF2 activity in a cell relative to the absence of the compound Gr-5a or an analogue, prodrug, or derivative thereof. In embodiments, the method increases the level of NRF2 activity in a cell relative to the absence of the compound Gr-5b or an analogue, prodrug, or derivative thereof. In embodiments, the method increases the level of NRF2 activity in a cell relative to the absence of the compound Gr-5d or an analogue, prodrug, or derivative thereof. In embodiments, the method increases the level of NRF2 activity in a cell relative to the absence of the compound Gr-6b. In embodiments, the method increases the level of NRF2 activity in a cell relative to the absence of the compound Gr-7c or an analogue, prodrug, or derivative thereof. In embodiments, the method increases the level of NRF2 activity in a cell relative to the absence of the compound O6 or an analogue, prodrug, or derivative thereof. In embodiments, the method increases the level of NRF2 activity in a cell relative to the absence of the compound O13 or an analogue, prodrug, or derivative thereof. In embodiments, the method increases the level of NRF2 activity in a cell relative to the absence of the compound O15 or an analogue, prodrug, or derivative thereof. In embodiments, the method increases the level of NRF2 activity in a cell relative to the absence of the compound O18 or an analogue, prodrug, or derivative thereof. In embodiments, the method increases the level of NRF2 activity in a cell relative to the absence of the compound O20 or an analogue, prodrug, or derivative thereof.

In embodiments, the method of increasing the level of NRF2 activity in a cell includes contacting the cell with the compound Gr-4a, Gr-5b, Gr-5c, Gr-4d or an analogue, prodrug, or derivative thereof (of any one of the compounds). In embodiments, the method of increasing the level of NRF2 activity in a cell includes contacting the cell with the compound Gr-4a or an analogue, prodrug, or derivative thereof. In embodiments, the method of increasing the level of NRF2 activity in a cell includes contacting the cell with the compound Gr-4b or an analogue, prodrug, or derivative thereof. In embodiments, the method of increasing the level of NRF2 activity in a cell includes contacting the cell with the compound Gr-4c or an analogue, prodrug, or derivative thereof. In embodiments, the method of increasing the level of NRF2 activity in a cell includes contacting the cell with the compound G4d or an analogue, prodrug, or derivative thereof.

In embodiments, the method of increasing the level of autophagy in a cell includes contacting the cell with the compound Gr-1a, Gr-1c, Gr-1d, Gr-1g, O11, O23 or an analogue, prodrug, or derivative thereof (of any one of the compounds). In embodiments, the method of increasing the level of autophagy in a cell includes contacting the cell with the compound Gr-1a or an analogue, prodrug, or derivative thereof. In embodiments, the method of increasing the level of autophagy in a cell includes contacting the cell with the compound Gr-1c or an analogue, prodrug, or derivative thereof. In embodiments, the method of increasing the level of autophagy in a cell includes contacting the cell with the compound Gr-1d or an analogue, prodrug, or derivative thereof. In embodiments, the method of increasing the level of autophagy in a cell includes contacting the cell with the compound Gr-1g or an analogue, prodrug, or derivative thereof. In embodiments, the method of increasing the level of autophagy in a cell includes contacting the cell with the compound O11 or an analogue, prodrug, or derivative thereof. In embodiments, the method of increasing the level of autophagy in a cell includes contacting the cell with the compound O23 or an analogue, prodrug, or derivative thereof.

In embodiments, the method of increasing the lifespan in a subject in need includes administering a compound Gr-4a, Gr-4b, Gr-4c, Gr-4d or an analogue, prodrug, or derivative thereof (of any one of the compounds). In embodiments, the method of increasing the lifespan in a subject in need includes administering a compound Gr-4a or an analogue, prodrug, or derivative thereof. In embodiments, the method of increasing the lifespan in a subject in need includes administering a compound Gr-4b or an analogue, prodrug, or derivative thereof. In embodiments, the method of increasing the lifespan in a subject in need includes administering a compound Gr-4c or an analogue, prodrug, or derivative thereof. In embodiments, the method of increasing the lifespan in a subject in need includes administering a compound Gr-4d or an analogue, prodrug, or derivative thereof.

In embodiments, the method increases the level of NRF2 activity in a cell relative to the absence of the compound Gr-4a, Gr-5b, Gr-5c, Gr-4d or an analogue, prodrug, or derivative thereof (of any one of the compounds). In embodiments, the method increases the level of NRF2 activity in a cell relative to the absence of the compound Gr-4a or an analogue, prodrug, or derivative thereof. In embodiments, the method increases the level of NRF2 activity in a cell relative to the absence of the compound Gr-4b or an analogue, prodrug, or derivative thereof. In embodiments, the method increases the level of NRF2 activity in a cell relative to the absence of the compound Gr-4c or an analogue, prodrug, or derivative thereof. In embodiments, the method increases the level of NRF2 activity in a cell relative to the absence of the compound G4d or an analogue, prodrug, or derivative thereof.

In embodiments, the compound (e.g., compound capable of increasing lifespan) is G1e, G3a, G3b, G3c, G6c, G7a, O12, O13, O14, O17 and O23 or an analogue, prodrug, or derivative thereof. In embodiments, the compound (e.g., compound capable of increasing lifespan) is G1e or an analogue, prodrug, or derivative thereof. In embodiments, the compound (e.g., compound capable of increasing lifespan) is G3a or an analogue, prodrug, or derivative thereof. In embodiments, the compound (e.g., compound capable of increasing lifespan) is G3b or an analogue, prodrug, or derivative thereof. In embodiments, the compound (e.g., compound capable of increasing lifespan) is G3c or an analogue, prodrug, or derivative thereof. In embodiments, the compound (e.g., compound capable of increasing lifespan) is G6c or an analogue, prodrug, or derivative thereof. In embodiments, the compound (e.g., compound capable of increasing lifespan) is G7a or an analogue, prodrug, or derivative thereof. In embodiments, the compound (e.g., compound capable of increasing lifespan) is O12 or an analogue, prodrug, or derivative thereof. In embodiments, the compound (e.g., compound capable of increasing lifespan) is O13 or an analogue, prodrug, or derivative thereof. In embodiments, the compound (e.g., compound capable of increasing lifespan) is O14 or an analogue, prodrug, or derivative thereof. In embodiments, the compound (e.g., compound capable of increasing lifespan) is O17 or an analogue, prodrug, or derivative thereof. In embodiments, the compound (e.g., compound capable of increasing lifespan) is O23 or an analogue, prodrug, or derivative thereof.

In embodiments, the compound (e.g., compound capable of increasing lifespan) is G1e, G3a, G3b, G3c, G6c, G7a, O12, O13, O14, O17 and O23. In embodiments, the compound (e.g., compound capable of increasing lifespan) is G1e. In embodiments, the compound (e.g., compound capable of increasing lifespan) is G3a. In embodiments, the compound (e.g., compound capable of increasing lifespan) is G3b. In embodiments, the compound (e.g., compound capable of increasing lifespan) is G3c. In embodiments, the compound (e.g., compound capable of increasing lifespan) is G6c. In embodiments, the compound (e.g., compound capable of increasing lifespan) is G7a. In embodiments, the compound (e.g., compound capable of increasing lifespan) is O12. In embodiments, the compound (e.g., compound capable of increasing lifespan) is O13. In embodiments, the compound (e.g., compound capable of increasing lifespan) is O14. In embodiments, the compound (e.g., compound capable of increasing lifespan) is O17. In embodiments, the compound (e.g., compound capable of increasing lifespan) is O23.

EMBODIMENTS

Embodiment P1

A method of increasing resistance to cellular stress in a subject, said method comprising administering an effective amount of a stress resistance increasing compound to said subject.

Embodiment P2

The method of Embodiment P1, wherein said cellular stress is oxidative stress.

Embodiment P3

The method of Embodiment P1, wherein said cellular stress is associated with DNA damage.

Embodiment P4

A method of increasing lifespan in a subject in need, said method comprising administering a stress resistance increasing compound to said subject.

Embodiment P5

A method of treating an age associated disease in a subject in need, said method comprising administering a stress resistance increasing compound to said subject.

Embodiment P6

The method of Embodiment P5, wherein age associated disease is a cancer, neurodegenerative disease, cardiovascular disease, metabolic disease, or inflammatory disease.

Embodiment P7

The method of Embodiment P6, wherein the neurodegenerative disease is Alzheimer's Disease, Parkinson's Disease, amyotrophic lateral sclerosis, or Huntington's Disease.

Embodiment P8

The method of Embodiment P6, wherein the metabolic disease is type II diabetes.

Embodiment P9

The method of Embodiment P6, wherein the cancer is lung cancer.

Embodiment P10

The method of Embodiment P6, wherein the cancer is non-small cell lung cancer.

Embodiment P11

The method of Embodiment P6, wherein the cancer is adenosquamous carcinoma.

Embodiment P12

A method of inhibiting proliferation of cancer cells, said method comprising contacting said cell with a stress resistance increasing compound.

Embodiment P13

A method of inhibiting survival of cancer cells, said method comprising contacting said cell with a stress resistance increasing compound.

Embodiment P14

The method of one of Embodiments P12 to P13, wherein said cancer cells are EGFR positive, PIK3CA positive, RB1 negative, and TP53 negative.

Embodiment P15

A method of increasing the level of FOXO3 activity in a cell, said method comprising contacting the cell with a stress resistance increasing compound.

Embodiment P16

A method of increasing the level of NRF2 activity in a cell, said method comprising contacting the cell with a stress resistance increasing compound.

Embodiment P17

A method of increasing the level of autophagy in a cell, said method comprising contacting the cell with a stress resistance increasing compound.

Embodiment P18

A method of reducing the level of mTOR activity in a cell, said method comprising contacting the cell with a stress resistance increasing compound.

Embodiment P19

The method of one of Embodiments P1 to P18, wherein the stress resistance increasing compound has the formula:

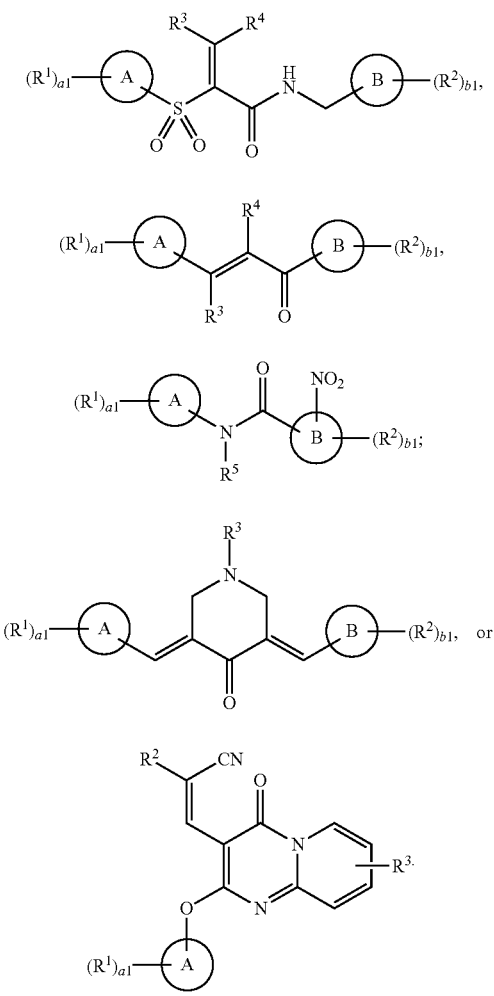

wherein

Ring A is aryl or heteroaryl;

Ring B is aryl or heteroaryl;

$R^1$ is independently a halogen, $-CX^1_3$, $-CN$, $-SO_{n1}R^{10}$, $-SO_{v1}NR^7R^8$, $-NHNH_2$, $-ONR^7R^8$, $-NHC=(O)NHNH_2$, $-NHC=(O)NR^7R^8$, $-N(O)_{m1}$, $-NR^7R^8$, $-C(O)R^9$, $-C(O)-OR^9$, $-C(O)NR^7R^8$, $-OR^{10}$, $-NR^7SO_2R^{10}$, $-NR^7C=(O)R^9$, $-NR^7C(O)-OR^9$, $-NR^7OR^9$, $-OCX^1_3$, $-OCHX^1_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

$R^2$ is independently a halogen, $-CX^2_3$, $-CN$, $-SO_{n2}R^{14}$, $-SO_{v2}NR^{11}R^{12}$, $-NHNH_2$, $-ONR^{11}R^{12}$, $-NHC=(O)NHNH_2$, $-NHC=(O)NR^{11}R^{12}$, $-N(O)_{m2}$, $-NR^{11}R^{12}$, $-C(O)R^{13}$, $-C(O)-OR^{13}$, $-C(O)NR^{11}R^{12}$, $-OR^{14}$, $-NR^{11}SO_2R^{14}$, $-NR^{11}C=(O)R^{13}$, $-NR^{11}C(O)-OR^{13}$, $-NR^{11}OR^{13}$, $-OCX^2_3$, $-OCHX^2_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl;

$R^3$ are independently hydrogen, halogen, $-CX^{33}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^3_3$, $-OCHX^3_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ are independently hydrogen, halogen, $-CX^4_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^4_3$, $-OCHX^4_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is hydrogen, substituted or unsubstituted $C_1$-$C_6$ alkyl, or substituted or unsubstituted 2 to 6 membered heteroalkyl; $R^5$ may optionally be joined to an $R^1$ substituent ortho to the $-N(R^5)-$ to form a substituted or unsubstituted 5 to 6 membered heterocycloalkyl or substituted or unsubstituted 5 to 6 membered heteroaryl;

$R^7$, $R^8$, $R^9$, $R^{10}$, $R^{11}$, $R^{12}$, $R^{13}$, and $R^{14}$ are independently hydrogen, halogen, $-CX_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX_3$, $-OCHX_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl;

a1 is independently an integer from 0 to 7;

b1 is independently an integer from 0 to 7;

m1, m2, v1, and v2 are independently 1 or 2;

n1 and n2 are independently an integer from 0 to 4;

X, $X^1$, $X^2$, $X^3$, and $X^4$ are independently $-Cl$, $-Br$, $-I$, or $-F$.

Embodiment P20

The method of Embodiment P19, wherein the stress resistance increasing compound has the formula:

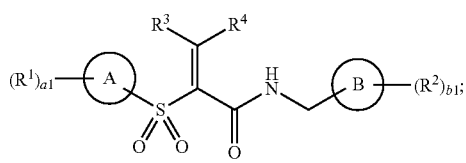
(I)

wherein

Ring A is phenyl;

Ring B is 5 or 6 membered heteroaryl;

$R^1$ is independently a halogen, $-CX^1_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^1_3$, $-OCHX^1_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^1$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl;

$R^2$ is independently a halogen, $-CX^2_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^2_3$, $-OCHX^2_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^2$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl;

$R^3$ is independently hydrogen, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl;

$R^4$ is independently hydrogen, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl;

a1 is independently an integer from 0 to 5;

b1 is independently an integer from 0 to 4;

$X^1$ and $X^2$ are independently $-Cl$, $-Br$, $-I$, or $-F$.

Embodiment P21

The method of Embodiment P20, wherein Ring B is pyridyl.

Embodiment P22

The method of Embodiment P20, wherein the stress resistance increasing compound has the formula:

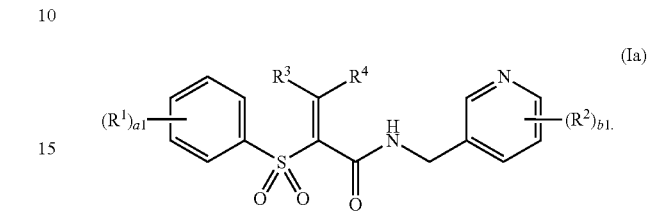
(Ia)

Embodiment P23

The method of one of Embodiments P20 to P22, wherein $R^3$ is independently hydrogen, substituted or unsubstituted phenyl, or substituted or unsubstituted 5 to 6 membered heteroaryl.

Embodiment P24

The method of one of Embodiments P20 to P22, wherein $R^3$ is independently substituted or unsubstituted 5 to 6 membered heteroaryl.

Embodiment P25

The method of one of Embodiments P20 to P22, wherein $R^3$ is independently substituted or unsubstituted furanyl.

Embodiment P26

The method of one of Embodiments P20 to P22, wherein $R^3$ is independently $R^{26}$-substituted or unsubstituted furanyl; and $R^{26}$ is halogen, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment P27

The method of one of Embodiments P20 to P26, wherein $R^4$ is independently hydrogen, substituted or unsubstituted phenyl, or substituted or unsubstituted 5 to 6 membered heteroaryl.

Embodiment P28

The method of one of Embodiments P20 to P26, wherein $R^4$ is independently substituted or unsubstituted phenyl.

Embodiment P29

The method of one of Embodiments P20 to P26, wherein $R^4$ is independently $R^{29}$-substituted or unsubstituted phenyl; and $R^{29}$ is halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, phenoxy, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment P30

The method of Embodiment P19, wherein the stress resistance increasing compound is:

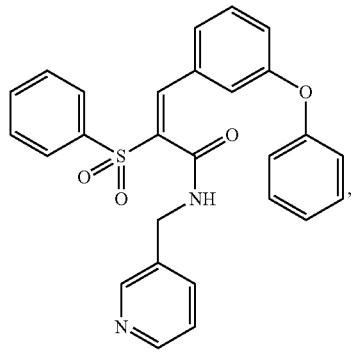

(Gr-7a)

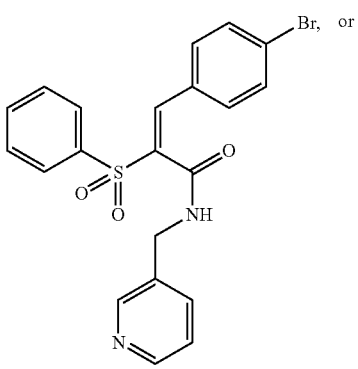

(Gr-7b)

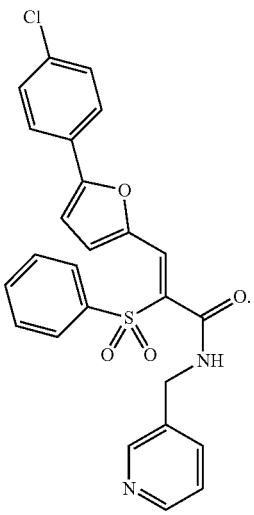

(Gr-7c)

Embodiment P31

The method of Embodiment P19, wherein the stress resistance increasing compound has the formula:

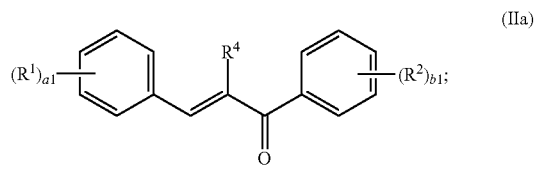

(IIa)

wherein $R^1$ is independently a halogen, —$CX^1_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^1_3$, —$OCHX^1_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^1$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl;

$R^2$ is independently a halogen, —$CX^2_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^2_3$, —$OCHX^2_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^2$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl;

$R^4$ is independently hydrogen, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl;

a1 is independently an integer from 0 to 5;
b1 is independently an integer from 0 to 5;
$X^1$ and $X^2$ are independently —Cl, —Br, —I, or —F.

Embodiment P32

The method of Embodiment P31, wherein $R^4$ is independently hydrogen, substituted or unsubstituted $C_6$-$C_{10}$ aryl, or substituted or unsubstituted 5 to 10 membered heteroaryl.

Embodiment P33

The method of Embodiment P31, wherein $R^4$ is independently substituted or unsubstituted 5 or 10 membered heteroaryl.

Embodiment P34

The method of Embodiment P31, wherein $R^4$ is independently $R^{29}$-substituted or unsubstituted benzimidazolyl; and $R^{29}$ is halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, phenoxy, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment P35

The method of Embodiment P19, wherein the stress resistance increasing compound has the formula:

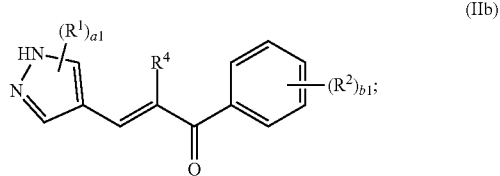

(IIb)

wherein $R^1$ is independently a halogen, —$CX^1_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^1_3$, —$OCHX^1_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^1$ substituents may optionally be joined to form a substituted or unsubstituted 5 to 6 membered heterocycloalkyl or substituted or unsubstituted 5 to 6 membered heteroaryl;

$R^2$ is independently a halogen, —$CX^2_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^2_3$, —$OCHX^2_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^2$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl;

$R^4$ is independently hydrogen, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl;

a1 is independently an integer from 0 to 5;
b1 is independently an integer from 0 to 5;
$X^1$ and $X^2$ are independently —Cl, —Br, —I, or —F.

Embodiment P36

The method of Embodiment P35, wherein $R^4$ is independently hydrogen.

Embodiment P37

The method of Embodiment P35, wherein $R^1$ is independently a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment P38

The method of Embodiment P19, wherein the stress resistance increasing compound has the formula:

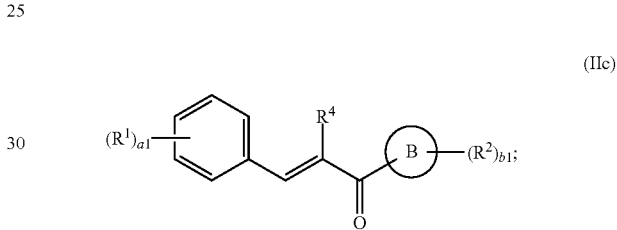

(IIc)

wherein

Ring B is a pyridyl;

$R^1$ is independently a halogen, —$CX^1_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^1_3$, —$OCHX^1_2$, substituted or unsubstituted $C_1$-$C_3$ alkyl, or substituted or unsubstituted 2 to 3 membered heteroalkyl;

$R^2$ is independently a halogen, —$CX^2_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^2_3$, —$OCHX^2_2$, substituted or unsubstituted $C_1$-$C_3$ alkyl, or substituted or unsubstituted 2 to 3 membered heteroalkyl;

$R^4$ is independently hydrogen;
a1 is independently an integer from 0 to 5;
b1 is independently an integer from 0 to 5;
$X^1$ and $X^2$ are independently —Cl, —Br, —I, or —F.

Embodiment P39

The method of Embodiment P38, wherein $R^1$ is independently a halogen.

Embodiment P40

The method of one of Embodiment P38 to P39, wherein $R^2$ is independently an —OH, unsubstituted $C_1$-$C_3$ alkyl, or unsubstituted 2 to 3 membered heteroalkyl.

111

Embodiment P41

The method of Embodiment P19, wherein the compound is:

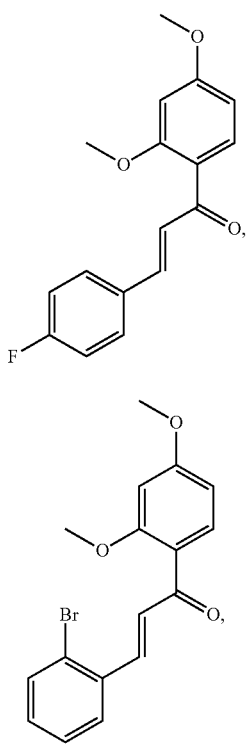

(Gr-4a)

(Gr-4b)

(Gr-4c)

(Gr-4d)

112

-continued

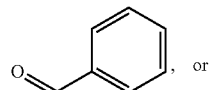

(Gr-6b)

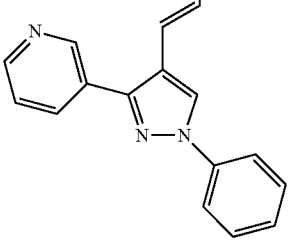

O18

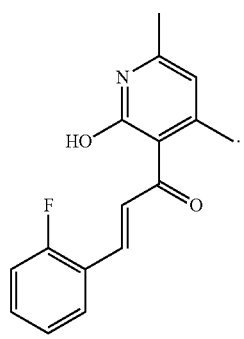

Embodiment P42

The method of Embodiment P19, wherein the stress resistance increasing compound has the formula:

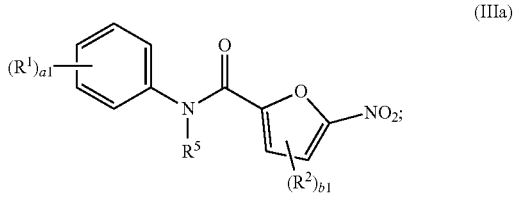

(IIIa)

wherein
R¹ is independently a halogen, —CX¹₃, —CN, —OH, —NH₂, —COOH, —CONH₂, —NO₂, —SH, —SO₃H, —SO₄H, —SO₂NH₂, —NHNH₂, —ONH₂, —NHC═(O) NHNH₂, —NHC═(O)NH₂, —NHSO₂H, —NHC═(O)H, —NHC(O)—OH, —NHOH, —OCX¹₃, —OCHX¹₂, substituted or unsubstituted C₁-C₆ alkyl, substituted or unsubstituted 2 to 6 membered heteroalkyl, substituted or unsubstituted C₃-C₆ cycloalkyl, substituted or unsubstituted 3 to 6 membered heterocycloalkyl, substituted or unsubstituted phenyl, or substituted or unsubstituted 5 to 6 membered heteroaryl; two adjacent R¹ substituents may optionally be joined to form a substituted or unsubstituted C₃-C₆ cycloalkyl, substituted or unsubstituted 3 to 6 membered heterocycloalkyl, substituted or unsubstituted phenyl, or substituted or unsubstituted 5 or 6 membered heteroaryl;
R² is independently a halogen, —CX²₃, —CN, —OH, —NH₂, —COOH, —CONH₂, —NO₂, —SH, —SO₃H, —SO₄H, —SO₂NH₂, —NHNH₂, —ONH₂, —NHC═(O) NHNH₂, —NHC═(O)NH₂, —NHSO₂H, —NHC═(O)H, —NHC(O)—OH, —NHOH, —OCX²₃, —OCHX²₂, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl;

$R^5$ is hydrogen or $R^5$ may optionally be joined to an $R^1$ substituent ortho to the —N($R^5$)— to form an unsubstituted 5 membered heterocycloalkyl or unsubstituted 5 membered heteroaryl;

a1 is independently an integer from 0 to 5;

b1 is independently an integer from 0 to 2;

$X^1$ and $X^2$ are independently —Cl, —Br, —I, or —F.

Embodiment P43

The method of Embodiment P19, wherein the compound is:

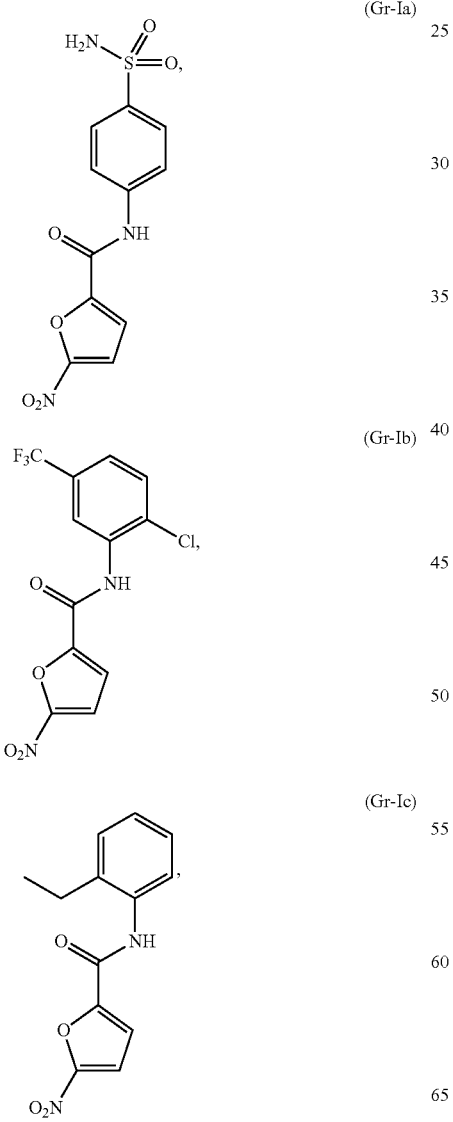

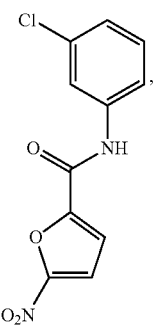

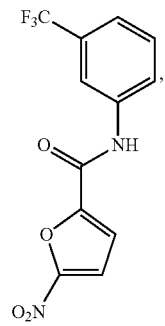

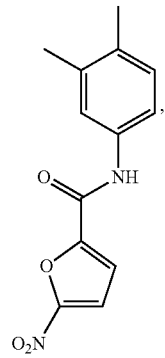

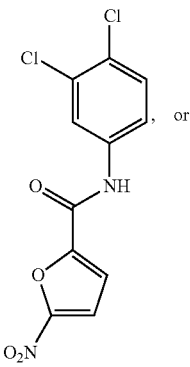

(O13)

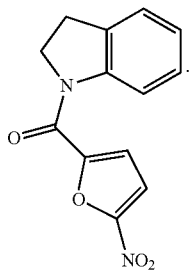

Embodiment P44

The method of one of Embodiment P19 to P43, wherein $R^1$ is independently a halogen, —$CX^1_3$, —CN, —OH, —$NH_2$, —COOH, —$CONH_2$, —$NO_2$, —SH, —$SO_2NH_2$, —$OCX^1_3$, —$OCHX^1_2$, substituted or unsubstituted $C_1$-$C_4$ alkyl, or substituted or unsubstituted 2 to 4 membered heteroalkyl.

Embodiment P45

The method of one of Embodiment P19 to P43, wherein $R^1$ is independently a halogen, —$CF_3$, —$SO_2NH_2$, unsubstituted $C_1$-$C_4$ alkyl, or unsubstituted 2 to 4 membered heteroalkyl.

Embodiment P46

The method of one of Embodiment P19 to P45, wherein $R^2$ is independently a halogen, —$CX^1_3$, —CN, —OH, —$NH_2$, —COOH, —$CONH_2$, —$NO_2$, —SH, —$SO_2NH_2$, —$OCX^1_3$, —$OCHX^1_2$, substituted or unsubstituted $C_1$-$C_4$ alkyl, or substituted or unsubstituted 2 to 4 membered heteroalkyl.

Embodiment P47

The method of one of Embodiment P19 to P45, wherein $R^2$ is independently a halogen, unsubstituted $C_1$-$C_4$ alkyl, or unsubstituted 2 to 4 membered heteroalkyl.

Embodiment P48

The method of Embodiment P19, wherein the stress resistance increasing compound has the formula:

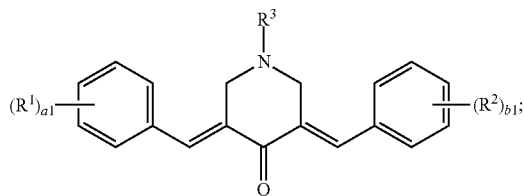

(IVa)

wherein
$R^1$ is independently a halogen, —$CX^1_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^1_3$, —$OCHX^1_2$, substituted or unsubstituted $C_1$-$C_6$ alkyl, or substituted or unsubstituted 2 to 6 membered heteroalkyl;
$R^2$ is independently a halogen, —$CX^2_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^2_3$, —$OCHX^2_2$, substituted or unsubstituted $C_1$-$C_6$ alkyl, or substituted or unsubstituted 2 to 6 membered heteroalkyl;
$R^3$ is independently unsubstituted $C_1$-$C_6$ alkyl or unsubstituted 2 to 6 membered heteroalkyl;
a1 is independently an integer from 0 to 5;
b1 is independently an integer from 0 to 5;
$X^1$ and $X^2$ are independently —Cl, —Br, —I, or —F.

Embodiment P49

The method of Embodiment P48, wherein $R^1$ is independently a halogen, —$CX^1_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^1_3$, —$OCHX^1_2$, unsubstituted $C_1$-$C_4$ alkyl, or unsubstituted 2 to 4 membered heteroalkyl.

Embodiment P50

The method of one of Embodiment P48 to P49, $R^2$ is independently a halogen, —$CX^2_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^2_3$, —$OCHX^2_2$ unsubstituted $C_1$-$C_4$ alkyl, or unsubstituted 2 to 4 membered heteroalkyl.

Embodiment P51

The method of one of Embodiment P48 to P50, wherein $R^3$ is unsubstituted $C_1$-$C_4$ alkyl.

Embodiment P52

The method of Embodiment P19, wherein the compound is:

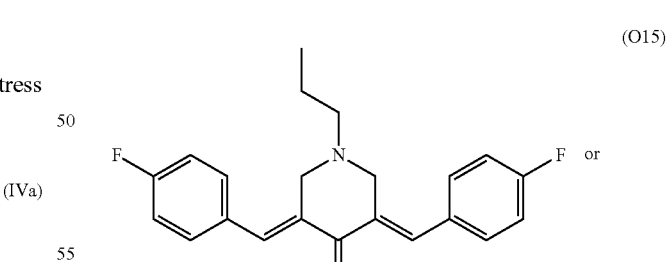

(O15)

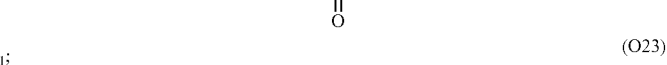

(O23)

Embodiment P53

The method of Embodiment P19, wherein the stress resistance increasing compound has the formula:

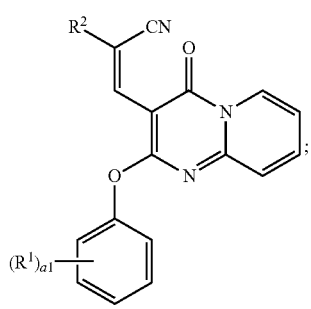

(Va)

wherein

R$^1$ is independently a halogen, —CX$^1{}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^1{}_3$, —OCHX$^1{}_2$, substituted or unsubstituted C$_1$-C$_6$ alkyl, or substituted or unsubstituted 2 to 6 membered heteroalkyl;

R$^2$ is independently —SO$_2$R$^{14}$, —C(O)NR$^{11}$R$^{12}$, or substituted or unsubstituted 2 to 6 membered heteroalkyl;

R$^{11}$, R$^{12}$, and R$^{14}$ are independently hydrogen, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl;

a1 is independently an integer from 0 to 5; and

X$^1$ is independently —Cl, —Br, —I, or —F.

Embodiment P54

The method of Embodiment P53, wherein R$^1$ is independently a halogen, unsubstituted C$_1$-C$_4$ alkyl, or unsubstituted 2 to 4 membered heteroalkyl.

Embodiment P55

The method of Embodiment P19, wherein the stress resistance increasing compound is:

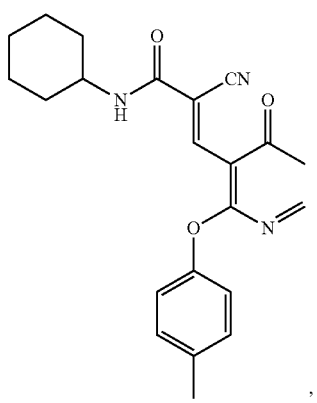

(Gr-5a)

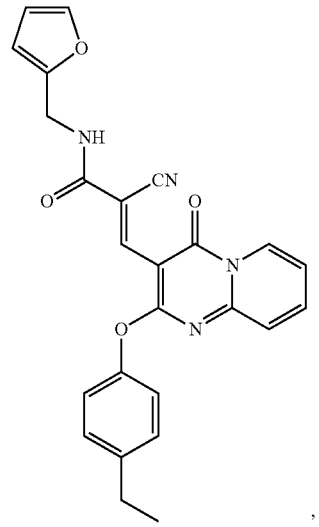

(Gr-5b)

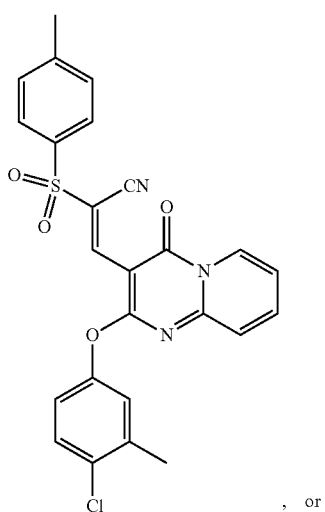

(Gr-5c)

, or

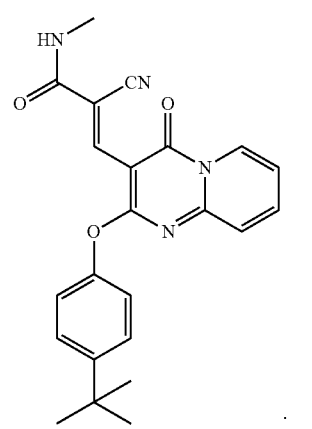

(Gr-5d)

119

Embodiment P56

The method of one of Embodiment P19 to P55, wherein a1 is 2.

Embodiment P57

The method of one of Embodiment P19 to P55, wherein a1 is 1.

Embodiment P58

The method of one of Embodiment P19 to P55, wherein a1 is 0.

Embodiment P59

The method of one of Embodiment P19 to P58, wherein b1 is 2.

Embodiment P60

The method of one of Embodiment P19 to P58, wherein b1 is 1.

Embodiment P61

The method of one of Embodiment P19 to P58, wherein b1 is 0.

Embodiment P62

The method of one of Embodiment P1 to P18, wherein the stress resistance increasing compound has the formula:

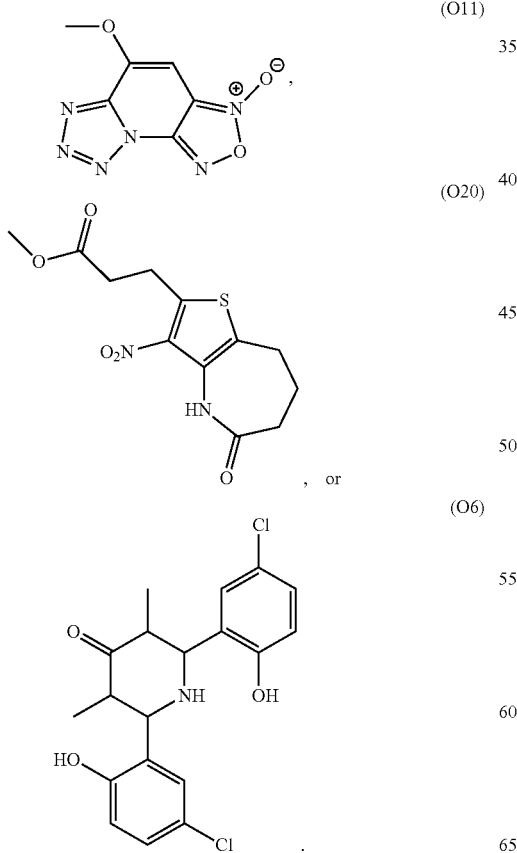

120

Embodiment P63

The method of Embodiment P15, wherein the stress resistance increasing compound has the formula:

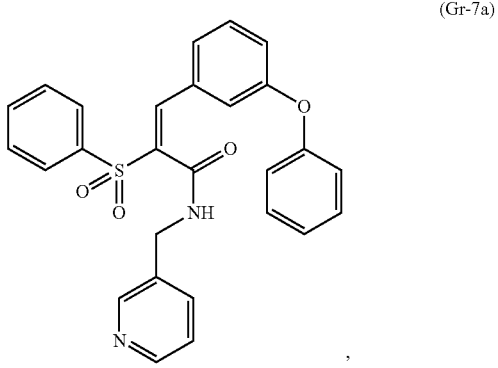

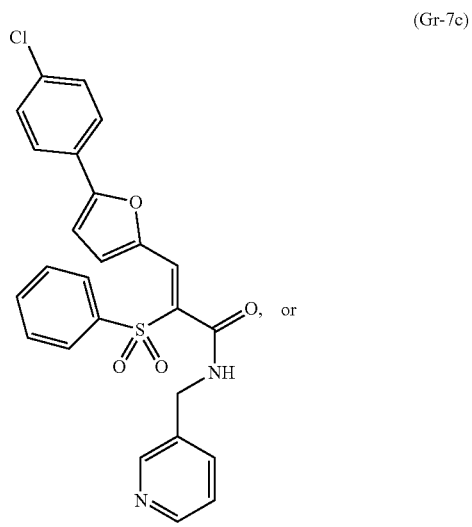

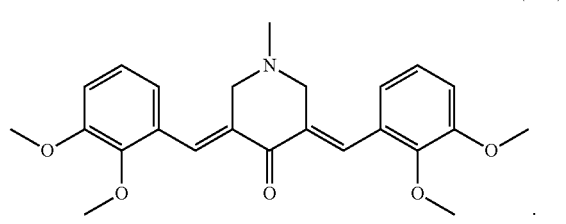

Embodiment P64
The method of Embodiment P16, wherein the stress resistance increasing compound has the formula:
(Gr-5a)
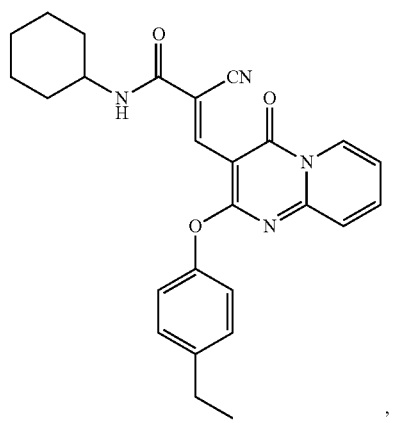
(Gr-5b)
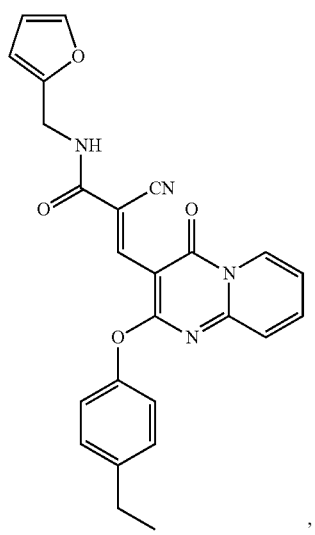
(Gr-5d)
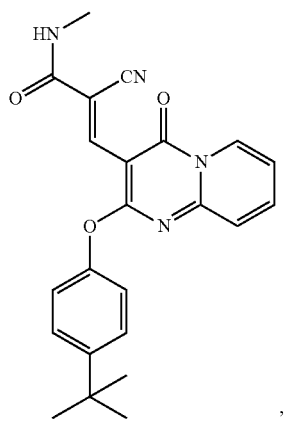
(Gr-6b)
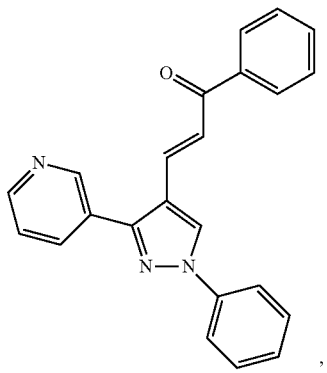
(Gr-7c)
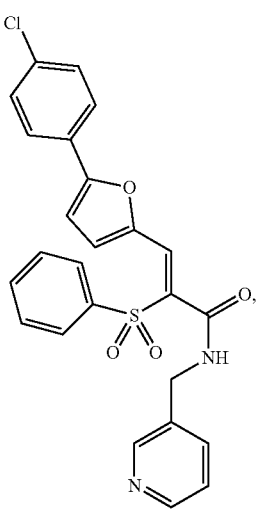
(O6)
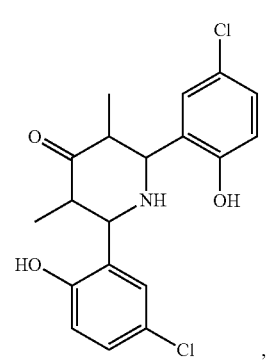
(O13)
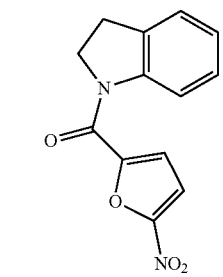

(O15)
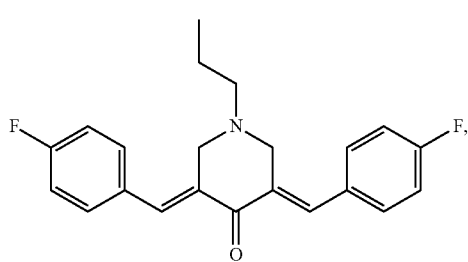
(O18)
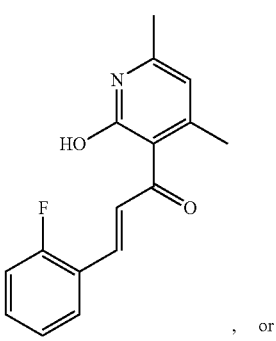
, or
(O20)
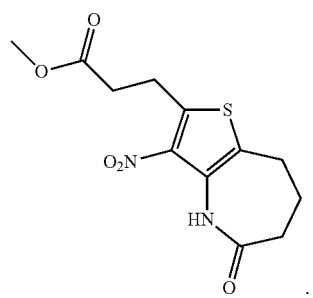
Embodiment P65
The method of Embodiment P16, wherein the stress resistance increasing compound has the formula:
(Gr-4a)
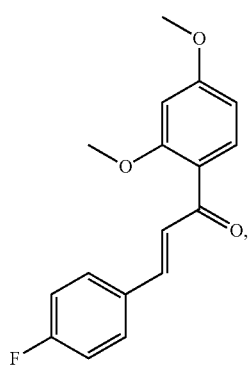
(Gr-4b)
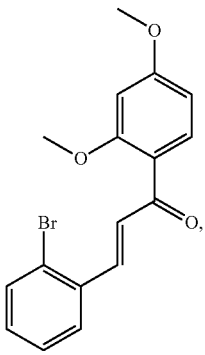
(Gr-4c)
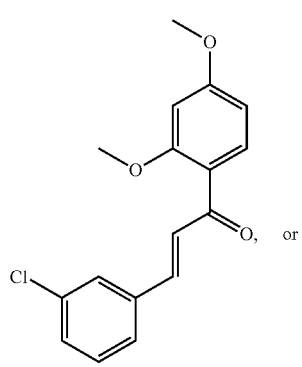
, or
(Gr-4d)
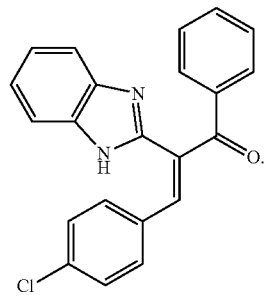
Embodiment P66
The method of Embodiment P17, wherein the stress resistance increasing compound has the formula:
(Gr-1a)
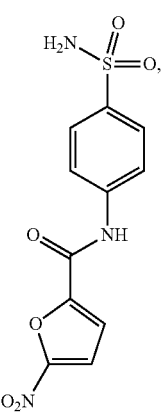

-continued (Gr-1c)
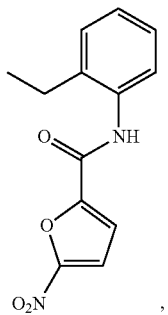

(Gr-1d)
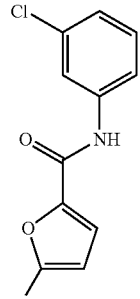

(Gr-1g)
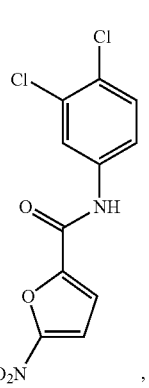

(O11)
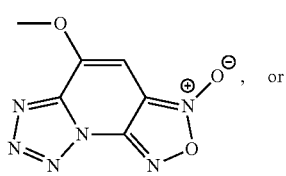 or (O23)
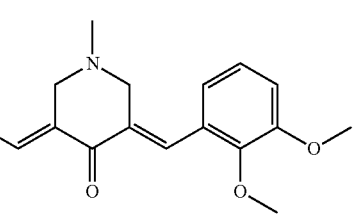

Embodiment P67

The method of Embodiment P4, wherein the stress resistance increasing compound is Gr-1e, Gr-3a, Gr-3b, Gr-3c, Gr-6c, Gr-7a, O12, O13, O14, O17, or O23.

Embodiment P68

The method of Embodiment P4, wherein the stress resistance increasing compound is:

(Gr-4d)
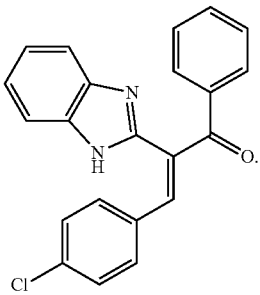

ADDITIONAL EMBODIMENTS

Embodiment 1

A method of increasing resistance to cellular stress in a subject, said method comprising administering an effective amount of a stress resistance increasing compound to said subject.

Embodiment 2

The method of embodiment 1, wherein said cellular stress is oxidative stress.

Embodiment 3

The method of embodiment 1, wherein said cellular stress is associated with DNA damage.

Embodiment 4

A method of increasing lifespan in a subject in need, said method comprising administering a stress resistance increasing compound to said subject.

Embodiment 5

A method of treating an age associated disease in a subject in need, said method comprising administering a stress resistance increasing compound to said subject.

Embodiment 6

The method of embodiment 5, wherein age associated disease is a cancer, neurodegenerative disease, cardiovascular disease, metabolic disease, or inflammatory disease.

Embodiment 7

The method of embodiment 6, wherein the neurodegenerative disease is Alzheimer's Disease, Parkinson's Disease, amyotrophic lateral sclerosis, or Huntington's Disease.

Embodiment 8

The method of embodiment 6, wherein the metabolic disease is type II diabetes.

Embodiment 9

The method of embodiment 6, wherein the cancer is lung cancer.

Embodiment 10

The method of embodiment 6, wherein the cancer is non-small cell lung cancer.

Embodiment 11

The method of embodiment 6, wherein the cancer is adenosquamous carcinoma.

Embodiment 12

A method of inhibiting proliferation of cancer cells, said method comprising contacting said cell with a stress resistance increasing compound.

Embodiment 13

A method of inhibiting survival of cancer cells, said method comprising contacting said cell with a stress resistance increasing compound.

Embodiment 14

The method of one of embodiments 12 to 13, wherein said cancer cells are EGFR positive, PIK3CA positive, RB1 negative, and TP53 negative.

Embodiment 15

A method of increasing the level of FOXO3 activity in a cell, said method comprising contacting the cell with a stress resistance increasing compound.

Embodiment 16

A method of increasing the level of NRF2 activity in a cell, said method comprising contacting the cell with a stress resistance increasing compound.

Embodiment 17

A method of increasing the level of autophagy in a cell, said method comprising contacting the cell with a stress resistance increasing compound.

Embodiment 18

A method of reducing the level of mTOR activity in a cell, said method comprising contacting the cell with a stress resistance increasing compound.

Embodiment 19

The method of one of embodiments 1 to 18, wherein the stress resistance increasing compound has the formula:

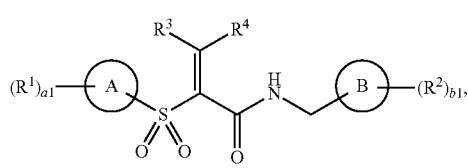

(I)

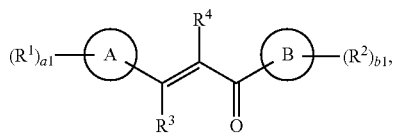

(II)

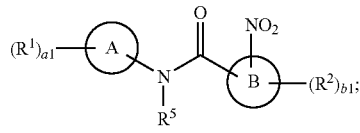

(III)

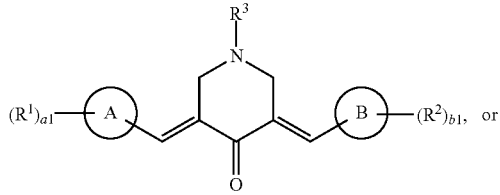

(IV)

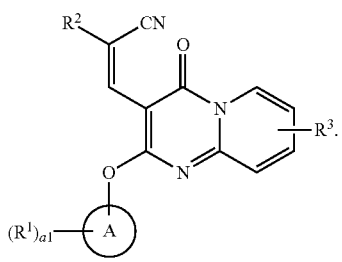

(V)

wherein Ring A is a aryl or heteroaryl; Ring B is a aryl or heteroaryl; $R^1$ is independently a halogen, $-CX^1_3$, $-CN$, $-SO_{n1}R^{10}$, $-SO_{v1}NR^7R^8$, $-NHNH_2$, $-ONR^7R^8$, $-NHC=(O)NHNH_2$, $-NHC=(O)NR^7R^8$, $-N(O)_{m1}$, $-NR^7R^8$, $-C(O)R^9$, $-C(O)-OR^9$, $-C(O)NR^7R^8$, $-OR^{10}$, $-NR^7SO_2R^{10}$, $-NRC=(O)R^9$, $-NR^7C(O)-OR^9$, $-NR^7OR^9$, $-OCX^1_3$, $-OCHX^1_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl; $R^2$ is independently a halogen, $-CX^2_3$, $-CN$, $-SO_{n2}R^{14}$, $-SO_{v2}NR^{11}R^{12}$, $-NHNH_2$, $-ONR^{11}R^{12}$, $-NHC=(O)NHNH_2$, $-NHC=(O)NR^{11}R^{12}$, $-N(O)_{m2}$, $-NR^{11}R^{12}$, $-C(O)R^{13}$, $-C(O)-OR^{13}$, $-C(O)NR^{11}R^{12}$, $-OR^{14}$, $-NR^{11}SO_2R^{14}$, $-NR^{11}C=(O)R^{13}$, $-NR^{11}C(O)-OR^{13}$, $-NR^{11}OR^{13}$, $-OCX^2_3$, $-OCHX^2_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl; $R^3$ are independently hydrogen, halogen, $-CX^{33}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^3_3$, $-OCHX^3_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ are independently hydrogen, halogen, $-CX^4_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^4_3$, $-OCHX^4_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ is hydrogen, substituted or unsubstituted $C_1$-$C_6$ alkyl, or substituted or unsubstituted 2 to 6 membered heteroalkyl; $R^5$ may optionally be joined to an $R^1$ substituent ortho to the $-N(R^5)-$ to form a substituted or unsubstituted 5 to 6 membered heterocycloalkyl or substituted or unsubstituted 5 to 6 membered heteroaryl; $R^7$, $R^8$, $R^9$, $R^{10}$, $R^{11}$, $R^{12}$, $R^{13}$, and $R^{14}$ are independently hydrogen, halogen, $-CX_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX_3$, $-OCHX_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; a1 is independently an integer from 0 to 7; b1 is independently an integer from 0 to 7; m1, m2, v1, and v2 are independently 1 or 2; n1 and n2 are independently an integer from 0 to 4; X, $X^1$, $X^2$, $X^3$, and $X^4$ are independently $-Cl$, $-Br$, $-I$, or $-F$.

Embodiment 20

The method of embodiment 19, wherein the stress resistance increasing compound has the formula:

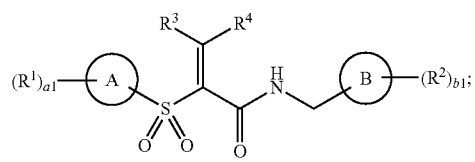

(I)

wherein Ring A is a phenyl; Ring B is a 5 or 6 membered heteroaryl; $R^1$ is independently a halogen, $-CX^1_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^1_3$, $-OCHX^1_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^1$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; $R^2$ is independently a halogen, $-CX^2_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^2_3$, $-OCHX^2_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^2$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; $R^3$ is independently hydrogen, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; $R^4$ is independently hydrogen, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; a1 is independently an integer from 0 to 5; b1 is independently an integer from 0 to 4; $X^1$ and $X^2$ are independently $-Cl$, $-Br$, $-I$, or $-F$.

Embodiment 21

The method of embodiment 20, wherein Ring B is a pyridyl.

Embodiment 22

The method of embodiment 20, wherein the stress resistance increasing compound has the formula:

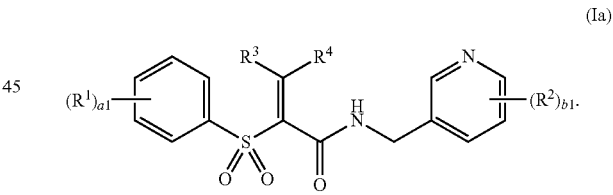

(Ia)

Embodiment 23

The method of one of embodiments 20 to 22, wherein $R^3$ is independently hydrogen, substituted or unsubstituted phenyl, or substituted or unsubstituted 5 to 6 membered heteroaryl.

Embodiment 24

The method of one of embodiments 20 to 22, wherein $R^3$ is independently substituted or unsubstituted 5 to 6 membered heteroaryl.

Embodiment 25

The method of one of embodiments 20 to 22, wherein $R^3$ is independently substituted or unsubstituted furanyl.

Embodiment 26

The method of one of embodiments 20 to 22, wherein $R^3$ is independently $R^{26}$-substituted or unsubstituted furanyl; and $R^{26}$ is halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 27

The method of one of embodiments 20 to 26, wherein $R^4$ is independently hydrogen, substituted or unsubstituted phenyl, or substituted or unsubstituted 5 to 6 membered heteroaryl.

Embodiment 28

The method of one of embodiments 20 to 26, wherein $R^4$ is independently substituted or unsubstituted phenyl.

Embodiment 29

The method of one of embodiments 20 to 26, wherein $R^4$ is independently $R^{29}$-substituted or unsubstituted phenyl; and $R^{29}$ is halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, phenoxy, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 30

The method of embodiment 19, wherein the stress resistance increasing compound is:

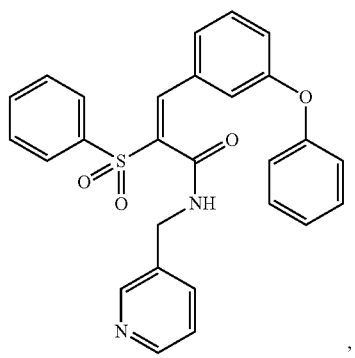

(Gr-7a)

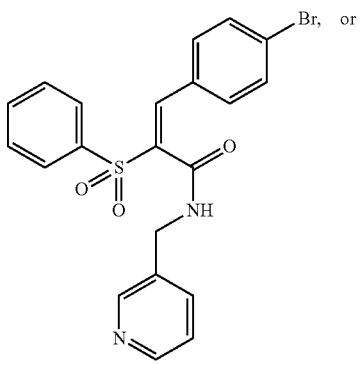

(Gr-7b)

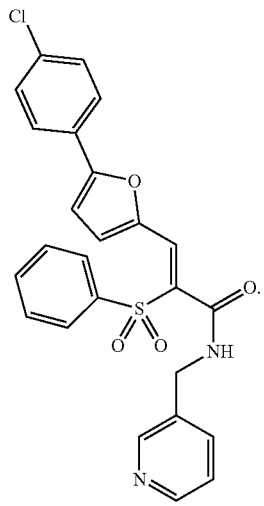

(Gr-7c)

Embodiment 31

The method of embodiment 19, wherein the stress resistance increasing compound has the formula:

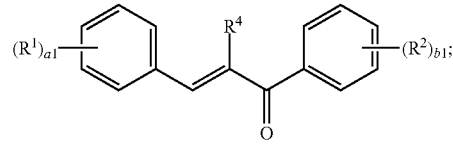

(IIa)

wherein $R^1$ is independently a halogen, —$CX^1_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^1_3$, —$OCHX^1_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^1$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl;

$R^2$ is independently a halogen, —CX$^2_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^2_3$, —OCHX$^2_2$, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^2$ substituents may optionally be joined to form a substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl; $R^4$ is independently hydrogen, substituted or unsubstituted C$_3$-C$_6$ cycloalkyl, substituted or unsubstituted 3 to 6 membered heterocycloalkyl, substituted or unsubstituted C$_6$-C$_{10}$ aryl, or substituted or unsubstituted 5 to 10 membered heteroaryl; a1 is independently an integer from 0 to 5; b1 is independently an integer from 0 to 5; $X^1$ and $X^2$ are independently —Cl, —Br, —I, or —F.

Embodiment 32

The method of embodiment 31, wherein $R^4$ is independently hydrogen, substituted or unsubstituted C$_6$-C$_{10}$ aryl, or substituted or unsubstituted 5 to 10 membered heteroaryl.

Embodiment 33

The method of embodiment 31, wherein $R^4$ is independently substituted or unsubstituted 5 or 10 membered heteroaryl.

Embodiment 34

The method of embodiment 31, wherein $R^4$ is independently $R^{29}$-substituted or unsubstituted benzimidazolyl; and $R^{29}$ is halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, phenoxy, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 35

The method of embodiment 19, wherein the stress resistance increasing compound has the formula:

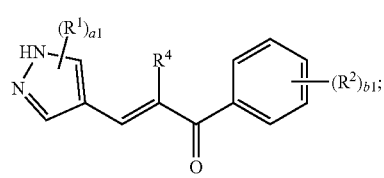

(IIb)

wherein $R^1$ is independently a halogen, —CX$^1_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^1_3$, —OCHX$^1_2$, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^1$ substituents may optionally be joined to form a substituted or unsubstituted 5 to 6 membered heterocycloalkyl or substituted or unsubstituted 5 to 6 membered heteroaryl; $R^2$ is independently a halogen, —CX$^2_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(ONH$_2$, —NHSO$_2$H, —NHC=(O)H, —NHC(O)—OH, —NHOH, —OCX$^2_3$, —OCHX$^2_2$, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl; two adjacent $R^2$ substituents may optionally be joined to form a substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl; $R^4$ is independently hydrogen, substituted or unsubstituted C$_3$-C$_6$ cycloalkyl, substituted or unsubstituted 3 to 6 membered heterocycloalkyl, substituted or unsubstituted C$_6$-C$_{10}$ aryl, or substituted or unsubstituted 5 to 10 membered heteroaryl; a1 is independently an integer from 0 to 5; b1 is independently an integer from 0 to 5; $X^1$ and $X^2$ are independently —Cl, —Br, —I, or —F.

Embodiment 36

The method of embodiment 35, wherein $R^4$ is independently hydrogen.

Embodiment 37

The method of embodiment 35, wherein $R^1$ is independently a substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 38

The method of embodiment 19, wherein the stress resistance increasing compound has the formula:

(IIc)

wherein Ring B is a pyridyl; $R^1$ is independently a halogen, $-CX^1_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^1_3$, $-OCHX^1_2$, substituted or unsubstituted $C_1$-$C_3$ alkyl, or substituted or unsubstituted 2 to 3 membered heteroalkyl; $R^2$ is independently a halogen, $-CX^2_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^2_3$, $-OCHX^2_2$, substituted or unsubstituted $C_1$-$C_3$ alkyl, or substituted or unsubstituted 2 to 3 membered heteroalkyl; $R^4$ is independently hydrogen; a1 is independently an integer from 0 to 5; b1 is independently an integer from 0 to 5; $X^1$ and $X^2$ are independently $-Cl$, $-Br$, $-I$, or $-F$.

Embodiment 39

The method of embodiment 38, wherein $R^1$ is independently a halogen.

Embodiment 40

The method of one of embodiments 38 to 39, wherein $R^2$ is independently an $-OH$, unsubstituted $C_1$-$C_3$ alkyl, or unsubstituted 2 to 3 membered heteroalkyl.

Embodiment 41

The method of embodiment 19, wherein the compound is:

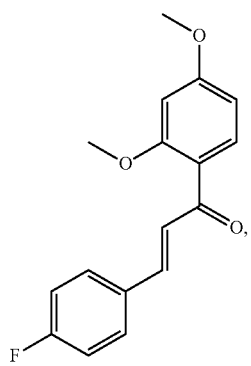

(Gr-4a)

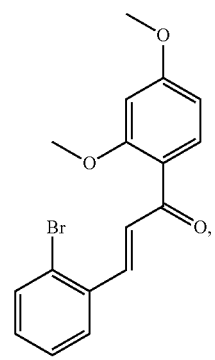

(Gr-4b)

(Gr-4c)

(Gr-4d)

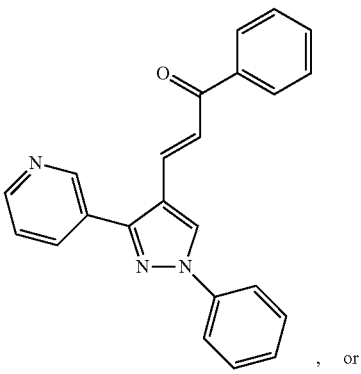

, or (Gr-6b)

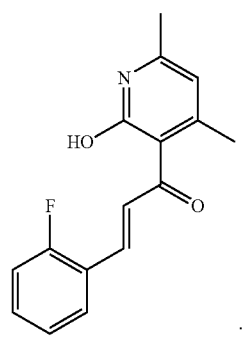

(O18)

Embodiment 42

The method of embodiment 19, wherein the stress resistance increasing compound has the formula:

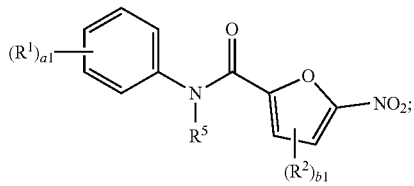

(IIIa)

wherein R¹ is independently a halogen, —CX¹₃, —CN, —OH, —NH₂, —COOH, —CONH₂, —NO₂, —SH, —SO₃H, —SO₄H, —SO₂NH₂, —NHNH₂, —ONH₂, —NHC═(O)NHNH₂, —NHC═(O)NH₂, —NHSO₂H, —NHC═(O)H, —NHC(O)—OH, —NHOH, —OCX¹₃, —OCHX¹₂, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; two adjacent R¹ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 or 6 membered heteroaryl; R² is independently a halogen, —CX²₃, —CN, —OH, —NH₂, —COOH, —CONH₂, —NO₂, —SH, —SO₃H, —SO₄H, —SO₂NH₂, —NHNH₂, —ONH₂, —NHC═(O)NHNH₂, —NHC═(O)NH₂, —NHSO₂H, —NHC═(O)H, —NHC(O)—OH, —NHOH, —OCX²₃, —OCHX²₂, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; R⁵ is hydrogen or R⁵ may optionally be joined to an R¹ substituent ortho to the —N(R⁵)— to form an unsubstituted 5 membered heterocycloalkyl or unsubstituted 5 membered heteroaryl; a1 is independently an integer from 0 to 5; b1 is independently an integer from 0 to 2; X¹ and X² are independently —Cl, —Br, —I, or —F.

Embodiment 43

The method of embodiment 19, wherein the compound is:

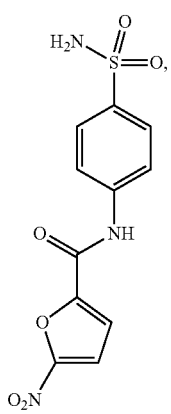

(Gr-1a)

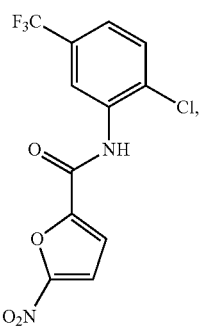

(Gr-1b)

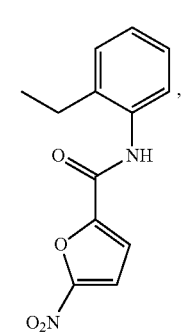

(Gr-1c)

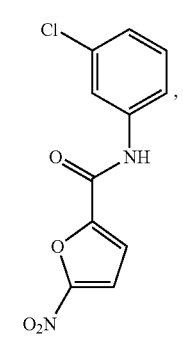

(Gr-1d)

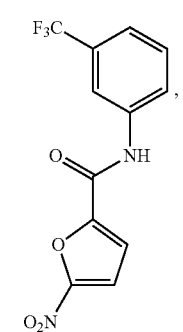

(Gr-1e)

(Gr-1f)

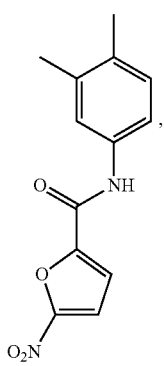

, (Gr-1g)

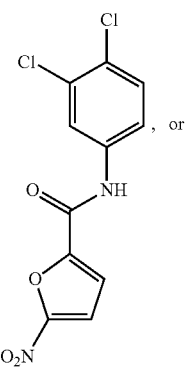

, or (O13)

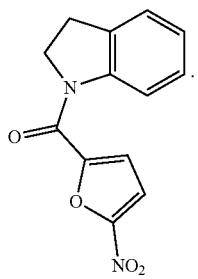

.

Embodiment 44

The method of one of embodiments 19 to 43, wherein $R^1$ is independently a halogen, —$CX^1_3$, —CN, —OH, —$NH_2$, —COOH, —$CONH_2$, —$NO_2$, —SH, —$SO_2NH_2$, —$OCX^1_3$, —$OCHX^1_2$, substituted or unsubstituted $C_1$-$C_4$ alkyl, or substituted or unsubstituted 2 to 4 membered heteroalkyl.

Embodiment 45

The method of one of embodiments 19 to 43, wherein $R^1$ is independently a halogen, —$CF_3$, —$SO_2NH_2$, unsubstituted $C_1$-$C_4$ alkyl, or unsubstituted 2 to 4 membered heteroalkyl.

Embodiment 46

The method of one of embodiments 19 to 45, wherein $R^2$ is independently a halogen, —$CX^1_3$, —CN, —OH, —$NH_2$, —COOH, —$CONH_2$, —$NO_2$, —SH, —$SO_2NH_2$, —$OCX^1_3$, —$OCHX^1_2$, substituted or unsubstituted $C_1$-$C_4$ alkyl, or substituted or unsubstituted 2 to 4 membered heteroalkyl.

Embodiment 47

The method of one of embodiments 19 to 45, wherein $R^2$ is independently a halogen, unsubstituted $C_1$-$C_4$ alkyl, or unsubstituted 2 to 4 membered heteroalkyl.

Embodiment 48

The method of embodiment 19, wherein the stress resistance increasing compound has the formula:

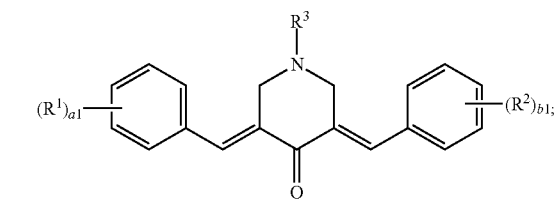

(IVa)

wherein $R^1$ is independently a halogen, —$CX^1_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^1_3$, —$OCHX^1_2$, substituted or unsubstituted $C_1$-$C_6$ alkyl, or substituted or unsubstituted 2 to 6 membered heteroalkyl; $R^2$ is independently a halogen, —$CX^2_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^2_3$, —$OCHX^2_2$, substituted or unsubstituted $C_1$-$C_6$ alkyl, or substituted or unsubstituted 2 to 6 membered heteroalkyl; $R^3$ is independently unsubstituted $C_1$-$C_6$ alkyl or unsubstituted 2 to 6 membered heteroalkyl; a1 is independently an integer from 0 to 5; b1 is independently an integer from 0 to 5; $X^1$ and $X^2$ are independently —Cl, —Br, —I, or —F.

Embodiment 49

The method of embodiment 48, wherein $R^1$ is independently a halogen, —$CX^1_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^1_3$, —$OCHX^1_2$, unsubstituted $C_1$-$C_4$ alkyl, or unsubstituted 2 to 4 membered heteroalkyl.

Embodiment 50

The method of one of embodiments 48 to 49, $R^2$ is independently a halogen, —$CX^2_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^2_3$, —$OCHX^2_2$ unsubstituted $C_1$-$C_4$ alkyl, or unsubstituted 2 to 4 membered heteroalkyl.

Embodiment 51

The method of one of embodiments 48 to 50, wherein $R^3$ is unsubstituted $C_1$-$C_4$ alkyl.

Embodiment 52

The method of embodiment 19, wherein the compound is:

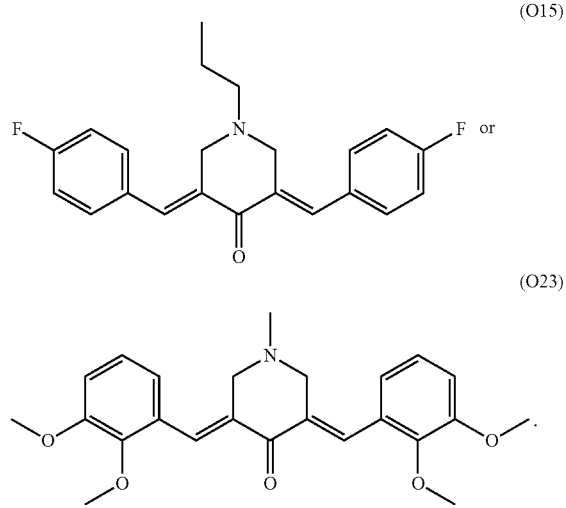

(O15)

(O23)

Embodiment 53

The method of embodiment 19, wherein the stress resistance increasing compound has the formula:

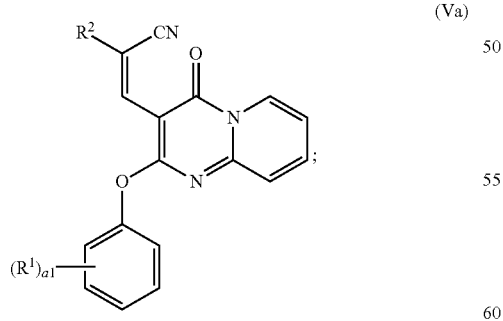

(Va)

wherein $R^1$ is independently a halogen, —$CX^1_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^1_3$, —$OCHX^1_2$, substituted or unsubstituted $C_1$-$C_6$ alkyl, or substituted or unsubstituted 2 to 6 membered heteroalkyl; $R^2$ is independently —$SO_2R^{14}$, —C(O)$NR^{11}R^{12}$, or substituted or unsubstituted 2 to 6 membered heteroalkyl; $R^{11}$, $R^{12}$, and $R^{14}$ are independently hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; a1 is independently an integer from 0 to 5; and $X^1$ is independently —Cl, —Br, —I, or —F.

Embodiment 54

The method of embodiment 53, wherein $R^1$ is independently a halogen, unsubstituted $C_1$-$C_4$ alkyl, or unsubstituted 2 to 4 membered heteroalkyl.

Embodiment 55

The method of embodiment 19, wherein the stress resistance increasing compound is:

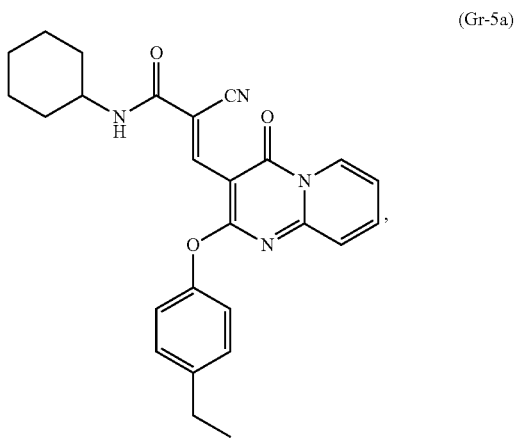 [SMILES: CCc1ccc(Oc2nc3ccccn3c(=O)c2/C=C(\C#N)C(=O)NC2CCCCC2)cc1]

(Gr-5a)

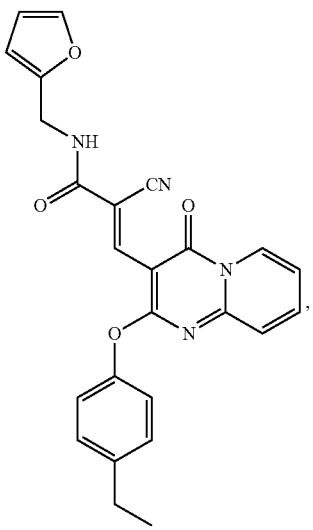

(Gr-5b)

143

-continued (Gr-5c)

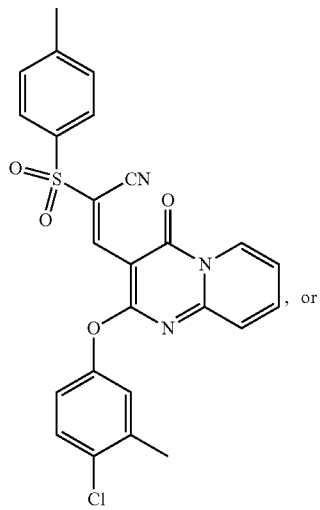

, or (Gr-5d)

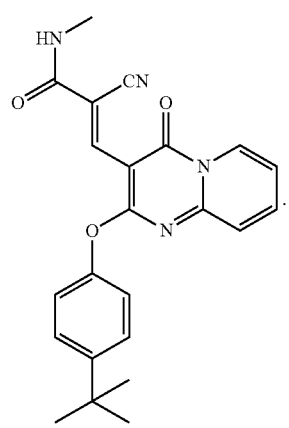

.

Embodiment 56

The method of one of embodiments 19-29, 31-40, 42, 44-51, 53, or 54, wherein a1 is 2.

Embodiment 57

The method of one of embodiments 19-29, 31-40, 42, 44-51, 53, or 54, wherein a1 is 1.

Embodiment 58

The method of one of embodiments 19-29, 31-40, 42, 44-51, 53, or 54, wherein a1 is 0.

Embodiment 59

The method of one of embodiments 19-29, 31-40, 42, or 44-51, wherein b1 is 2.

Embodiment 60

The method of one of embodiments 19-29, 31-40, 42, or 44-51, wherein b1 is 1.

144

Embodiment 61

The method of one of embodiments 19-29, 31-40, 42, or 44-51, wherein b1 is 0.

Embodiment 62

The method of one of embodiments 1 to 18, wherein the stress resistance increasing compound has the formula:

(O11)

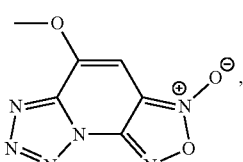

(O20)

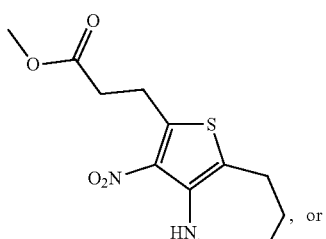

, or (O6)

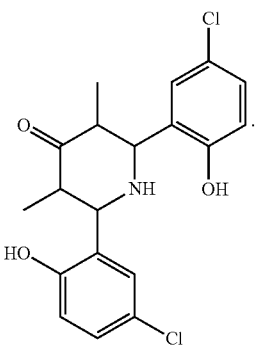

.

Embodiment 63

The method of embodiment 15, wherein the stress resistance increasing compound has the formula:

(Gr-7a)

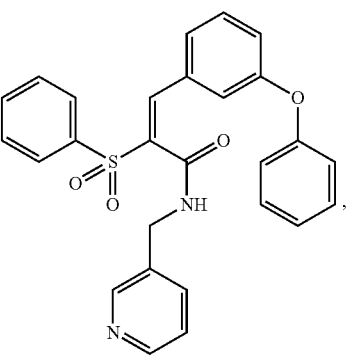

, (Gr-7c)
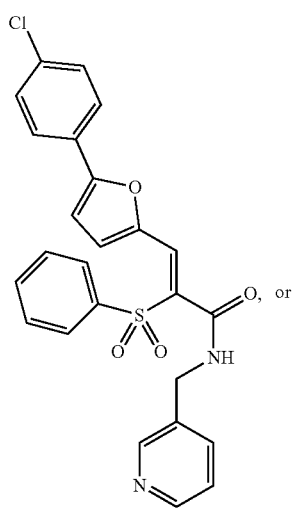
(O23)
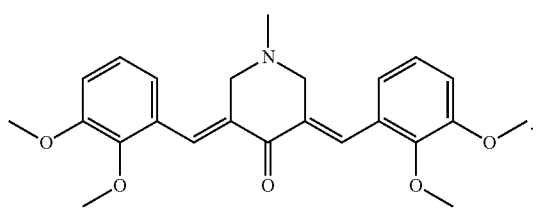
Embodiment 64
The method of embodiment 16, wherein the stress resistance increasing compound has the formula:
(Gr-5a)
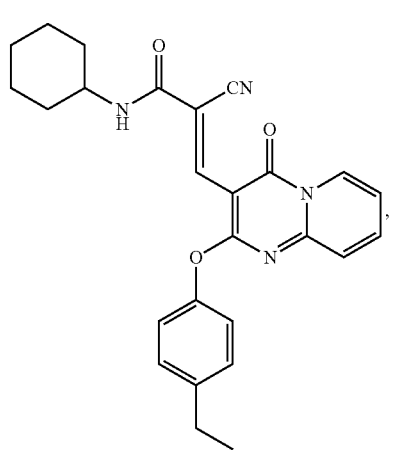
(Gr-5b)
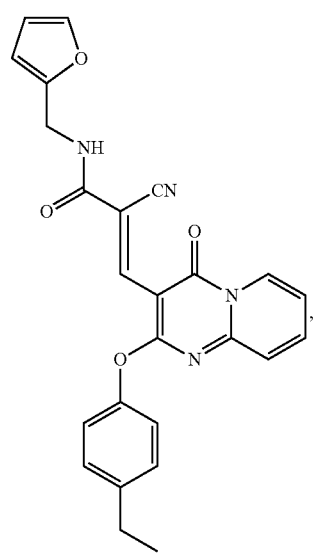
(Gr-5d)
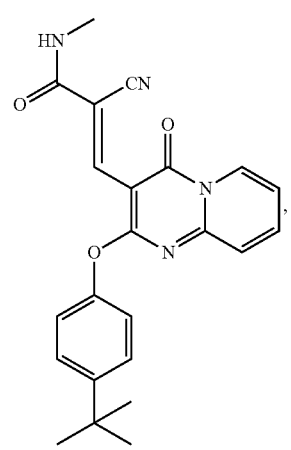
(Gr-6b)
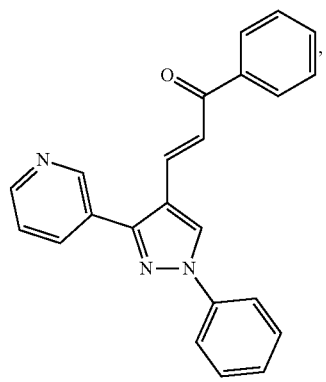

(Gr-7c)
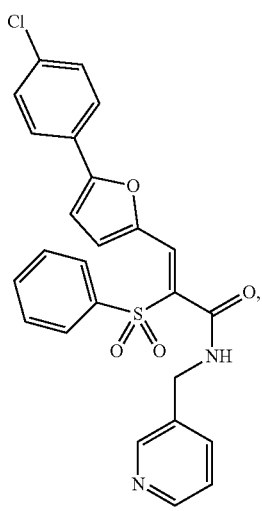
(O6)
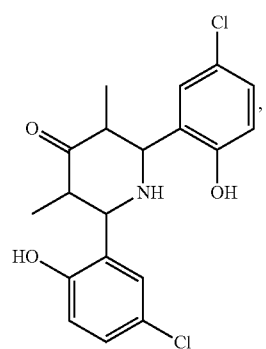
(O13)
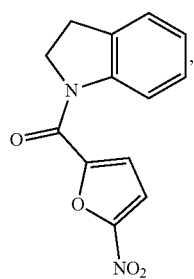
(O15)
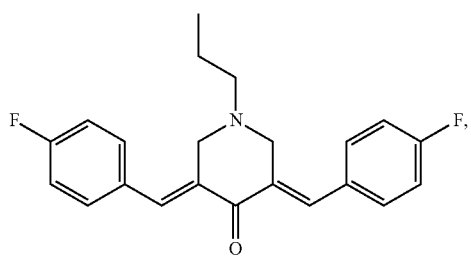
(O18)
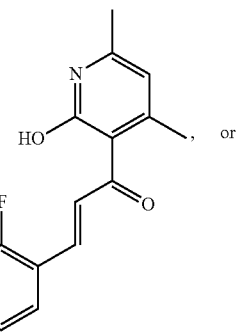
, or
(O20)
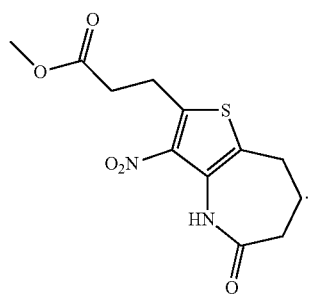
Embodiment 65
The method of embodiment 16, wherein the stress resistance increasing compound has the formula:
(Gr-4a)
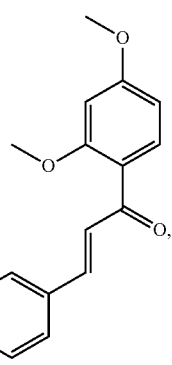
(Gr-4b)
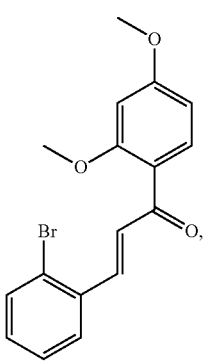

-continued
(Gr-4c)
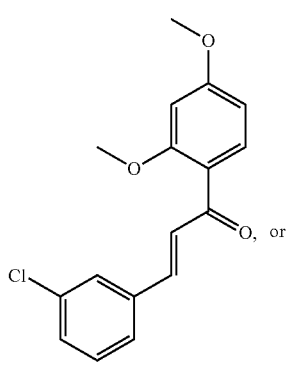
, or
(Gr-4d)
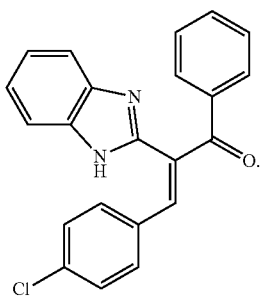
Embodiment 66
The method of embodiment 17, wherein the stress resistance increasing compound has the formula:
(Gr-1a)
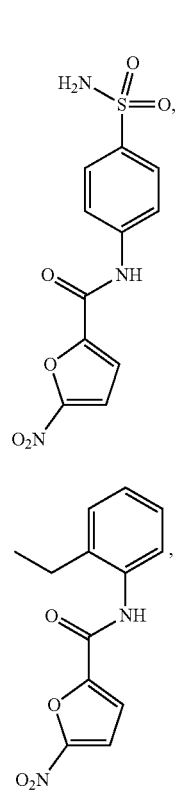
(Gr-1c)
-continued
(Gr-1d)
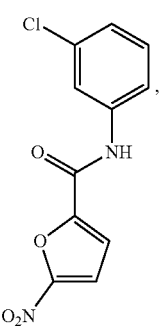
(Gr-1g)
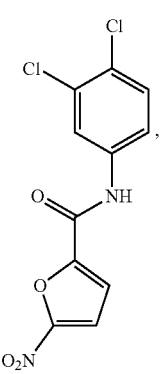
(O11)
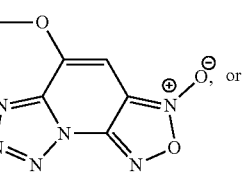
, or
(O23)
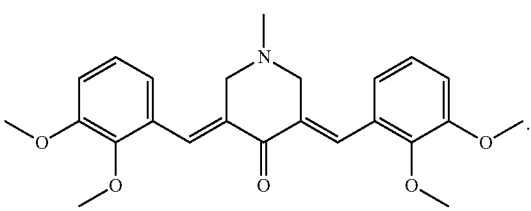
Embodiment 67
The method of embodiment 4, wherein the stress resistance increasing compound is Gr-1e, Gr-3a, Gr-3b, Gr-3c, Gr-6c, Gr-7a, O12, O13, O14, O17, or O23.

Embodiment 68

The method of embodiment 4, wherein the stress resistance increasing compound is:

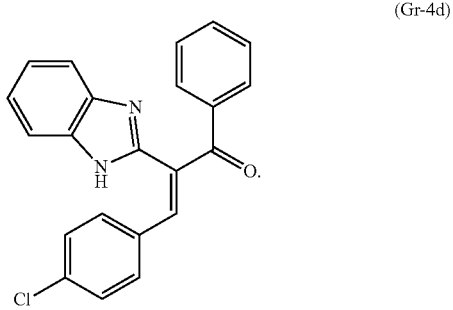 [SMILES: O=C(/C(=C/c1ccc(Cl)cc1)c1nc2ccccc2[nH]1)c1ccccc1]

(Gr-4d)

EXAMPLES

Example 1. High-Throughput Screen Identifies Small Molecules that Promote Stress Resistance and Link to Aging Increased resistance to environmental stress at the cellular level is often correlated with organismal longevity, as seen for cells from long-lived mutants and wild animal species. Likewise, in many experimental organisms, screens for increased stress resistance have yielded mutants that are long-lived. To find small molecules that could potentially promote healthy aging in humans, applicants have screened 104,121 small molecules in a human primary fibroblast cell line and identified 61 that increased oxidative stress resistance. Thirty hits fall into seven structurally related chemical groups, suggesting that they may promote stress resistance by acting on common targets. Three small molecules increased C. elegans' stress resistance, and at least twelve extended their lifespan (from ~10% to ~50%). In human cells, some small molecules affect the activities of FOXO3, NRF2, and/or mTOR, proteins whose activation or inhibition can extend lifespan in model organisms.

In animals, single-gene mutations in many nutrient, energy and stress-sensing genes, such as genes affecting IGF-1 and mTOR signalling, extend youthfulness and lifespan and counter age-related diseases (Bartke, 2011; Fontana et al., 2010; Kenyon, 2010b). Intriguingly, these genes lie in the center of intertwined networks that consist of multiple components, many of which could serve as targets for pharmacological interventions to slow aging and extend healthy lifespan. In fact, in lieu of genetic approaches to inhibit mTOR, or to activate AMPK or sirtuins, small molecules (rapamycin, metformin, resveratrol) that modulate these proteins have been observed to prolong lifespan in several different species (Bjedov et al., 2010; Cabreiro et al., 2013; De Haes et al., 2014; Harrison et al., 2009; Martin-Montalvo et al., 2013; Onken and Driscoll, 2010; Robida-Stubbs et al., 2012; Wilkinson et al., 2012). Remarkably, the same small molecules have been used in humans to treat cancer and diabetes, two prominent diseases that afflict a large size of aging population. Together, these findings highlight the possibility that certain therapeutical small molecules, by acting on longevity-influencing proteins, could extend the healthy life of humans.

Besides these genetic and pharmacological regulators, studies in experimental animals also have revealed phenotypes that correlate with an increased lifespan, such as enhanced resistance to different types of stresses. First, long-lived mutants (such as GH-receptor mutant mice) and their cells tend to be stress resistant (Miller, 2009). Second, cells from long-lived wild animals, such as brown bats and naked mole rats, are resistant to oxidizing radicals (e.g., hydrogen peroxide), heavy metals, and DNA-damaging agents (Harper et al., 2007; Lewis et al., 2012; Salmon et al., 2008). Third, forkhead box O (FOXO) proteins (such as FOXO3) and nuclear factor erythroid 2-related factor 2 (NFE2L2/NRF2), key regulators of stress responses, are also crucial to promote longevity in several species, including worms (Bishop and Guarente, 2007; Kenyon et al., 1993; Libina et al., 2003; Ogg et al., 1997; Tullet et al., 2008), flies (Giannakou et al., 2004; Hwangbo et al., 2004; Sykiotis and Bohmann, 2008), and mice (Leiser and Miller, 2010; Shimokawa et al., 2015; Steinbaugh et al., 2012). In humans, exceptional longevity-associated FOXO3A polymorphisms have been identified in multiple cohorts of centenarians (Kenyon, 2010b), and NRF2 activation has been shown to delay senescence in human fibroblasts (Kapeta et al., 2010). From another perspective, approximately 10-15% of mutants selected for stress-resistance in genetic screens in yeast, worms, and plants, turn out to be long-lived (Cao et al., 2003; de Castro et al., 2004; Kennedy et al., 1995; Kim and Sun, 2007). Recently, by screening a library of compounds with known mammalian pharmacology, Ye and coworkers identified 60 that promoted longevity of C. elegans, and of these, 33 increased C. elegans' resistance to oxidative stress (Ye et al., 2014). These findings, again, appeared to corroborate the idea of enriching for longevity regulators by carrying out primary screens for stress resistance. In particular, this approach could be taken to identify small molecules that promote stress resistance in human cells, and some of these molecules, and particularly, those that have direct or indirect effects on known aging regulators, could be starting points for developing interventions that slow aging and counteract age-related disease in humans.

Applicants have isolated small molecules that enhanced the resistance of a human primary cell line to hydrogen peroxide. A substantial fraction of molecules were shown to affect FOXO3, NRF2, and/or mTOR activity, and also extended the lifespan of C. elegans.

PARP Inhibitor Assay.

The assay was performed with the HT Fluorescent Homogeneous PARP Inhibition Assay Kit (Trevigen), following manufacturer's instructions. Briefly, nicotinamide adenine dinucleotide, human PARP1 and activated-DNA solution was added onto a 96-well plate. 54 repurchased small molecules, at 10 µM final concentration, were introduced onto the 96-well assay plate and incubated in a humid chamber at room temperature for 30 min in dark. Cycling mixture, with resazurin and cycling enzyme diaphorase, was then added and incubated further for 1 hr in dark. Reaction was terminated by adding the stopping buffer. Fluorescence was then measured on a FlexStation 3 multi-mode microplate reader (544 nm excitation/590 nm emission).

qPCR Analysis & FOXO3 & NRF2 Interference to Address Dependency.

For qPCR analysis, WI-38 cells were treated with small molecules (at 10 µM) (biological quadruplicates) for 24 hrs and processed for RNA isolation and reverse transcription (RT) with the Cells-to-Ct Kit (Life Technologies), following manufacturer's instructions. RT products were diluted with H₂O and used for qPCR analysis on an ABI 7300 system (Life Technologies) (technical triplicates). Relative expression levels of target genes were normalized to the genes B2M, PPIA and GAPDH. To knock down the expression of FOXO3 or NRF2, WI-38 cells were transfected, using the RNAiMAX reagents (Life Technologies), with siRNA oligos (at 10 nM final concentration, 10 ml culture medium) for FOXO3 (Life Technologies) or NRF2 (Integrated DNA Technologies) on 10-cm petri dishes for 36 hrs, and then detached and aliquoted onto 96-well (for qPCR analysis) or 384-well plates (for H$_2$O$_2$-stress treatment). ~24 hrs later, small molecules were introduced and incubated with cells for 24 hrs. Cells were then either processed with the Cells-to-Ct Kit to prepare RT products for qPCR analysis or subjected to H$_2$O$_2$ (700 μM) for 3 hrs and assayed for viability. The knockdown efficiency of FOXO3 or NRF2 was checked at 36 hrs post-transfection and at the end as well.

mTOR Inhibition (RPS6 Phosphorylation Status) Analysis.

In-Cell Western assays were performed, following a standard immuno-staining protocol. Briefly, WI-38 cells were treated with small molecules for 24 hrs, and then processed and incubated with primary antibody cocktail (Cell Signaling, mouse anti-RPS, 1:25; rabbit-anti-pRPS6-(Ser-235/236), 1:100) overnight at 4° C. Next day, samples were processed and incubated with fluorophore-conjugated secondary antibodies (Cell Signaling, DyLight 680-goat anti-mouse, 1:500; DyLight 800-goat anti-rabbit, 1:1,000). Images were collected on an Odyssey Imager (LI-COR) and analyzed with the Image Studio Lite software (version 5.0.21).

Autophagy Induction Analysis.

Immuno-staining of LC3A/B was performed, following a standard protocol. Briefly, WI-38 cells were treated with small molecules for 24 hrs, and then processed and incubated with primary antibody (Cell Signaling, rabbit anti-LC3A/B, 1:100) overnight at 4° C. Next day, samples were processed and incubated with fluorophore-conjugated secondary antibody and further incubated with DAPI dye. Images were collected on the INCell Analyzer 2000 (Experiment 1: 10× objective; Experiment 2: 20× objective) and analyzed with the Developer Toolbox. For Experiment 2, lysosomal-associated membrane protein 2 (LAMP2) was also counter-stained to identify the LC3A/B puncta that colocalize with lysosome and the data were analyzed by the MetaXpress software (Molecular Devices, version 5.1). The intensity of total (Exp. 1) or LAMP2-colocalized LC3A/B puncta (Exp. 2) was normalized the total numbers nuclei in the fields.

Poly(Q) Toxicity & Viability Analysis.

Viability assays were performed as described before (Aiken et al., 2004). PC12 cells that stably express the inducible poly(Q)103-Htt-EGFP were grown in culture. Ponasterone A (Life Technologies), an ecdysone analog, was added to 10 μM final concentration to induce transgene expression, and formation of puncta was examined and confirmed using the Eclipse 200 fluorescent microscope (Nikon). Cell viability was analyzed 48 hrs later by measuring ATP content with CellTiter-Glo. The parental WT-PC12A cells that do not express the poly(Q)103-Htt-EGFP were used as the negative control to exclude the small molecules that may enhance viability in general.

Lifespan Assays.

Liquid culture-based lifespan assays were performed, following the protocol as described before (Solis and Petrascheck, 2011). Briefly, newly hatched wild-type worms were fed ampicillin-resistant OP50 bacteria (gift from Michael Petrascheck at Scripps) and treated with small molecules (67 μM final concentration, 0.2% DMSO) at the young adult stage. FUdR was used to block progeny production. The molecules were analyzed in 96-well plates, with 4 wells for each small molecule. Multiple control wells with DMSO (0.2% final concentration) were included. Likewise, small molecules were also analyzed for their ability to extend lifespan on solid agar, following procedures as described before (Cabreiro et al., 2013). Hypochlorite-synchronized temperature-sensitive sterile mutants, CF4059, (fer-15(b26) II rol-6(su1006)II; fem-1(hc17)IV), were raised on large agar plates seeded with OP50 bacteria at 25° C. Day 1 adults were transferred onto mini-plates, seeded with OP50 bacteria (UV-irradiated, kanamycin-treated) and supplemented with small molecules (~60 μM final concentration, 0.2% DMSO). Worms were scored every other day. Cumulative survival was analyzed using the STATA software (log-rank test).

We also tested the small molecules (at 67 μM) for their ability to confer H$_2$O$_2$-resistance. The worms were treated with the small molecules in liquid, with H$_2$O$_2$ (500 μM final concentration) added on day 4 of adulthood, and scored for viability everyday In vitro PARP inhibitor assays revealed 10 additional inhibitors of PARP1: Gr-2A, Gr-2B, Gr-2C, Gr-2D (note that these molecules belong to the same structural group, Gr-2), as well as Gr-6A (but not the other members of this group), O1, O3, O4, O12 and O22, among 54 repurchased small molecules.

A total of 11 molecules (Gr-1F, Gr-3A, Gr-3B, Gr-3C, Gr-4D, Gr-7C, O6, O13, O14, O18 and O22) have confirmed human protein targets, including NF-kappaB signaling components.

Characterization and Validation.

Applicants were able to obtain 54 small molecules for the follow-up characterizations. Applicants confirmed 52 fresh molecules by the ATP assay, and further validated 38 by the PI cell-death imaging assay. These 38 molecules then became the "core set" of compounds for further analyses in cells and in nematode Caenorhabditis elegans. A total of 37 of 38 validated molecules also protected primary human dermal fibroblasts (HDFp, isolated from the skin of pooled donors, from Zen-Bio) from H$_2$O$_2$, suggesting that their protective effects are not limited to a specific cell line.

Safety Concerns.

To inquire whether these molecules could adversely affect normal cells, applicants analyzed their effects on two DNA damage-associated cellular markers, phosphorylated histone variant γH2A.X and tumor protein p53 binding protein 1 (TP53BP1). Nine small molecules (Gr-1A, Gr-1C, Gr-1D, Gr-1F—these 4 belong to one structural class, Gr-1, —Gr-3A, Gr-3C, Gr-6C, O21 and O27) increased the percentage of both γH2A.X- and TP53BP1-positive cells in multiple independent assays (in the absence of H$_2$O$_2$). Consistent with these results, of these, 4 molecules (Gr-1C, Gr-1D, Gr-1F and O21) also increased the percentage of propidium iodide-positive (dead) cells under normal conditions.

High-Throughput Oxidative Stress Resistance Small-Molecule Screen.

Applicants used the WI-38 human primary fibroblast cell line for the screen because previous studies demonstrating the peroxide-, cadmium- and methyl methane sulfonate (MMS)-resistance of cells from long-lived mouse mutants and long-lived species employed primary skin fibroblasts (Harper et al., 2007; Harper et al., 2011; Salmon et al., 2005). Not all types of cells derived from long-lived and stress-resistant animals are stress-resistant in culture. Some, such as hepatocytes, are more likely to undergo apoptosis (Kennedy et al., 2003). Likewise, human mammary epithelial cells (HMECs) incubated in IGF-1-deficient serum are sensitized to die when exposed to hydrogen peroxide (Guevara-Aguirre et al., 2011). In addition, primary cells are expected to offer advantages over tumor cells, which, due to the profound heterogeneity of genetic alterations, could behave remarkably differently in a screen.

The initial screen was focused on identifying small molecules that can increase the resistance to hydrogen peroxide using ATP levels initially as a proxy for viability (CellTiterGlo assay). Applicants screened 104,121 small molecules selected to maximize the coverage of chemical space. WI-38 cells of an early population doubling level (PDL) were screened with small molecules at the 10 µM final concentration, a dose that has been shown to produce high structural diversity in many small-molecule screens (Walters and Namchuk, 2003). Applicants selected a three-hour treatment with 700 µM $H_2O_2$, and this condition consistently produced high Z' values. Importantly, small interfering RNAs (siRNAs) against the insulin/IGF-1 signal-transduction gene AKT1 and the NRF2 inhibitor gene KEAP1 both increased stress resistance under these conditions (to hydrogen peroxide, as well as cadmium and MMS) indicating that recovery of these types of perturbations that increase lifespan in animals.

A total of 104,121 compounds were analyzed on 327 microplates, each using DMSO as the negative control (n=16 wells), and the phosphatase inhibitor calyculin (50 nM) as the "positive control" (n=16 wells). The Z' numbers, which are determined by the difference between positive and negative controls and by the extent of variation, were used to evaluate assay robustness. Z' score, defined as 1−[(3× standard deviation of positive controls+3× standard deviation of negative controls)/(mean of positive controls−mean of negative controls)], is used to access the quality of a high-throughput screen assay. A Z' value greater than 0.5 indicates a robust assay, and the average Z' value was determined to be 0.61. A normalization value was calculated for each run (generally ~30 plates) to control for inter-day variation. Molecules were discarded, whereby stimulating proliferation could significantly increase ATP signals in the absence of $H_2O_2$. Altogether, a total of 209 small molecules were isolated (0.2% of molecules tested) that produced signals at least 2.5-fold higher than the DMSO control. We also analyzed these molecules in the absence of $H_2O_2$ and ruled out the possibility that, by stimulating proliferation, they can significantly increase ATP signals. Further testing of the candidates at six different final concentrations (0.6 µM to 20 µM) confirmed 127 small molecules that consistently produced protective effects against $H_2O_2$ at one or more of these doses. (Table 10)

To eliminate false positives that increased ATP levels but not cell viability (Thorne et al., 2010), we carried out a secondary cell-imaging assay. Propidium iodide (PI), a cell non-permeable dye, stains DNA in late apoptotic/necrotic cells when membrane integrity is lost. 107 hits, at 1.25 µM and/or 10 µM, were found to reduce the percentage of PI-positive dead cells, and were retained for analysis (Table 10).

Of 209 candidate hits, at least 40 are derivatives of 8-hydroxyquinoline, a well-known reactive-oxygen species (ROS) scavenger that can protect cells from $H_2O_2$ stress (Wang et al., 2010). Therefore, applicants carried out an ROS scavenger assay, using 2,2-diphenyl-1-picrylhydrazyl (DPPH) (Sharma and Bhat, 2009), a radical-containing purple dye that can be reduced by ROS scavengers. After the ROS-scavenger and PI retests, 61 top hits were identified that passed the retests and did not show obvious ROS scavenger activities. Intriguingly, besides 31 orphan compounds, 30 of these molecules fall into one of seven structural classes (with at least 3 members in one group), suggesting that they may act on common targets in the cells to promote $H_2O_2$-resistance. In addition, the orphan compounds, O7 and O22 are similar to each other, as are O15 and O23.

In multiple independent experiments, applicants confirmed that 52 fresh small molecules could increase the viability of WI-38 cells upon $H_2O_2$ stress. By performing Amplex Red assays, it was verified that the molecules did not quench $H_2O_2$ and excluded this possible explanation for their protective effects (FIG. 1). PI-imaging assays confirmed that 38 molecules could protect WI-38 cells at multiple time points (3, 4, 5 hours) during $H_2O_2$ treatment (Table 11). These 38 compounds also protected primary human dermal fibroblasts (HDFs; isolated from the skin of multiple donors) from $H_2O_2$, suggesting that the protective capacity of these molecules is not limited to the WI-38 cell line. Thus, these 38 small molecules became the core of the following characterizations.

For many stress conditions tested previously, one significant correlation to longevity is the cellular resistance to $H_2O_2$ or $CdCl_2$. Applicants then tested these small molecules, at five different final concentrations (0.25 µM to 20 µM), for cadmium and MMS resistance in WI-38 cells. Two (Gr-6A and O22) of 38 molecules reproducibly conferred multiplex resistance to cadmium, MMS and $H_2O_2$, and 13 did not confer resistance to either cadmium or MMS in the assays used (Tables 5, 8, and 12). 21 molecules increased the resistance to both cadmium and $H_2O_2$ only, likely due to ROS-producing ability of both $H_2O_2$ and heavy metals as seen in Tables described herein.

Potential Toxicity of the Small Molecules.

To predict the long-term effects of our molecules on human cells, we introduced small molecules (at 10 µM final concentration) to WI-38 fibroblasts and assayed for viability by measuring ATP levels during a course of 5 days of continuous treatment (in the absence of $H_2O_2$; the ability of these molecules to promoted $H_2O_2$-resistance was confirmed by testing a portion of the cells on day 2 of treatment). In addition, cell death was scored by PI-imaging on day 2 and day 5 of treatment.

Of 38 "core set" molecules, at least 10, including Gr-1F, Gr-3B, Gr-3C, Gr-6C, Gr-7A, Gr-7C, O11, O21, O23 & O27, reduced the ATP content by more than 30% after 5 days of continuous incubation (Table 13), suggesting potential anti-proliferative activity and/or cell toxicity of these molecules under the conditions tested. Consistent with this interpretation, as indicated by the examination of cell population and morphology, as well as cell death-imaging, 7 molecules (Gr-3B, Gr-6C, Gr-7C, O11, O21 & O27) reduced cell number substantially and increased the fraction of PI-positive dead cells under the conditions tested. Likewise, most cells treated with another two (Gr-7A & O23) were not viable under the tested conditions. In contrast, rapamycin (5 uM), a potent inhibitor of mTOR, reduced the ATP content by ~50%, yet did not significantly increase cell death under the conditions tested.

To ask whether our molecules could adversely affect cells by causing DNA damage, we analyzed their effects on two DNA damage-associated cell markers, phosphorylated histone variant γH2A.X and tumor protein p53 binding protein 1 (TP53BP1). γH2A.X is required for checkpoint-mediated cell cycle arrest and DNA repair following double-stranded DNA breaks. Phosphorylation of γH2A.X by a group of PI3K-like kinases (ATM, ATR, and DNA-PK) occurs rapidly in response to DNA damage (Perez-Cadahia et al., 2010). Likewise, in response to DNA damages, TP53BP1 is phosphorylated and translocated into the nucleus; retention of TP53BP1 at DNA breaks requires phosphorylated γH2A.X (Panier and Boulton, 2014). We found that 9 small molecules [Gr-1A, Gr-1C, Gr-1D, Gr-1F (these 4 belong to one structural class), Gr-3A, Gr-3C, Gr-6C, O21 and O27] increased the percentage of both γH2A.X- and TP53BP1-positive cells under the assayed conditions in at least two independent experiments (Table 14).

We found that 4 of these molecules (Gr-1C, Gr-1D, Gr-1F and O21) increased the percentage PI-positive dead cells under normal conditions (Gr-1C, 3.5±1.3%, P=0.002; Gr-1D, 4.2±1.4%, P=0.001; Gr-1F, 3.3±0.8%, P=3.26E-14; and O21, 1.1±0.4%, P=0.008; vs. control, 0.4±0.2%) (Table 11).

In addition, the PI-positive fraction was also increased for WI-38 cells treated with another 7 small molecules (Gr-1B, 1.0%±0.3%, P=0.006; Gr-1G, 7.1%±1.1%, P=2.09E-05; Gr-7B, 3.6%±0.7%, P=8.77E-05; O11, 1.9%±0.7%, P=0.004; O15, 3.8%±0.7%, P=5.30E-05; O20 0.7%±0.3%, P=0.030; and O23, 2.6%±1.4%, P=0.011), though these did not appear to increase both γH2A.X and TP53BP1 foci in treated cells (Table 14).

In summary, 15 of the 38 molecules (4 of Group 1 but not the other 3 of this group, all 3 of Group 3, all 3 of Group 7, plus other 5 molecules) we chose to study in greater depth kill cells and damage DNA upon longer exposure under the conditions tested. The finding that small molecules that increase stress resistance also damage DNA suggests that they may protect cells from $H_2O_2$ by inducing cell-protective responses, a "hormesis" mechanism. Increased DNA damage could elevate the risk of malignant transformation when affected cells do not undergo senescence and apoptosis. However, even if this is the case, these DNA-damaging small molecules could be valuable, as they may act like certain cytotoxic agents (e.g., doxorubicin) and produce toxicity on highly proliferative tumor cells in vivo. Consistent with this hypothesis, our preliminary data indicated that two small molecules, Gr-7A and Gr-7B, when examined in both WI-38 and other tumor cell lines at a given dose (10 μM), exerted more pronounced toxicity on the HTB-178 lung tumor cells (EGFR+, PIK3CA+, RB1−, TP53−).

Properties of Newly Identified Small Molecules That Increase Oxidative Stress Resistance. We used both MetaDrug data-mining pathway tool (Ekins et al., 2007) and Similarity Ensemble Approach (SEA) statistical method (Keiser et al., 2007) to ask whether any of our compounds resemble known therapeutic drugs. Although the screen library was not designed to contain known drugs, we recovered several PARP (poly-(ADP ribose) polymerase) inhibitors and chalcones.

Screen Hits and Longevity Regulators.

Remarkably, FOXO3A DNA variants have been associated with exceptional human longevity in at least eight different populations around the world, though how these variants exactly affect FOXO3 activity is not known.

We have taken the strategy to identify the first compounds that activate any one of many life-extending pathways. This is a great strength: In animals, FOXO can extend life not only in response to reduced insulin or IGF-1 signaling, but in response to increased activity of AMP kinase (Apfeld et al., 2004; Greer et al., 2007), the heat-shock transcription factor (Hsu et al., 2003; Morley and Morimoto, 2004), certain microRNAs (Smith-Vikos and Slack, 2012), a longevity pathway regulated by the reproductive system (Kenyon, 2010a), and, in some studies, sirtuins (Berdichevsky et al., 2006; Rizki et al., 2011).

Other conditions extend life independently of daf-16/foxo, like increased activity of the SKN-1/NRF2 oxidative-stress and xenobiotic phase II detoxification-regulator. SKN-1/NRF2 promotes longevity in insulin/IGF-1-pathway mutant (Tullet et al., 2008) and calorically restricted worms (Bishop and Guarente, 2007) and in fly keap1 mutants (Sykiotis and Bohmann, 2008). It is activated in long-lived IGF-1-pathway mouse mutants (Steinbaugh et al., 2012), and in long-lived mice lacking the glutathione S-transferase gene mGsta4 (Singh et al., 2010). More recently, constitutive Nrf2-signaling activity has been found to be associated with maximum lifespan potential of several rodent species, including the naked mole rats (Lewis et al., 2015), and enhanced cell signaling via Nrf2 and p53 has been suggested to be protective against spontaneous neoplasia and tumorigenesis in the naked mole rats (Lewis et al., 2012).

The enrichment of NRF2-activating small molecules is consistent with the anti-oxidative role of NRF2, and it may have implications for human aging as well. In human fibroblasts, declined NRF2 function has been shown to occur in replicative senescence and NRF2 silencing led to premature senescence (Kapeta et al., 2010). Conversely, NRF2 activation enhanced the survival of cells following oxidative stress and extended replicative lifespan of human fibroblasts. (Hybertson et al., 2011). Thus, small molecule modulators of the KEAP1-NRF2-ARE pathway could be potential preventive and therapeutic agents (Magesh et al., 2012).

Small Molecule Screen Library.

Applicants screened a "diversity library" that contains 104,121 small molecules (~24K from ChemBridge; ~50K from ChemDiv; and ~30K from SPECS) selected to maximize the coverage of chemical space. These compounds were provided as 10 mM stock by the Small Molecule Discovery Center (SMDC) at UCSF, with information in the database for query purpose. Applicants screened WI-38 cells (human fibroblasts, lung-derived, ATCC, CCL-75) at an early population doubling level (PDL) with 104,121 small molecules selected to maximize the coverage of chemical space. Compounds were provided as 10 mM stocks by the Small Molecule Discovery Center (SMDC), and chemical information, including the structures, simplified molecular-input line-entry system (SMILES) IDs, PubChem links and possible in silico docking, is available for query. Cells were incubated with small molecules, at 10 μM final concentration, for 24 hours and then subject to 700 μM $H_2O_2$ for 3 hours. Applicants identified 209 (0.20%) small molecules that significantly enhanced the viability of $H_2O_2$-stressed cells, by measuring the ATP content (2.5-fold cutoff, normalized to the DMSO negative controls). Applicants retested and confirmed 127 (0.12%) hits, and then, validated 107 (0.10%) by a secondary propidium iodide (PI) cell-death imaging assay for cell viability. Applicants further eliminated potential scavengers of reactive oxygen species (ROS), using the 2,2-diphenyl-1-picrylhydrazyl (DPPH) assay, and confirmed 61 (0.06%) top hits that passed the series of retests. To eliminate false positives that increased ATP levels (Thorne et al., 2010), applicants also carried out a secondary imaging assay for cell viability. Propidium iodide (PI), a cell non-permeable dye, stains DNA in late apoptotic/necrotic cells when membrane integrity is lost. A total of 107 hits, at 1.25 µM and/or 10 µM, were found to reduce the percentage of PI-positive dead cells, with statistically significant effects.

Chemical Data Analysis:

Applicants used the SARvision (CHEMapps) software and found that, of 61 top hits, 30 molecules fall into 7 structurally related chemical groups (with at least 3 members in one group), suggesting that they may promote stress resistance by acting on common targets. In addition, O7 and O22, as well O15 and O23, are similar to each other. These molecules were named according to their respective groups, for example, Gr-1A, Gr-1B, etc; and the other orphan molecules as O1, O2, etc. Applicants used both the MetaDrug data-mining pathway tool and the Similarity Ensemble Approach (SEA) statistical method to ask whether any of our compounds resembles a known therapeutic drug. Although the screen library was not designed to contain known drugs, several PARP [poly-(ADP ribose) polymerase] inhibitors and chalcones were recovered.

Cell Culture & $H_2O_2$-Resistance Screen.

Human fetus lung-derived WI-38 cells (ATCC) at an early population doubling level (PDL ~30; these cells reach complete senescence at PDL ~50) were used for the screen. To reduce the influence of culture variations, sufficient amount of cells of the same PDL (initial PDL ~23) were propagated, frozen as stocks in liquid nitrogen, and then used later for the whole screen as well as for subsequent characterizations of isolated small molecules.

Cells were cultured in OptiMEM (Life Technologies) supplemented with 10% fetal bovine serum (FBS). In a 384 multi-well format, ~2,000 cells were added per well by WellMate (Thermo Fisher) liquid dispenser and cultured in a $CO_2$ incubator at 37° C. for 24 hours. Then small molecules were introduced from stock plate with pin-tool on a Biomek FXP (Beckman) automation workstation at 10 µM final concentration, 0.1% DMSO. Twenty four hours later, the cells were subject to a three-hour treatment with 700 µM $H_2O_2$, and CellTiter-Glo reagent (Promega) was added at the end and the luminescence signals were analyzed using an Analyst HT plate reader (Molecule Devices). Control seeding plates were always prepared and analyzed for ATP content in the end. In the absence of $H_2O_2$, the variation is typically less than 10%.

$CdCl_2$ and MMS Resistance Assays.

The setups on 384-well plates and incubation times were the same as for $H_2O_2$ until the time of incubation with the stressors, which was 12 hours for both cadmium and MMS assays. Applicants tested several conditions, including conditions used to assay fibroblasts from long-lived animals (Salmon et al., 2005). These conditions produced better results with the positive controls (KEAP1 and AKT1 siRNAs) in the MMS assay. Thus, for MMS, the cells were shifted from growth media—OptiMEM+10% FBS, to DMEM (Gibco)+2% BSA (no serum) just before adding small molecules, which occurred 24 hours before MMS addition.

Isolated small molecules were tested for MMS and cadmium resistance twice in two independent assays. Each small molecule was analyzed at five different concentrations (0.25 µM to 20 µM final concentration), with technical triplicates for each dose. Data were analyzed using a global variance t-test.

DPPH Assay.

The assay was performed, following procedures as described in a review (Sharma and Bhat, 2009). DPPH (Sigma) stock solution (25 mM) was prepared in methanol and diluted to 50 µM in acetic acid-buffered methanol (0.1 M, pH 5.5). 50 µl solution was dispensed by WellMate liquid dispenser onto three 384-well plates (technical triplicates). 209 primary hits were introduced onto the 384-well assay plates by pin-tool on a Biomek FXP automation workstation at 10 µM final concentration. Plates were sealed and incubated in a humid chamber at 30° C. in dark. Absorbance at 519 nm was measured on a FlexStation 3 multi-mode microplate reader (Molecular Devices) 3 hrs and 24 hrs later. Several known ROS scavenager, including N-acetyl cysteine (NAC), amodiaquin dihydrochloride (AmD) and 8-hydroxyquinoline quinoline (Sigma), were used as the controls and assayed at several doses (1 µM, 10 µM, 100 µM). These controls, at 10 µM final concentration, could reduce the readings (normalized to DMSO negative control) by ~20% to 50% in 3 hrs. Small molecules that consistently reduced the absorbance by 10% or more were considered as potential ROS scavengers.

Imaging Analysis.

WI-38 cells were seeded on 384-well plates for 24 hrs and then incubated with small molecules for 24 hrs. $H_2O_2$ (700 µM final concentration) prepared in OptiMEM or OptiMEM only was added and incubated further for 3 hours, and Hoechst 33342 (Life Technologies) (10 µg/ml final concentration) and propidium iodide (Life Technologies) (2.5 µM final concentration) were added for the last 30 minutes. Images were collected on an INCell Analyzer 2000 (GE) and analyzed with the Developer software. In a typical $H_2O_2$-stress assay, ~23.7±6.9% DMSO-treated control cells scored positive for propidium-iodide staining (~1.0±0.8% for non-stressed cells).

DNA Damage Marker Analysis.

WI-38 cells were seeded on 96-well plates and cultured for 24 hrs and then incubated with small molecules for another 24 hrs. As the positive control to damage DNA, $H_2O_2$ was supplemented at 700 µM final concentration for the last 3 hrs. Cells were washed with phosphate-buffered saline (PBS), fixed with 4% paraformaldehyde and then blocked with 5% normal goat serum (Cell Signaling), plus 0.3% Triton X-100, for 1 hr. Primary antibody cocktail (rabbit anti-phospho-histone γH2A.X (Ser-139), 1:100; anti-phospho-TP53BP1 (Ser-1778), 1:100), prepared in 1% BSA and 0.3% Triton X-100/PBS, was then introduced and incubated overnight at 4 C. Next day, samples were washed with PBS and further incubated with fluorophore-conjugated secondary antibody (1:1,000) for 1 hr in the dark. Samples were then washed and incubated with DAPI dye (Life Technologies) (4 µg/ml final concentration) for the last 10 minutes. Images were collected on an INCell Analyzer 2000 (GE) and analyzed with the Developer software. In a representative experiment, the percentages of cells that scored positive for these DNA damage markers were: γH2A.X: DMSO, ~1.7±0.4%; $H_2O_2$, ~50.9±4.2%. TP53BP1: DMSO, ~1.0±0.2%; $H_2O_2$, ~45.8±5.1%.

WI-38 cells were seeded (~8,000 cells per well) on 96-well plates and cultured for 24 hrs and then incubated with small molecules for another 24 hrs. Doxorubicin (300 nM, 24 hrs) and $H_2O_2$ (700 µM, 3 hrs) were also introduced as the positive controls to damage DNA. Cells were washed with phosphate-buffered saline (PBS), fixed with 4% paraformaldehyde for 30 min and then blocked with 5% normal goat serum (Cell Signaling) and 0.3% Triton X-100 for 1 hr. Primary antibody cocktail (Cell Signaling, rabbit anti-phospho-histone γH2A.X (Ser-139), 1:100; anti-phospho-TP53BP1 (Ser-1778), 1:100) was prepared in PBS with 1% BSA and 0.3% Triton X-100 and incubated overnight at 4° C. Next day, samples were washed with PBS and further incubated with fluorophore-conjugated secondary antibody (1:1,000) for 1 hr in dark. Samples were then washed and incubated with DAPI dye (Life Technologies) (4 µg/ml final concentration) for 30 minutes. Images were collected on the INCell Analyzer 2000 (10× objective) and analyzed with the Developer Toolbox. Cells that showed immuno-staining intensity above a software-defined threshold were scored.

AmplexRed Assay.

The assay was performed using the Amplex Red Hydrogen Peroxide/Peroxidase Assay Kit (Life Technologies), following manufacturer's instructions. Briefly, small molecules (at 10 µM final concentration) were pre-incubated with 700 µM $H_2O_2$ in water for 3 hrs in a 37° C. $CO_2$ incubator. Amplex Red reagent was mixed with horseradish peroxidase (HRP) in buffer and then incubated with 1:10 diluted small molecule/$H_2O_2$ mixture for 30 min in dark. Fluorescence at 590 nm was measured on a FlexStation 3 multi-mode microplate reader (Molecular Devices).

The objective of this example is to screen for a cellular phenotype that is common to cells from many long-lived animal mutants, and from long-lived species of mammals and birds to identify resistance to multiple forms of environmental stress. A total of 104,121 small molecules were screened for their ability to protect primary human fibroblasts from a lethal dose of hydrogen peroxide, and then approximately 60 hits were reexamined for their ability to protect cells from the DNA-damaging agent MMS and the heavy metal cadmium. Many of these compounds conferred resistance to multiple stressors, and a number inhibited TOR activity and appeared to affect FOXO3 and/or NRF2 activities, and/or extended C. elegans' lifespan.

Recently, it has been realized that pan assay interference compounds (PAINS), due to their reactive chemical features, could introduce promiscuous results and misleading readouts in chemical screens (Baell and Walters, 2014; Baell and Holloway, 2010). After examination of the small molecules, 7 of 61 screen hits as well as 5 of 38 validated hits (Gr-6C, O6, O15, O21 and O23), contained at least part of the PAINS moieties (Tables 1a-1f, and Table 5). Of these, Gr-6C contains a rhodanine moiety and O23 shows both enone and catechol structures, and they extended C. elegans' lifespan in 3 of 3 and 3 of 4 trials, respectively. O6 (phenolic Mannich base) and O15 (enone) induce both HMOX1 and NQO1 by more than 1.5-fold. In fact, O15 induced HMOX1 by almost 50-fold and it also protected worms from hydrogen peroxide. O21, with rhodanine structure, scored positive for DNA-damage markers and promoted $H_2O_2$-resistance in a NRF2-dependent fashion.

The screen did not enrich for PAINS (P=0.068, hypergeometric distribution probability, for all 61 hits). Certain molecules identified as PAINS-like, in that they enhance stress resistance, induce expression of FOXO3- and NRF2-regulated genes, and extend the lifespan of C. elegans. In this regard, these PAINS-like molecules may produce global benefits, a specific biological context, in the whole animal.

Screen Hits and Longevity Regulators.

This screen was designed to isolated small molecules that promote resistance to multiplex stress, and of the top 38 hits, a number of molecules had effects on several key regulators of aging, including FOXO3 (3), NRF2 (14) and mTOR (4).

The rate of aging can be influenced by many factors, including a network of signaling proteins and transcription factors that also sense nutrients, energy levels and stress. Perturbing many genes in this network can extend healthy youthfulness and increase disease-resistance and lifespan (Bartke, 2011; Fontana et al., 2010). The insulin/IGF-1 pathway, which regulates growth and metabolism, was the first lifespan pathway to be identified (Kenyon et al., 1993).

Mutations in the Insulin/IGF-1-receptor daf-2 gene doubled the lifespan of C. elegans, in a manner that requires daf-16 (Kenyon et al., 1993), which encodes a FOXO transcription factor that extends lifespan by regulating a diverse collection of cell-protective, proteostasis, metabolic, innate-immunity and other genes (Murphy et al., 2003). This endocrine regulation of has been shown to be conserved among many different experimental animals (Kenyon, 2010b).

In humans, in a population of Ashkenazi Jews, partial loss-of-function IGF-1-receptor mutations (Tazearslan et al., 2011) and other IGF-1-pathway mutations (Yousin Suh, pers. comm.) are more frequently found in centenarians. Similarly, a pathway-level analysis of GWAS longevity data highlighted core insulin and IGF-1-pathway genes (Deelen et al., 2013). Remarkably, FOXO3A DNA variants have been associated with exceptional human longevity in at least eight different populations around the world, though how these variants exactly affect FOXO3 activity is not known.

We have taken a strategy to identify the first compounds that activate any one of many life-extending pathways. This is a great strength: In animals, FOXO can extend life not only in response to reduced insulin or IGF-1 signaling, but in response to increased activity of AMP kinase (Apfeld et al., 2004; Greer et al., 2007), the heat-shock transcription factor (Hsu et al., 2003; Morley and Morimoto, 2004), certain microRNAs (Smith-Vikos and Slack, 2012), a longevity pathway regulated by the reproductive system (Kenyon, 2010a), and, in some studies, sirtuins (Berdichevsky et al., 2006; Rizki et al., 2011).

Other conditions extend life independently of daf-16/foxo, like increased activity of the SKN-1/NRF2 oxidative-stress and xenobiotic phase II detoxification-regulator. SKN-1/NRF2 promotes longevity in insulin/IGF-1-pathway mutant (Tullet et al., 2008) and calorically restricted worms (Bishop and Guarente, 2007) and in fly keap1 mutants (Sykiotis and Bohmann, 2008). It is activated in long-lived IGF-1-pathway mouse mutants (Steinbaugh et al., 2012), and in long-lived mice lacking the glutathione S-transferase gene mGsta4 (Singh et al., 2010). More recently, constitutive Nrf2-signaling activity has been found to be associated with maximum lifespan potential of several rodent species, including the naked mole rats (Lewis et al., 2015), and enhanced cell signaling via Nrf2 and p53 has been suggested to be protective against spontaneous neoplasia and tumorigenesis in the naked mole rats (Lewis et al., 2012).

The enrichment of NRF2-activating small molecules is consistent with the anti-oxidative role of NRF2, and it may have implications for human aging as well. In human fibroblasts, declined NRF2 function has been shown to occur in replicative senescence and NRF2 silencing could lead to premature senescence (Kapeta et al., 2010). Conversely, NRF2 activation could enhance the survival of cells following oxidative stress and extended replicative lifespan of human fibroblasts. Thus, small molecule modulators of the KEAP1-NRF2-ARE pathway could be potential preventive and therapeutic agents (Magesh et al., 2012).

Potential Mechanism(s) of Action.

At least 11 small molecules (Gr-1F, Gr-3A, Gr-3B, Gr-3C, Gr-4D, Gr-7C, O6, O13, O14, O18 and O22) have been identified with confirmed human protein targets (Tables 1a-1f). Besides, the behavior of these molecules appeared to be rather different form other outstanding PAINS that present overwhelmingly in different bioassays. A summary of compounds and targets are located in Table 2 and Table 9.

NF-kappaB Signaling. Of 11 molecules with potential targets, Gr-3C had been identified as a molecule that induced the NF-kappaB inhibitor NFKBIA in two screens ($EC_{50}$, 8.5

μM and 11.0 μM), coherent with its role as an RELA inhibitor (IC$_{50}$, 2.0 μM) in HUVEC cells in another study. These studies also isolated and confirmed Gr-3A (EC50, 11.0 μM and 12.0 μM) as an NFKBIA-inducing compound. These results are consistent with in silico docking analysis, using the ZINC software (Irwin et al., 2012), which predicted that Gr-3C could bind to both NFKBIA and RELA. Interestingly, applicants have found that siRNA knockdown of NFKB2, a related member of the NF-kappaB/REL family (Chen and Greene, 2004), promoted H$_2$O$_2$-resistance in our siRNA screen.

NF-kappaB signaling pathway controls cell survival, differentiation, and proliferation. Key components of the pathway have been shown be crucially involved in inflammation (Lawrence, 2009) and have been implicated in many diseases, including cancer, autoimmune diseases, neurodegenerative diseases, cardiovascular diseases, and diabetes, etc (Hayden and Ghosh, 2012). Recently, prevention of aging-related hypothalamic or brain IKK-beta and NF-kappaB activation has been shown to retard aging and extend lifespan in mice (Zhang et al., 2013), providing more evidence to highlight the significance of chronic inflammation in aging (Jenny, 2012; Salminen et al., 2008). Given these notes, our small molecules that could inhibit NF-kappaB signaling may provide the reagents for future analysis in animals. In fact, it is noted that all three molecules could extend *C. elegans*' lifespan (3 of 3 trials, ~8% to 33%).

Cancer.

Many long-lived animal mutants are resistant to age-related diseases (Le Couteur et al., 2012), including cancer (Ikeno et al., 2009), protein-aggregation diseases (Cohen et al., 2009; Morley et al., 2002) and heart disease (Birse et al., 2010; Harrington et al., 2007; Wessells et al., 2004). Thus, the small molecules sought after may counter multiple age-related diseases. Different species in nature have very different lifespans, but within each, the elderly are most susceptible to cancer. This correlation in nature between slow aging and delayed cancer suggests that the same pathways that slow aging may antagonize cancer, and, in fact, many longevity pathways have anti-cancer activity. Importantly, these pathways inhibit a wide variety of cancers, which is predicted for our small molecules. Preliminary data indicated that two small molecules (Gr-7A and Gr-7B, both of which demonstrating mTOR-inhibiting activities, at 10 μM) could significantly reduce the viability of the HTB-178 lung tumor cells. Furthermore, another small molecule (O17, at 5 μM) could significantly reduce cell viability in two breast cancer-derived tumor cell lines that harbor different sets of mutations.

Example 2. PARP Modulating Compounds

PARP Inhibitors.

PARP mediates the cellular responses and executes the actions to different stress signals upon many types of stresses (oxidative, genotoxic, inflammatory, metabolic, etc) (Luo and Kraus, 2012). PARP inhibitors, by preventing PARP from diverting NAD+ to the synthesis of poly(ADP-ribose), could significantly modulate the stress-related consequences, from cell death, tissue damage, to age-associated dysfunction and oxidative damage-related pathologies. PARP inhibitors can also kill certain tumor types because of their effects on DNA repair pathways (Chan et al., 2010; Mason et al., 2014; Rouleau et al., 2010), and specifically, they have been shown to be effective in clinical trials among cancer patients carrying BRCA1/2 mutations (Fong et al., 2009).

PARP inhibition is known to increase resistance to DNA-damaging agents such as hydrogen peroxide (Zhang et al., 2007). (Banasik et al., 1992), (Costantino et al., 2001). By in vitro assays for PARP inhibition, we identified, from the 38 "core set" hits, Gr-6A (but not the other members of this group), O1, O14 and O22 (structurally similar to O7) as inhibitors of PARP1 (FIG. 2) When we extended the analysis to the other members of the original group of 54 molecules, we found, besides O7, additional PARP inhibitors as well (Gr-2A, Gr-2B, Gr-2C, Gr-2E—note that these molecules belong to the same structural group, O3 and O4). All 11 PARP inhibitors preserved ATP upon H$_2$O$_2$ stress.

Recently, several studies have revealed very interesting features of PARP inhibition in the perspective of promoting health. First, deletion of Parp1 has been shown to increase mitochondrial metabolism through NAD+ preservation and SIRT1 activation and protect animals from metabolic disease (Bai et al., 2011). Second, long-term treatment with PARP inhibitors has been found to enhance mitochondrial functions and improve fitness of skeletal muscles in mice, and also, reverse mitochondrial defects in primary myotubes of obese humans and attenuate metabolism defects in NDUFS1 mutant fibroblasts (Pirinen et al., 2014). Third, disruption of the worm orthologue pme-1, as well as PARP inhibitors, could induce the mitochondria unfolded protein response (mtUPR) and extend lifespan in a manner that requires both sir-2.1 and daf-16/foxo in *C. elegans* (Mouchiroud et al., 2013). Consistent with the previous reports, applicants also found that several of the identified PARP inhibitors extended *C. elegans*' lifespan (for example, O7, ~10%-34%, 4 of 4 trials; O14, ~10% or more, 3 of 3 trials).

PARP Inhibitors & Protein SUMOylation.

The isolation of multiple PARP-inhibiting small molecules, including several with structures distinct from known classes of PARP inhibitors, is consistent with the role of PARP in DNA damage response. Inhibition of PARP-1 has been shown to preserve ATP levels and improve antioxidant status, and maintain anti-apoptotic Bcl-x levels in the kidney following chemotherapy-induced injury (Weaver and Yang, 2013). Consistent with the recent findings of PARP inhibition-associated benefits, preservation of NAD+, which declines with age, has also been shown to restores mitochondrial function in muscles of aged mice (Gomes et al., 2013). Interestingly, the neuroprotective P7C3 aminopropyl carbazole chemicals have been shown to, by activating NAMPT and improving NAD+ salvage, promote survival of neurons in rodent models of neurodegeneration or nerve cell injury (Wang et al., 2014a). Here, the DNA-damaging doxorubicin has been shown to reduce intracellular NAD+ levels, most likely by activating PARP. In addition, PARP-1, via activation of NF-kappaB, has been shown to enhance amyloid beta peptide-induced neuronal damages (Martire et al., 2013). PAPR inhibition could attenuate ischemia/reperfusion-induced neurodegeneration in the retina (Li et al., 2012) and reduce alpha-synuclein- and MPP+-induced cytotoxicity in a cellular model of Parkinson's disease (Outeiro et al., 2007). These findings have suggested potential neuroprotective effects of PAPR inhibitors in neurodegenerative diseases.

Two molecules (Gr-1F and O13) have been identified in other screens and confirmed to inhibit SUMO/sentrin specific peptidases (SENPs) (Gr-1F: SENP6, 2 screens, ~80% inhibition at 10.0 μM or 12. μM; SENP7, 2 screens, ~90% inhibition at 5.0 μM or 12. μM; SENP8, 3 screens, ~60%-

80% inhibition at 10.0 µM to 12. µM. O13: SENP6, 2 screens, ~50% inhibition at 10. µM or 12. µM; SENP8, 1 screen, ~50% inhibition at 20. µM). Small ubiquitin-related modifiers (SUMOs) are ubiquitin-like proteins that can be covalently attached to a variety of target proteins (Geiss-Friedlander and Melchior, 2007). SENPs, a class of SUMO-specific proteases, are required to remove SUMOylation modification of target proteins, which affect many cellular processes, including apoptosis, DNA damage repair, ribosome maturation, and transcription, etc (Hickey et al., 2012; Yeh, 2009). SUMOylation of many proteins increases greatly following certain cellular stresses, such as heat shock and hydrogen peroxide (Zhou et al., 2004), yet the underlying mechanisms and cellular consequences are not fully understood. Perturbed SUMOylation balance has been implicated in various diseases including cancer, atherosclerosis and heart diseases, and the designing and developing of novel SENP inhibitors have gained increased interests recently (Kumar and Zhang, 2015).

The concurrent isolation of PARP inhibitors and potential SUMO-modulators in this screen could be interesting. It is known that SUMOylation of PARP could block its acetylation and restrain the consequent activation of NF-kappaB (Messner et al., 2009). Thereby, SENP inhibitors are expected to, by maintaining SUMOylation levels, block PARP-mediate NF-kappaB activation. In addition, it has been shown that senescent cells develop a PARP-1 and NF-kappaB-associated secretome (PNAS), and inhibition of PARP-1 or NF-kappaB prevents the pro-invasive properties of the secretome (Ohanna et al., 2011).

PARP Inhibitors.

PARP mediates the formation of poly(ADP-ribose) in response to various cellular stresses (oxidative, genotoxic, inflammatory, metabolic, etc) (Luo and Kraus, 2012), thereby initiating protective DNA-repair and other processes. PARP inhibitors, by preventing PARP from diverting $NAD^+$ to the synthesis of poly(ADP-ribose), can significantly modulate consequences of stress, affecting cell death, tissue damage, and age-associated dysfunction and oxidative damage-related pathologies. PARP inhibitors can also kill certain tumor types because of their effects on DNA repair pathways (Chan et al., 2010; Mason et al., 2014; Rouleau et al., 2010); specifically, they have been shown to be effective in clinical trials among cancer patients carrying BRCA1/2 mutations (Fong et al., 2009).

Figure 2:
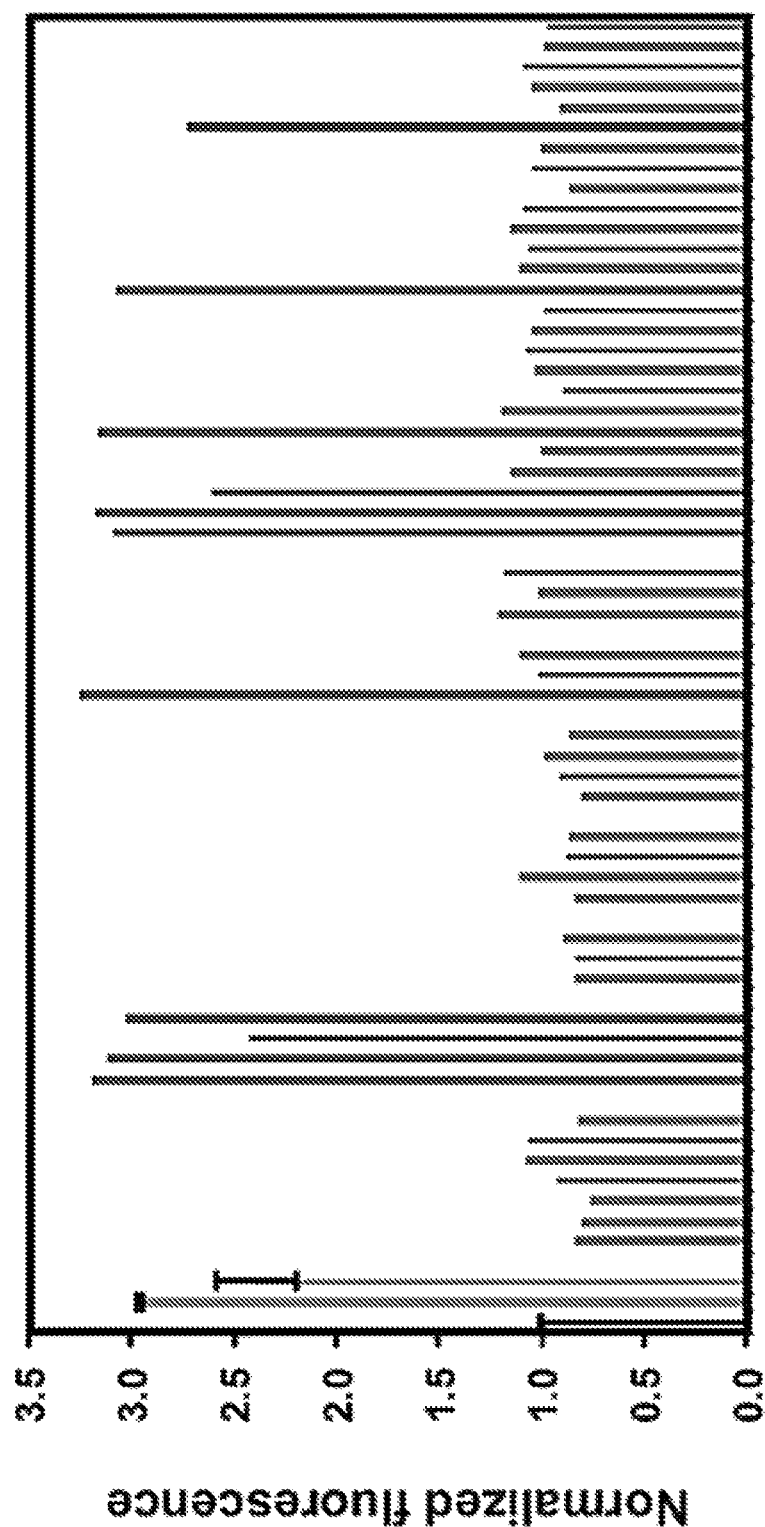
FIG. 2. Certain small molecules inhibit the activity of human PARP1. Two known PARP inhibitors, including PJ-34 (Tocris) ($IC_{50}$: ~20 nM) and MK-4827 ($IC_{50}$: ~3.8 nM), were used as the controls at 200 nM and 40 nM, respectively. 11 of the 54 repurchased molecules inhibited PARP1. Note that all the molecules from Group 2, plus the 4-amino-1,8-naphthalimide PARP inhibitor analogs O7 and O22, were confirmed as PARP inhibitors by this assay. Molecules tested in this assay (as identified on the x axis) are in order left to right: Control, PJ34, MK-4827, Gr-1A, Gr-1B, Gr-1C, Gr-1D, Gr-1E, Gr-1F, Gr-1G, Gr-2A, Gr-2B, Gr-2C, Gr-2D, Gr-2E, Gr-3A, Gr-3B, Gr-3C, Gr-4A, Gr-4B, Gr-4C, Gr-4D, Gr-5A, Gr-5B, Gr-5C, Gr-5D, Gr-6A, Gr-6B, Gr-6C, Gr-7A, Gr-7B, Gr-7C, O1, O2, O3, O4, O5, O6, O7, O8, O9, O10, O11, O12, O13, O14, O15, O16, O17, O18, O19, O20, O21, O22, O23, O24, O25, O26, and O27, respectively.

PARP inhibition is known to increase resistance to DNA-damaging agents such as hydrogen peroxide (Zhang et al., 2007). (Banasik et al., 1992), (Costantino et al., 2001). By in vitro assays for PARP inhibition, we identified, from the 38 "core set" hits, Gr-6A (but not the other members of this group), O1, O14 and O22 (structurally similar to O7) as inhibitors of PARP1 (FIG. 2). When we extended the analysis to the other members of the original group of 54 molecules, we found, besides O7, additional PARP inhibitors as well (Gr-2A, Gr-2B, Gr-2C, Gr-2E—note that these molecules belong to the same structural group, O3 and O4). All 11 PARP inhibitors preserved ATP upon $H_2O_2$ stress.

Recently, several studies have revealed very interesting features of PARP inhibition with potential health benefits. First, deletion of Parp1 has been shown to increase mitochondrial metabolism through $NAD^+$ preservation and SIRT1 activation and to protect animals from metabolic disease (Bai et al., 2011). Second, long-term treatment with PARP inhibitors has been found to enhance mitochondrial function and improve fitness of skeletal muscles in mice. Moreover, PARP inhibition can reverse mitochondrial defects in primary myotubes of obese humans and attenuate metabolic defects in NDUFS1-mutant fibroblasts (Pirinen et al., 2014). Third, disruption of the C. elegans PARP orthologue pme-1, as well as PARP inhibitors, could induce the mitochondria unfolded protein response (mtUPR) and extend lifespan in a manner that requires both sir-2.1 and daf-16/foxo (Mouchiroud et al., 2013). Consistent with these previous reports, we found that several of our PARP inhibitors extended C. elegans' lifespan (specifically, O7, ~10%-34%, 4 of 4 trials; and O14, ~10% or more, 3 of 3 trials).

PARP Inhibitor Assay.

The assay was performed with the HT Fluorescent Homogeneous PARP Inhibition Assay Kit (Trevegen), following manufacturer's instructions. Briefly, nicotinamide adenine dinucleotide, human PARP1 and activated-DNA solution was added onto a 96-well plate. 54 repurchased small molecules, at 10 µM final concentration, were introduced onto the 96-well assay plate and incubated in a humid chamber at room temperature for 30 min in dark. Cycling mixture, with resazurin and cycling enzyme diaphorase, was then added and incubated further for 1 hr in dark. Reaction was stopped by adding the stopping buffer. Fluorescence was measured on a FlexStation 3 multi-mode microplate reader (544 nm excitation/590 nm emission). Two known PARP inhibitors, including PJ-34 (Tocris) ($IC_{50}$: ~20 nM) (200 nM) and MK-4827 ($IC_{50}$: ~3.8 nM), were used as the controls at 200 nM and 40 nM, respectively. These PARP inhibitors could increase the readings to 2.4- to 3.0-fold (normalized to DMSO negative control).

14 identified PARP inhibitors, including the 4-amino-1, 8-naphthalimide analog, represented a significant fraction of our total 61 hits. A few validated PARP inhibitors, consistent with previous reports, extended C. elegans' lifespan (for example, O7, ~10%-34%, 4 of 4 trials; O14, ~10% or more, 3 of 3 trials). Furthermore, some of these are structurally different from known PARP inhibitors and do not appear to have been identified by others. PARP inhibitors have been tested in clinical trials, particularly for cancer patients carrying mutation in the BRCA1 and BRCA2 DNA repair genes. Recently, several studies have revealed very interesting features of PARP inhibition in the perspective of promoting health, and our findings of novel PARP inhibitors could provide us with the necessary reagents to pursue this possibility.

Recently, several studies have revealed very interesting features of PARP inhibition with potential health benefits. First, deletion of Parp1 has been shown to increase mitochondrial metabolism through $NAD^+$ preservation and SIRT1 activation and to protect animals from metabolic disease (Bai et al., 2011). Second, long-term treatment with PARP inhibitors has been found to enhance mitochondrial function and improve fitness of skeletal muscles in mice. Moreover, PARP inhibition can reverse mitochondrial defects in primary myotubes of obese humans and attenuate metabolic defects in NDUFS1-mutant fibroblasts (Pirinen et al., 2014). Third, disruption of the C. elegans PARP orthologue pme-1, as well as PARP inhibitors, could induce the mitochondria unfolded protein response (mtUPR) and extend lifespan in a manner that requires both sir-2.1 and daf-16/foxo (Mouchiroud et al., 2013). Consistent with these previous reports, we found that several of our PARP inhibitors extended C. elegans' lifespan (specifically, O7, ~10%-34%, 4 of 4 trials; and O14, ~10% or more, 3 of 3 trials).

Example 3. Chalcones

Chalcones.

Chalcones are aromatic ketones (1,3-diaryl-2-propen-1-ones). They have many beneficial health effects, including anti-cancer, anti-HIV, anti-malarial, anti-inflammatory, and anti-allergic activities (Batovska and Todorova, 2010; Sahu et al., 2012). Chalcones have a wide variety of molecular targets, many of which have relevance for cancer, which could explain their anti-proliferative activities against cell lines derived from many types of tumors (Solomon and Lee, 2012; Yadav et al., 2011). Several proteins, including HSF-1, FOXO3 and NRF2, as well as the chaperone machinery, have been shown to mediate the beneficial effects of chalcones.

The 104,121-compound library contained 71 chalcones, with exact core structure match. Of these, 4 were in our top 61 $H_2O_2$-resistant hits (Gr-4A, Gr-4B, Gr-4C and Gr-4D—the chalcone group), and one of these, Gr-4D (see Table 1a-1f) appeared particularly interesting, as it could induce both FOXO3- and NRF2-regulated genes. This molecule also increased lifespan (up to ~50%, 4 of 4 trials) consistently in worms. (Table 7). (Calamini et al., 2012). Several proteins, including HSF-1, FOXO3 and NRF2, as well as the chaperone machinery, have been shown to mediate the beneficial effects of chalcones. Likewise, the effects of our chalcone compounds on these key regulators of stress response may explain, at least in part, the benefits that we have observed in cells and in worms.

Example 4. FOXO Modulating Compounds

Effects on Longevity-Modulating Proteins.

Applicants examined our molecules in many cellular assays to score them in the context of aging. Specifically, it is important to understand whether these molecules could activate proteins, including FOXO3 and NRF2, known to extend lifespan, inhibit mTOR (another potential cause of life extension), induce autophagy (strong association with longevity in experimental species), and/or attenuate toxic protein aggregation, etc.

qPCR Analysis & FOXO3 & NRF2 Interference.

For qPCR analysis, WI-38 cells were treated with small molecules (at 10 µM) (biological quadruplicate) for 24 hrs and processed for RNA isolation and reverse transcription (RT) with the Cells-to-Ct Kit (Life Technologies), following manufacturer's instructions. RT products were diluted with $H_2O$ and used for qPCR analysis on a LightCycler 480 system (Roche) (technical triplicates). Relative expression levels of target genes were normalized to the genes B2M, PPIA and GAPDH. To knock down the expression of FOXO3 or NRF2, WI-38 cells were transfected with siRNA oligos (at 10 nM final concentration) for FOXO3 (Life Technologies) or NRF2 on 10-cm petri dish for 36 hrs, and then detached and aliquoted onto 96-well plates. ~24 hrs later, small molecules were introduced and incubated with cells for 24 hrs. Cells were then processed with the Cells-to-Ct Kit to prepare RT products for qPCR analysis. The knockdown efficiency of FOXO3 or NRF2 was checked at 36 hrs post-transfection and at the end as well.

qPCR analyses indicated that 13 molecules (Gr-1A, Gr-1B, Gr-1C, Gr-1E, Gr-4A, Gr-4C, Gr-4D, O11, O12, O13, O14, O15, O20) could produce significant induction of at least two (of five selected) representative FOXO3-regulated genes. Another 3 (Gr-7A, Gr-7C and O23) could induce robust expression (greater than 1.5-fold) of at least 2 FOXO3 target genes. By analyzing stress resistance upon FOXO3-knockdown, applicants also found that at least 4 molecules (Gr-7A, Gr-7C, O15 and O20) required FOXO3 to promote $H_2O_2$-resistance of WI-38 cells (in at least 2 of 3 independent experiments).

Many perturbations that increase lifespan and stress resistance in animals do so in a FOXO-dependent fashion (Kenyon, 2010c). Humans have several FOXO genes, but FOXO3, which promotes stress resistance in mammalian cell culture (Kops et al., 2002; Nemoto and Finkel, 2002; Tran et al., 2003), is the one that has been linked to exceptional longevity in humans (Anselmi et al., 2009; Flachsbart et al., 2009; Li et al., 2009; Pawlikowska et al., 2009; Soerensen et al., 2010; Willcox et al., 2008). FOXO1, in contrast, appears to be responsible for some symptoms of diabetes in mouse models (Cheng and White, 2011). For this reason, applicants have focused on analyzing potential ability of our small molecules to activate FOXO3. Of 38 small molecules, we found 10 (Gr-1A, Gr-1B, Gr-1E, Gr-4A, Gr-4C, Gr-4D, O11, O13, O15, O20) that produced significant, induction of at least two of five FOXO3-regulated genes analyzed, including SOD2 (superoxide dismutase), GADD45A (cell cycle regulator), CAT (catalase), DDB1 (damage-specific DNA binding protein), and TXNIP (thioredoxin interacting protein) (Table 1a-1f). Another 4 molecules (Gr-7A, Gr-7C, O12 and O23) could induce robust expression (greater than 1.5-fold) of at least 2 FOXO3 target genes.

Figure 3:
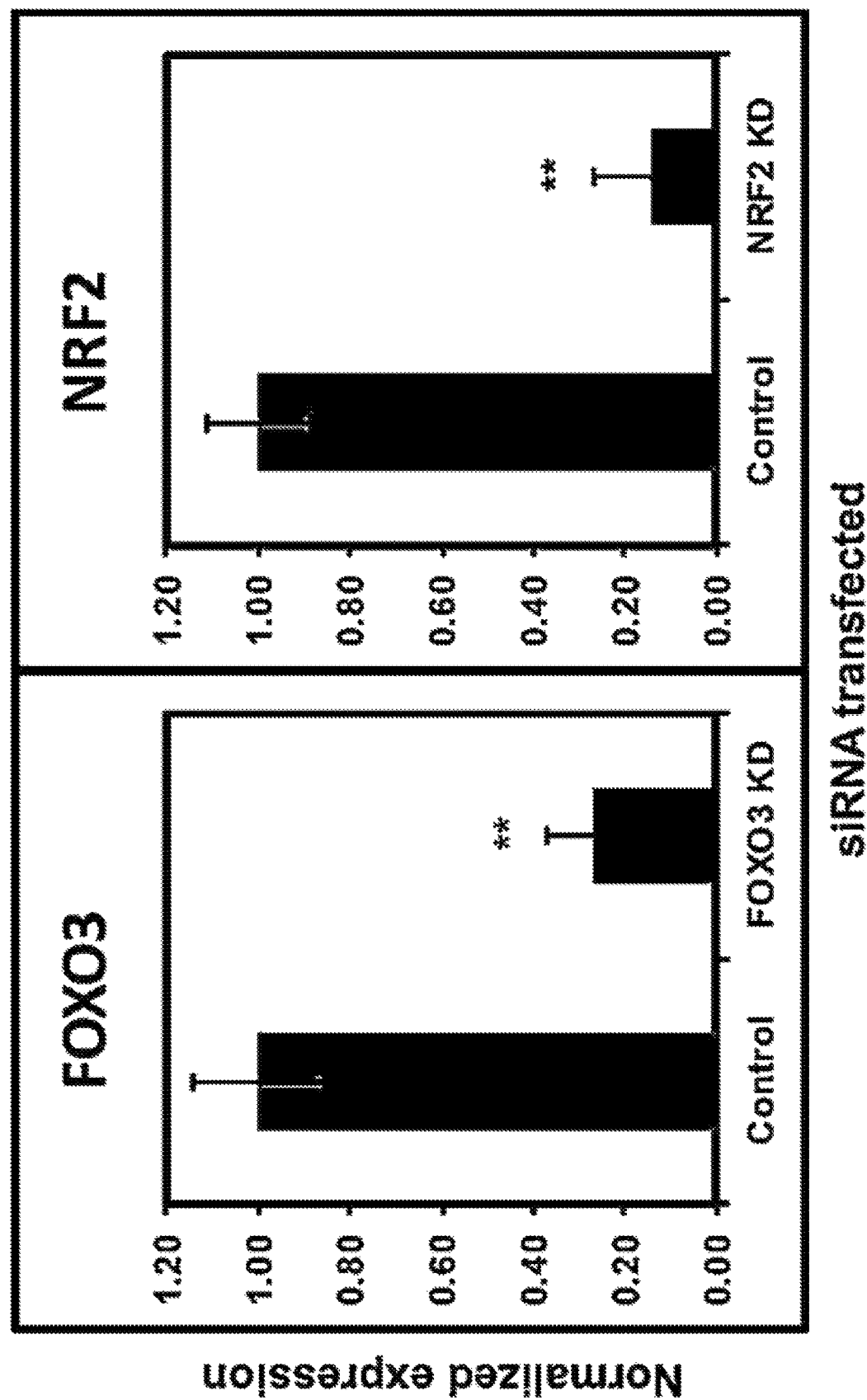
FIG. 3. Knockdown efficiencies for FOXO3 and NRF2 in WI-38 cells were analyzed. siRNA oligos for FOXO3 or NRF2 were used to transfect WI-38 cells (10 nM final concentration) and then analyzed by qPCR for they ability to knock down the expression of target genes. Upon ~36 hrs of transfection (the time point to start small molecule incubation), the knockdown efficiency is typically ~50% to 60% for FOXO3 (~70% at 60 hrs or longer), and ~80% to 90% for NRF2 (~90% at 60 hrs or longer). Representative data from at least 3 independent transfection experiments are shown (72 hrs of transfection, normalized to B2M, error bar is for standard deviation for all the figures, n=3. ** P<0.01, Student's t-test). See Table 6 for additional data.
Figure 4A:
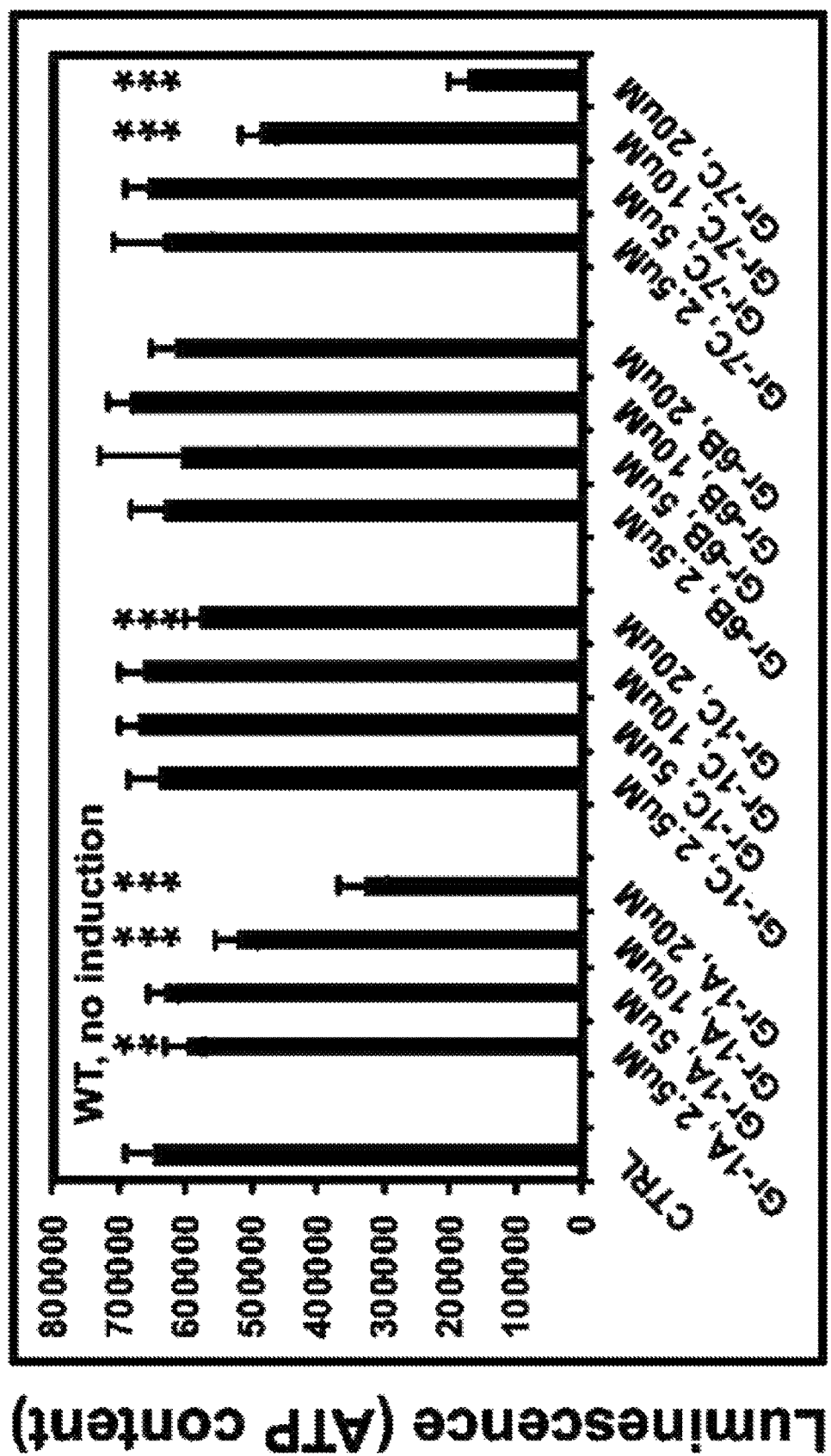
FIG. 4A-4D. Certain small molecules attenuated poly-Q toxicity in a cellular model of Huntington's. 54 repurchased molecules (initially at 10 µM) were introduced to neuron-like PC12 cells that express poly(Q)-tagged GFP (Q103-Htt-EGFP), and candidates showing protective effects were further retested at multiple doses (2.5 µM, 5 µM, 10 µM and 20 µM) to address their effects on cell viability upon the induction of toxic poly(Q)103-Htt-EGFP aggregates. The parental PC12 cells (WT) that do not express poly(Q) were used as the control to demonstrate the specificity of protective effects. Note that induction of poly(Q)103-Htt-EGFP reduced cell viability substantially (right, bottom panel), and several small molecules produced modest yet significant effects to enhance viability. (n=6. Student's t-test, * P<0.001;  P<0.01; * P<0.05).
Figure 4B:
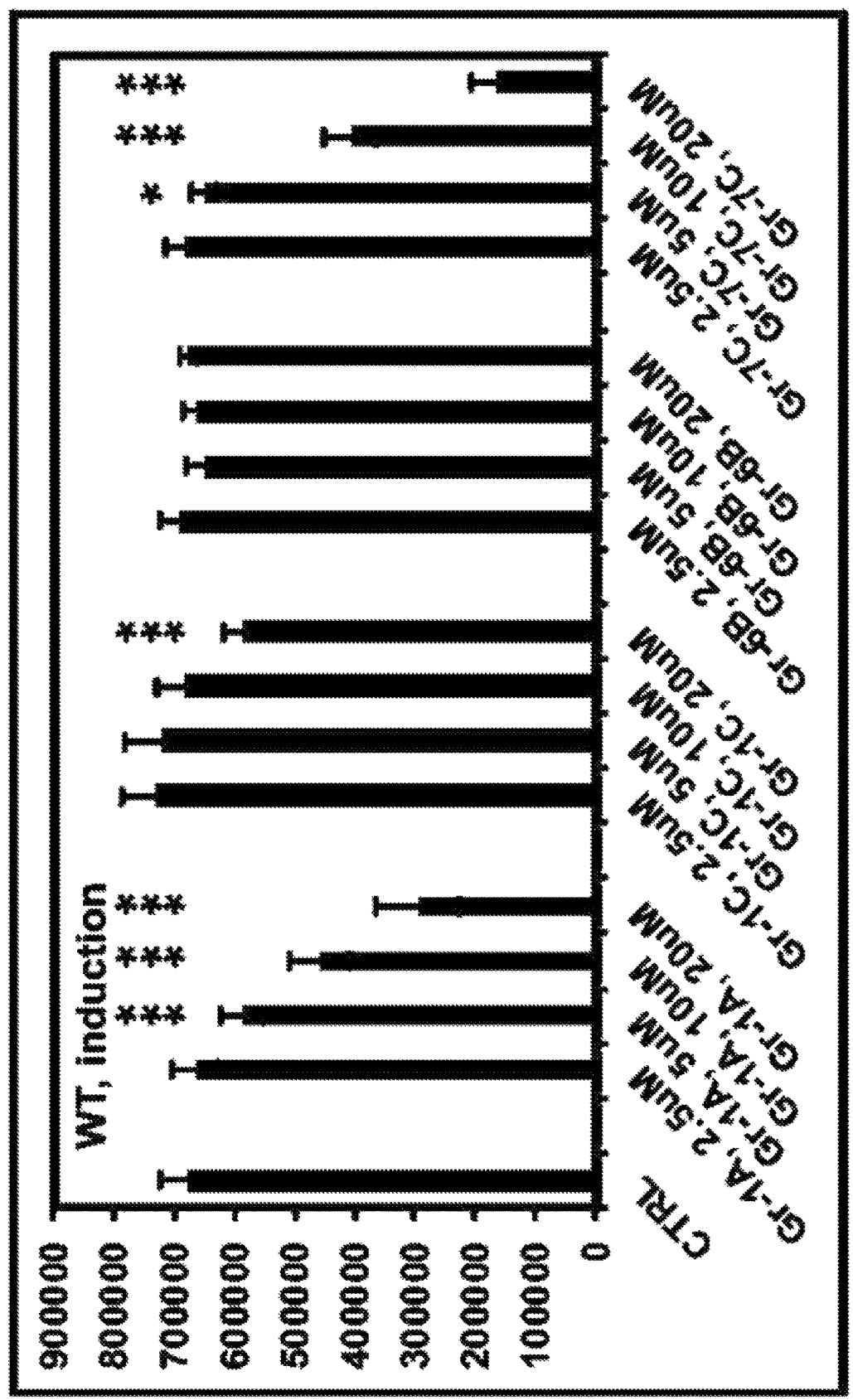
Figure 4C:
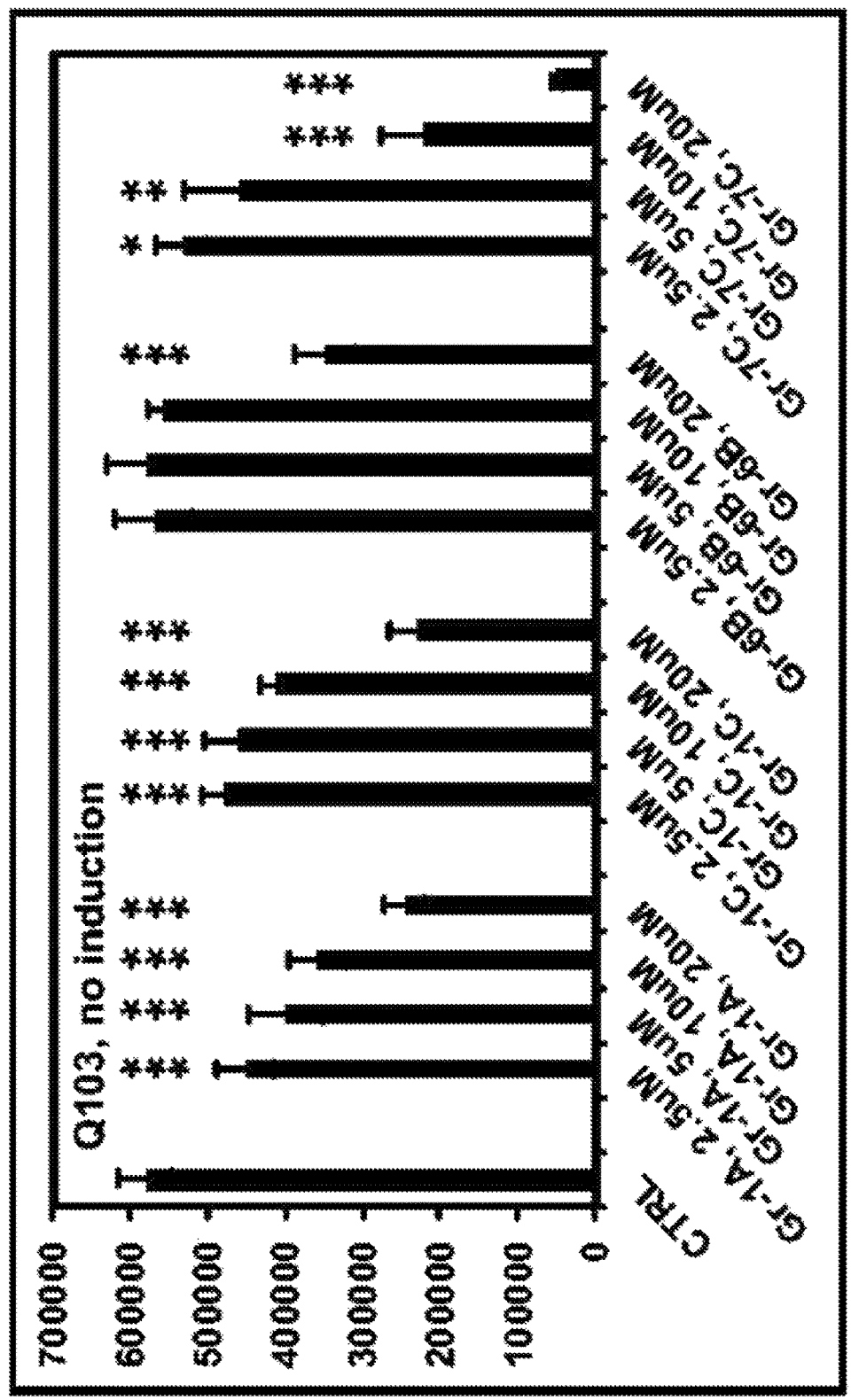
Figure 4D:
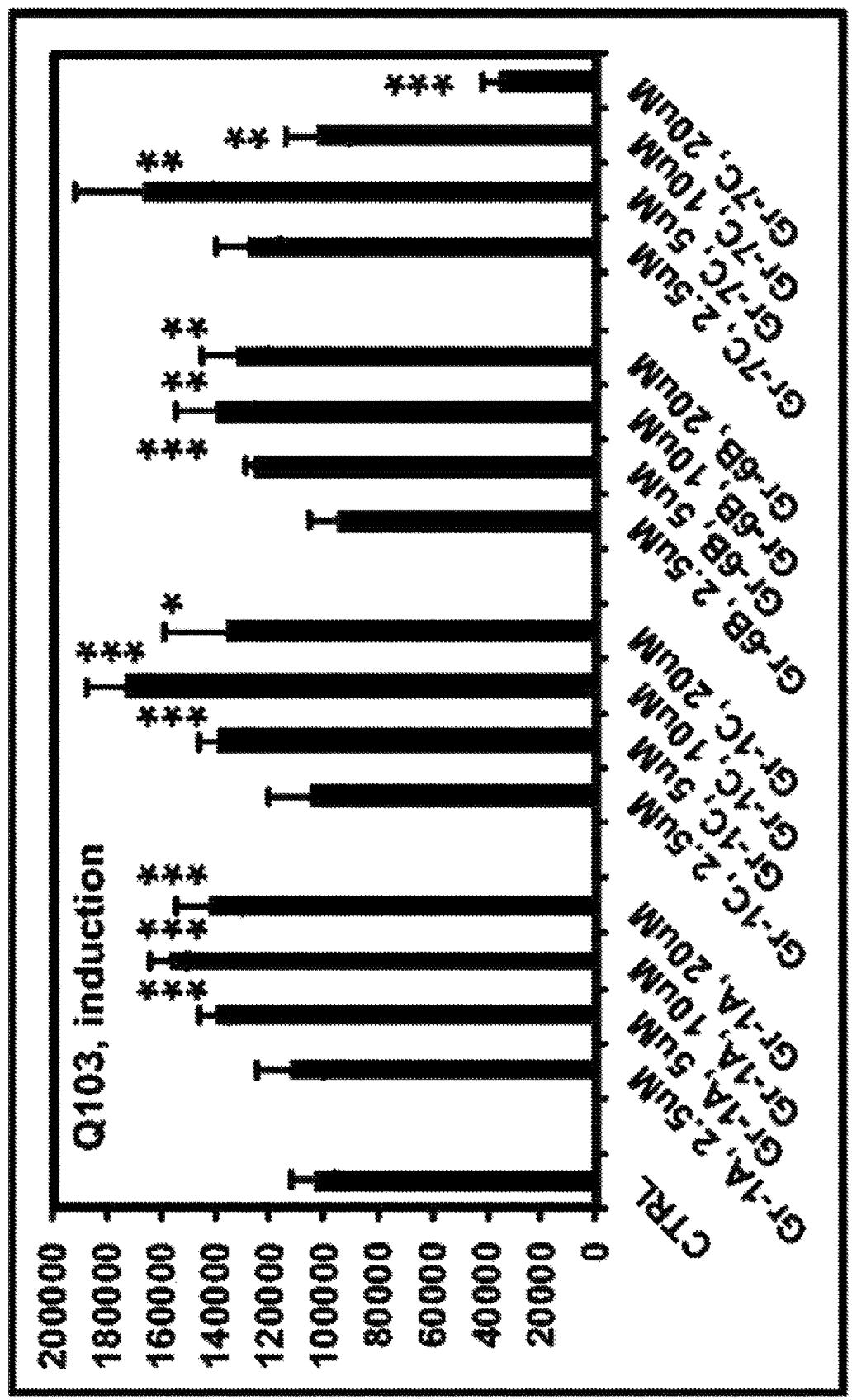
Figure 5:
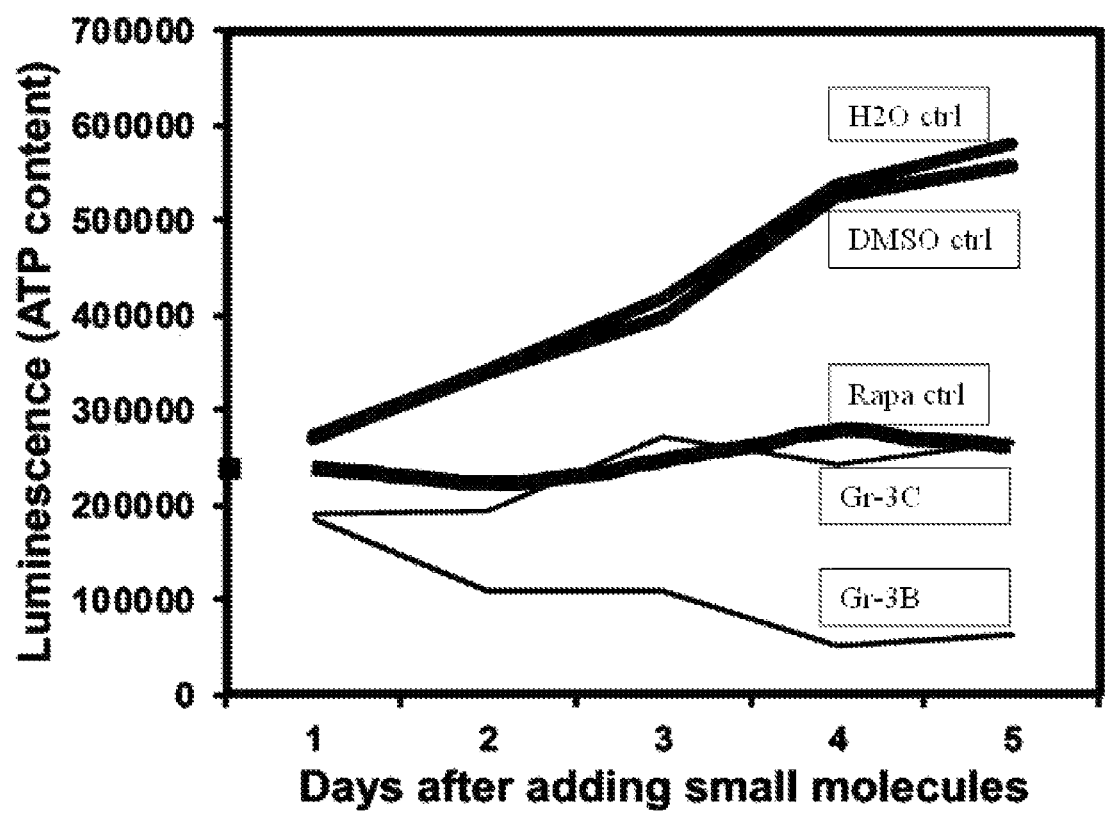
FIG. 5. Long-term effects of small molecules on cell viability. 38 "core set" small molecules were analyzed and confirmed, in two batches (a) 31 and (b) 2, to promote $H_2O_2$-resistance of WI-38 cells. Their effects on cell viability were then analyzed upon prolonged incubation (up to 5 days), by measuring ATP levels (n=6 for each molecule). ATP levels were marked on the y axis for day 0-24 hrs after seeding, before adding small molecules. Note that rapamycin reduced the ATP level by ~50% on day 5 of treatment. At least 11 small molecules also reduced the ATP level by more than 30%, and unlike rapamycin, most of them showed cell toxicity (by cell morphology examination and cell death-imaging). See Table 13 for details.
Figure 6A:
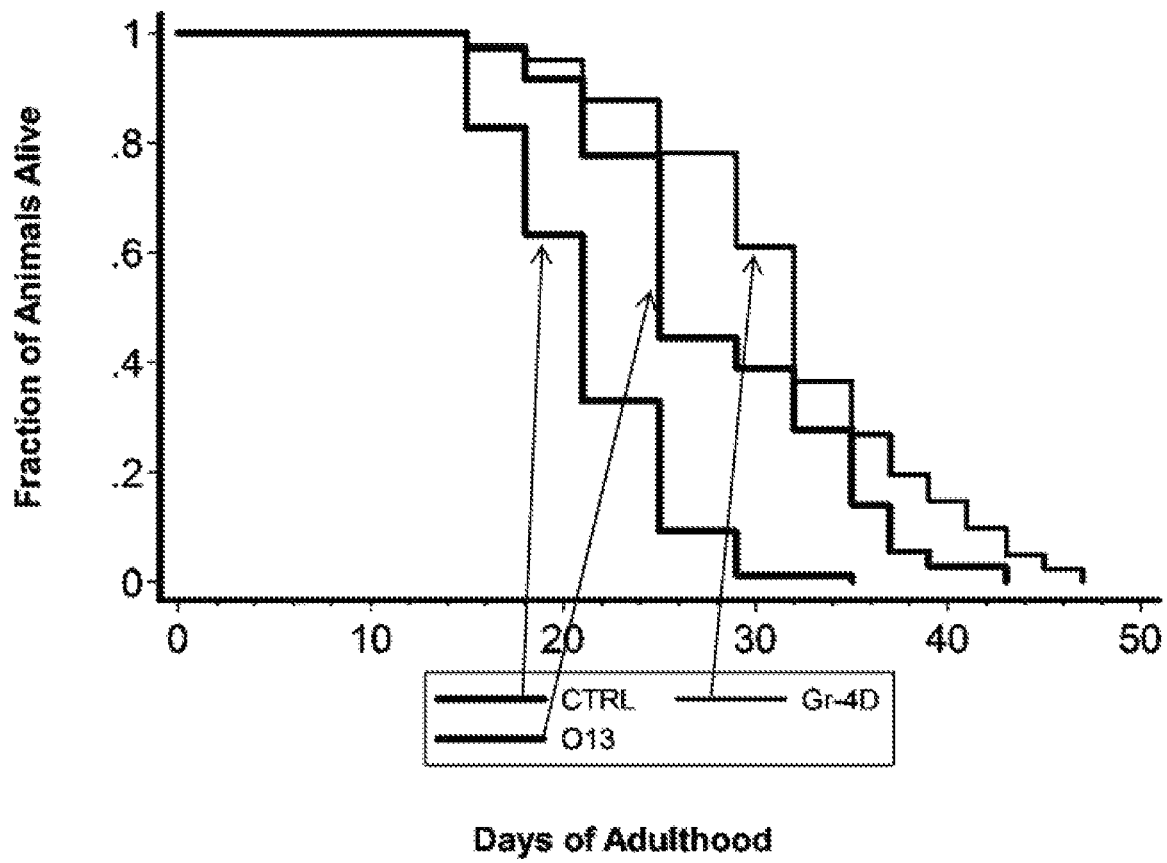
FIG. 6A-6B. Small molecules extend *C. elegans*' lifespan. Small molecules were analyzed for their ability to extend the lifespan of *C. elegans*. Given the caveat of lifespan assay variations for *C. elegans* studies, different culture conditions (in liquid and on plate, food concentrations, live or UV- & kanamycin-treated bacteria) were introduced in the assays. Molecules were analyzed at the highest dose (~60 µM, 0.3% DMSO, as higher DMSO concentration has been reported to extend lifespan of *C. elegans*). Two small molecules that consistently extended lifespan in multiple independent assays are shown.
Figure 6B:
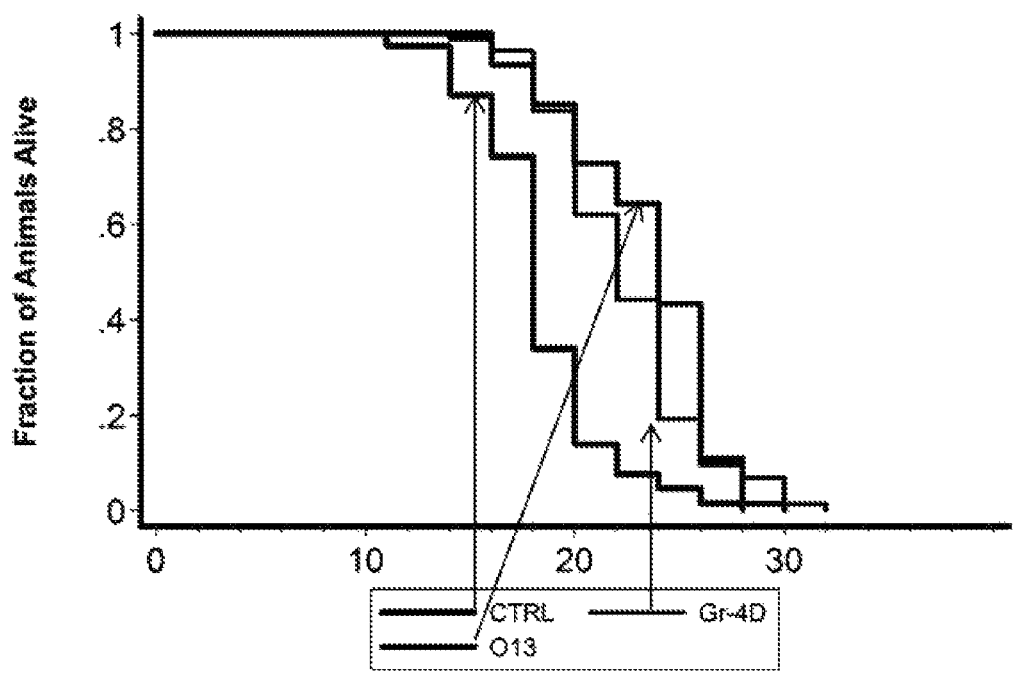

Applicants used siRNA to knock down FOXO3 expression by ~70% in an attempt to identify whether the activation of these genes depends on activity of FOXO3 and/or NRF2. Here, a negative result does not mean that FOXO proteins are not activated: in flies, dfoxo inhibition prevents insulin/IGF-1-pathway mutations from increasing lifespan but not from increasing oxidative stress resistance (Slack et al., 2011). We used siRNA to knock down FOXO3 expression by ~60% to 70% (FIG. 3; see data in Table 6). At least 4 small molecules (Gr-7A, Gr-7C, O15 and O20) required FOXO3 to promote $H_2O_2$-resistance of WI-38 cells (in at least 2 of 3 independent experiments) (Table 1a-1f) under conditions tested. (Given the caveat that FOXO3 was not fully knocked down, partial dependency was scored when the $H_2O_2$-resistance capacity was reduced by at least 25% but less than 50% upon siRNA knockdown). At least for Gr-7A and Gr-7C, which are structurally related, the observed FOXO3-dependency for $H_2O_2$-resistance is consistent with their strong effects to induce FOXO3 target genes (Tables 1a-1f, Table 6, & Table 15), including SOD2 and GADD45A.

Example 5. NRF2 Modulating Compounds

NRF2/SKN-1, the oxidative stress and xenobiotic phase 2 detoxification protein, can extend animal lifespan (Sykiotis and Bohmann, 2008; Tullet et al., 2008). Applicants analyzed these small molecules for their ability to increase the expression of NRF2-regulated genes, including HMOX1 (heme oxygenase (decycling) 1; anti-oxidant), NQO1 (NAD (P)H dehydrogenase, quinone 1; phase 2 detoxification enzyme), GCLC (glutamate-cysteine ligase, catalytic) and GSTM1 (glutathionine S transferase) (Hur and Gray, 2011; Suzuki et al., 2013).

3 small molecules (Gr-1C, O11, O17) could induce expression of at least two genes above. To our surprise, 15 additional molecules (Gr-1A, Gr-4A, Gr-4B, Gr-4C, Gr-4D, Gr-5A, Gr-5B, Gr-5D, Gr-6B, Gr-7C, O6, O13, O15, O18 and O20) could induce, by more than 1.5-fold, the expression of at least two NRF2 target genes. These data indicate an enrichment for NRF2-activating small molecules in our screen. Of these, all the chalcones (group 4) induced several NRF2-regulated genes (Tables 1a-1f), including HMOX1 (>=4.0-fold) and NQO1 (>=2.0-fold). These findings are consistent with the notion that chalcones, as known electrophilic Michael acceptors, could block KEAP1 through Michael addition reactions with its cysteine sulfhydryl groups, and thereby, activate NRF2 and downstream xenobiotic stress responses. Conversely, none the PARP inhibitors caused obvious increased expression of either FOXO3 or NRF2 target genes under the conditions tested, suggesting that they act through other pathways to promote stress resistance.

Consistent with the observation of multiple NRF2-activating molecules, applicants then found that NRF2 siRNA knockdown (by ~90% or more, FIG. 3) could significantly attenuate the ability of at least 12 small molecules (Gr-1A, Gr-6B, Gr-7A, Gr-7B, Gr-7C, O1, O15, O18, O20, O21, O22 and O23) to promote $H_2O_2$-resistance of WI-38 cells (in at least 2 of 3 independent experiments) (Tables 1a-1f). Of these, O15 and O20 consistently (in 3 of 3 experiments) required NRF2 to promote $H_2O_2$-resistance, and their resistance capacities were reduced by ~90% on average upon NRF2 knockdown under conditions tested. O15 is a small molecule that could induce HMOX1 by almost 50-fold in WI-38 cells, and it also protected C. elegans from hydrogen peroxide (in 2 of 2 trials). In addition, the ability of chalcone Gr-4D to promote $H_2O_2$-resistance appeared to be partially dependent on NRF2, but not FOXO3 under conditions tested. Applicants also noted that several small molecules, including Gr-1A, Gr-7A, Gr-7C and O23, but not the others, could reduce the survival of NRF2 siRNA-transfected cells in the absence of $H_2O_2$ under conditions tested.

Example 6. MTOR Modulating Compounds mTOR Inhibition.

Mammalian target of rapamycin (mTOR) is a crucial regulator of cell growth and metabolism and has been implicated in aging and many diseases, including cancer, diabetes and neurological diseases (Dazert and Hall, 2011; Zoncu et al., 2011). The strong connections between mTOR and diseases and aging have stimulated the interests to develop novel mTORC1/2 inhibitors, besides rapamycin, ATP-competitive, phosphatidic acid-competitive, and farnesyltransferase-inhibiting, etc (Benjamin et al., 2011). In addition, the anti-diabetes drug metformin (Kalender et al., 2010), as well as other AMPK activators such as 2-deoxy-D-glucose (Inoki et al., 2003) and AICAR (Shaw et al., 2004), could inhibit mTORC1. Applicants examined the effects of our molecules (at three doses, 5 µM, 10 µM and 20 µM) on the phosphorylation status of ribosomal protein S6 (RPS6), a readout of mTOR activity, to ask whether they could inhibit mTOR. Rapamycin, as a control, could substantially reduce the phosphorylated form of RPS6 (normalized, by 95%). Quantitative analysis indicated that, 4 of 38 small molecules (Gr-7A, Gr-7B, Gr-7C and O27) consistently reduced the ratios of phosphorylated RPS6 (p-RPS6) to total RPS6 (30%-60%, at 10 µM, (Tables 1a-1f)). This group of small molecules, like rapamycin, appeared to have anti-proliferative activities and may have significant long-term toxicity on cells under the conditions tested. Conversely, the PARP inhibitors nor the chalcones reduced the p-RPS6/RPS6 ratio, suggesting that our different hits affect the cells in different ways.

Sestrin.

Through direct effects on anti-oxidant peroxiredoxins and through the AMPK and mTOR pathways, sestrins could suppress ROS production and protect cells from oxidative stress, transformation, and genomic instability (Budanov and Karin, 2008). Studies have indicated that sestrin could be a pro-longevity factor. RNAi inhibition of the sestrin gene sesn-1 has been shown to shorten lifespan, while its overexpression promotes longevity of C. elegans (Yang et al., 2013). Loss of Drosophila dSesn has been shown to lead to age-associated pathologies, including fat accumulation, mitochondrial dysfunction, muscle degeneration, and cardiac malfunction, which could be blocked by pharmacological activation of AMPK or inhibition of TOR (Lee et al., 2010). Likewise, sestrin deficiencies in mice led to exacerbated obesity-induced diabetic conditions (Lee et al., 2013; Lee et al., 2012). Furthermore, sestrins have been shown to activate Nrf2, by promoting p62-dependent autophagic degradation of Keap1, and prevent oxidative damage in the liver of mice (Bae et al., 2013)). In this study, at least 9 small molecules (Gr-1A, Gr-1C, Gr-1D, Gr-1F, Gr-4D, O11, O20, O21 and O27) were found to induce the expression (more than 1.5-fold) of SESN1, which could count for, at least in part, their anti-oxidative capacity. Of the 9 small molecules, 6 (Gr-1A, Gr-1C, Gr-1D, Gr-1F, O21 and O27) scored positive for the DNA damage-markers γH2A.X and TP53BP1, which appeared to be consistent with previous findings that genotoxic stress, through the induction of p53, could up-regulate sestrins (Budanov and Karin, 2008). Nonetheless, both p53 and Nrf2 are highly expressed in the long-lived, stress-resistant naked mole rats, which could explain the prevention of cancer in these animals (Lewis et al., 2012). In this regard, it is possible that even the small molecules that may induce sestrin through p53 activation could still be beneficial.

Sestrin genes are regulated by FOXO3 (Nogueira et al., 2008), NRF2 (Shin et al., 2012) and p53 (Budanov et al., 2004). In a parallel siRNA screen, 83 siRNA clones that increased the H2O2-resistance of WI-38 cells. Of these, approximately 65 clones could induce SESN1 by at least 1.5-fold—this raises the alert that some of these clones may cause DNA damages in cells. Interestingly, no observations were made regarding substantial attenuation of SESN1 induction by these siRNA clones upon FOXO3 or NRF2 knockdown, indicating that neither FOXO3 nor NRF2 under conditions tested.

We examined the effects of our molecules (at three doses, 5 µM, 10 µM and 20 µM) on the phosphorylation status of ribosomal protein S6 (RPS6), a downstream readout of mTOR activity, to ask whether they could inhibit mTOR. Rapamycin, as a control, substantially reduced the phosphorylated form of RPS6 (normalized, by 95%). Quantitative analysis indicated that 4 of 38 small molecules (Gr-7A, Gr-7B, Gr-7C and O27) consistently reduced the ratios of phosphorylated RPS6 (p-RPS6) to total RPS6 (30%-60%, at 10 µM, Table 16). Conversely, neither the PARP inhibitors nor the chalcones reduced the p-RPS6/RPS6 ratio under the conditions tested, again suggesting that our different hits affect the cells in different ways. However, we noted that this group of mTOR-inhibiting small molecules appeared to have long-term toxicity on cells (Table 13).

mTOR Inhibition (RPS6 Phosphorylation Status) Methods and Analysis.

In-Cell Western assays were performed, following the same procedures to analyze DNA-damage markers. WI-38 cells were incubated with small molecules for 24 hrs, and then processed and incubated with primary antibody cocktail (mouse anti-RPS, 1:25; rabbit-anti-pRPS6, 1:100) overnight at 4° C. Next day, samples were processed and incubated with fluorophore-conjugated secondary antibodies (goat anti-mouse, 1:500; goat anti-rabbit, 1:1,000) in antibody dilution buffer. Images were collected on an Odyssey Imager (LI-COR) and analyzed with the Image Studio Lite software. Rapamycin was used as the control, at 2.5 µM, 5 µM and 10 µM, and reduced the ratio of pRPS6/RPS6 by 90% or more (normalized to DMSO negative control).

Quantitative In-Cell Western imaging analysis indicated that 4 of 38 molecules (Gr-7A, Gr-7B, Gr-7C and O27) consistently reduced the ratios of phosphorylated ribosomal protein S6 (p-RPS6) to total RPS6, a readout of mTOR activity.

Example 7. Autophagy Modulating Compounds

Autophagy Induction.

The induction of autophagy, a cytoprotective self-eating process, has been observed consistently in long-lived animals, including calorically restricted, in which nutrient and growth-related signaling pathway activities are reduced (de Cabo et al., 2014; Madeo et al., 2015). Key regulators of the autophagy process have been shown to influence longevity in many experimental organisms, including yeast, worms, and flies (de Cabo et al., 2014). Recently, it has been shown that naked mole rats, compared with lab mice, have high levels of autophagy in their livers (Zhao et al., 2014). In addition, like rapamycin, polyamine spermidine has been shown to, by inducing autophagy, extend lifespan in several species (Eisenberg et al., 2009). Applicants examined the small molecules for their ability to increase the formation of autophagy-associated LC3A/B puncta in cells. Applicants found at least 6 small molecules (Gr-1A, Gr-1C, Gr-1D, Gr-1G, O11 and O23) that could induce LC3A/B puncta by 2-fold or more (Tables 1a-1f, Table 17). As noted above, the Group 1 molecules enhanced the levels of DNA-damage markers and reduced the total numbers of cells (Tables 1a-1f, Tables 13 & 14). Additionally, 4 of these molecules (Gr-1A, Gr-1C, O11 and O23) also induce FOXO3-regulated genes, while FOXO3 activation is known to promote autophagy (Feng et al., 2015).

Autophagy Induction Analysis.

These assays were performed, following the same procedures to analyze DNA-damage markers. WI-38 cells were incubated with small molecules for 24 hrs, and then processed and incubated with primary antibody (rabbit anti-LC3A/B, 1:100) overnight at 4 C. The next day, samples were processed and incubated with fluorophore-conjugated secondary antibody and further incubated with DAPI dye. Images were collected on an INCell Analyzer 2000 and analyzed with the Developer software. Total LC3A/B puncta intensity was normalized the total numbers of DAPI-positive nuclei.

Example 8. Neurodegernative Disease Modulating Compounds

Poly-Q Toxicity Attenuation.

Toxic protein aggregation is a key feature of many age-related neurodegenerative diseases, including Alzheimer's and Huntington's disease (Caughey and Lansbury, 2003; Ross and Poirier, 2004). A number of animal models (Phillips et al., 2009) and cell models (Schlachetzki et al., 2013) have been established to study these diseases. For this purpose, PC12 rat pheochromocytoma cells display neuronal features and produce neurotransmitters and have been used extensively to study neuronal phenotypes, including synaptic transmission and neurological diseases. PC12 cells, stably expressing GFP fused to the poly(Q) tract (exon 1) of mutant human huntingtin gene HTT (Q103-Htt-EGFP), has been engineered to establish a cellular model of Huntington's disease (HD) (Aiken et al., 2004). In this model, induced expression of poly(Q)103-Htt-EGFP could lead to the formation of aggregates and exert substantial toxicity in cells. Applicants screened our 54 molecules (initially at 10 µM) in this HD model, and then by testing several candidates at multiple doses (2.5 µM, 5 µM, 10 µM and 20 µM), found 4 (Gr-1A, Gr-1C, Gr-6B and Gr-7C) that consistently increased the viability of PC12 cells upon the induction of toxic poly(Q)103-Htt-EGFP aggregates. Except for Gr-6B, the others appeared to cause toxicity to PC12 cells under non-induced conditions, (Table 13 & 14).

In these cells, induced expression of poly(Q)103-Htt-EGFP leads to the formation of aggregates and exert substantial toxicity. (Aiken et al., 2004), (Aso and Ferrer, 2014; Booz, 2011). We analyzed our molecules (initially at 10 µM) in this HD model, and then by retesting several candidates at multiple doses (2.5 µM, 5 µM, 10 µM and 20 µM), found 4 (Gr-1A, Gr-1C, Gr-6B and Gr-7C) that consistently increased the viability of PC12 cells upon the induction of toxic poly(Q)103-Htt-EGFP aggregates (FIG. 4).

Poly(Q) Toxicity & Viability Analysis.

Viability assays were performed as described before (Aiken et al., 2004). PC12 cells that stably express the inducible poly(Q)103-Htt-EGFP were grown in culture. Ponasterone A (Life Technologies), an ecdysone analog, was added to 10 µM final concentration to induce transgene expression, and formation of puncta was examined and confirmed using the Eclipse 200 fluorescent microscope (Nikon). Cell viability was analyzed 48 hrs later by measuring ATP content with CellTiter-Glo. The parental WT-PC12A cells that do not express the poly(Q)103-Htt-EGFP were used as the negative control to exclude the small molecules that could enhance viability in general.

Effects on Toxic Protein Aggregation.

In an established cellular model of Huntington's disease (HD), 4 molecules (Gr-1A, Gr-1C, Gr-6B and Gr-7C) consistently increased the viability of PC12 cells upon the induction of toxic polyQ(103)-Htt-EGFP aggregates.

Example 9. Lifespan Modulating Compounds

Hydrogen Peroxide Resistance on *C. elegans*.

In two independent trials, 54 small molecules were tested and found that at least 3 (Gr-7A, O15 and O17; 2 of 2 trials) could protect *C. elegans* from hydrogen peroxide of lethal dose.

Hydrogen Peroxide Resistance.

In two independent trials, we tested our 54 small molecules and found that at least 3 (Gr-7A, O15 and O17; 2 of 2 trials) could protect *C. elegans* from hydrogen peroxide of lethal dose (Table 12). This appeared to be rather surprising. However, our molecules were isolated with human cells, while their pharmacological kinetics and dynamics could be totally different in between human cells and worms. Moreover, stress resistance at the cellular level and organismal level may not be perfectly correlated with each other.

Lifespan Extension on *C. elegans*.

To test the molecules in more diverse experimental scope, different assay conditions were used, (i.e. in liquid or on plate, non-irradiated or UV-irradiated bacteria, FuDR-treated or genetically-induced sterile animals). In multiple independent experiments, 12 of 38 small molecules (Gr-1E, Gr-3A, Gr-3B, Gr-3C, Gr-4D, Gr-6C, Gr-7A, O12, O13, O14, O17, and O23) could extend animal's lifespan (in at least 3 to 4 trials) (from ~10% to ~50%) (Tables 1a-1f). Of these, O14 is an identified PARP inhibitor (Mouchiroud et al., 2013). Furthermore, the chalcone Gr-4D and another orphan compound O13 consistently produced significant life-extending effects (Gr-4D, 24.0%; O13, 18.2%; average increase) in 4 or more trials.

In this study, we have screened for a cellular phenotype that is common to cells from many long-lived animal mutants, and from long-lived species of mammals and birds: resistance to multiple forms of environmental stress. We screened 104,121 small molecules for their ability to protect primary human fibroblasts from a lethal dose of hydrogen peroxide, and then retested our top ~60 hits for their ability to protect cells from the DNA-damaging agent MMS and the heavy metal cadmium. Many of these compounds conferred resistance to multiple stressors, and a number inhibited TOR activity and appeared to affect FOXO3 and/or NRF2 activities, and/or extended *C. elegans*' lifespan (see the summary in Table 4).

Table 4 is a summary for characterization of screen hits. 38 "core set" small molecules are listed and are assigned a score, based on the result for each individual characterization. From our small molecule screen for $H_2O_2$-resistance, we isolated 61 top hits. Of these, 38 repurchased molecules were further validated and analyzed as the "core set" in multiple phenotypical assays that have been shown to be longevity-related in experimental systems (including animals). Specifically, a 2-point score was assigned to the most well-known and prominent longevity-related phenotypes, such as multiplex resistance, activation of FOXO3 and/or NRF2, and down-regulation of mTOR. Small molecules were also analyzed for their ability to extend *C. elegans*' lifespan in 4 to 6 independent trials, and the lifespan score scale is from 0 to 2: 0 for no obvious effects, 1 for lifespan extension observed in 2 trials, 2 for observed in more than 2 trials. Certain molecules appeared to have DNA-damaging effects and/or potential cell-toxicity in cultured human cells, and they receive a negative point.

No observations were made regarding the obvious reduction in pumping rates for worms treated with the life-extending molecules. Consistent with this, these animals did not appear to be pale, a feature that is often seen in calorically restricted animals.

Example 10. Proliferation Modulating Compounds

To understand to what extent these molecules could adversely affect cells under normal conditions, applicants analyzed the small molecule's effects on two DNA damage-associated cellular markers: phosphorylated histone variant γH2A.X and tumor protein p53 binding protein 1 (TP53BP1). γH2A.X is required for checkpoint-mediated cell cycle arrest and DNA repair following double-stranded DNA breaks, and phosphorylation of γH2A.X by a group of PI3K-like kinases (ATM, ATR, and DNA-PK) occurs rapidly in response to DNA damages (Perez-Cadahia et al., 2010). Likewise, in response to DNA damages, TP53BP1 is phosphorylated and translocated into the nucleus, and retention of TP53BP1 at DNA breaks requires phosphorylated γH2A.X (Panier and Boulton, 2014). Applicants found that 10 small molecules (Gr-1A, Gr-1C, Gr-1D, Gr-1F (these 4 belong to one structural class), Gr-3A, Gr-3C, Gr-6C, O21 and O27) increased the percentage of both γH2A.X- and TP53BP1-positive cells under the assayed conditions in multiple independent experiments (Tables 1a-1f). Consistent with these results, of these, 4 molecules (Gr-1C, Gr-1D, Gr-1F and O21) increased the percentage of propidium iodide-positive death cells under normal conditions (Gr-1C, 3.5±1.3%, P=0.002; Gr-1D, 4.2±1.4%, P=0.001; Gr-1F, 3.3±0.8%, P=3.26E-14; and O21, 1.1±0.4%, P=0.008; vs. control, 0.4±0.2%). Besides, PI-positive fraction was also increased for WI-38 cells treated with another 7 small molecules (Gr-1B, 1.0%±0.3%, P=0.006; Gr-1G, 7.1%±1.1%, P=2.09E-05; Gr-7B, 3.6%±0.7%, P=8.77E-05; O11, 1.9%±0.7%, P=0.004; O15, 3.8%±0.7%, P=5.30E-05; O20 0.7%±0.3%, P=0.030; and O23, 2.6%±1.4%, P=0.011), while these did not appear to increase both γH2A.X and TP53BP1 foci in treated cells. Applicants did not observe obvious reduction in viability of WI-38 cells that had been incubated up to 5 days with our molecules (for example, of 11 analyzed, Gr-1C, Gr-1D, Gr-1E, Gr-6A, Gr-7A, O1, O11, O12, O14, O20 and O22: Gr-1C and Gr-1D showed some toxicity under conditions tested.

In this case, by inducing modest level of stress, small molecules may protect cells from $H_2O_2$ through "hormesis" mechanism. However, such type of small molecules could result in increased DNA damages, which elevate the risk of malignant transformation when affected cells do not undergo senescence and apoptosis. But, even if so, these DNA-damaging small molecules could also be interesting, as they may act like certain cytotoxic agents (e.g., doxorubicin) and produce toxicity on highly proliferative tumor cells in vivo.

Longterm Proliferation Assay.

Applicants introduced molecules (at 10 uM final concentration) to WI-38 fibroblasts and then assayed cell viability (through ATP measurement) everyday, during a course of 5 days of continuous treatment. At least 14 of 38 molecules, including Gr-1A, Gr-1B, Gr-1F, Gr-3A, Gr-3B, Gr-3C, Gr-6C, Gr-7A, Gr-7B, Gr-7C, O11, O21, O23 and O27, could reduce the ATP content by more than 40% after 5 days of continuous incubation. These data suggested potential anti-proliferative activity and/or cell toxicity for these molecules under conditions tested. Applicants also examined the morphology and scored cell death (propidium iodide staining) for cells treated with the above molecules. Of these 14 molecules, some appeared to cause cell toxicity. For Gr-1B, Gr-3A, Gr-3B, Gr-6C, Gr-7C, O11, O21 & O27, there were less cells, and more cells scored positive for propidium iodide. Gr-7A, Gr-7B & O23: many cells are dead and necrotic. Rapamycin (5 uM), a potent inhibitor of mTOR, reduced the ATP content by more than 50%, yet did not significantly increase the fraction of PI-positive dead cells under the conditions tested. Many Group 1 molecules scored positive for DNA-damaging markers (phosphorylation of H2AX and 53BP1), and Group 7 molecules significantly reduce the phosphorylation of RPS6 and exerted toxicity on the HTB-178 lung tumor cell line. Furthermore, preliminary analysis with comet assay, which assesses DNA damages by assaying the electrophoresis behavior of DNA, indicated that, at least Gr-7A significantly increased the fraction of damaged DNA with long comet tails. Despite the observed long-term toxicity, these molecules are still interesting as they may act as anti-tumor agents in vivo, should they have more pronounced cytotoxicity on highly proliferative tumor cells. When cells were incubated with these molecules for ~24 hrs and then subject to hydrogen peroxide for 3 hrs, these molecules are all protective. Of the 38 core hits, a few small molecules, including Gr-1A, Gr-3A, O11, O15, O20, O23 and O27, may have some cell toxicity and/or DNA-damaging effects under certain conditions. Some of these small molecules may be toxic by themselves under certain conditions, but by inducing protective mechanisms, they may trigger "hormesis" and therefore protect cells from oxidative stress.

Lifespan Assays Methods.

Liquid culture-based lifespan assays were performed, following the protocol as described before (Solis and Petrascheck, 2011). Briefly, newly hatched wild-type N2 worms were fed ampicillin-resistant OP50 bacteria and treated with small molecules (67 µM final concentration, 0.2% DMSO) at the young adult stage. FUdR was used to block progeny production. The molecules were analyzed in 96-well plates, with 4 wells for each small molecule. Multiple control wells with DMSO (0.2% final concentration) were included. Likewise, small molecules were also analyzed for their ability to extend lifespan on solid agar, following procedures as described before (Cabreiro et al., 2013). Hypochlorite-synchronized temperature-sensitive sterile mutants, CF4059, (fer-15(b26)II rol-6(su1006)II; fem-1(hc17)IV), were raised on large agar plates seeded with OP50 bacteria at 25° C. Day 1 adults were transferred onto mini-plates, seeded with OP50 bacteria (UV-irradiated, kanamycin-treated) and supplemented with small molecules (~60 µM final concentration, 0.2% DMSO). Worms were scored every other day. Cumulative survival was analyzed using the STATA software (log-rank test). The small molecules were tested (at 67 µM) for their ability to confer $H_2O_2$-resistance. The worms were treated with the small molecules in liquid, with $H_2O_2$ (500 µM final concentration) added on day 4 of adulthood, and scored for viability every day.

TABLE 1A

Index, SMDC ID, Cmpd ID, Structure and Group Hit Structure (it will be understood that the R moieties (e.g., R1, R2, R3) shown in the Group Hit Structures of Table 1A do not necessarily correspond to the R moieties (e.g., $R^1$, $R^2$, $R^3$) of the compounds described herein (e.g., in the Compound section above). It will be further understood that the formulae of the Group Hit Structures may be embodiments of the compounds described herein (e.g., in aspects or embodiments of the Compound section above) wherein a person of ordinary skill will readily recognize which R moieties of the Group Hit Structures correspond to which R moieties described in the Compound section when a Group Hit Structure is fit to a formulae of the Compound section above).

| Index | SMDC ID | Cmpd ID | Structure | Group hit and Structure |
|---|---|---|---|---|
| 4 | 43368 | Gr-1A | 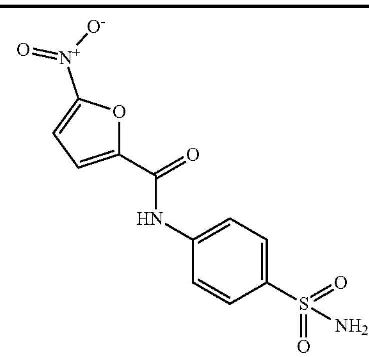 | Group 1: 7 hits |
| 5 | 45705 | Gr-1B | 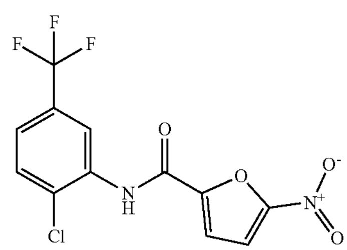 [SMILES: O=C(Nc1cc(C(F)(F)F)ccc1Cl)c1ccc([N+](=O)[O-])o1] | |
| 6 | 34365 | Gr-1C | 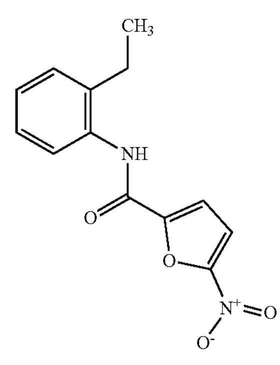 [SMILES: CCc1ccccc1NC(=O)c1ccc([N+](=O)[O-])o1] | |

TABLE 1A-continued

Index, SMDC ID, Cmpd ID, Structure and Group Hit Structure (it will be understood that the R moieties (e.g., R1, R2, R3) shown in the Group Hit Structures of Table 1A do not necessarily correspond to the R moieties (e.g., $R^1$, $R^2$, $R^3$) of the compounds described herein (e.g., in the Compound section above). It will be further understood that the formulae of the Group Hit Structures may be embodiments of the compounds described herein (e.g., in aspects or embodiments of the Compound section above) wherein a person of ordinary skill will readily recognize which R moieties of the Group Hit Structures correspond to which R moieties described in the Compound section when a Group Hit Structure is fit to a formulae of the Compound section above).

| Index | SMDC ID | Cmpd ID | Structure | Group hit and Structure |
|---|---|---|---|---|
| 7 | 43139 | Gr-1D | 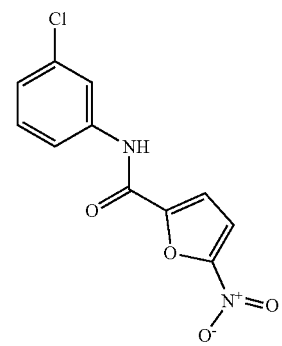 [SMILES: O=C(Nc1cccc(Cl)c1)c1ccc([N+](=O)[O-])o1] | |
| 8 | 45496 | Gr-1E | 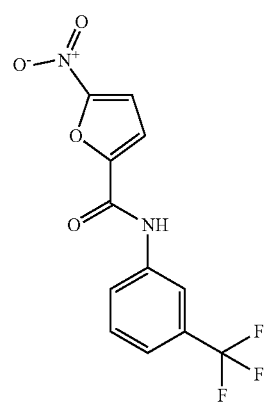 [SMILES: O=C(Nc1cccc(C(F)(F)F)c1)c1ccc([N+](=O)[O-])o1] | |
| 9 | 44811 | Gr-1F | 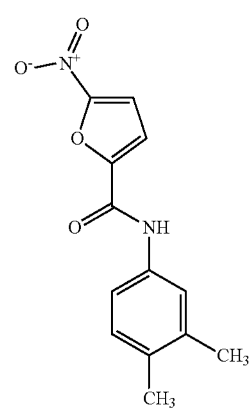 [SMILES: Cc1ccc(NC(=O)c2ccc([N+](=O)[O-])o2)cc1C] | |

TABLE 1A-continued

Index, SMDC ID, Cmpd ID, Structure and Group Hit Structure (it will be understood that the R moieties (e.g., R1, R2, R3) shown in the Group Hit Structures of Table 1A do not necessarily correspond to the R moieties (e.g., $R^1$, $R^2$, $R^3$) of the compounds described herein (e.g., in the Compound section above). It will be further understood that the formulae of the Group Hit Structures may be embodiments of the compounds described herein (e.g., in aspects or embodiments of the Compound section above) wherein a person of ordinary skill will readily recognize which R moieties of the Group Hit Structures correspond to which R moieties described in the Compound section when a Group Hit Structure is fit to a formulae of the Compound section above).

| Index | SMDC ID | Cmpd ID | Structure | Group hit and Structure |
|---|---|---|---|---|
| 10 | 44542 | Gr-1G | 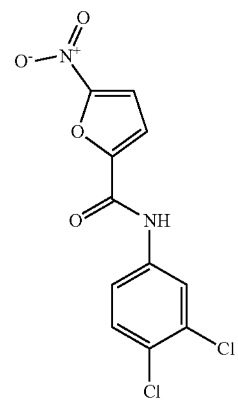 [SMILES: O=C(Nc1ccc(Cl)c(Cl)c1)c1ccc([N+](=O)[O-])o1] | |
| 11 | 152226 | Gr-2A | 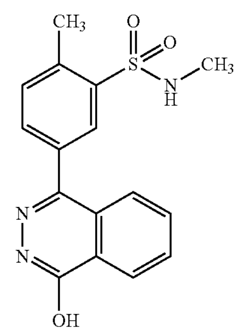 [SMILES: CNS(=O)(=O)c1cc(-c2nnc(O)c3ccccc23)ccc1C] | Group 2: 6 hits |
| 12 | 29688 | Gr-2B | 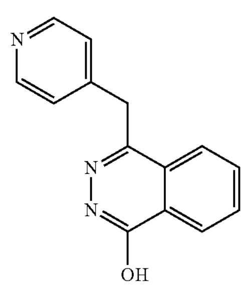 [SMILES: Oc1nnc(Cc2ccncc2)c2ccccc12] | |
| 13 | 30271 | Gr-2C | 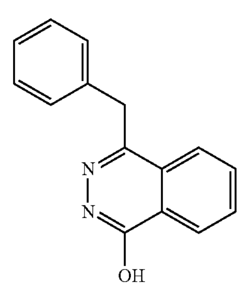 [SMILES: Oc1nnc(Cc2ccccc2)c2ccccc12] | |

TABLE 1A-continued

Index, SMDC ID, Cmpd ID, Structure and Group Hit Structure (it will be understood that the R moieties (e.g., R1, R2, R3) shown in the Group Hit Structures of Table 1A do not necessarily correspond to the R moieties (e.g., $R^1$, $R^2$, $R^3$) of the compounds described herein (e.g., in the Compound section above). It will be further understood that the formulae of the Group Hit Structures may be embodiments of the compounds described herein (e.g., in aspects or embodiments of the Compound section above) wherein a person of ordinary skill will readily recognize which R moieties of the Group Hit Structures correspond to which R moieties described in the Compound section when a Group Hit Structure is fit to a formulae of the Compound section above).

| Index | SMDC ID | Cmpd ID | Structure | Group hit and Structure |
|---|---|---|---|---|
| 14 | 164559 | Gr-2D | 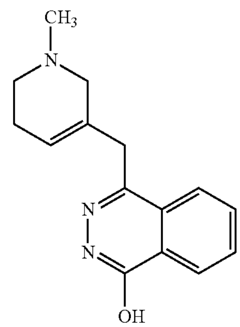 [SMILES: CN1CCC=C(Cc2nnc(O)c3ccccc23)C1] | |
| 15 | 182737 | Gr-2E | 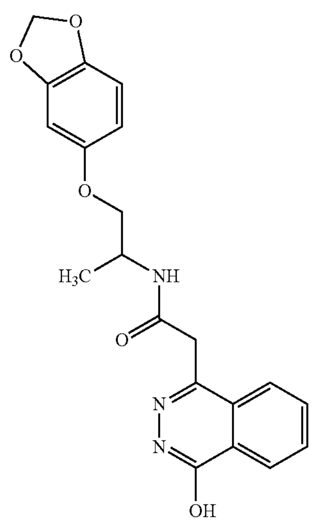 [SMILES: CC(COc1ccc2c(c1)OCO2)NC(=O)Cc1nnc(O)c2ccccc12] | |
| 16 | 29031 | Gr-3A | 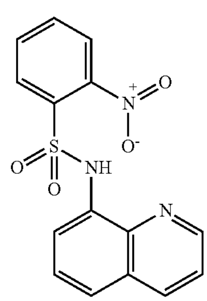 | Group3: 4 hits |

TABLE 1A-continued

Index, SMDC ID, Cmpd ID, Structure and Group Hit Structure (it will be understood that the R moieties (e.g., R1, R2, R3) shown in the Group Hit Structures of Table 1A do not necessarily correspond to the R moieties (e.g., $R^1$, $R^2$, $R^3$) of the compounds described herein (e.g., in the Compound section above). It will be further understood that the formulae of the Group Hit Structures may be embodiments of the compounds described herein (e.g., in aspects or embodiments of the Compound section above) wherein a person of ordinary skill will readily recognize which R moieties of the Group Hit Structures correspond to which R moieties described in the Compound section when a Group Hit Structure is fit to a formulae of the Compound section above).

| Index | SMDC ID | Cmpd ID | Structure | Group hit and Structure |
|---|---|---|---|---|
| 17 | 28636 | Gr-3B | 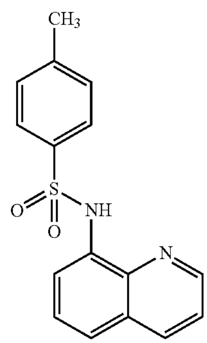 [SMILES: Cc1ccc(S(=O)(=O)Nc2cccc3cccnc23)cc1] | |
| 18 | 29041 | Gr-3C | 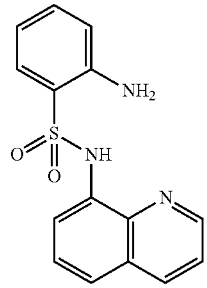 [SMILES: Nc1ccccc1S(=O)(=O)Nc1cccc2cccnc12] | |
| 19 | 118836 | Gr-3D | 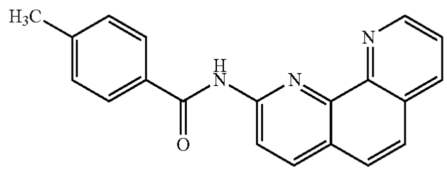 [SMILES: Cc1ccc(C(=O)Nc2ccc3ccc4cccnc4c3n2)cc1] | |
| 20 | 29513 | Gr-4A | 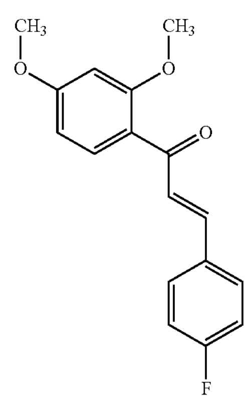 [SMILES: COc1ccc(C(=O)/C=C/c2ccc(F)cc2)c(OC)c1] | Group 4: 4 hits (chalcones) |

TABLE 1A-continued

Index, SMDC ID, Cmpd ID, Structure and Group Hit Structure (it will be understood that the R moieties (e.g., R1, R2, R3) shown in the Group Hit Structures of Table 1A do not necessarily correspond to the R moieties (e.g., $R^1$, $R^2$, $R^3$) of the compounds described herein (e.g., in the Compound section above). It will be further understood that the formulae of the Group Hit Structures may be embodiments of the compounds described herein (e.g., in aspects or embodiments of the Compound section above) wherein a person of ordinary skill will readily recognize which R moieties of the Group Hit Structures correspond to which R moieties described in the Compound section when a Group Hit Structure is fit to a formulae of the Compound section above).

| Index | SMDC ID | Cmpd ID | Structure | Group hit and Structure |
|---|---|---|---|---|
| 21 | 33179 | Gr-4B | 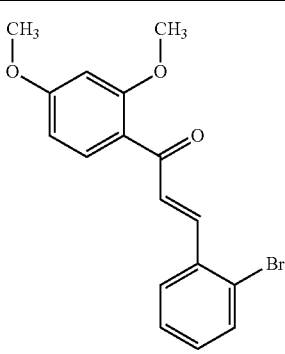 | |
| 22 | 32955 | Gr-4C | 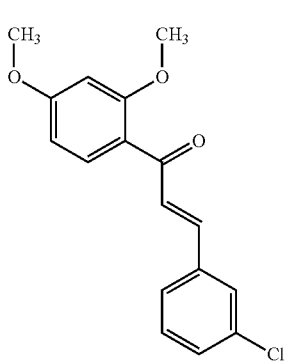 [SMILES: COc1ccc(C(=O)/C=C/c2cccc(Cl)c2)c(OC)c1] | |
| 23 | 28213 | Gr-4D | 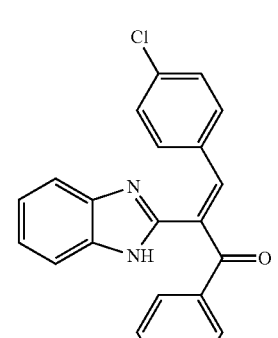 | |

TABLE 1A-continued

Index, SMDC ID, Cmpd ID, Structure and Group Hit Structure (it will be understood that the R moieties (e.g., R1, R2, R3) shown in the Group Hit Structures of Table 1A do not necessarily correspond to the R moieties (e.g., $R^1$, $R^2$, $R^3$) of the compounds described herein (e.g., in the Compound section above). It will be further understood that the formulae of the Group Hit Structures may be embodiments of the compounds described herein (e.g., in aspects or embodiments of the Compound section above) wherein a person of ordinary skill will readily recognize which R moieties of the Group Hit Structures correspond to which R moieties described in the Compound section when a Group Hit Structure is fit to a formulae of the Compound section above).

| Index | SMDC ID | Cmpd ID | Structure | Group hit and Structure |
|---|---|---|---|---|
| 24 | 158211 | Gr-5A | 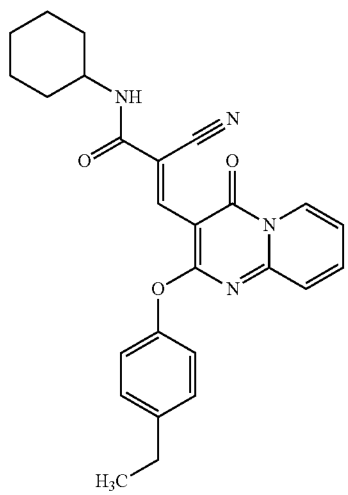 [SMILES: CCc1ccc(Oc2nc3ccccn3c(=O)c2/C=C(\C#N)C(=O)NC2CCCCC2)cc1] | Group 5: 4 hits |
| 25 | 158201 | Gr-5B | 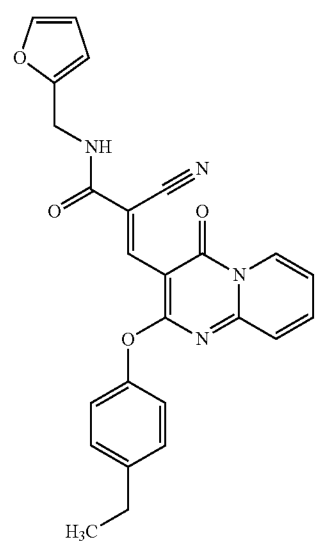 [SMILES: CCc1ccc(Oc2nc3ccccn3c(=O)c2/C=C(\C#N)C(=O)NCc2ccco2)cc1] | |

TABLE 1A-continued

Index, SMDC ID, Cmpd ID, Structure and Group Hit Structure (it will be understood that the R moieties (e.g., R1, R2, R3) shown in the Group Hit Structures of Table 1A do not necessarily correspond to the R moieties (e.g., $R^1$, $R^2$, $R^3$) of the compounds described herein (e.g., in the Compound section above). It will be further understood that the formulae of the Group Hit Structures may be embodiments of the compounds described herein (e.g., in aspects or embodiments of the Compound section above) wherein a person of ordinary skill will readily recognize which R moieties of the Group Hit Structures correspond to which R moieties described in the Compound section when a Group Hit Structure is fit to a formulae of the Compound section above).

| Index | SMDC ID | Cmpd ID | Structure | Group hit and Structure |
|---|---|---|---|---|
| 26 | 158206 | Gr-5C | 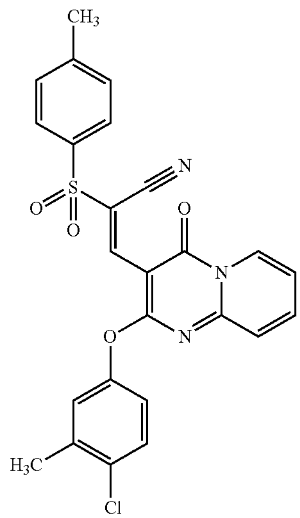 [SMILES: Cc1ccc(S(=O)(=O)/C(C#N)=C/c2c(Oc3ccc(Cl)c(C)c3)nc3ccccn3c2=O)cc1] | |
| 27 | 158125 | Gr-5D | 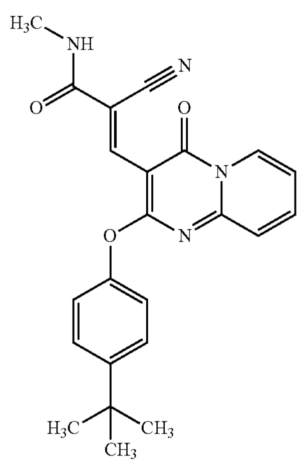 [SMILES: CNC(=O)/C(C#N)=C/c1c(Oc2ccc(C(C)(C)C)cc2)nc2ccccn2c1=O] | |
| 28 | 50328 | Gr-6A | 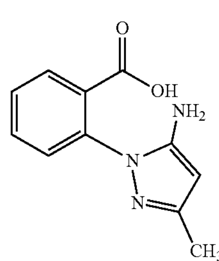 | Group 6: 3 hits |

TABLE 1A-continued

Index, SMDC ID, Cmpd ID, Structure and Group Hit Structure (it will be understood that the R moieties (e.g., R1, R2, R3) shown in the Group Hit Structures of Table 1A do not necessarily correspond to the R moieties (e.g., $R^1$, $R^2$, $R^3$) of the compounds described herein (e.g., in the Compound section above). It will be further understood that the formulae of the Group Hit Structures may be embodiments of the compounds described herein (e.g., in aspects or embodiments of the Compound section above) wherein a person of ordinary skill will readily recognize which R moieties of the Group Hit Structures correspond to which R moieties described in the Compound section when a Group Hit Structure is fit to a formulae of the Compound section above).

| Index | SMDC ID | Cmpd ID | Structure | Group hit and Structure |
|---|---|---|---|---|
| 29 | 150533 | Gr-6B | 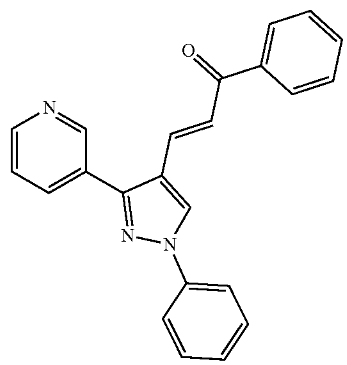 [SMILES: O=C(/C=C/c1cn(-c2ccccc2)nc1-c1cccnc1)c1ccccc1] | |
| 30 | 162159 | Gr-6C | 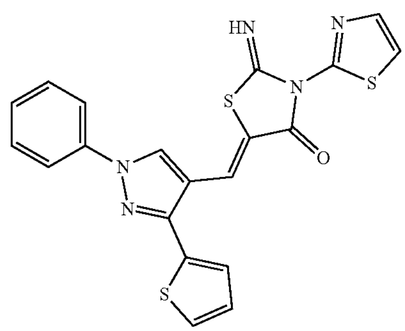 [SMILES: N=C1S/C(=C\c2cn(-c3ccccc3)nc2-c2cccs2)C(=O)N1c1nccs1] | |
| 31 | 152946 | Gr-7A | 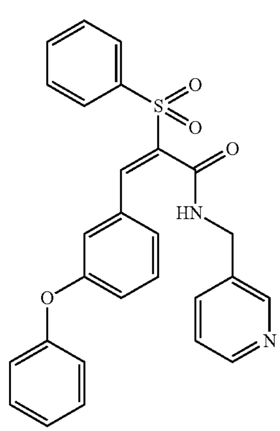 [SMILES: O=C(NCc1cccnc1)/C(=C\c1cccc(Oc2ccccc2)c1)S(=O)(=O)c1ccccc1] | Group 7: 3 hits |

TABLE 1A-continued

Index, SMDC ID, Cmpd ID, Structure and Group Hit Structure (it will be understood that the R moieties (e.g., R1, R2, R3) shown in the Group Hit Structures of Table 1A do not necessarily correspond to the R moieties (e.g., $R^1$, $R^2$, $R^3$) of the compounds described herein (e.g., in the Compound section above). It will be further understood that the formulae of the Group Hit Structures may be embodiments of the compounds described herein (e.g., in aspects or embodiments of the Compound section above) wherein a person of ordinary skill will readily recognize which R moieties of the Group Hit Structures correspond to which R moieties described in the Compound section when a Group Hit Structure is fit to a formulae of the Compound section above).

| Index | SMDC ID | Cmpd ID | Structure | Group hit and Structure |
|---|---|---|---|---|
| 32 | 152936 | Gr-7B | 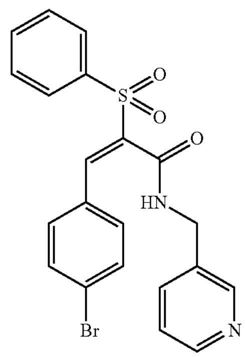 [SMILES: O=C(NCc1cccnc1)/C(=C\c1ccc(Br)cc1)S(=O)(=O)c1ccccc1] | |
| 33 | 152926 | Gr-7C | 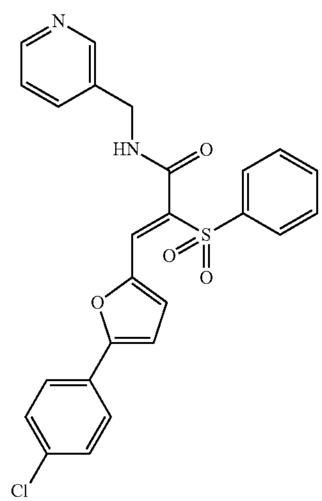 [SMILES: O=C(NCc1cccnc1)/C(=C/c1ccc(-c2ccc(Cl)cc2)o1)S(=O)(=O)c1ccccc1] | |
| 35 | 39959 | O1 | 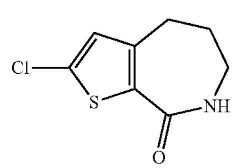 [SMILES: O=C1NCCCc2cc(Cl)sc21] | |
| 36 | 169199 | O2 | 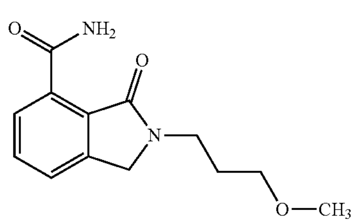 [SMILES: COCCCN1Cc2cccc(C(N)=O)c2C1=O] | |

TABLE 1A-continued

Index, SMDC ID, Cmpd ID, Structure and Group Hit Structure (it will be understood that the R moieties (e.g., R1, R2, R3) shown in the Group Hit Structures of Table 1A do not necessarily correspond to the R moieties (e.g., $R^1$, $R^2$, $R^3$) of the compounds described herein (e.g., in the Compound section above). It will be further understood that the formulae of the Group Hit Structures may be embodiments of the compounds described herein (e.g., in aspects or embodiments of the Compound section above) wherein a person of ordinary skill will readily recognize which R moieties of the Group Hit Structures correspond to which R moieties described in the Compound section when a Group Hit Structure is fit to a formulae of the Compound section above).

| Index | SMDC ID | Cmpd ID | Structure | Group hit and Structure |
|---|---|---|---|---|
| 37 | 127091 | O3 | 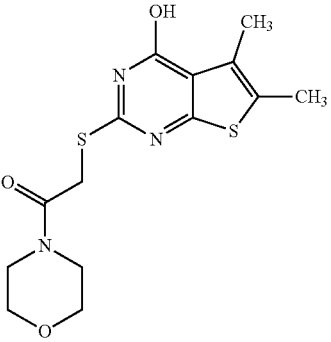 [SMILES: Cc1sc2nc(SCC(=O)N3CCOCC3)nc(O)c2c1C] | |
| 38 | 194447 | O4 | 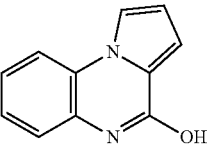 [SMILES: Oc1nc2ccccc2n2cccc12] | |
| 39 | 151482 | O5 | 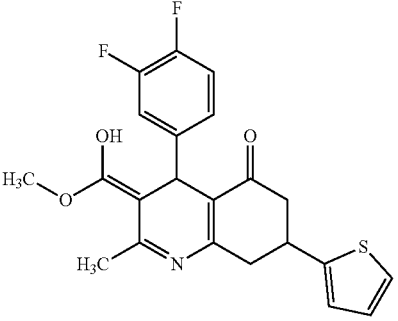 [SMILES: CO/C(O)=C1\C(C)=NC2=C(C(=O)CC(c3cccs3)C2)C1c1ccc(F)c(F)c1] | |
| 40 | 166246 | O6 | 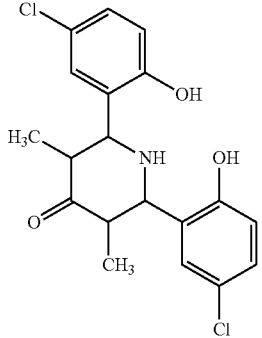 [SMILES: CC1C(=O)C(C)C(c2cc(Cl)ccc2O)NC1c1cc(Cl)ccc1O] | |
| 41 | 148098 | O7 | 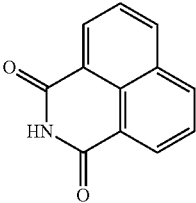 [SMILES: O=C1NC(=O)c2cccc3cccc1c23] | |

TABLE 1A-continued

Index, SMDC ID, Cmpd ID, Structure and Group Hit Structure (it will be understood that the R moieties (e.g., R1, R2, R3) shown in the Group Hit Structures of Table 1A do not necessarily correspond to the R moieties (e.g., $R^1$, $R^2$, $R^3$) of the compounds described herein (e.g., in the Compound section above). It will be further understood that the formulae of the Group Hit Structures may be embodiments of the compounds described herein (e.g., in aspects or embodiments of the Compound section above) wherein a person of ordinary skill will readily recognize which R moieties of the Group Hit Structures correspond to which R moieties described in the Compound section when a Group Hit Structure is fit to a formulae of the Compound section above).

| Index | SMDC ID | Cmpd ID | Structure | Group hit and Structure |
|---|---|---|---|---|
| 42 | 173384 | O8 | 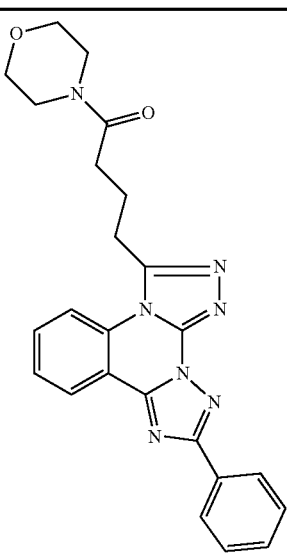 | |
| 43 | 178510 | O9 | 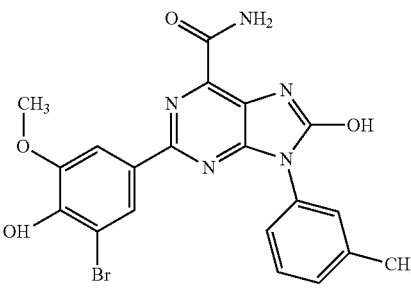 | |
| 44 | 41334 | O10 | 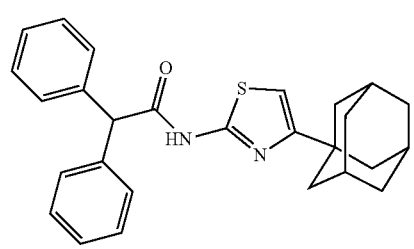 [SMILES: O=C(Nc1nc(C23CC4CC(CC(C4)C2)C3)cs1)C(c1ccccc1)c1ccccc1] | |
| 45 | 157343 | O11 | 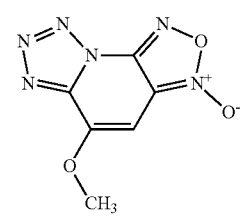 | |
| 46 | 122572 | O12 | 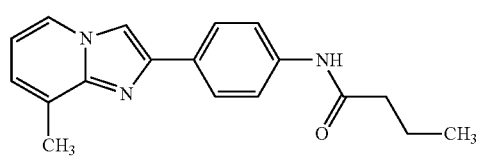 [SMILES: CCCC(=O)Nc1ccc(-c2cn3cccc(C)c3n2)cc1] | |

TABLE 1A-continued

Index, SMDC ID, Cmpd ID, Structure and Group Hit Structure (it will be understood that the R moieties (e.g., R1, R2, R3) shown in the Group Hit Structures of Table 1A do not necessarily correspond to the R moieties (e.g., $R^1$, $R^2$, $R^3$) of the compounds described herein (e.g., in the Compound section above). It will be further understood that the formulae of the Group Hit Structures may be embodiments of the compounds described herein (e.g., in aspects or embodiments of the Compound section above) wherein a person of ordinary skill will readily recognize which R moieties of the Group Hit Structures correspond to which R moieties described in the Compound section when a Group Hit Structure is fit to a formulae of the Compound section above).

| Index | SMDC ID | Cmpd ID | Structure | Group hit and Structure |
|---|---|---|---|---|
| 47 | 30228 | O13 | 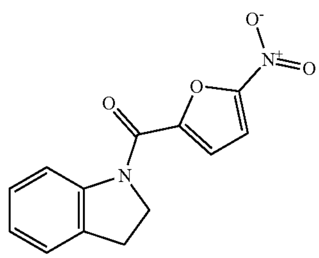 [SMILES: O=C(c1ccc([N+](=O)[O-])o1)N1CCc2ccccc21] | |
| 48 | 38610 | O14 | 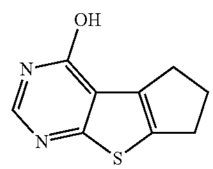 [SMILES: Oc1ncnc2sc3c(c12)CCC3] | |
| 49 | 29424 | O15 | 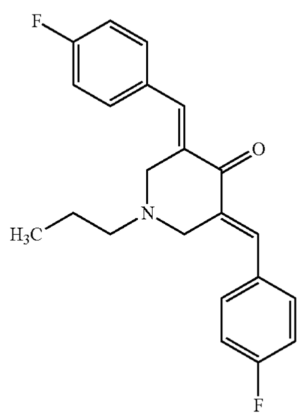 [SMILES: CCCN1C/C(=C\c2ccc(F)cc2)C(=O)/C(=C/c2ccc(F)cc2)C1] | |
| 50 | 194820 | O16 | 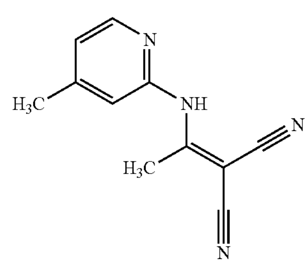 | |
| 51 | 157154 | O17 | 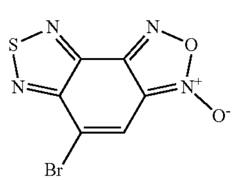 [SMILES: [O-][n+]1onc2c3nsnc3c(Br)cc21] | |

TABLE 1A-continued

Index, SMDC ID, Cmpd ID, Structure and Group Hit Structure (it will be understood that the R moieties (e.g., R1, R2, R3) shown in the Group Hit Structures of Table 1A do not necessarily correspond to the R moieties (e.g., $R^1$, $R^2$, $R^3$) of the compounds described herein (e.g., in the Compound section above). It will be further understood that the formulae of the Group Hit Structures may be embodiments of the compounds described herein (e.g., in aspects or embodiments of the Compound section above) wherein a person of ordinary skill will readily recognize which R moieties of the Group Hit Structures correspond to which R moieties described in the Compound section when a Group Hit Structure is fit to a formulae of the Compound section above).

| Index | SMDC ID | Cmpd ID | Structure | Group hit and Structure |
|---|---|---|---|---|
| 52 | 31883 | O18 | 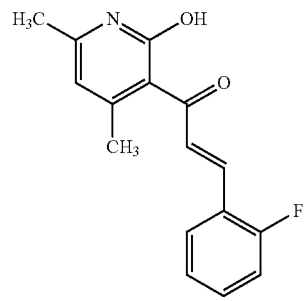 [SMILES: Cc1cc(C)c(C(=O)/C=C/c2ccccc2F)c(O)n1] | |
| 53 | 47511 | O19 | 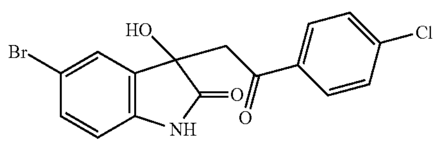 [SMILES: O=C(CC1(O)C(=O)Nc2ccc(Br)cc21)c1ccc(Cl)cc1] | |
| 54 | 39793 | O20 | 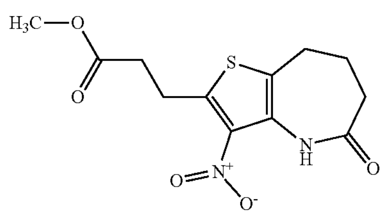 [SMILES: COC(=O)CCc1sc2c(c1[N+](=O)[O-])NC(=O)CCC2] | |
| 55 | 128071 | O21 | 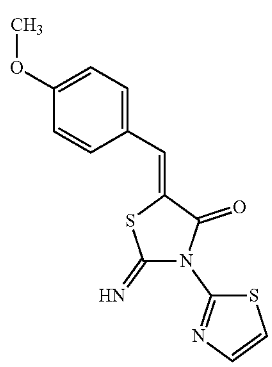 [SMILES: COc1ccc(/C=C2\SC(=N)N(c3nccs3)C2=O)cc1] | |

TABLE 1A-continued

Index, SMDC ID, Cmpd ID, Structure and Group Hit Structure (it will be understood that the R moieties (e.g., R1, R2, R3) shown in the Group Hit Structures of Table 1A do not necessarily correspond to the R moieties (e.g., $R^1$, $R^2$, $R^3$) of the compounds described herein (e.g., in the Compound section above). It will be further understood that the formulae of the Group Hit Structures may be embodiments of the compounds described herein (e.g., in aspects or embodiments of the Compound section above) wherein a person of ordinary skill will readily recognize which R moieties of the Group Hit Structures correspond to which R moieties described in the Compound section when a Group Hit Structure is fit to a formulae of the Compound section above).

| Index | SMDC ID | Cmpd ID | Structure | Group hit and Structure |
|---|---|---|---|---|
| 56 | 115873 | O22 | 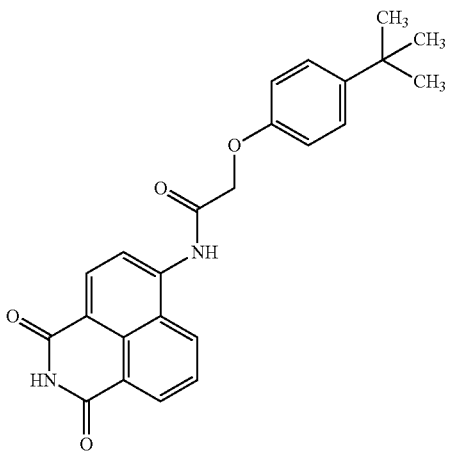 [SMILES: CC(C)(C)c1ccc(OCC(=O)Nc2ccc3c4c(cccc24)C(=O)NC3=O)cc1] | |
| 57 | 165151 | O23 | 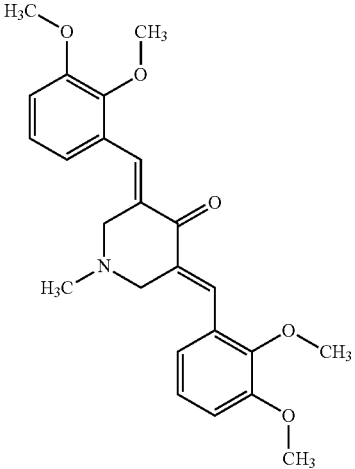 [SMILES: COc1cccc(/C=C2\CN(C)C/C(=C\c3cccc(OC)c3OC)C2=O)c1OC] | |
| 58 | 184478 | O24 | 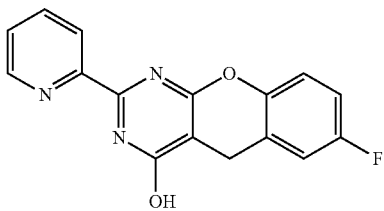 [SMILES: Oc1nc(-c2ccccn2)nc2c1Cc1cc(F)ccc1O2] | |
| 59 | 119430 | O25 | 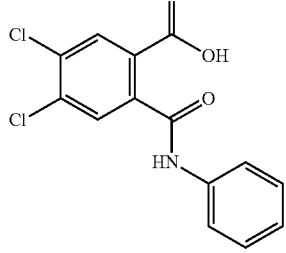 | |

TABLE 1A-continued

Index, SMDC ID, Cmpd ID, Structure and Group Hit Structure (it will be understood that the R moieties (e.g., R1, R2, R3) shown in the Group Hit Structures of Table 1A do not necessarily correspond to the R moieties (e.g., $R^1$, $R^2$, $R^3$) of the compounds described herein (e.g., in the Compound section above). It will be further understood that the formulae of the Group Hit Structures may be embodiments of the compounds described herein (e.g., in aspects or embodiments of the Compound section above) wherein a person of ordinary skill will readily recognize which R moieties of the Group Hit Structures correspond to which R moieties described in the Compound section when a Group Hit Structure is fit to a formulae of the Compound section above).

| Index | SMDC ID | Cmpd ID | Structure | Group hit and Structure |
|---|---|---|---|---|
| 60 | 49713 | O26 | 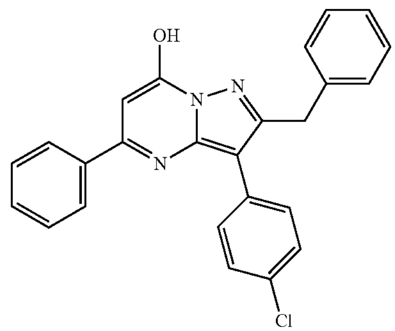 [SMILES: Oc1cc(-c2ccccc2)nc2c(-c3ccc(Cl)cc3)c(Cc3ccccc3)nn12] | |
| 61 | 34215 | O27 | 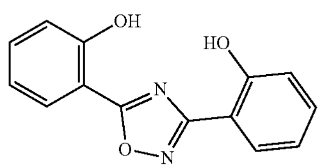 [SMILES: Oc1ccccc1-c1noc(-c2ccccc2O)n1] | |
| 62 | 43877 | O28 | 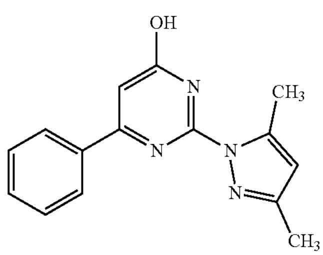 [SMILES: Cc1cc(C)n(-c2nc(O)cc(-c3ccccc3)n2)n1] | |
| 63 | 29261 | O29 | 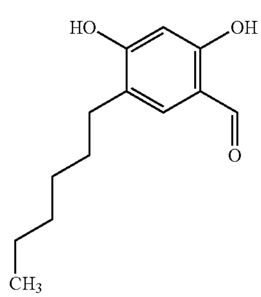 [SMILES: CCCCCCc1cc(C=O)c(O)cc1O] | |

TABLE 1A-continued

Index, SMDC ID, Cmpd ID, Structure and Group Hit Structure (it will be understood that the R moieties (e.g., R1, R2, R3) shown in the Group Hit Structures of Table 1A do not necessarily correspond to the R moieties (e.g., $R^1$, $R^2$, $R^3$) of the compounds described herein (e.g., in the Compound section above). It will be further understood that the formulae of the Group Hit Structures may be embodiments of the compounds described herein (e.g., in aspects or embodiments of the Compound section above) wherein a person of ordinary skill will readily recognize which R moieties of the Group Hit Structures correspond to which R moieties described in the Compound section when a Group Hit Structure is fit to a formulae of the Compound section above).

| Index | SMDC ID | Cmpd ID | Structure | Group hit and Structure |
|---|---|---|---|---|
| 64 | 155615 | O30 | 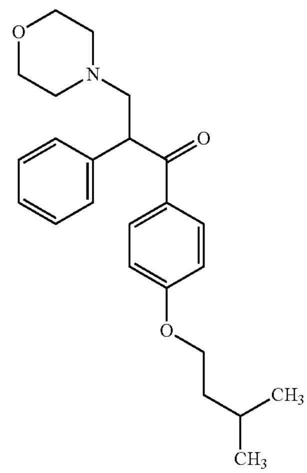 [SMILES: CC(C)CCOc1ccc(C(=O)C(CN2CCOCC2)c2ccccc2)cc1] | |
| 65 | 160962 | O31 | 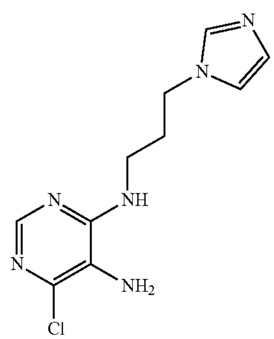 [SMILES: Nc1c(Cl)ncnc1NCCCn1ccnc1] | |

TABLE 1B

Screening Compounds.

| Index | SMDC ID | Cmpd ID | Screen 1(a) | Screen 2(b) | Screen 3(c) | Est. $ED_{50}$ (μM) |
|---|---|---|---|---|---|---|
| 4 | 43368 | Gr-1A | 2.89 | 3.66 | 3.44 | 2.53 |
| 5 | 45705 | Gr-1B | 4.12 | 3.18 | 3.40 | 2.65 |
| 6 | 34365 | Gr-1C | 5.35 | 2.67 | 3.27 | 2.66 |
| 7 | 43139 | Gr-1D | 5.99 | 4.84 | 4.85 | 2.68 |
| 8 | 45496 | Gr-1E | 17.87 | 11.83 | 6.59 | 2.76 |
| 9 | 44811 | Gr-1F | 26.35 | 3.47 | 7.92 | 2.88 |
| 10 | 44542 | Gr-1G | 33.25 | 7.81 | 4.96 | 2.95 |
| 11 | 152226 | Gr-2A | 2.94 | 1.87 | 2.57 | 3.05 |
| 12 | 29688 | Gr-2B | 3.15 | 2.18 | 3.00 | 3.05 |
| 13 | 30271 | Gr-2C | 3.59 | 3.60 | 5.83 | 3.12 |
| 14 | 164559 | Gr-2D | 3.81 | 5.66 | 8.11 | 3.42 |
| 15 | 182737 | Gr-2E | 4.74 | 5.33 | 8.81 | 3.82 |
| 16 | 29031 | Gr-3A | 5.16 | 1.43 | 1.88 | 4.21 |
| 17 | 28636 | Gr-3B | 20.47 | 2.18 | 2.68 | 4.24 |
| 18 | 29041 | Gr-3C | 24.00 | 5.93 | 1.74 | 4.60 |
| 19 | 118836 | Gr-3D | 36.08 | 38.43 | 29.38 | 4.96 |
| 20 | 29513 | Gr-4A | 2.71 | 1.98 | 2.48 | 4.97 |
| 21 | 33179 | Gr-4B | 2.94 | 1.93 | 2.10 | 5.33 |
| 22 | 32955 | Gr-4C | 6.06 | 2.33 | 2.90 | 6.45 |
| 23 | 28213 | Gr-4D | 14.99 | 3.48 | 6.13 | 8.90 |
| 24 | 158211 | Gr-5A | 3.52 | 1.27 | 1.40 | 10.24 |
| 25 | 158201 | Gr-5B | 3.62 | 1.60 | 1.90 | 14.30 |
| 26 | 158206 | Gr-5C | 4.94 | 1.72 | 2.13 | 15.73 |
| 27 | 158125 | Gr-5D | 12.42 | 1.57 | 1.77 | 18.69 |
| 28 | 50328 | Gr-6A | 9.69 | 3.20 | 5.82 | 40.54 |
| 29 | 150533 | Gr-6B | 17.34 | 1.29 | 2.00 | 45.06 |
| 30 | 162159 | Gr-6C | 50.99 | 1.37 | 10.83 | 48.52 |
| 31 | 152946 | Gr-7A | 3.01 | 2.80 | 9.45 | 58.35 |
| 32 | 152936 | Gr-7B | 3.36 | 1.29 | 2.61 | 24.70 |
| 33 | 152926 | Gr-7C | 23.04 | 1.46 | 2.83 | 2.59 |
| 35 | 39959 | O1 | 2.53 | 1.87 | 2.91 | 13.2 |
| 36 | 169199 | O2 | 2.65 | 4.23 | 7.85 | 20.0 |
| 37 | 127091 | O3 | 2.66 | 1.67 | 2.90 | 20.0 |
| 38 | 194447 | O4 | 2.68 | 2.67 | 4.84 | 11.2 |
| 39 | 151482 | O5 | 2.76 | 1.88 | 0.99 | 20.0 |
| 40 | 166246 | O6 | 2.88 | 1.50 | 1.95 | 9.8 |

TABLE 1B-continued

Screening Compounds.

| Index | SMDC ID | Cmpd ID | Screen 1(a) | Screen 2(b) | Screen 3(c) | Est. ED$_{50}$ (μM) |
|---|---|---|---|---|---|---|
| 41 | 148098 | O7 | 2.95 | 2.23 | 2.14 | 5.5 |
| 42 | 173384 | O8 | 3.05 | 0.95 | 0.80 | 20.0 |
| 43 | 178510 | O9 | 3.05 | 1.11 | 1.59 | 14.2 |
| 44 | 41334 | O10 | 3.12 | 1.83 | 2.32 | 9.5 |
| 45 | 157343 | O11 | 3.42 | 6.71 | 3.00 | 4.4 |
| 46 | 122572 | O12 | 3.82 | 5.74 | 9.57 | 1.0 |
| 47 | 30228 | O13 | 4.21 | 1.50 | 2.09 | 10.1 |
| 48 | 38610 | O14 | 4.24 | 2.32 | 3.77 | 12.5 |
| 49 | 29424 | O15 | 4.60 | 1.57 | 2.32 | 20.0 |
| 50 | 194820 | O16 | 4.96 | 0.93 | 1.88 | 20.0 |
| 51 | 157154 | O17 | 4.97 | 1.96 | 2.22 | 8.5 |
| 52 | 31883 | O18 | 5.33 | 1.73 | 2.22 | 9.8 |
| 53 | 47511 | O19 | 6.45 | 1.28 | 1.34 | 20.0 |
| 54 | 39793 | O20 | 8.90 | 1.41 | 1.82 | 12.9 |
| 55 | 128071 | O21 | 10.24 | 1.59 | 8.46 | 18.1 |
| 56 | 115873 | O22 | 14.30 | 3.28 | 5.11 | 20.0 |
| 57 | 165151 | O23 | 15.73 | 2.82 | 1.44 | 4.9 |
| 58 | 184478 | O24 | 18.69 | 27.09 | 30.94 | 7.5 |
| 59 | 119430 | O25 | 40.54 | 34.84 | 43.28 | 8.5 |
| 60 | 49713 | O26 | 45.06 | 1.05 | 0.68 | 20.0 |
| 61 | 34215 | O27 | 48.52 | 10.45 | 43.23 | 12.7 |
| 62 | 43877 | O28 | 58.35 | 46.91 | 41.23 | 5.4 |
| 63 | 29261 | O29 | 24.70 | 4.10 | 44.54 | 15.3 |
| 64 | 155615 | O30 | 2.59 | 2.03 | 2.14 | 4.2 |
| 65 | 160962 | O31 | 3.22 | 2.00 | 2.68 | 10.6 |

(a)Screen 1: Screening, at 10 uM (viability assay by ATP measurement, normalized fold-change shown, >=2.5);
(b)Screen 2: Dose response, at 10 uM (viability assay by ATP measurement, normalized fold-change shown, >=1.5);
(c)Screen 3: Dose response, at 20 uM (viability assay by ATP measurement, normalized fold-change shown).

TABLE 1C

Cellular Assays.

| SMDC ID | Cmpd ID | Assay 1(d) | Assay 2(e) | Assay 3(f) | Assay 4(g) | Assay 5(h) | Assay 6(i) | Assay 7(j) |
|---|---|---|---|---|---|---|---|---|
| 43368 | Gr-1A | YES | YES | YES | YES | YES | YES | YES |
| 45705 | Gr-1B | YES | YES | NO * | YES | YES | YES | YES |
| 34365 | Gr-1C | YES | YES | NO | YES | NO | YES | YES |
| 43139 | Gr-1D | YES | YES | YES | YES | YES | YES | YES |
| 45496 | Gr-1E | YES | YES | NO * | YES | YES | YES | YES |
| 44811 | Gr-1F | YES | YES | YES | YES | YES | YES | YES |
| 44542 | Gr-1G | YES | YES | NO | YES | NO | YES | YES |
| 152226 | Gr-2A | YES | YES | YES | YES | YES | YES | NO |
| 29688 | Gr-2B | YES | YES | YES | YES | YES | YES | NO |
| 30271 | Gr-2C | YES | YES | YES | YES | YES | YES | NO |
| 164559 | Gr-2D | N/A | N/A | N/A | N/A | N/A | — | — |
| 182737 | Gr-2E | YES | YES | NO | YES | NO | YES | NO |
| 29031 | Gr-3A | YES | YES | YES | YES | YES | YES | YES |
| 28636 | Gr-3B | NO | NO | NO | NO | NO | YES | YES |
| 29041 | Gr-3C | NO | NO | NO | NO | NO | YES | YES |
| 118836 | Gr-3D | N/A | N/A | N/A | N/A | N/A | — | — |
| 29513 | Gr-4A | YES | YES | NO | YES | NO | YES | YES |
| 33179 | Gr-4B | YES | YES | YES | YES | YES | YES | YES |
| 32955 | Gr-4C | YES | YES | YES | YES | YES | YES | YES |
| 28213 | Gr-4D | YES | YES | YES | YES | YES | YES | YES |
| 158211 | Gr-5A | NO | NO | NO | | NO | YES | YES |
| 158201 | Gr-5B | NO | NO | NO | NO | NO | YES | YES |
| 158206 | Gr-5C | NO | NO | NO | NO | NO | YES | NO |
| 158125 | Gr-5D | YES | YES | YES | YES | YES | YES | YES |
| 50328 | Gr-6A | YES | YES | YES | YES | YES | YES | YES |
| 150533 | Gr-6B | YES | YES | YES | YES | YES | YES | YES |
| 162159 | Gr-6C | NO | NO | NO | NO | NO | YES | YES |
| 152946 | Gr-7A | YES | YES | NO | YES | NO | YES | YES |
| 152936 | Gr-7B | YES | YES | NO | YES | NO | YES | YES |
| 152926 | Gr-7C | YES | YES | NO | YES | NO | YES | YES |
| 39959 | O1 | YES | YES | NO | YES | NO | YES | YES |
| 169199 | O2 | N/A | N/A | N/A | N/A | N/A | — | — |
| N/A | | | | | | | | |
| 127091 | O3 | YES | YES | YES | YES | YES | YES | NO |
| 194447 | O4 | YES | YES | YES | YES | YES | YES | NO |
| 151482 | O5 | YES | YES | YES | YES | YES | YES | NO |
| 166246 | O6 | YES | YES | NO | YES | NO | YES | YES |
| 148098 | O7 | YES | YES | YES | YES | YES | YES | NO |
| 173384 | O8 | NO | NO | NO | NO | NO | YES | NO |
| 178510 | O9 | YES | YES | YES | YES | YES | NO | NO |
| 41334 | O10 | YES | YES | NO | YES | NO | YES | YES |
| 157343 | O11 | YES | YES | NO | YES | NO | YES | YES |
| 122572 | O12 | NO | NO * | NO | NO | NO | YES | YES |
| 30228 | O13 | YES | YES | YES | YES | YES | YES | YES |

TABLE 1C-continued

Cellular Assays.

| SMDC ID | Cmpd ID | Assay 1(d) | Assay 2(e) | Assay 3(f) | Assay 4(g) | Assay 5(h) | Assay 6(i) | Assay 7(j) |
|---|---|---|---|---|---|---|---|---|
| 38610 | O14 | YES | YES | YES | YES | YES | YES | YES |
| 29424 | O15 | YES | YES | NO | YES | NO | YES | YES |
| 194820 | O16 | NO | NO | NO | NO | NO | YES | NO |
| 157154 | O17 | NO | NO | NO | NO | NO | YES | YES |
| 31883 | O18 | YES | YES | YES | YES | YES | NO | YES |
| 47511 | O19 | NO | N/A | N/A | N/A | NO | YES | NO |
| 39793 | O20 | YES | YES | YES | YES | YES | YES | YES |
| 128071 | O21 | NO | NO | NO |  | NO | YES | YES |
| 115873 | O22 | YES | YES | YES | YES | YES | YES | YES |
| 165151 | O23 | YES | YES | NO | YES | NO | YES | YES |
| 184478 | O24 | YES | YES | YES | YES | YES | YES | NO |
| 119430 | O25 | NO | N/A | N/A | N/A | NO | YES | NO |
| 49713 | O26 | NO | N/A | NO | NO | NO | NO | NO |
| 34215 | O27 | YES | YES | N/A | YES | YES | YES | YES |
| 43877 N/A | O28 | N/A | N/A | N/A | N/A | N/A | — | — |
| 29261 N/A | O29 | N/A | N/A | N/A | N/A | N/A | — | — |
| 155615 N/A | O30 | N/A | N/A | N/A | N/A | N/A | — | — |
| 160962 N/A | O31 | N/A | N/A | N/A | N/A | N/A | — | — |

(d)Assay: H2O2-resistant (If scored NO, possibly due to repeated freezing/thawing that compromise the stocks);
(e)Assay: Cadmium-resistant;
(f)Assay: MMS-resistant;
(g)Assay: H2O2- & Cd-resistant;
(h)Assay: Triple resistant;
(i)Assay: $H_2O_2$-resistant, at 10 uM, human dermal fibroblast (HDF) primary cells;
(j)Assay: $H_2O_2$-resistant, at 10 uM, validated by propidium iodide (PI) cell-death imaging (w/$H_2O_2$, 3 hrs/4 hrs/5 hrs).
* indicates partial.

TABLE 1D

Cellular Assays.

| SMDC ID | Cmpd ID | Assay 8(k) | Assay 9(l) | Assay 10(m) | Assay 11(n) | Assay 12(o) | Assay 13(p) | Assay 14(q) |
|---|---|---|---|---|---|---|---|---|
| 43368 | Gr-1A | NO | YES | CAT 1.36, $p < 0.01$; DDB1 1.16, $p < 0.05$; SESN1 1.93, $p < 0.05$ | NO | GCLC 1.48, $p < 0.01$; GSTM1 1.45, $p < 0.01$ |  | NO |
| 45705 | Gr-1B | YES | NO | TXNIP 1.52, $p < 0.01$; CAT 1.40, $p < 0.01$ | NO | GCLC 1.24, $p < 0.05$; NQO1 1.19, $p < 0.05$; GSTM1 1.44, $p < 0.01$ |  | NO |
| 34365 | Gr-1C | YES | YES | CAT 1.41, $p < 0.05$; GADD45A 0.60, $p < 0.01$; DDB1 1.14, $p < 0.01$; SESN1 1.59, $p < 0.001$ | NO | GCLC 1.65, $p < 0.01$; NQO1 1.33, $p < 0.01$ |  | NO |
| 43139 | Gr-1D | YES | YES | DDB1 1.13, $p < 0.05$; SESN1 1.91, $p < 0.001$ | NO | NO |  | NO |
| 45496 | Gr-1E | NO | NO | TXNIP 1.33, $p < 0.05$; CAT 1.38, $p < 0.05$; GADD45A 0.62, | NO | HMOX1 0.79, $p < 0.05$, GCLC 1.36, $p < 0.05$ |  | NO |

TABLE 1D-continued

Cellular Assays.

| SMDC ID | Cmpd ID | Assay 8(k) | Assay 9(l) | Assay 10(m) | Assay 11(n) | Assay 12(o) | Assay 13(p) | Assay 14(q) |
|---|---|---|---|---|---|---|---|---|
| 44811 | Gr-1F | YES | YES | $p < 0.01$; SESN1 1.34, $p < 0.01$ GADD45A 0.80, $p < 0.05$; DDB1 1.12, $p < 0.05$; SESN1 1.64, $p < 0.01$ | NO | HMOX1 0.82, $p < 0.05$; GCLC 1.35, $p < 0.05$; GSTM1 1.28, $p < 0.05$ | | NO |
| 44542 | Gr-1G | YES | NO | SOD2 0.76, $p < 0.05$; CAT 1.35, $p < 0.05$; GADD45A 0.60, $p < 0.01$ | NO | HMOX1 0.50, $p < 0.05$; GCLC 1.57, $p < 0.05$ | | NO |
| 152226 | Gr-2A | NO | NO | NO | NO | NO | NO | NO |
| 29688 | Gr-2B | NO | NO | NO | NO | NO | NO | NO |
| 30271 | Gr-2C | NO | NO | TXNIP 1.20, $p < 0.01$ | NO | HMOX1 1.23, $p < 0.01$ | NO | NO |
| 164559 | Gr-2D | — | — | — | — | — | — | — |
| 182737 | Gr-2E | NO | NO | NO | NO | NO | NO | NO |
| 29031 | Gr-3A | NO | YES | TXNIP 0.64, $p < 0.01$; CAT 0.83, $p < 0.05$; DDB1, 0.81, $p < 0.01$; SESN1 1.21, $p < 0.05$ | NO | NQO1 1.30, $p < 0.01$ | NO | NO |
| 28636 | Gr-3B | NO | NO | NO | NO | NO | NO | NO |
| 29041 | Gr-3C | NO | YES | DDB1 0.79, $p < 0.01$ | NO | HMOX1 0.86, $p < 0.05$ | NO | NO |
| 118836 | Gr-3D | — | — | — | — | — | — | — |
| 29513 | Gr-4A | NO | NO | CAT 1.26, $p < 0.05$; DDB1 1.20, $p < 0.05$ | NO | HMOX1 5.24, $p < 0.05$; NQO1 2.73, $p < 0.001$; GSTM1 1.24, $p < 0.05$ | YES | NO |
| 33179 | Gr-4B | NO | NO | NO | NO | HMOX1 4.51, $p > 0.05$; NQO1 2.36, $p < 0.05$ | YES | NO |
| 32955 | Gr-4C | NO | NO | TXNIP 0.18, $p < 0.05$; CAT 1.19, $p < 0.05$; GADD45A 1.23, $p < 0.05$; DDB1 1.51, $p < 0.001$; SESN1 1.42, $p < 0.05$ | NO | HMOX1 89.48, $p < 0.01$; GCLC 2.51, $p < 0.001$; NQO1 5.00, $p < 0.001$; GSTM1 1.63, $p < 0.01$ | YES | NO |
| 28213 | Gr-4D | NO | NO | SOD2 1.20, $p < 0.05$; CAT 1.37, $p < 0.01$; GADD45A 2.11, $p < 0.001$; DDB1 1.41, $p < 0.01$; SESN1 2.16, $p < 0.01$ | NO | HMOX1 4.55, $p < 0.01$; NQO1 2.56, $p < 0.01$; GSTM1 1.52, $p < 0.05$ | YES | NO |
| 158211 | Gr-5A | NO | NO | NO | NO | HMOX1 2.06, $p < 0.01$; NQO1 1.55, $p < 0.01$ | YES | NO |
| 158201 | Gr-5B | NO | NO | NO | NO | HMOX1 1.73, $p < 0.05$; NQO1 1.94, $p < 0.01$; GSTM1 1.27, $p < 0.05$ | YES | NO |

TABLE 1D-continued

Cellular Assays.

| SMDC ID | Cmpd ID | Assay 8(k) | Assay 9(l) | Assay 10(m) | Assay 11(n) | Assay 12(o) | Assay 13(p) | Assay 14(q) |
|---|---|---|---|---|---|---|---|---|
| 158206 | Gr-5C | YES | NO | NO | NO | HMOX1 1.67, $p < 0.001$; NQO1 1.49, $p < 0.001$ | NO | NO |
| 158125 | Gr-5D | NO | NO | NO | NO | HMOX1 2.49, $p < 0.01$; NQO1 1.78, $p < 0.001$; TXNIP 0.67, $p < 0.01$ | YES | NO |
| 50328 | Gr-6A | NO | NO | GADD45A 0.79, $p < 0.05$ | NO | NO | NO | NO |
| 150533 | Gr-6B | NO | NO | DDB1 1.19, $p < 0.05$ | NO | HMOX1 1.88, $p < 0.05$; NQO1 1.52, $p < 0.01$ | YES | NO |
| 162159 | Gr-6C | NO | YES | TXNIP 0.57, $p < 0.01$; SESN1 1.42, $p < 0.05$ | NO | HMOX1 2.09, $p < 0.01$; GCLC 0.33, $p < 0.001$ | NO | NO |
| 152946 | Gr-7A | NO | NO | TXNIP 0.12, $p < 0.001$; SOD2 1.78, $p < 0.01$; GADD45A 1.91, $p < 0.01$ | YES | HMOX1 15.23, $p < 0.01$; GCLC 0.60, $p < 0.001$; NQO1 0.78, $p < 0.05$ | NO | YES |
| 152936 | Gr-7B | YES | NO | TXNIP 0.26, $p < 0.001$; GADD45A 2.07, $p > 0.05$ | NO | HMOX1 17.90, $p < 0.01$ | NO | YES |
| 152926 | Gr-7C | NO | NO | TXNIP 0.07, $p < 0.001$; SOD2 2.67, $p < 0.05$; CAT 1.43, $p < 0.01$; GADD45A 10.86, $p < 0.01$; DDB1 1.36, $p < 0.05$ | YES | HMOX1 28.05, $p < 0.01$; GCLC 2.27, $p < 0.01$; GSTM1 0.78, $p < 0.05$ | YES | YES |
| 39959 | O1 | NO | NO | NO | NO | NO | NO | NO |
| 169199 | O2 | — | — | — | — | — | — | — |
| 127091 | O3 | NO | NO | NO | NO | NQO1 1.21, $p < 0.05$ | NO | NO |
| 194447 | O4 | NO | NO | NO | NO | NO | NO | NO |
| 151482 | O5 | YES | NO | SOD2 0.77, $p < 0.01$; GADD45A 0.45 $p < 0.05$ | NO | HMOX1 2.15, $p < 0.001$ | NO | NO |
| 166246 | O6 | NO | NO | NO | NO | HMOX1 3.85, $p < 0.001$; NQO1 1.62, $p < 0.001$ | YES | NO |
| 148098 | O7 | NO | NO | NO | NO | NO | NO | NO |
| 173384 | O8 | NO | NO | SOD2 1.07, $p < 0.05$ | NO | GSTM1 0.82, $p < 0.05$ | NO | NO |
| 178510 | O9 | NO | NO | TXNIP 1.72, $p < 0.05$; SOD2 1.15, $p < 0.05$; SESN1 1.19, $p < 0.05$ | NO | HMOX1 1.97, $p < 0.001$; NQO1 1.32, $p < 0.05$ | NO | NO |
| 41334 | O10 | NO | NO | NO | NO | NO | NO | NO |
| 157343 | O11 | YES | NO | TXNIP 1.35, $p < 0.05$; CAT 1.41, $p < 0.05$; DDB1 1.31, $p < 0.05$; SESN1 1.77, $p < 0.05$ | NO | NQO1 2.03, $p < 0.01$; GSTM1 1.30, $p < 0.01$ | NO | NO |

TABLE 1D-continued

Cellular Assays.

| SMDC ID | Cmpd ID | Assay 8(k) | Assay 9(l) | Assay 10(m) | Assay 11(n) | Assay 12(o) | Assay 13(p) | Assay 14(q) |
|---|---|---|---|---|---|---|---|---|
| 122572 | O12 | NO | NO | SOD2 1.35, $p < 0.001$; CAT 0.82, $p < 0.05$, GADD45A 1.44, $p < 0.01$; DDB1 0.86, $p < 0.05$ | NO | HMOX1 0.76, $p < 0.05$; GCLC 0.54, $p < 0.01$; NQO1 0.66, $p < 0.01$ | NO | NO |
| 30228 | O13 | NO | NO | CAT 1.33, $p < 0.05$; GADD45A 1.20, $p < 0.05$; DDB1 1.27, $p < 0.01$ | NO | HMOX1 5.52, $p < 0.01$; GCLC 1.99, $p < 0.01$, NQO1 2.95, $p < 0.001$; GSTM1 1.31, $p < 0.01$ | YES | NO |
| 38610 | O14 | NO | NO | TXNIP 1.27, $p < 0.05$; SOD2 1.06, $p < 0.05$ | NO | NO | NO | NO |
| 29424 | O15 | YES | NO | TXNIP 0.22, $p < 0.001$; CAT 1.28, $p < 0.05$; GADD45A 2.72, $p < 0.01$; SESN1 0.80, $p < 0.05$ | NO | HMOX1 48.69, $p < 0.001$; NQO1 1.60, $p < 0.05$ | YES | NO |
| 194820 | O16 | NO | NO | NO | NO | NO | NO | NO |
| 157154 | O17 | NO | NO | GADD45A 0.85, $p < 0.05$ | NO | GCLC 1.36, $p < 0.05$; NQO1 1.47, $p < 0.01$ | NO | NO |
| 31883 | O18 | NO | NO | TXNIP 0.30, $p < 0.001$ | NO | HMOX1 23.76, $p < 0.05$; GCLC 2.10, $p < 0.05$; NQO1 2.94, $p < 0.01$; GSTM1 1.52, $p < 0.01$ | YES | NO |
| 47511 | O19 | NO | NO | GADD45A 0.84, $p < 0.05$ | NO | NQO1 1.91, $p < 0.001$ | NO | NO |
| 39793 | O20 | YES | NO | CAT 1.35, $p < 0.01$; DDB1 1.25, $p < 0.05$; SESN1 1.73, $p < 0.05$ | NO | GCLC 1.76, $p < 0.05$; NQO1 2.49, $p < 0.01$ | YES | NO |
| 128071 | O21 | YES | YES | SESN1 1.88, $p < 0.05$ | NO | HMOX1 3.02, $p < 0.05$; GCLC 0.51, $p < 0.001$; GSTM1 1.25, $p < 0.01$ | NO | NO |
| 115873 | O22 | NO | NO | GADD45A 1.23, $p < 0.01$ | NO | GCLC 0.66, $p < 0.05$ | NO | NO |
| 165151 | O23 | YES | NO | TXNIP 0.07, $p < 0.001$; SOD2 2.04 $p < 0.01$; GADD45 7.22, $p < 0.01$ | YES | HMOX1 12.86, $p < 0.05$; GCLC 0.67, $p < 0.01$; NQO1 0.48, $p < 0.001$; GSTM1 0.60, $p < 0.001$ | NO | NO |
| 184478 | O24 | NO | NO | TXNIP 0.61, $p < 0.01$; SOD2 1.20, $p < 0.001$; SESN1 1.93, $p < 0.001$ | NO | HMOX1 9.55, $p > 0.05$; GCLC 0.70, $p < 0.05$; NQO1 1.48, $p < 0.01$; GSTM1 1.24, $p < 0.01$ | NO | NO |

TABLE 1D-continued

Cellular Assays.

| SMDC ID | Cmpd ID | Assay 8(k) | Assay 9(l) | Assay 10(m) | Assay 11(n) | Assay 12(o) | Assay 13(p) | Assay 14(q) |
|---|---|---|---|---|---|---|---|---|
| 119430 | O25 | NO | NO | NO | NO | NO | NO | NO |
| 49713 | O26 | NO | YES | TXNIP 1.16, $p < 0.05$; GADD45A 3.36, $p < 0.01$; SESN1 2.21, $p < 0.01$ | NO | NQO1 0.44, $p < 0.001$; GSTM1 0.85, $p < 0.05$ | NO | NO |
| 34215 | O27 | NO | YES | SESN1 1.54, $p < 0.05$ | NO | HMOX1 1.71, $p < 0.05$ | NO | YES |
| 43877 | O28 | — | — | — | — | — | — | — |
| 29261 | O29 | — | — | — | — | — | — | — |
| 155615 | O30 | — | — | — | — | — | — | — |
| 160962 | O31 | — | — | — | — | — | — | — |

(k)Assay: Without $H_2O_2$, at 10 uM, PI cell-death imaging (indicating potential toxicity);
(l)Assay: Score positive for both H2A.X & 53BP1, at 10 uM (indicating potential DNA-damaging effects);
(m)Assay: Induction of FOXO3-regulated genes (5 analyzed), at 10 uM (2012 July qPCR analysis) (normalized fold-change and p value shown);
(n)Assay: Potential FOXO3 Activation (>=2 target genes induced, by >=1.5-fold);
(o)Assay: Induction of NRF2-regulated genes (4 analyzed), at 10 uM (2012 July qPCR analysis) (normalized fold-change and p value shown);
(p)Assay: Potential NRF2 Activation (>=2 target genes induced, by >=1.5-fold);
(q)Assay: mTOR down-regulation by p-RPS6 assays, at 5 uM, 10 uM & 20 uM.

TABLE 1E

Cellular Assays.

| SMDC ID | Cmpd ID | Assay 15(r) | Assay 16(s) | Assay 17(t) | Assay 18(u) | Assay 19(v) | Assay 20(w) | Assay 21(x) |
|---|---|---|---|---|---|---|---|---|
| 43368 | Gr-1A | YES | NO | YES | | | YES | NO |
| 45705 | Gr-1B | NO | NO | NO | | | NO | NO |
| 34365 | Gr-1C | YES | NO | NO | | | YES | NO |
| 43139 | Gr-1D | YES | NO | NO | | | NO | NO |
| 45496 | Gr-1E | NO | NO | NO | | | NO | NO |
| 44811 | Gr-1F | NO | NO | NO | | | NO | NO |
| 44542 | Gr-1G | YES | NO | NO | | | NO | NO |
| 152226 | Gr-2A | NO | NO | NO | | | NO | NO |
| 29688 | Gr-2B | NO | NO | NO | | | NO | NO |
| 30271 | Gr-2C | NO | NO | NO | | | NO | NO |
| 164559 | Gr-2D | — | — | — | — | — | — | — |
| 182737 | Gr-2E | NO | NO | YES | | | NO | NO |
| 29031 | Gr-3A | NO | NO | NO | | | NO | NO |
| 28636 | Gr-3B | NO | NO | NO | | | NO | NO |
| 29041 | Gr-3C | NO | NO | NO | | | NO | NO |
| 118836 | Gr-3D | — | — | — | — | — | — | — |
| 29513 | Gr-4A | NO | NO | NO | | | NO | NO |
| 33179 | Gr-4B | NO | NO | NO | | | NO | NO |
| 32955 | Gr-4C | NO | NO | NO | | | NO | NO |
| 28213 | Gr-4D | NO | NO | NO | | | NO | NO |
| 158211 | Gr-5A | NO | NO | NO | | | NO | NO |
| 158201 | Gr-5B | NO | NO | NO | | | NO | NO |
| 158206 | Gr-5C | NO | NO | NO | | | NO | NO |
| 158125 | Gr-5D | NO | NO | NO | | | NO | NO |
| 50328 | Gr-6A | NO | NO | NO | | | NO | NO |
| 150533 | Gr-6B | NO | NO | YES | | | YES | NO |
| 162159 | Gr-6C | NO | NO | NO | | | NO | NO |
| 152946 | Gr-7A | NO | YES | YES | | | NO | YES |
| 152936 | Gr-7B | NO | NO | YES | | | NO | YES |
| 152926 | Gr-7C | NO | YES | YES | | | YES | NO |
| 39959 | O1 | NO | NO | YES | | | NO | NO |
| 169199 | O2 | — | — | — | — | — | — | — |
| 127091 | O3 | NO | NO | NO | | | NO | NO |
| 194447 | O4 | NO | NO | YES | | | NO | NO |
| 151482 | O5 | NO | NO | NO | | | NO | NO |
| 166246 | O6 | NO | NO | NO | | | NO | NO |
| 148098 | O7 | NO | NO | NO | | | YES | NO |
| 173384 | O8 | NO | NO | NO | | | NO | NO |
| 178510 | O9 | NO | NO | NO | | | NO | NO |

TABLE 1E-continued

Cellular Assays.

| SMDC ID | Cmpd ID | Assay 15(r) | Assay 16(s) | Assay 17(t) | Assay 18(u) | Assay 19(v) | Assay 20(w) | Assay 21(x) |
|---|---|---|---|---|---|---|---|---|
| 41334 | O10 | NO | NO | NO | | | NO | NO |
| 157343 | O11 | YES | NO | NO | | | NO | NO |
| 122572 | O12 | NO | NO | NO | | | NO | NO |
| 30228 | O13 | NO | NO | NO | | | NO | NO |
| 38610 | O14 | NO | NO | NO | | | NO | NO |
| 29424 | O15 | NO | YES | YES | | | NO | NO |
| 194820 | O16 | NO | NO | NO | | | NO | NO |
| 157154 | O17 | NO | NO | NO | | | NO | NO |
| 31883 | O18 | NO | NO | YES | | | NO | NO |
| 47511 | O19 | NO | NO | NO | | | NO | NO |
| 39793 | O20 | NO | YES | YES | | | NO | NO |
| 128071 | O21 | NO | NO | YES | | | NO | NO |
| 115873 | O22 | NO | NO | YES | | | NO | NO |
| 165151 | O23 | YES | NO | YES | | | NO | NO |
| 184478 | O24 | NO | NO | NO | | | NO | NO |
| 119430 | O25 | NO | NO | NO | | | NO | NO |
| 49713 | O26 | NO | NO | YES | | | NO | NO |
| 34215 | O27 | NO | NO | NO | | | NO | YES |
| 43877 N/A | O28 | — | — | — | | | — | — |
| 29261 N/A | O29 | — | — | — | | | — | — |
| 155615 N/A | O30 | — | — | — | | | — | — |
| 160962 N/A | O31 | — | — | — | | | — | — |

(r)Assay: Potential autophagy induction by LC3A/B puncta assays, at 10 uM & 20 uM;
(s)Assay: FOXO3-dependency for $H_2O_2$-resistance, at 10 uM;
(t)Assay: NRF2-dependency for $H_2O_2$-resistance, at 10 uM;
(u)Assay: FOXO3-dependency for target gene induction, at 10 uM;
(v)Assay: NRF2-dependency for target gene induction, at 10 uM;
(w)Assay: Huntington's poly-Q toxicity attenuation, at 10 uM;
(x)Assay: Potential killing effects on HTB-178 tumor cells (EGFR+ & PIK3CA+ & RB1– & TP53–) at 10 uM.

TABLE 1F

*C. elegans* Assays.

| SMDC ID | Cmpd ID | Assay 1(y) | Assay 2(z) | Assay 3(aa) | Assay 4(ab) | Assay 5(ac) | Assay 6(ad) | Assay 7(ae) |
|---|---|---|---|---|---|---|---|---|
| 43368 | Gr-1A | 1st, YES; 2nd, NO. | −1.3% | +0.2% | +14.2% | N/A | N/A | N/A |
| 45705 | Gr-1B | NO | +12.9% | +8.0% | +15.1% | N/A | N/A | N/A |
| 34365 | Gr-1C | NO | +14.4% | +1.7% | +14.7% | N/A | N/A | N/A |
| 43139 | Gr-1D | NO | +18.2% | −0.5% | +10.5% | N/A | N/A | N/A |
| 45496 | Gr-1E | NO | +17.4% | +6.3% | +13.8% | N/A | N/A | N/A |
| 44811 | Gr-1F | NO | +22.3% | +0.6% | +11.3% | N/A | N/A | N/A |
| 44542 | Gr-1G | NO | +1.3% | +10.2% | +24.7% | +5.8% | N/A | N/A |
| 152226 | Gr-2A | NO | +22.7% | +10.8% | +11.4% | N/A | N/A | N/A |
| 29688 | Gr-2B | 1st, YES; 2nd, NO. | +2.5% | −1.1% | +14.1% | N/A | N/A | N/A |
| 30271 | Gr-2C | NO | +15.3% | +0.1% | +7.6% | N/A | N/A | N/A |
| 164559 | Gr-2D | — | — | — | — | — | — | — |
| 182737 | Gr-2E | 1st, YES; 2nd, NO. | +3.3% | +4.0% | +9.7% | N/A | N/A | N/A |
| 29031 | Gr-3A | NO | +33.4% | +14.2% | +16.3% | +8.4% | N/A | N/A |
| 28636 | Gr-3B | 1st, YES; 2nd, NO. | +13.7% | +12.5% | +8.1% | N/A | N/A | N/A |
| 29041 | Gr-3C | NO | +18.9% | +11.9% | +8.0% | N/A | N/A | N/A |
| 118836 | Gr-3D | — | — | — | — | — | — | — |
| 29513 | Gr-4A | NO | −21.4% | +1.2% | −0.1% | N/A | N/A | N/A |
| 33179 | Gr-4B | NO | +8.1% | +14.5% | +10.7% | N/A | N/A | N/A |

TABLE 1F-continued

C. elegans Assays.

| SMDC ID | Cmpd ID | Assay 1(y) | Assay 2(z) | Assay 3(aa) | Assay 4(ab) | Assay 5(ac) | Assay 6(ad) | Assay 7(ae) |
|---|---|---|---|---|---|---|---|---|
| 32955 | Gr-4C | NO | −14.9% | +3.1% | −1.7% | N/A | N/A | N/A |
| 28213 | Gr-4D | 1st, YES; 2nd, NO. | +50.8% | +9.0% | +22.2% | +11.3% | +39.4% | +11.1% |
| 158211 | Gr-5A | 1st, YES; 2nd, NO. | +25.8% | −1.4% | −8.3% | N/A | N/A | N/A |
| 158201 | Gr-5B | NO | +37.2% | +2.0% | +1.7% | N/A | N/A | N/A |
| 158206 | Gr-5C | NO | +32.6% | +1.6% | −6.9% | N/A | N/A | N/A |
| 158125 | Gr-5D | NO | +29.5% | +5.8% | −5.3% | N/A | N/A | N/A |
| 50328 | Gr-6A | 1st, YES; 2nd, NO. | +5.5% | +6.8% | +16.9% | −2.7% | N/A | N/A |
| 150533 | Gr-6B | NO | +3.0% | +0.2% | +20.6% | −1.3% | N/A | N/A |
| 162159 | Gr-6C | NO | +20.5% | +12.4% | +9.4% | N/A | N/A | N/A |
| 152946 | Gr-7A | 1st, YES; 2nd, YES. | +40.6% | +16.2% | +13.9% | +2.7% | N/A | N/A |
| 152936 | Gr-7B | 1st, YES; 2nd, NO. | +1.3% | +3.5% | +14.9% | N/A | N/A | N/A |
| 152926 | Gr-7C | NO | −29.1% | +10.1% | −41.6% | N/A | N/A | N/A |
| 39959 | O1 | NO | +1.8% | −1.7% | +22.1% | −2.2% | N/A | N/A |
| 169199 | O2 | — | — | — | — | — | — | — |
| 127091 | O3 | NO | +14.1% | +14.8% | +15.9% | +12.0% | +8.7% | +1.4% |
| 194447 | O4 | NO | +26.3% | +8.0% | +18.5% | −0.9% | N/A | N/A |
| 151482 | O5 | NO | +48.9% | +18.9% | +46.2% | +46.3% | +10.2% | +32.0% |
| 166246 | O6 | 1st, YES; 2nd, NO. | +28.3% | +10.3% | +3.9% | N/A | N/A | N/A |
| 148098 | O7 | NO | +19.7% | +26.0% | +33.7% | +10.2% | +5.8% | −10.5% |
| 173384 | O8 | 1st, YES; 2nd, NO. | +6.6% | +3.8% | +10.0% | N/A | N/A | N/A |
| 178510 | O9 | 1st, YES; 2nd, YES. | +6.6% | +1.3% | −0.3% | N/A | N/A | N/A |
| 41334 | O10 | NO | +5.9% | −6.2% | +9.5% | N/A | N/A | N/A |
| 157343 | O11 | 1st, YES; 2nd, NO. | +14.9% | +6.0% | +21.0% | +9.0% | N/A | N/A |
| 122572 | O12 | 1st, YES; 2nd, NO. | +36.8% | +9.6% | +6.6% | N/A | N/A | N/A |
| 30228 | O13 | 1st, YES; 2nd, NO. | +32.7% | +10.3% | +27.3% | +15.0% | +8.4% | +15.3% |
| 38610 | O14 | NO | +13.7% | +5.8% | +11.3% | N/A | N/A | N/A |
| 29424 | O15 | 1st, YES; 2nd, YES. | +38.0% | +6.6% | +14.6% | N/A | N/A | N/A |
| 194820 | O16 | 1st, YES; 2nd, YES. | +16.8% | +11.4% | +19.7% | +9.8% | +9.9% | +12.1% |
| 157154 | O17 | 1st, YES; 2nd, YES. | +1.7% | +22.6% | +19.7% | +17.8% | +15.2% | +20.8% |
| 31883 | O18 | NO | +22.1% | +11.8% | +3.8% | N/A | N/A | N/A |
| 47511 | O19 | NO | — | — | — | — | — | — |

TABLE 1F-continued

C. elegans Assays.

| SMDC ID | Cmpd ID | Assay 1(y) | Assay 2(z) | Assay 3(aa) | Assay 4(ab) | Assay 5(ac) | Assay 6(ad) | Assay 7(ae) |
|---|---|---|---|---|---|---|---|---|
| 39793 | O20 | NO | +18.8% | +3.4% | +11.3% | N/A | N/A | N/A |
| 128071 | O21 | NO | +7.9% | −0.5% | +12.2% | N/A | N/A | N/A |
| 115873 | O22 | NO | −24.5% | −2.3% | −52.8% | N/A | N/A | N/A |
| 165151 | O23 | 1st, YES; 2nd, NO. | +36.2% | +17.4% | +21.6% | −0.3% | N/A | N/A |
| 184478 | O24 | NO | +13.0% | +2.3% | N/A | N/A | N/A | N/A |
| 119430 | O25 | NO | — | — | — | — | — | — |
| 49713 | O26 | NO | +23.9% | +4.6% | +27.1% | +8.3% | N/A | N/A |
| 34215 | O27 | NO | −35.1% | −17.8% | −69.3% | N/A | N/A | N/A |
| 43877 | O28 | — | — | — | — | — | — | — |
| 29261 | O29 | — | — | — | — | — | — | — |
| 155615 | O30 | — | — | — | — | — | — | — |
| 160962 | O31 | — | — | — | — | — | — | — |

(y)Assay: Potential killing effects on HTB-178 tumor cells (EGFR+ & PIK3CA+ & RB1− & TP53−) at 10 uM;
(z)Assay: Lifespan assay in liquid, at 66 uM, $1.0 \times 10^9$ bacteria/ml, wild type + FuDR (2012 July) ($p < 0.05$ highlighted);
(aa)Assay: Lifespan assay in liquid, at 66 uM, $2.5 \times 10^9$ bacteria/ml, wild type + FuDR ($p < 0.05$ highlighted);
(ab)Assay: Lifespan assay on plates, at 66 uM, $2.0 \times 10^{10}$ bacteria/ml, CF512 worms, no FuDR ($p < 0.05$ highlighted);
(ac)Assay: Lifespan assay on plates, at 66 uM, $1.0 \times 10^{11}$ bacteria/ml, CF512 worms, no FuDR ($p < 0.05$ highlighted);
(ad)Assay: Lifespan assay on plates, at 66 uM, $2.0 \times 10^{10}$ bacteria/ml, CF512 worms, no FuDR ($p < 0.05$ highlighted);
(ae)Assay: Lifespan assay on plates, at 66 uM, $1.0 \times 10^{11}$ bacteria/ml, CF512 worms, no FuDR ($p < 0.05$ highlighted).

TABLE 2

Target Summary.

| Cmpd | Target competency(a) | Targets |
|---|---|---|
| Gr-1F | 11/23/446/653 | SENP8, SENP7, JAK2, CFTR, TDP1, IDH1, CASP3, IL1B, GMNN, STAT1, SENP6 |
| Gr-3A | 21/25/285/423 | NFE2L2, ADRBK1, BARD1, MDM2, DRD3, MDM4, TDP1, RELA, OPRK1, CCR6, SMAD3, NOD2, IL1B, GMNN, BAZ2B, NOD1, APLNR, RBBP8, SIX1, BRCA1, NFKBIA, |
| Gr-3B | 39/44/482/772 | NFE2L2, NR2E3, TLR9, NOD2, OPRM1, BARD1, HTT, CFTR, MDM2, DRD3, MDM4, TDP1, OPRD1, GOPC, CHRM4, MITF, EPAS1, OPRK1, CCR6, MAP1LC3A, TNF, TARDBP, SMAD3, S1PR4, S1PR1, SLC12A5, NOD2, IL1B, CXCR6, TACC3, NOD1, APLNR, RIPK2, PRNP, HIF1A, AGTR1, ADRB2, ARNT, SIX1, BRCA1 |
| Gr-3C | 3/7/27/39 | RELA, GAPDH, NFKBIA |
| Gr-4D | 32/41/473/700 | TNFRSF10B, RELA, ATXN2, PLIN5, BARD1, MAPT, HTT, CFTR, MDM2, DRD3, MDM4, TDP1, CHRM4, IDH1, MITF, EPAS1, CHRM1, NFKB1, ABHD5, HNF4A, TUBB, TNF, SMAD3, CYP2C9, CYP3A4, NOD2, IL1B, GMNN, NOD1, GPR183, HIF1A, BRCA |
| Gr-7C | 41/52/478/718 | NFE2L2, KCNJ1, NR2E3, ATXN2, S1PR2, NPBWR1, NOD2, PLIN5, BARD1, CFTR, MDM2, MDM4, TDP1, VDR, CHRM4, IDH1, NPSR1, MITF, EPAS1, NCOA3, ABHD5, HNF4A, TNF, NCOA1, NR5A1, S1PR4, NR2F2, S1PR1, NOD2, IL1B, GMNN, NCOA2, NOD1, GPR183, RIPK2, NPY2R, NPY1R, HIF1A, NR5A2, CYP2C19, ADRB2, BRCA1 |

TABLE 2-continued

Target Summary.

| Cmpd | Target competency(a) | Targets |
|---|---|---|
| O6 (phenolic mannich) - PAINS | 9/15/361/498 | KCNE1, ATXN2, NTSR1, ADAM17, IDH1, KCNQ1, IL1B, ADAM10, GLP1R |
| O13 | 10/19/363/521 | SENP8, HCRTR1, TDP1, NR5A1, CASP3, GMNN, SSP1, NR5A2, DRD2, SENP6 |
| O14 | 1/1/421/581 | TRHR |
| O18 | 1/1/1/1 | JAK2 |
| O22 | 8/11/395/561 | OPRM1, CFTR, TDP1, OPRD1, NCOA3, APOBEC3F, PPARG, S1PR4 |

(a)Target competency: Human Protein Targets (confirmed)/Protein Targets (confirmed)/Total Protein Targets/Total BioAssays - query on PubChem.

TABLE 3

Summary of 20 compounds.

| ID | A | B | C | D | E | F | G | H | I | J | K | L | M | N | O | P | Q |
|---|---|---|---|---|---|---|---|---|---|---|---|---|---|---|---|---|---|
| Gr-7A | 1 | 0 | 1 | 0 | 2 | 0 | 2 | 0 | 1 | 1 | 0 | 1 | 2 | 11 | 0 | 0 | 0 |
| O20 | 1 | 1 | 1 | 2 | 0 | 2 | 0 | 0 | 1 | 1 | 0 | 0 | 1 | 10 | 1 | 0 | 1 |
| Gr-4D | 1 | 1 | 1 | 2 | 0 | 2 | 0 | 0 | 0 | 0 | 0 | 0 | 2 | 9 | 0 | 0 | 0 |
| Gr-6B | 1 | 1 | 1 | 2 | 0 | 2 | 0 | 0 | 0 | 1 | 1 | 0 | 0 | 9 | 0 | 0 | 0 |
| O13 | 1 | 1 | 1 | 2 | 0 | 2 | 0 | 0 | 0 | 0 | 0 | 0 | 2 | 9 | 0 | 0 | 0 |
| O18 | 1 | 1 | 1 | 2 | 0 | 2 | 0 | 0 | 0 | 1 | 0 | 0 | 1 | 9 | 0 | 0 | 0 |
| Gr-1A | 1 | 1 | 1 | 2 | 0 | 0 | 0 | 1 | 0 | 1 | 1 | 0 | 0 | 8 | 0 | 1 | 1 |
| O23 | 1 | 0 | 1 | 0 | 2 | 0 | 0 | 1 | 0 | 1 | 0 | 0 | 2 | 8 | 1 | 0 | 1 |
| O15 | 1 | 0 | 1 | 0 | 0 | 2 | 0 | 0 | 1 | 1 | 0 | 1 | 1 | 8 | 1 | 0 | 1 |
| Gr-5D | 1 | 1 | 1 | 2 | 0 | 2 | 0 | 0 | 0 | 0 | 0 | 0 | 0 | 7 | 0 | 0 | 0 |
| O14 | 1 | 1 | 1 | 2 | 0 | 0 | 0 | 0 | 0 | 0 | 0 | 0 | 2 | 7 | 0 | 0 | 0 |
| Gr-3A | 1 | 1 | 1 | 2 | 0 | 0 | 0 | 0 | 0 | 0 | 0 | 0 | 2 | 7 | 0 | 1 | 1 |
| O22 | 1 | 1 | 1 | 2 | 0 | 0 | 0 | 0 | 1 | 0 | 0 | 0 | 0 | 6 | 0 | 0 | 0 |
| O6 | 1 | 0 | 1 | 0 | 0 | 2 | 0 | 0 | 0 | 0 | 0 | 0 | 1 | 5 | 0 | 0 | 0 |
| O27 | 1 | 0 | 1 | 0 | 0 | 0 | 2 | 0 | 0 | 0 | 0 | 0 | 0 | 4 | 0 | 1 | 1 |
| O11 | 1 | 0 | 1 | 0 | 0 | 0 | 0 | 1 | 0 | 0 | 0 | 0 | 1 | 4 | 1 | 0 | 1 |
| O17 | 0 | 0 | 0 | 0 | 0 | 0 | 0 | 0 | 0 | 0 | 0 | 1 | 2 | 3 | 0 | 0 | 0 |
| O1 | 1 | 0 | 1 | 0 | 0 | 0 | 0 | 0 | 1 | 0 | 0 | 0 | 0 | 3 | 0 | 0 | 0 |
| O12 | 0 | 0 | 0 | 0 | 0 | 0 | 0 | 0 | 0 | 0 | 0 | 0 | 2 | 2 | 0 | 0 | 0 |
| O10 | 1 | 0 | 1 | 0 | 0 | 0 | 0 | 0 | 0 | 0 | 0 | 0 | 2 | 0 | 0 | 0 | |

A = Cadmium resistant; B = MMS resistant; C = H2O2- & Cd-resistant; D = Triple resistant; E = Potential FOXO3 Activation; F = Potential NRF2 Activation; G = mTOR down-regulation; H = Potential Autophagy Induction; I = FOXO3-dependency for H2O2-resistance; J = NRF2-dependency for H2O2-resistance; K = Huntington's poly-Q toxicity attenuation; L = H2O2-resistance in worms; M = Lifespan-extending scores in worms; N = Sum of Positive Scores; O = Potential toxicity; P = Potential DNA-damaging; Q = Sum of Negative Scores.

TABLE 4

Summary of 38 core scores.

| ID | A | B | C | D | E | F | G | H | I | J | K | L | M | N | O | P | Q |
|---|---|---|---|---|---|---|---|---|---|---|---|---|---|---|---|---|---|
| Gr-7A | 1 | 0 | 1 | 0 | 2 | 0 | 2 | 0 | 1 | 1 | 0 | 1 | 2 | 11 | 0 | 0 | 0 |
| Gr-7C | 1 | 0 | 1 | 0 | 2 | 2 | 2 | 0 | 1 | 1 | 1 | 0 | 0 | 11 | 0 | 0 | 0 |
| O20 | 1 | 1 | 1 | 2 | 0 | 2 | 0 | 0 | 1 | 1 | 0 | 0 | 1 | 10 | 1 | 0 | 1 |
| Gr-4D | 1 | 1 | 1 | 2 | 0 | 2 | 0 | 0 | 0 | 0 | 0 | 0 | 2 | 9 | 0 | 0 | 0 |
| Gr-6B | 1 | 1 | 1 | 2 | 0 | 2 | 0 | 0 | 0 | 1 | 1 | 0 | 0 | 9 | 0 | 0 | 0 |
| O13 | 1 | 1 | 1 | 2 | 0 | 2 | 0 | 0 | 0 | 0 | 0 | 0 | 2 | 9 | 0 | 0 | 0 |
| O18 | 1 | 1 | 1 | 2 | 0 | 2 | 0 | 0 | 0 | 1 | 0 | 0 | 1 | 9 | 0 | 0 | 0 |
| Gr-4B | 1 | 1 | 1 | 2 | 0 | 2 | 0 | 0 | 0 | 0 | 0 | 0 | 1 | 8 | 0 | 0 | 0 |
| Gr-1A | 1 | 1 | 1 | 2 | 0 | 0 | 0 | 1 | 0 | 1 | 1 | 0 | 0 | 8 | 0 | 1 | 1 |
| O23 | 1 | 0 | 1 | 0 | 2 | 0 | 0 | 1 | 0 | 1 | 0 | 0 | 2 | 8 | 1 | 0 | 1 |
| O15 | 1 | 0 | 1 | 0 | 0 | 2 | 0 | 0 | 1 | 1 | 0 | 1 | 1 | 8 | 1 | 0 | 1 |
| Gr-4C | 1 | 1 | 1 | 2 | 0 | 2 | 0 | 0 | 0 | 0 | 0 | 0 | 0 | 7 | 0 | 0 | 0 |
| Gr-5D | 1 | 1 | 1 | 2 | 0 | 2 | 0 | 0 | 0 | 0 | 0 | 0 | 0 | 7 | 0 | 0 | 0 |
| O14 | 1 | 1 | 1 | 2 | 0 | 0 | 0 | 0 | 0 | 0 | 0 | 0 | 2 | 7 | 0 | 0 | 0 |
| Gr-3A | 1 | 1 | 1 | 2 | 0 | 0 | 0 | 0 | 0 | 0 | 0 | 0 | 2 | 7 | 0 | 1 | 1 |
| Gr-1D | 1 | 1 | 1 | 2 | 0 | 0 | 0 | 1 | 0 | 0 | 0 | 0 | 1 | 7 | 1 | 1 | 2 |
| O22 | 1 | 1 | 1 | 2 | 0 | 0 | 0 | 0 | 0 | 1 | 0 | 0 | 0 | 6 | 0 | 0 | 0 |

TABLE 4-continued

Summary of 38 core scores.

| ID | A | B | C | D | E | F | G | H | I | J | K | L | M | N | O | P | Q |
|---|---|---|---|---|---|---|---|---|---|---|---|---|---|---|---|---|---|
| Gr-1F | 1 | 1 | 1 | 2 | 0 | 0 | 0 | 0 | 0 | 0 | 0 | 0 | 1 | 6 | 1 | 1 | 2 |
| Gr-6A | 1 | 1 | 1 | 2 | 0 | 0 | 0 | 0 | 0 | 0 | 0 | 0 | 0 | 5 | 0 | 0 | 0 |
| O6 | 1 | 0 | 1 | 0 | 0 | 2 | 0 | 0 | 0 | 0 | 0 | 0 | 1 | 5 | 0 | 0 | 0 |
| Gr-7B | 1 | 0 | 1 | 0 | 0 | 0 | 2 | 0 | 0 | 1 | 0 | 0 | 0 | 5 | 1 | 0 | 1 |
| Gr-1C | 1 | 0 | 1 | 0 | 0 | 0 | 0 | 1 | 0 | 0 | 1 | 0 | 1 | 5 | 1 | 1 | 2 |
| Gr-1E | 1 | 0 | 1 | 0 | 0 | 0 | 0 | 0 | 0 | 0 | 0 | 0 | 2 | 4 | 0 | 0 | 0 |
| Gr-4A | 1 | 0 | 1 | 0 | 0 | 2 | 0 | 0 | 0 | 0 | 0 | 0 | 0 | 4 | 0 | 0 | 0 |
| Gr-1G | 1 | 0 | 1 | 0 | 0 | 0 | 0 | 1 | 0 | 0 | 0 | 0 | 1 | 4 | 1 | 0 | 1 |
| O27 | 1 | 0 | 1 | 0 | 0 | 0 | 2 | 0 | 0 | 0 | 0 | 0 | 0 | 4 | 0 | 1 | 1 |
| O11 | 1 | 0 | 1 | 0 | 0 | 0 | 0 | 1 | 0 | 0 | 0 | 0 | 1 | 4 | 1 | 0 | 1 |
| O17 | 0 | 0 | 0 | 0 | 0 | 0 | 0 | 0 | 0 | 0 | 0 | 1 | 2 | 3 | 0 | 0 | 0 |
| O1 | 1 | 0 | 1 | 0 | 0 | 0 | 0 | 0 | 0 | 1 | 0 | 0 | 0 | 3 | 0 | 0 | 0 |
| Gr-1B | 1 | 0 | 1 | 0 | 0 | 0 | 0 | 0 | 0 | 0 | 0 | 0 | 1 | 3 | 1 | 0 | 1 |
| Gr-3B | 0 | 0 | 0 | 0 | 0 | 0 | 0 | 0 | 0 | 0 | 0 | 0 | 2 | 2 | 0 | 0 | 0 |
| Gr-5A | 0 | 0 | 0 | 0 | 0 | 2 | 0 | 0 | 0 | 0 | 0 | 0 | 0 | 2 | 0 | 0 | 0 |
| Gr-5B | 0 | 0 | 0 | 0 | 0 | 2 | 0 | 0 | 0 | 0 | 0 | 0 | 0 | 2 | 0 | 0 | 0 |
| O12 | 0 | 0 | 0 | 0 | 0 | 0 | 0 | 0 | 0 | 0 | 0 | 0 | 2 | 2 | 0 | 0 | 0 |
| O10 | 1 | 0 | 1 | 0 | 0 | 0 | 0 | 0 | 0 | 0 | 0 | 0 | 0 | 2 | 0 | 0 | 0 |
| Gr-3C | 0 | 0 | 0 | 0 | 0 | 0 | 0 | 0 | 0 | 0 | 0 | 0 | 2 | 2 | 0 | 1 | 1 |
| Gr-6C | 0 | 0 | 0 | 0 | 0 | 0 | 0 | 0 | 0 | 0 | 0 | 0 | 2 | 2 | 0 | 1 | 1 |
| O21 | 0 | 0 | 0 | 0 | 0 | 0 | 0 | 0 | 0 | 1 | 0 | 0 | 0 | 1 | 1 | 1 | 2 |

A = Cadmium resistant; B = MMS resistant; C = H2O2- & Cd-resistant; D = Triple resistant; E = Potential FOXO3 Activation; F = Potential NRF2 Activation; G = mTOR down-regulation; H = Potential Autophagy Induction; I = FOXO3-dependency for H2O2-resistance; J = NRF2-dependency for H2O2-resistance; K = Huntington's poly-Q toxicity attenuation; L = H2O2-resistance in worms; M = Lifespan-extending scores in worms; N = Sum of Positive Scores; O = Potential toxicity; P = Potential DNA-damaging; Q = Sum of Negative Scores.

TABLE 5

List of 38 "core set" small molecule hits, some of which increased the resistance to other stress conditions, including heavy metal cadmium and DNA-damaging agent MMS.

| Small Molecule ID | $H_2O_2$-resistant | $CdCl_2$-resistant | MMS-resistant | $H_2O_2$ & $CdCl_2$-resistant | Triple resistant |
|---|---|---|---|---|---|
| Group 1: 7 hits (Gr-1A) | YES | YES | NO | YES | NO |
| Gr-1B | YES | YES | NO | YES | NO |
| Gr-1C | YES | YES | NO | YES | NO |
| Gr-1D | YES | YES | NO | YES | NO |
| Gr-1E | YES | YES | NO | YES | NO |
| Gr-1F | YES | YES | NO | YES | NO |
| Gr-1G | YES | YES | NO | YES | NO |
| Group 3: 4 hits (3 available) (Gr-3A) | YES | YES | NO | YES | NO |
| Gr-3B | YES | NO | NO | NO | NO |
| Gr-3C | YES | NO | NO | NO | NO |
| Group 4: 4 hits (chalcones) (Gr-4A) | YES | YES | NO | YES | NO |
| Gr-4B | YES | YES | NO | YES | NO |
| Gr-4C | YES | NO | NO | NO | NO |
| Gr-4D | YES | YES | NO | YES | NO |
| Group 5: 4 hits (3 validated) (Gr-5A) | YES | YES | NO | YES | NO |
| Gr-5B | YES | NO | NO | NO | NO |
| Gr-5D | YES (*) | N/A | N/A | N/A | N/A |
| Group 6: 3 hits (Gr-6A) | YES | YES | YES | YES | YES |
| Gr-6B | YES | YES | NO | YES | NO |
| Gr-6C, rhodanines - PAINS | YES (*) | N/A | N/A | N/A | N/A |
| Group 7: 3 hits (Gr-7A) | YES (*) | NO | NO | NO | NO |
| Gr-7B | YES (*) | NO | NO | NO | NO |
| Gr-7C | YES | NO | NO | NO | NO |
| O1 | YES | YES | NO | YES | NO |
| O6, phenolic mannich - PAINS | YES | YES | NO | YES | NO |
| O10 | YES | YES | NO | YES | NO |
| O11 | YES | YES | NO | YES | NO |
| O12 | YES | YES | NO | YES | NO |
| O13 | YES | NO | NO | NO | NO |
| O14 | YES | YES | NO | YES | NO |
| O15, enones - PAINS | YES (*) | NO | NO | NO | NO |
| O17 | YES | NO | NO | NO | NO |
| O18 | YES | NO | NO | NO | NO |
| O20 | YES | YES | NO | YES | NO |
| O21, rhodanines - PAINS | YES | NO | NO | NO | NO |
| O22 | YES | YES | YES | YES | YES |
| O23, enones, catechols - PAINS | YES (*) | NO | NO | NO | NO |
| O27 | YES | YES | NO | YES | NO |

Note:
asterisks indicate the loss of the ability of several small molecules to protect cells from $H_2O_2$, which could be due to compromised stability of compound assayed over time.
24 of the 54 repurchased compounds are not shown because: 1) Two orphan compounds (O19 and O25) scored negatively in all tests, even the hydrogen peroxide retest, and were discarded. 2) the other twenty-two, including all Group 2 compounds that were confirmed to be PARP inhibitors, increased stress resistance, but did not score positive for the cell death-imaging assay.

TABLE 6

Effects of small molecules on FOXO3- and NRF2-regulated genes and analysis of the requirement for FOXO3 and NRF2 to promote $H_2O_2$-reistance. Small molecules (at 10 μM, n = 4) were introduced to WI-38 cells for 24 hrs and then analyzed by qPCR assays to address their effects on the expression levels of FOXO3- and NRF2-regulated genes. Relative levels were normalized to the genes B2M (summary of normalized fold changes for genes analyzed is shown, Student's t-test), PPIA and GAPDH (see Table 15 for additional details). To ask whether small molecules require FOXO3 and/or NRF2 to increase the resistance to $H_2O_2$, FOXO3 or NRF2 was first knocked down in WI-38 cells, and then cell viability was assayed following small molecule incubation and $H_2O_2$ stress treatment. Small molecules were analyzed in three independent gene knockdown experiments (1 & 2, with $H_2O_2$ only; 3 with and without $H_2O_2$). Dependency on FOXO3 or NRF2 is scored when the $H_2O_2$-resistance capacity of a given small molecule was reduced by at least 50% upon gene knockdown, and partial dependency is scored when it falls in between 25% and 50%.

| Small Molecule ID | A | B | C | D | E | F |
|---|---|---|---|---|---|---|
| Group 1: 7 hits (Gr-1A) | CAT 1.31, p < 0.01; DDB1 1.36, p < 0.05; SESN1 2.12, p < 0.01 | GCLC 1.61, p < 0.01; NQO1 1.79, p < 0.01; GSTM1 1.45, p < 0.01 | No | No | 1st, NO; 2nd, partial | YES (note: viability of non-stressed cells, reduced by 30%) |
| Gr-1B | TXNIP 1.94, p < 0.05; CAT 1.40, p < 0.01; SESN1 1.30, p < 0.01 | NQO1 1.31, p < 0.05; GSTM1 2.00, p > 0.05 | NO | N/A | NO | N/A |
| Gr-1C | CAT 1.44, p < 0.05 | GCLC 1.82, p < 0.05; NQO1 1.46, p < 0.01 | NO | N/A | NO | N/A |
| Gr-1D | TXNIP 0.62, p < 0.05; DDB1 1.18, p < 0.05; SESN1 1.73, p < 0.01 | HMOX1 4.68, p > 0.10 | NO | N/A | NO | N/A |
| Gr-1E | TXNIP 2.02, p > 0.05; CAT 1.45, p < 0.05; SESN1 1.40, p < 0.01 | GSTM1 2.11, p > 0.10 | NO | N/A | NO | N/A |
| Gr-1F | CAT 1.35, p < 0.05; SESN1 2.00, p < 0.05 | GCLC 1.62, p < 0.05 | NO | YES | NO | YES (note: viability of non-stressed cells, reduced by 50%) |
| Gr-1G | SOD2 0.76, p < 0.05; CAT 1.35, p < 0.05; GADD45A 0.60, p < 0.01 | HMOX1 0.50, p < 0.05; GCLC 1.57, p < 0.05 | NO | N/A | 1st, YES; 2nd, NO. | N/A |
| Group 3: 4 hits (3 available) (Gr-3A) | TXNIP 0.75, p < 0.05; CAT 0.87, p < 0.05; SESN1 1.18, p < 0.05 | HMOX1, 1.41, p < 0.05; NQO1 1.37, p < 0.01 | NO | N/A | NO | N/A |
| Gr-3B | NO | NO | NO | N/A | NO | N/A |
| Gr-3C | CAT 0.87, p < 0.05 | NO | NO | N/A | NO | N/A |
| Group 4: 4 hits (chalcones) (Gr-4A) | CAT 1.26, p < 0.05; DDB1 1.20, p < 0.05 | HMOX1 5.24, p < 0.05; NQO1 2.73, p < 0.001; GSTM1 1.24, p < 0.05 | NO | N/A | NO | N/A |
| Gr-4B | NO | HMOX1 4.51, p > 0.05; NQO1 2.36, p < 0.05 | NO | N/A | NO | N/A |

TABLE 6-continued

Effects of small molecules on FOXO3- and NRF2-regulated genes and analysis of the requirement for FOXO3 and NRF2 to promote $H_2O_2$-reistance. Small molecules (at 10 μM, n = 4) were introduced to WI-38 cells for 24 hrs and then analyzed by qPCR assays to address their effects on the expression levels of FOXO3- and NRF2-regulated genes. Relative levels were normalized to the genes B2M (summary of normalized fold changes for genes analyzed is shown, Student's t-test), PPIA and GAPDH (see Table 15 for additional details). To ask whether small molecules require FOXO3 and/or NRF2 to increase the resistance to $H_2O_2$, FOXO3 or NRF2 was first knocked down in WI-38 cells, and then cell viability was assayed following small molecule incubation and $H_2O_2$ stress treatment. Small molecules were analyzed in three independent gene knockdown experiments (1 & 2, with $H_2O_2$ only; 3 with and without $H_2O_2$). Dependency on FOXO3 or NRF2 is scored when the $H_2O_2$-resistance capacity of a given small molecule was reduced by at least 50% upon gene knockdown, and partial dependency is scored when it falls in between 25% and 50%.

| Small Molecule ID | A | B | C | D | E | F |
|---|---|---|---|---|---|---|
| Gr-4C | TXNIP 0.18, $p < 0.05$; CAT 1.19, $p < 0.05$; GADD45A 1.23, $p < 0.05$; DDB1 1.51, $p < 0.001$; SESN1 1.42, $p < 0.05$ | HMOX1 89.48, $p < 0.01$; GCLC 2.51, $p < 0.001$; NQO1 5.00, $p < 0.001$; GSTM1 1.63, $p < 0.01$ | NO | N/A | NO | N/A |
| Gr-4D | SOD2 1.20, $p < 0.05$; CAT 1.37, $p < 0.01$; GADD45A 2.11, $p < 0.001$; DDB1 1.41, $p < 0.01$; SESN1 2.16, $p < 0.01$ | HMOX1 4.55, $p < 0.01$; NQO1 2.56, $p < 0.01$; GSTM1 1.52, $p < 0.05$ | NO | Partial | NO | Partial |
| Group 5: 4 hits (3 validated) (Gr-5A) | NO | HMOX1 2.06, $p < 0.01$; NQO1 1.55, $p < 0.01$ | NO | N/A | NO | N/A |
| Gr-5B | NO | HMOX1 1.73, $p < 0.05$; NQO1 1.94, $p < 0.01$; GSTM1 1.27, $p < 0.05$ | NO | N/A | NO | N/A |
| Gr-5D | TXNIP 0.67, $p < 0.01$ | HMOX1 2.49, $p < 0.01$; NQO1 1.78, $p < 0.001$; TXNIP 0.67, $p < 0.01$ | NO | N/A | NO | N/A |
| Group 6: 3hits (Gr-6A) | GADD45A 0.79, $p < 0.05$ | NO | NO | N/A | NO | N/A |
| Gr-6B | DDB1 1.19, $p < 0.05$ | HMOX1 1.88, $p < 0.05$; NQO1 1.52, $p < 0.01$ | NO | NO | 1st, NO; 2nd, partial. | YES |
| Gr-6C, rhodanines - PAINS | TXNIP 0.57, $p < 0.01$; GADD45A 2.17, $p > 0.10$; SESN1 1.42, $p < 0.05$ | HMOX1 2.09, $p < 0.01$; GCLC 0.33, $p < 0.001$ | NO | N/A | 1st, NO; 2nd, partial. | N/A |
| Group 7: 3 hits (Gr-7A) | TXNIP 0.12, $p < 0.001$; SOD2 1.78, $p < 0.01$; GADD45A 1.91, $p < 0.01$ | HMOX1 15.23, $p < 0.01$; GCLC 0.60, $p < 0.001$; NQO1 0.78, $p < 0.05$ | 1st, partial; 2nd, YES. | YES | 1st, YES; 2nd, YES. | YES (note: viability of non-stressed cells, reduced by 84%) |

TABLE 6-continued

Effects of small molecules on FOXO3- and NRF2-regulated genes and analysis of the requirement for FOXO3 and NRF2 to promote $H_2O_2$-reistance. Small molecules (at 10 μM, n = 4) were introduced to WI-38 cells for 24 hrs and then analyzed by qPCR assays to address their effects on the expression levels of FOXO3- and NRF2-regulated genes. Relative levels were normalized to the genes B2M (summary of normalized fold changes for genes analyzed is shown, Student's t-test), PPIA and GAPDH (see Table 15 for additional details). To ask whether small molecules require FOXO3 and/or NRF2 to increase the resistance to $H_2O_2$, FOXO3 or NRF2 was first knocked down in WI-38 cells, and then cell viability was assayed following small molecule incubation and $H_2O_2$ stress treatment. Small molecules were analyzed in three independent gene knockdown experiments (1 & 2, with $H_2O_2$ only; 3 with and without $H_2O_2$). Dependency on FOXO3 or NRF2 is scored when the $H_2O_2$-resistance capacity of a given small molecule was reduced by at least 50% upon gene knockdown, and partial dependency is scored when it falls in between 25% and 50%.

| Small Molecule ID | A | B | C | D | E | F |
|---|---|---|---|---|---|---|
| Gr-7B | TXNIP 0.26, p < 0.001; GADD45A 2.07, p > 0.05 | HMOX1 54.15, p < 0.05 | NO | N/A | 1st, partial; 2nd, partial. | N/A |
| Gr-7C | TXNIP 0.07, p < 0.001; SOD2 2.67, p < 0.05; CAT 1.43, p < 0.01; GADD45A 10.86, p < 0.01; DDB1 1.36, p < 0.05 | HMOX1 28.05, p < 0.01; GCLC 2.27, p < 0.01; GSTM1 0.78, p < 0.05 | 1st, YES; 2nd, NO. | Partial | 1st, YES; 2nd, NO. | YES (note: viability of non-stressed cells, reduced by 60%) |
| O1 | NO | NO | NO | N/A | 1st, partial; 2nd, partial. | N/A |
| O6, phenolic mannich - PAINS | NO | HMOX1 3.85, p < 0.001; NQO1 1.62, p < 0.001 | NO | N/A | NO | N/A |
| O10 | NO | NO | NO | N/A | NO | N/A |
| O11 | TXNIP 1.35, p < 0.05; CAT 1.41, p < 0.05; DDB1 1.31, p < 0.05; SESN1 1.77, p < 0.05 | NQO1 2.03, p < 0.01; GSTM1 1.30, p < 0.01 | NO | N/A | NO | N/A |
| O12 | SOD2 1.52, p < 0.05; CAT 0.80, p < 0.01; GADD45A 1.69, p < 0.05 | HMOX1 0.82, p < 0.05; GCLC 0.53, p < 0.01; NQO1 0.69, p < 0.01 | NO | N/A | NO | N/A |
| O13 | CAT 1.33, p < 0.05; GADD45A 1.20, p < 0.05; DDB1 1.27, p < 0.01 | HMOX1 5.52, p < 0.01; GCLC 1.99, p < 0.01, NQO1 2.95, p < 0.001; GSTM1 1.31, p < 0.01 | NO | N/A | NO | N/A |
| O14 | TXNIP 1.39, p < 0.05 | NO | NO | N/A | NO | N/A |
| O15, enones - PAINS | TXNIP 0.22, p < 0.001; CAT 1.28, p < 0.05; GADD45A 2.72, p < 0.01; SESN1 0.80, p < 0.05 | HMOX1 48.69, p < 0.001; NQO1 1.60, p < 0.05 | 1st, YES; 2nd, NO. | YES | 1st, YES; 2nd, YES. | YES |

TABLE 6-continued

Effects of small molecules on FOXO3- and NRF2-regulated genes and analysis of the requirement for FOXO3 and NRF2 to promote $H_2O_2$-reistance. Small molecules (at 10 μM, n = 4) were introduced to WI-38 cells for 24 hrs and then analyzed by qPCR assays to address their effects on the expression levels of FOXO3- and NRF2-regulated genes. Relative levels were normalized to the genes B2M (summary of normalized fold changes for genes analyzed is shown, Student's t-test), PPIA and GAPDH (see Table 15 for additional details). To ask whether small molecules require FOXO3 and/or NRF2 to increase the resistance to $H_2O_2$, FOXO3 or NRF2 was first knocked down in WI-38 cells, and then cell viability was assayed following small molecule incubation and $H_2O_2$ stress treatment. Small molecules were analyzed in three independent gene knockdown experiments (1 & 2, with $H_2O_2$ only; 3 with and without $H_2O_2$). Dependency on FOXO3 or NRF2 is scored when the $H_2O_2$-resistance capacity of a given small molecule was reduced by at least 50% upon gene knockdown, and partial dependency is scored when it falls in between 25% and 50%.

| Small Molecule ID | A | B | C | D | E | F |
|---|---|---|---|---|---|---|
| O17 | GADD45A 0.85, $p < 0.05$ | GCLC 1.36, $p < 0.05$; NQO1 1.47, $p < 0.01$ | NO | N/A | NO | N/A |
| O18 | TXNIP 0.30, $p < 0.001$ | HMOX1 23.76, $p < 0.05$; GCLC 2.10, $p < 0.05$; NQO1 2.94, $p < 0.01$; GSTM1 1.52, $p < 0.01$ | NO | YES | 1st, NO; 2nd, partial. | YES |
| O20 | CAT 1.35, $p < 0.01$; DDB1 1.25, $p < 0.05$; SESN1 1.73, $p < 0.05$ | GCLC 1.76, $p < 0.05$; NQO1 2.49, $p < 0.01$ | 1st, NO; 2nd, YES. | YES | 1st, YES; 2nd, YES. | YES |
| O21, rhodanines - PAINS | SESN1 1.88, $p < 0.05$ | HMOX1 3.02, $p < 0.05$; GCLC 0.51, $p < 0.001$; GSTM1 1.25, $p < 0.01$ | NO | YES | 1st, partial; 2nd, NO. | YES |
| O22 | GADD45A 1.23, $p < 0.01$ | GCLC 0.66, $p < 0.05$ | NO | N/A | 1st, partial; 2nd, partial. | N/A |
| O23, enones, catechols - PAINS | TXNIP 0.07, $p < 0.001$; SOD2 2.04 $p < 0.01$; GADD45 7.22, $p < 0.01$ | HMOX1 12.86, $p < 0.05$; GCLC 0.67, $p < 0.01$; NQO1 0.48, $p < 0.001$; GSTM1 0.60, $p < 0.001$ | NO | YES | 1st, YES; 2nd, YES. | YES (note: yet viability of non-stressed cells, reduced by 40%) |
| O27 | SESN1 1.54, $p < 0.05$ | HMOX1 1.71, $p < 0.05$ | NO | N/A | NO | N/A |

A = Summary of effects on FOXO3- regulated genes, at 10 uM; B = Summary of effects on NRF2-regulated genes, at 10 uM; C = FOXO3-dependency for H2O2- resistance, at 10 uM (experiment 1 & 2) - with H2O2; D = FOXO3-dependency for H2O2- resistance, at 10 uM (experiment 3) - with & without H2O2; E = NRF2-dependency for H2O2-resistance, at 10 uM (experiment 1 & 2) -with H2O2; F = NRF2-dependency for H2O2-resistance, at 10 uM (experiment 3) - with & without H2O2.

TABLE 7

Small molecules extend C. elegans' lifespan, and a few also promoted $H_2O_2$-resistance. Multiple independent trials were conducted to analyze the effects of small molecules (at 60 μM final concentration, 0.3% DMSO) on lifespan. Trial 1 (1.0 × 10^9 bacteria/ml) & 2 (2.5 × 10^9 bacteria/ml): wild type, with FuDR; Trial 3 (2.0 × 10^10 bacteria/ml, 100 μl) & 4 (1.0 × 10^11 bacteria/ml, 100 μl) (UV-irradiated, plus kanamycin), on plate, CF512 temperature-sensitive sterile mutant animals, no FuDR; Confirmative trials 5 (2.0 × 10^10 bacteria/ml, 100 μl) & 6 (1.0 × 10^11 bacteria/ml, 100 μl), same as trials 3 or 4, three molecules analyzed. Compared with control animals, relative changes of mean lifespan are shown (color code indicate statistical significant differences). Similarly, $H_2O_2$-resistance assays were conducted for all the small molecules in liquid (60 μM final concentration) and molecules that scored positive in two independent experiments are reported.

| Small Molecule ID | A | B | C | D | E | F | G |
|---|---|---|---|---|---|---|---|
| Group 1: 7 hits (Gr-1A) | −1.3% | +0.2% | +14.2% | N/A | N/A | N/A | 1st, YES; 2nd, NO. |
| Gr-1B | +12.9% | +8.0% | +15.1% | N/A | N/A | N/A | NO |
| Gr-1C | +14.4% | +1.7% | +14.7% | N/A | N/A | N/A | NO |
| Gr-1D | +18.2% | −0.5% | +10.5% | N/A | N/A | N/A | NO |
| Gr-1E | +17.4% | +6.3% | +13.8% | N/A | N/A | N/A | NO |
| Gr-1F | +22.3% | +0.6% | +11.3% | N/A | N/A | N/A | NO |
| Gr-1G | +1.3% | +10.2% | +24.7% | +5.8% | N/A | N/A | NO |
| Group 3: 4 hits (3 available) | +33.4% | +14.2% | +16.3% | +8.4% | N/A | N/A | NO |
| Gr-3B | +13.7% | +12.5% | +8.1% | N/A | N/A | N/A | 1st, YES; 2nd, NO. |
| Gr-3C | +18.9% | +11.9% | +8.0% | N/A | N/A | N/A | NO |
| Group 4: 4 hits (chalcones) (Gr-4A) | −21.4% | +1.2% | −0.1% | N/A | N/A | N/A | NO |
| Gr-4B | +8.1% | +14.5% | +10.7% | N/A | N/A | N/A | NO |
| Gr-4C | −14.9% | +3.1% | −1.7% | N/A | N/A | N/A | NO |
| Gr-4D | +50.8% | +9.0% | +22.2% | +11.3% | +39.4% | +11.1% | 1st, YES; 2nd, NO. |
| Group 5: 4 hits (3 validated) (Gr-5A) | +25.8% | −1.4% | −8.3% | N/A | N/A | N/A | 1st, YES; 2nd, NO. |
| Gr-5B | +37.2% | +2.0% | +1.7% | N/A | N/A | N/A | NO |
| Gr-5D | +29.5% | +5.8% | −5.3% | N/A | N/A | N/A | NO |
| Group 6: 3 hits (Gr-6A) | +5.5% | +6.8% | +16.9% | −2.7% | N/A | N/A | 1st, YES; 2nd, NO. |
| Gr-6B | +3.0% | +0.2% | +20.6% | −1.3% | N/A | N/A | NO |
| Gr-6C, rhodanines - PAINS | +20.5% | +12.4% | +9.4% | N/A | N/A | N/A | NO |
| Group 7: 3 hits (Gr-7A) | +40.6% | +16.2% | +13.9% | +2.7% | N/A | N/A | 1st, YES; 2nd, NO. |
| Gr-7B | +1.3% | +3.5% | +14.9% | N/A | N/A | N/A | 1st, YES; 2nd, NO. |
| Gr-7C | −29.1% | +10.1% | −41.6% | N/A | N/A | N/A | NO |
| O1 | +1.8% | −1.7% | +22.1% | −2.2% | N/A | N/A | NO |
| O6, phenolic mannich - PAINS | +28.3% | +10.3% | +3.9% | N/A | N/A | N/A | 1st, YES; 2nd, NO. |
| O10 | +5.9% | −6.2% | +9.5% | N/A | N/A | N/A | NO |
| O11 | +14.9% | +6.0% | +21.0% | +9.0% | N/A | N/A | 1st, YES; 2nd, NO. |

TABLE 7-continued

Small molecules extend *C. elegans*' lifespan, and a few also promoted $H_2O_2$-resistance. Multiple independent trials were conducted to analyze the effects of small molecules (at 60 μM final concentration, 0.3% DMSO) on lifespan. Trial 1 (1.0 × 10^9 bacteria/ml) & 2 (2.5 × 10^9 bacteria/ml): wild type, with FuDR; Trial 3 (2.0 × 10^10 bacteria/ml, 100 μl) & 4 (1.0 × 10^11 bacteria/ml, 100 μl) (UV-irradiated, plus kanamycin), on plate, CF512 temperature-sensitive sterile mutant animals, no FuDR; Confirmative trials 5 (2.0 × 10^10 bacteria/ml, 100 μl) & 6 (1.0 × 10^11 bacteria/ml, 100 μl), same as trials 3 or 4, three molecules analyzed. Compared with control animals, relative changes of mean lifespan are shown (color code indicate statistical significant differences). Similarly, $H_2O_2$-resistance assays were conducted for all the small molecules in liquid (60 μM final concentration) and molecules that scored positive in two independent experiments are reported.

| Small Molecule ID | A | B | C | D | E | F | G |
|---|---|---|---|---|---|---|---|
| O12 | +36.8% | +9.6% | +6.6% | N/A | N/A | N/A | 1st, YES; 2nd, NO. |
| O13 | +32.7% | +10.3% | +27.3% | +15.0% | +8.4% | +15.3% | 1st, YES; 2nd, NO. |
| O14 | +13.7% | +5.8% | +11.3% | N/A | N/A | N/A | NO |
| O15, enones - PAINS | +38.0% | +6.6% | +14.6% | N/A | N/A | N/A | 1st, YES; 2nd, YES. |
| O17 | +1.7% | +22.6% | +19.7% | +17.8% | +15.2% | +20.8% | 1st, YES; 2nd, YES. |
| O18 | +22.1% | +11.8% | +3.8% | N/A | N/A | N/A | NO |
| O20 | +18.8% | +3.4% | +11.3% | N/A | N/A | N/A | NO |
| O21, rhodanines - PAINS | +7.9% | −0.5% | +12.2% | N/A | N/A | N/A | NO |
| O22 | −24.5% | −2.3% | −52.8% | N/A | N/A | N/A | NO |
| O23, enones, catechols - PAINS | +36.2% | +17.4% | +21.6% | −0.3% | N/A | N/A | 1st, YES; 2nd, NO. |
| O27 | −35.1% | −17.8% | −69.3% | N/A | N/A | N/A | NO |

A = Trial 1, in liquid, wild type, with FuDR; B = Trial 2, in liquid, wild type, with FuDR; C = Trial 3, on plate, temperature-sensitive sterile animals, without FuDR; D = Trial 4, on plate, temperature-sensitive sterile animals, without FuDR (11 analyzed); E = Trial 5, on plate, temperature-sensitive sterile animals, without FuDR (3 analyzed); F = Trial 6, on plate, temperature-sensitive sterile animals, without FuDR (3 analyzed); G = H2O2- resistance assay, in liquid, wild type, with FuDR.

TABLE 8

Summary for characterization of screen hits. 38 "core set" small molecules are listed and are assigned a score, based on the result for each individual characterization. From our small molecule screen for $H_2O_2$-resistance, we isolated 61 top hits. Of these, 38 repurchased molecules were further validated and analyzed as the "core set" in multiple phenotypical assays that have been shown to be longevity-related in experimental systems (including animals). Specifically, a 2-point score was assigned to the most well-known and prominent longevity-related phenotypes, such as multiplex resistance, activation of FOXO3 and/or NRF2, and down-regulation of mTOR. Small molecules were also analyzed for their ability to extend *C. elegans*' lifespan in 4 to 6 independent trials, and the lifespan score scale is from 0 to 2: 0 for no obvious effects, 1 for lifespan extension observed in 2 trials, 2 for observed in more than 2 trials. Certain molecules appeared to have DNA-damaging effects and/or potential cell-toxicity in cultured human cells, and they receive a negative point.

| ID | A | B | C | D | E | F | G | H | I | J | K | L | M | N | O | P | Q | R | S |
|---|---|---|---|---|---|---|---|---|---|---|---|---|---|---|---|---|---|---|---|
| Gr-1A | 1 | 0 | 1 | 0 | 0 | 2 | 0 | 1 | 0 | 1 | 1 | 0 | 1 | 0 | 0 | 8 | 0 | 1 | 1 |
| Gr-1B | 1 | 0 | 1 | 0 | 0 | 0 | 0 | 0 | 0 | 0 | 0 | 0 | 0 | 0 | 1 | 3 | 0 | 0 | 0 |
| Gr-1C | 1 | 0 | 1 | 0 | 0 | 0 | 0 | 1 | 0 | 0 | 0 | 0 | 1 | 0 | 1 | 5 | 0 | 1 | 1 |
| Gr-1D | 1 | 0 | 1 | 0 | 0 | 0 | 1 | 0 | 0 | 1 | 0 | 0 | 0 | 0 | 1 | 5 | 0 | 1 | 1 |
| Gr-1E | 1 | 0 | 1 | 0 | 0 | 0 | 0 | 0 | 0 | 0 | 0 | 0 | 0 | 0 | 2 | 4 | 0 | 0 | 0 |
| Gr-1F | 1 | 0 | 1 | 0 | 0 | 0 | 0 | 0 | 0 | 0 | 1 | 0 | 0 | 0 | 1 | 4 | 1 | 1 | 2 |
| Gr-1G | 1 | 0 | 1 | 0 | 0 | 0 | 0 | 0 | 1 | 0 | 0 | 0 | 0 | 0 | 1 | 4 | 0 | 0 | 1 |
| Gr-3A | 1 | 0 | 1 | 0 | 0 | 0 | 0 | 0 | 0 | 0 | 0 | 0 | 0 | 0 | 2 | 4 | 0 | 1 | 1 |
| Gr-3B | 0 | 0 | 0 | 0 | 0 | 0 | 0 | 0 | 0 | 0 | 0 | 0 | 0 | 0 | 2 | 2 | 1 | 0 | 0 |
| Gr-3C | 0 | 0 | 0 | 0 | 0 | 0 | 0 | 0 | 0 | 0 | 0 | 0 | 0 | 0 | 2 | 2 | 1 | 1 | 2 |
| Gr-4A | 1 | 0 | 1 | 0 | 0 | 2 | 0 | 0 | 0 | 0 | 0 | 0 | 0 | 0 | 0 | 4 | 0 | 0 | 0 |

TABLE 8-continued

Summary for characterization of screen hits. 38 "core set" small molecules are listed and are assigned a score, based on the result for each individual characterization. From our small molecule screen for $H_2O_2$-resistance, we isolated 61 top hits. Of these, 38 repurchased molecules were further validated and analyzed as the "core set" in multiple phenotypical assays that have been shown to be longevity-related in experimental systems (including animals). Specifically, a 2-point score was assigned to the most well-known and prominent longevity-related phenotypes, such as multiplex resistance, activation of FOXO3 and/or NRF2, and down-regulation of mTOR. Small molecules were also analyzed for their ability to extend C. elegans' lifespan in 4 to 6 independent trials, and the lifespan score scale is from 0 to 2: 0 for no obvious effects, 1 for lifespan extension observed in 2 trials, 2 for observed in more than 2 trials. Certain molecules appeared to have DNA-damaging effects and/or potential cell-toxicity in cultured human cells, and they receive a negative point.

| ID | A | B | C | D | E | F | G | H | I | J | K | L | M | N | O | P | Q | R | S |
|---|---|---|---|---|---|---|---|---|---|---|---|---|---|---|---|---|---|---|---|
| Gr-4B | 1 | 0 | 1 | 0 | 0 | 2 | 0 | 0 | 0 | 0 | 0 | 0 | 0 | 0 | 1 | 5 | 0 | 0 | 0 |
| Gr-4C | 0 | 0 | 0 | 0 | 0 | 2 | 0 | 0 | 0 | 0 | 0 | 0 | 0 | 0 | 0 | 2 | 0 | 0 | 0 |
| Gr-4D | 1 | 0 | 1 | 0 | 0 | 2 | 0 | 0 | 0 | 0 | 1 | 0 | 0 | 0 | 2 | 7 | 0 | 0 | 0 |
| Gr-5A | 1 | 0 | 1 | 0 | 0 | 2 | 0 | 0 | 0 | 0 | 0 | 0 | 0 | 0 | 0 | 4 | 0 | 0 | 0 |
| Gr-5B | 0 | 0 | 0 | 0 | 0 | 2 | 0 | 0 | 0 | 0 | 0 | 0 | 0 | 0 | 0 | 2 | 0 | 0 | 0 |
| Gr-5D | 0 | 0 | 0 | 0 | 0 | 2 | 0 | 0 | 0 | 0 | 0 | 0 | 0 | 0 | 0 | 2 | 0 | 0 | 0 |
| Gr-6A | 1 | 1 | 1 | 2 | 0 | 0 | 0 | 0 | 0 | 0 | 0 | 1 | 0 | 0 | 0 | 6 | 0 | 0 | 0 |
| Gr-6B | 1 | 0 | 1 | 0 | 0 | 2 | 0 | 0 | 0 | 1 | 0 | 0 | 1 | 0 | 0 | 6 | 0 | 0 | 0 |
| Gr-6C | 0 | 0 | 0 | 0 | 0 | 0 | 0 | 0 | 0 | 0 | 0 | 0 | 0 | 0 | 2 | 2 | 1 | 1 | 2 |
| Gr-7A | 0 | 0 | 0 | 0 | 2 | 0 | 2 | 0 | 1 | 1 | 0 | 0 | 0 | 1 | 2 | 9 | 1 | 0 | 1 |
| Gr-7B | 0 | 0 | 0 | 0 | 0 | 0 | 2 | 0 | 0 | 1 | 0 | 0 | 0 | 0 | 0 | 3 | 1 | 0 | 1 |
| Gr-7C | 0 | 0 | 0 | 0 | 2 | 2 | 2 | 0 | 1 | 1 | 0 | 0 | 1 | 0 | 0 | 9 | 1 | 0 | 1 |
| O1 | 1 | 0 | 1 | 0 | 0 | 0 | 0 | 0 | 0 | 1 | 0 | 1 | 0 | 0 | 0 | 4 | 0 | 0 | 0 |
| O6 | 1 | 0 | 1 | 0 | 0 | 2 | 0 | 0 | 0 | 0 | 0 | 0 | 0 | 0 | 1 | 5 | 0 | 0 | 0 |
| O10 | 1 | 0 | 1 | 0 | 0 | 0 | 0 | 0 | 0 | 0 | 0 | 0 | 0 | 0 | 0 | 2 | 0 | 0 | 0 |
| O11 | 1 | 0 | 1 | 0 | 0 | 0 | 0 | 1 | 0 | 0 | 1 | 0 | 0 | 0 | 1 | 5 | 1 | 0 | 1 |
| O12 | 1 | 0 | 1 | 0 | 2 | 0 | 0 | 0 | 0 | 0 | 0 | 0 | 0 | 0 | 2 | 7 | 0 | 0 | 0 |
| O13 | 0 | 0 | 0 | 0 | 0 | 2 | 0 | 0 | 0 | 0 | 0 | 0 | 0 | 0 | 2 | 4 | 0 | 0 | 0 |
| O14 | 1 | 0 | 1 | 0 | 0 | 0 | 0 | 0 | 0 | 0 | 1 | 0 | 0 | 0 | 2 | 5 | 0 | 0 | 0 |
| O15 | 0 | 0 | 0 | 0 | 0 | 2 | 0 | 0 | 1 | 1 | 0 | 0 | 0 | 1 | 1 | 6 | 0 | 0 | 0 |
| O17 | 0 | 0 | 0 | 0 | 0 | 0 | 0 | 0 | 0 | 0 | 0 | 0 | 0 | 1 | 2 | 3 | 0 | 0 | 0 |
| O18 | 0 | 0 | 0 | 0 | 0 | 2 | 0 | 0 | 0 | 1 | 0 | 0 | 0 | 0 | 1 | 4 | 0 | 0 | 0 |
| O20 | 1 | 0 | 1 | 0 | 0 | 2 | 0 | 0 | 1 | 1 | 1 | 0 | 0 | 0 | 1 | 8 | 0 | 0 | 0 |
| O21 | 0 | 0 | 0 | 0 | 0 | 0 | 0 | 0 | 1 | 1 | 0 | 0 | 0 | 0 | 2 | 1 | 1 | 1 | 2 |
| O22 | 1 | 1 | 1 | 2 | 0 | 0 | 0 | 0 | 1 | 0 | 1 | 0 | 0 | 0 | 7 | 0 | 0 | 0 |
| O23 | 0 | 0 | 0 | 0 | 2 | 0 | 0 | 1 | 0 | 1 | 0 | 0 | 0 | 0 | 2 | 6 | 1 | 0 | 1 |
| O27 | 1 | 0 | 1 | 0 | 0 | 0 | 2 | 0 | 0 | 0 | 1 | 0 | 0 | 0 | 0 | 5 | 1 | 1 | 2 |

A = Cadmium resistant; B = MMS resistant; C = H2O2- & Cd-resistant; D = Triple resistant; E = Potential FOXO3 Activation; F = Potential NRF2 Activation; G = mTOR down-regulation; H = Potential Autophagy Induction; I = FOXO3-dependency for H2O2-resistance; J = NRF2-dependency for H2O2-resistance; K = Sestrin induction; L = PARP inhibition; M = Huntington's poly-Q toxicity attenuation; N = H2O2-resistance in worms; O = Life span- extending scores in worms; P = Sum of Positive Scores; Q = Potential toxicity;
R = Potential DNA damaging; S = Sum of Negative scores.

TABLE 9

PubChem database queries indicate that at least 11 small molecules had been identified in multiple screens with confirmed human protein targets. Shown are the potential targets, which upon knocking down, may recapitulate the oxidative stress-resistance phenotype of our small molecules. Human Protein Targets (confirmed)/Protein Targets (confirmed)/Total Protein Targets/To 11/23/446/653 for Gr-1F; 21/25/285/423 for Gr-3A (note Gr-3A = AC1LEORR); 39/44/482/772 for Gr-3B; 3/7/27/39 for Gr-3C; tal BioAssays - query on PubChem 32/41/473/700 for Gr-4D; 41/52/4N78/718 for Gr-7C; 9/15/361/498 for O6 (note phenolic mannich - PAINS); 10/19/363/521 for O13; 1/1/421/581 for O14; 1/1/1/1 for O18; 8/11/395/561 for O22.

| | |
|---|---|
| Gr-1F | CASP3, CFTR, GMNN, IDH1, IL1B, JAK2, SENP6, SENP7, SENP8, STAT1, TDP1 |
| Gr-3A | ADRBK1, APLNR, BARD1, BAZ2B, BRCA1, CCR6, DRD3, GMNN, IL1B, MDM2, MDM4, NFE2L2, NFKBIA, NOD1, NOD2, OPRK1, RBBP8, RELA, SIX1, SMAD3, TDP1 |
| Gr-3B | ADRB2, AGTR1, APLNR, ARNT, BARD1, BRCA1, CCR6, CFTR, CHRM4, CXCR6, DRD3, EPAS1, GOPC, HIF1A, HTT, IL1B, MAP1LC3A, MDM2, MDM4, MITF, NFE2L2, NOD1, NOD2, NOD2, RR2E3, OPRD1, OPRK1, OPRM1, PRNP, RIPK2, S1PR1, S1PR4, SIX1, SLC12A5, SMAD3, TACC3, TARDBP, TDP1, TLR9, TNF |
| Gr-3C | GAPDH, NFKBIA, RELA |
| Gr-4D | ABHD5, ATXN2, BARD1, BRCA, CFTR, CHRM1, CHRM4, CYP2C9, CYP3A4, DRD3, EPAS1, GMNN, GPR183, HIF1A, HNF4A, HTT, IDH1, IL1B, MAPT, MDM2, MDM4, MITF, NFKB1, NOD1, NOD2, PLIN5, RELA, SMAD3, TDP1, TNF, TNFRSF10B, TUBB |

TABLE 9-continued

PubChem database queries indicate that at least 11 small molecules had been identified in multiple screens with confirmed human protein targets. Shown are the potential targets, which upon knocking down, may recapitulate the oxidative stress-resistance phenotype of our small molecules. Human Protein Targets (confirmed)/Protein Targets (confirmed)/Total Protein Targets/To 11/23/446/653 for Gr-1F; 21/25/285/423 for Gr-3A (note Gr-3A = AC1LEORR); 39/44/482/772 for Gr-3B; 3/7/27/39 for Gr-3C; tal BioAssays - query on PubChem 32/41/473/700 for Gr-4D; 41/52/4N78/718 for Gr-7C; 9/15/361/498 for O6 (note phenolic mannich - PAINS); 10/19/363/521 for O13; 1/1/421/581 for O14; 1/1/1/1 for O18; 8/11/395/561 for O22.

| | |
|---|---|
| Gr-7C | ABHD5, ADRB2, ATXN2, BARD1, BRCA1, CFTR, CHRM4, CYP2C19, EPAS1, GMNN, GPR183, HIF1A, HNF4A, IDH1, IL1B, KCNJ1, MDM2, MDM4, MITF, NCOA1, NCOA2, NCOA3, NFE2L2, NOD1, NOD2, NOD2, NPBWR1, NPSR1, NPY1R, NPY2R, NR2E3, NR2F2, NR5A1, NR5A2, PLIN5, RIPK2, S1PR1, S1PR2, TDP1, TNF, VDR |
| O6 | ADAM10, ADAM17, ATXN2, GLP1R, IDH1, IL1B, KCNE1, KCNQ1, NTSR1 |
| O13 | CASP3, DRD2, GMNN, HCRTR1, NR5A1, NR5A2, SENP6, SENP8, SSP1, TDP1 |
| O14 | TRHR |
| O18 | JAK2 |
| O22 | APOBEC3F, CFTR, NCOA3, OPRD1, OPRM1, PPARG, S1PR4, TDP1 |

TABLE 10

(related to Table 5). Dose response and cell death imaging analysis of library compounds identified in the screen. 209 candidate hits were cherry-picked from the screen library and retested at six different final concentrations (0.6 μM, 1.25 μM, 2.5 μM, 5 μM, 10 μM and 20 μM) to examine their ability to promote $H_2O_2$-resistance of WI-38 cells. Dose response curves and derived EC50 values are shown. This table includes the data for the 38 "core set" hits, including 23 that belong to 6 structural groups and 15 orphans. Potential pan assay interference compounds are also indicated. Cells pre-treated with these molecules (at 1.25 μM and 10 μM) were also analyzed by propidium iodide imaging to examine cell death upon 3.5 hours of $H_2O_2$ treatment. For DMSO pre-treated controls (n = 30), the percentages of PI-positive cells were 23.7% ± 6.9% (average ± standard deviation, 1.25 μM assay plate) and 27.4% ± 6.5% (average ± standard deviation, 10 μM assay plate). 107 hits were found to reduce [by one (*), two () or three (*) standard deviations] the percentage of PI-positive dead cells. Certain effective small molecules could have been missed in the imaging assays, as false negatives could arise due to potential stability issue of the library compounds. Note that significant reduction of performance (fold change < 1.50, highlighted in red) and high EC50 values were observed in certain cases.

| Small Molecule ID | Library Screening, at 10 uM (fold change) | Dose response retest, at 10 uM (fold change) | Dose response retest, at 20 uM (fold change) | EC50 (uM) | Percentage of propidium iodide-positive dead cells (under $H_2O_2$ stress treatment), at 1.25 uM | Percentage of propidium iodide-positive dead cells (under $H_2O_2$ stress treatment), at 10 uM |
|---|---|---|---|---|---|---|
| Group 1: 7 hits (Gr-1A) | 2.89 | 3.66 | 3.44 | 6.0 | 4.5% *** | 22.6% |
| Gr-1B | 4.12 | 3.18 | 3.40 | 6.2 | 3.7% *** | 38.1% |
| Gr-1C | 5.35 | 2.67 | 3.27 | 8.0 | 10.4% * | 7.8% ** |
| Gr-1D | 5.99 | 4.84 | 4.85 | 4.6 | 9.1% ** | 36.7% |
| Gr-1E | 17.87 | 11.83 | 6.59 | 3.7 | 5.1% *** | 18.8% * |
| Gr-1F | 26.35 | 3.47 | 7.92 | 14.8 | 5.6% ** | 11.2% ** |
| Gr-1G | 33.25 | 7.81 | 4.96 | 4.8 | 12.6% * | 34.4% * |
| Group 3: 4 hits (3 available) (Gr-3A) | 5.16 | 1.43 | 1.88 | 11.2 | 10.0% ** | 12.4% ** |
| Gr-3B | 20.47 | 2.18 | 2.68 | 8.5 | 20.8% | 2.6% *** |
| Gr-3C | 24.00 | 5.93 | 1.74 | 6.5 | 9.6% ** | 3.1% *** |
| Group 4: 4 hits (chalcones) (Gr-4A) | 2.71 | 1.98 | 2.48 | 9.1 | 6.2% ** | 1.9% ** |
| Gr-4B | 2.94 | 1.93 | 2.10 | 8.9 | 1.8% *** | 3.4% *** |
| Gr-4C | 6.06 | 2.33 | 2.90 | 8.4 | 3.5% *** | 17.4% * |
| Gr-4D | 14.99 | 3.48 | 6.13 | 10.6 | 4.5% *** | 19.8% * |
| Group 5: 4 hits (3 validated) (Gr-5A) | 3.52 | 1.27 | 1.40 | 20.0 | 9.5% ** | 3.7% *** |

TABLE 10-continued (related to Table 5). Dose response and cell death imaging analysis of library compounds identified in the screen. 209 candidate hits were cherry-picked from the screen library and retested at six different final concentrations (0.6 μM, 1.25 μM, 2.5 μM, 5 μM, 10 μM and 20 μM) to examine their ability to promote $H_2O_2$-resistance of WI-38 cells. Dose response curves and derived EC50 values are shown. This table includes the data for the 38 "core set" hits, including 23 that belong to 6 structural groups and 15 orphans. Potential pan assay interference compounds are also indicated. Cells pre-treated with these molecules (at 1.25 μM and 10 μM) were also analyzed by propidium iodide imaging to examine cell death upon 3.5 hours of $H_2O_2$ treatment. For DMSO pre-treated controls (n = 30), the percentages of PI-positive cells were 23.7% ± 6.9% (average ± standard deviation, 1.25 μM assay plate) and 27.4% ± 6.5% (average ± standard deviation, 10 μM assay plate). 107 hits were found to reduce [by one (*), two () or three (*) standard deviations] the percentage of PI-positive dead cells. Certain effective small molecules could have been missed in the imaging assays, as false negatives could arise due to potential stability issue of the library compounds. Note that significant reduction of performance (fold change < 1.50, highlighted in red) and high EC50 values were observed in certain cases.

| Small Molecule ID | Library Screening, at 10 uM (fold change) | Dose response retest, at 10 uM (fold change) | Dose response retest, at 20 uM (fold change) | EC50 (uM) | Percentage of propidium iodide-positive dead cells (under $H_2O_2$ stress treatment), at 1.25 uM | Percentage of propidium iodide-positive dead cells (under $H_2O_2$ stress treatment), at 10 uM |
|---|---|---|---|---|---|---|
| Gr-5B | 3.62 | 1.60 | 1.90 | 8.7 | 9.7% ** | 6.1% *** |
| Gr-5D | 12.42 | 1.57 | 1.77 | 20.0 | 11.4% * | 6.4% *** |
| Group 6: 3hits (Gr-6A) | 9.69 | 3.20 | 5.82 | 13.8 | 19.1% | 15.6% * |
| Gr-6B | 17.34 | 1.29 | 2.00 | 20.0 | 12.3% * | 2.1% *** |
| Gr-6C, rhodanines - PAINS | 50.99 | 1.37 | 10.83 | 16.2 | 11.2% * | 7.9% ** |
| Group 7: 3 hits (Gr-7A) | 3.01 | 2.80 | 9.45 | 16.1 | 15.9% | 9.9% ** |
| Gr-7B | 3.36 | 1.29 | 2.61 | 20.0 | 5.7% ** | 4.7% *** |
| Gr-7C | 23.04 | 1.46 | 2.83 | 14.2 | 26.8% | 12.5% ** |
| O1 | 2.53 | 1.87 | 2.91 | 13.2 | 13.7% * | 20.4% * |
| O6, phenolic mannich - PAINS | 2.88 | 1.50 | 1.95 | 9.8 | 17.5% | 16.8% * |
| O10 | 3.12 | 1.83 | 2.32 | 9.5 | 10.4% * | 3.6% *** |
| O11 | 3.42 | 6.71 | 3.00 | 4.4 | 2.6% *** | 26.5% |
| O12 | 3.82 | 5.74 | 9.57 | 1.0 | 3.0% *** | 0.4% *** |
| O13 | 4.21 | 1.50 | 2.09 | 10.1 | 16.4% | 4.8% *** |
| O14 | 4.24 | 2.32 | 3.77 | 12.5 | 5.6% ** | 12.7% ** |
| O15, enones - PAINS | 4.60 | 1.57 | 2.32 | 20.0 | 6.7% ** | 6.8% *** |
| O17 | 4.97 | 1.96 | 2.22 | 8.5 | 15.5% | 6.6% *** |
| O18 | 5.33 | 1.73 | 2.22 | 9.8 | 7.2% ** | 4.5% *** |
| O20 | 8.90 | 1.41 | 1.82 | 12.9 | 11.1% * | 9.4% ** |
| O21, rhodanines - PAINS | 10.24 | 1.59 | 8.46 | 18.1 | 13.0% * | 7.8% ** |
| O22 | 14.30 | 3.28 | 5.11 | 20.0 | 8.7% ** | 4.1% *** |
| O23, enones, catechols - PAINS | 15.73 | 2.82 | 1.44 | 4.9 | 8.3% ** | 10.2% ** |
| O27 | 48.52 | 10.45 | 43.23 | 12.7 | 10.1% ** | 0.5% *** |

TABLE 11

(related to Table 5). Cell death-imaging analysis and effects on primary HDF cells for repurchased small molecules. Repurchased small molecules were analyzed first by LC-MS for quality check. Except for three molecules (Gr-6A, O12 and O17 - these molecules also protected human cells from $H_2O_2$ and were included for subsequent analyses), their masses matched with predicted values. Potential pan assay interference compounds are also indicated. Consistent with the results of ATP assay for cell viability, the 38 "core set" small molecules reduced the fraction of propidium iodide-positive cells upon $H_2O_2$ stress treatment (n = 6 for each molecule, Student's t-test, three consecutive time points - 3 hrs, 4 hrs and 5 hrs of $H_2O_2$ treatment). Representative data, normalized fold-changes for ATP measurements and PI-positive fractions, are shown for at least three independent experiments. Small molecules were also analyzed in primary human dermal fibroblasts (HDFs, from multiple donors), along with the WI-38 cells, and found to protect these primary cells from $H_2O_2$.

| Small Molecule ID | A | B | C | D | E | F | G | H | I |
|---|---|---|---|---|---|---|---|---|---|
| Group 1: 7 hits (Gr-1A) | OK | 0.72 | 0.79% ± 0.36%, p = 0.054 | 3.77 | 1.44% ± 0.52%, p = 2.54E−09; 3.18% ± 0.52%, p = 2.59E−20; 7.49% ± 2.56%, p = 7.31E−06 | 8.58 | 3.89 | 12.06 | 52.51 |
| Gr-1B | | 0.94 | 1.03% ± 0.34%, p = 0.006 | 2.17 | 2.69% ± 0.61%, p = 2.36E−06; 11.16% ± 1.4 2%, p = 2.00−E05; 17.61% ± 4.1 4%, p = 0.033 | 8.53 | 0.51 | 24.58 | 53.68 |
| Gr-1C | OK | 0.81 | 3.51% ± 1.28%, p = 0.002 | 11.38 | 2.49% ± 0.45%, p = 7.52E−09; 3.10% ± 0.87%, p = 5.28E−14; 4.05% ± 0.87%, p = 1.24E−16 | 7.64 | 15.23 | 24.98 | 49.13 |
| Gr-1D | OK | 0.91 | 4.16% ± 1.39%, p = 0.001 | 6.98 | 6.27% ± 2.02%, p = 0.365; 5.83% ± 2.40%, p = 3.28E−05; 10.70% ± 2.6 0%, p = 3.51E−05 | 8.31 | 2.79 | 18.93 | 49.32 |
| Gr-1E | OK | 0.96 | 0.71% ± 0.28%, p = 0.090 | 4.14 | 1.68% ± 0.25%, p = 1.73E−14; 2.95% ± 0.51%, p = 1.16E−20; 3.44% ± 0.33%, p = 4.87E−23 | 8.22 | 1.40 | 28.54 | 30.96 |
| Gr-1F | OK | 0.60 | 3.27% ± 0.82%, p = 3.26E−14 | 14.64 | 3.55% ± 0.60%, p = 6.99E−05; 3.07% ± 0.60%, p = 3.72E−19; 4.57% ± 0.78%, p = 3.39E−18 | 8.10 | 5.84 | 23.26 | 52.28 |
| Gr- = 1G | | 0.82 | 7.07% ± 1.09%, p = 2.09E−05 | 19.33 | 8.40% ± 1.51%, p = 0.004; 7.74% ± 1.37%, p = 2.63E−07; 10.69% ± 2.1 5%, p = 6.53E−06 | 8.14 | 8.66 | 25.76 | 39.84 |
| Group 3: 4 hits (3 available) (Gr-3A) | OK | 0.98 | 0.54% ± 0.16%, p = 0.195 | 1.08 | 5.54% ± 1.00%, p = 0.085; 13.94% ± 1.3 0%, p = 0.001; 16.88% ± 4.5 6%, p = 0.029 | 8.12 | 2.38 | 2.69 | 1.67 |
| Gr-3B | OK | 0.90 | 0.47% ± 0.20%, p = 0.647 | 1.08 | 4.63% ± 0.81%, p = 0.063; 13.01% ± 1.1 8%, p = 6.56E−05; 15.17% ± 4.8 8%, p = 0.014 | 7.78 | 3.10 | 7.53 | 1.59 |
| Gr-3C | OK | 0.95 | 0.57% ± 0.24%, p = 0.269 | 1.11 | 5.13% ± 1.50%, p = 0.645; 15.61% ± 2.0 2%, p = 0.224; 16.25% ± 4.3 9%, p = 0.017 | 8.22 | 6.59 | 11.18 | 1.69 |

TABLE 11-continued (related to Table 5). Cell death-imaging analysis and effects on primary HDF cells for repurchased small molecules. Repurchased small molecules were analyzed first by LC-MS for quality check. Except for three molecules (Gr-6A, O12 and O17 - these molecules also protected human cells from $H_2O_2$ and were included for subsequent analyses), their masses matched with predicted values. Potential pan assay interference compounds are also indicated. Consistent with the results of ATP assay for cell viability, the 38 "core set" small molecules reduced the fraction of propidium iodide-positive cells upon $H_2O_2$ stress treatment (n = 6 for each molecule, Student's t-test, three consecutive time points - 3 hrs, 4 hrs and 5 hrs of $H_2O_2$ treatment). Representative data, normalized fold-changes for ATP measurements and PI-positive fractions, are shown for at least three independent experiments. Small molecules were also analyzed in primary human dermal fibroblasts (HDFs, from multiple donors), along with the WI-38 cells, and found to protect these primary cells from $H_2O_2$.

| Small Molecule ID | A | B | C | D | E | F | G | H | I |
|---|---|---|---|---|---|---|---|---|---|
| Group 4: 4 hits (chalcones) (Gr-4A) | OK | 1.08 | 0.39% ± 0.14%, p = 0.645 | 3.00 | 1.87% ± 0.73%, p = 2.53E−06; 11.36% ± 4.8 0%, p = 0.038; 20.42% ± 1.4 0%, p = 0.013 | 2.48 | 7.16 | 30.86 | 2.35 |
| Gr-4B | OK | 1.18 | 0.36% ± 0.13%, p = 0.357 | 2.83 | 3.31% ± 0.73%, p = 1.69E−4; 14.49% ± 1.1 0%, p = 0.008; 19.91% ± 1.7 9%, p = 0.014 | 1.89 | 13.73 | 9.20 | 55.59 |
| Gr-4C | OK | 1.08 | 0.47% ± 0.20%, p = 0.653 | 6.93 | 4.02% ± 1.94%, p = 0.135; 6.21% ± 2.69%, p = 9.42E−4; 16.65% ± 2.4 6%, p = 0.001 | 1.99 | 4.32 | 19.28 | 3.15 |
| Gr-4D | OK | 1.11 | 0.42% ± 0.15%, p = 0.945 | 1.21 | 1.58% ± 0.57%, p = 1.98E−08; 7.44% ± 1.55%, p = 1.13E−4; 15.47% ± 2.3 7%, p = 3.67E−04 | 2.58 | 1.06 | 5.09 | 2.00 |
| Group 5: 4 hits (3 validated) (Gr-5A) | Expected mass, 2 peaks | 1.14 | 0.48% ± 0.20%, p = 0.589 | 1.28 | 1.64% ± 0.43%, p = 5.23E−11; 8.97% ± 1.09%, p = 1.51E−08; 17.12% ± 1.1 4%, p = 1.31E−06 | 1.69 | 2.95 | 16.36 | 2.00 |
| Gr-5B | Expected mass, 2 peaks | 1.19 | 0.45% ± 0.15%, p = 0.798 | 1.43 | 1.18% ± 0.29%, p = 4.63E−15; 6.19% ± 0.62%, p = 1.30E−16; 24.15% ± 1.5 2%, P = 0.048 | 1.70 | 9.16 | 7.69 | 13.33 |
| Gr-5D | OK | 1.14 | 0.51% ± 0.18%, p = 0.384 | 1.40 | 3.28% ± 0.58%, p = 1.39E−05; 17.57% ± 1.7 5%, p = 0.366; 24.13% ± 0.7 7%, p = 0.003 | 1.22 | 0.18 | 1.90 | 2.66 |
| Group 6: 3 hits (Gr-6A) | | 1.10 | 0.41% ± 0.17%, p = 0.854 | 6.26 | 4.38% ± 0.31%, p = 1.25E−4; 15.21% ± 0.4 9%, p = 4.85E−04; 26.95% ± 2.3 7%, p = 0.004 | 2.47 | 10.28 | 3.53 | 39.34 |
| Gr-6B | Expected mass, 2 peaks | 1.10 | 0.46% ± 0.25%, p = 0.766 | 1.95 | 2.62% ± 0.86%, p = 9.76E−5; 12.57% ± 2.1 3%, p = 0.003; 21.75% ± 0.9 4%, p = 0.177 | 1.80 | 3.60 | 22.79 | 57.65 |
| Gr-6C, rhodanines - PAINS | Expected mass, 2 peaks | .096 | 0.66% ± 0.26%, p = 0.079 | 8.07 | 1.17% ± 0.19%, p = 8.63E−16; 1.39% ± 0.35%, p = 4.01E−22; 6.12% ± 1.95%, p = 2.37E−07 | 1.23 | 0.01 | 5.39 | 50.65 |

TABLE 11-continued (related to Table 5). Cell death-imaging analysis and effects on primary HDF cells for repurchased small molecules. Repurchased small molecules were analyzed first by LC-MS for quality check. Except for three molecules (Gr-6A, O12 and O17 - these molecules also protected human cells from $H_2O_2$ and were included for subsequent analyses), their masses matched with predicted values. Potential pan assay interference compounds are also indicated. Consistent with the results of ATP assay for cell viability, the 38 "core set" small molecules reduced the fraction of propidium iodide-positive cells upon $H_2O_2$ stress treatment (n = 6 for each molecule, Student's t-test, three consecutive time points - 3 hrs, 4 hrs and 5 hrs of $H_2O_2$ treatment). Representative data, normalized fold-changes for ATP measurements and PI-positive fractions, are shown for at least three independent experiments. Small molecules were also analyzed in primary human dermal fibroblasts (HDFs, from multiple donors), along with the WI-38 cells, and found to protect these primary cells from $H_2O_2$.

| Small Molecule ID | A | B | C | D | E | F | G | H | I |
|---|---|---|---|---|---|---|---|---|---|
| Group 7: 3 hits (Gr-7A | OK | 0.78 | | 6.36 | 2.78% ± 0.77%, p = 0.002; 2.32% ± 0.57%, p = 3.50E−20; 3.52% ± 1.16%, p = 1.81E−12 | 0.68 | 1.20 | 18.20 | 4.11 |
| Gr-7B | OK | 0.56 | | 0.77 | 5.88% ± 1.30%, p = 0.464; 6.44% ± 2.24%, p = 2.05E−04; 18.93% ± 1.0 9%, p = 3.90E−05 | .059 | 3.71 | 3.82 | 3.35 |
| Gr-7C | OK | 0.87 | | 31.87 | 0.82% ± 0.19%, p = 3.15E−16; 2.36% ± 1.09%, p = 6.06E−09; 3.73% ± 0.66%, p = 7.55E−21 | 1.24 | .074 | 27.90 | 8.33 |
| O1 | OK | 0.92 | 0.30% ± 0.13%, p = 0.122 | 2.14 | 5.80% ± 1.09%, p = 0.484; 18.65% ± 1.5 4%, p = 0.032; 28.70% ± 1.8 7%, p = 1.25E−04 | 1.65 | 2.95 | 2.46 | 17.83 |
| O6, phenolic mannich - PAINS | OK | 1.07 | 0.36% ± 0.10%, p = 0.270 | 1.89 | 0.80% ± 0.24%, p = 1.80E−16; 4.92% ± 1.47%, p = 7.74E−08; 9.82% ± 2.06%, p = 2.59E−06 | 2.57 | 284.95 | 2.91 | 22.22 |
| O10 | OK | 1.08 | 0.54% ± 0.16%, p = 0.188 | 1.34 | 2.19% ± 0.35%, p = 1.22E−11; 4.27% ± 0.66%, p = 3.71E−17; 11.58% ± 1.4 4%, p = 6.62E−08 | 2.51 | 12.60 | 13.37 | 8.91 |
| O11 | OK | 0.75 | 1.86% ± 0.71%, p = 0.004 | 7.18 | 2.19% ± 0.35%, p = 7.15E−05; 2.80% ± 0.49%, p = 5.87E−21; 2.90% ± 0.70%, p = 1.72E−20 | 2.52 | 16.57 | 28.12 | 55.68 |
| O12 | Mass NOT matched | 1.01 | 0.45% ± 0.05%, p = 0.744 | 9.31 | 0.74% ± 0.33%, p = 4.15E−15; 0.77% ± 0.17%, p = 1.19E−20; 1.33% ± 0.20%, p = 2.24E−22 | 7.61 | 264.49 | 9.99 | 49.22 |
| O13 | OK | 1.09 | 0.69% ± 0.12%, p = 0.002 | 1.96 | 1.13% ± 0.40%, p = 1.29E−12; 2.56% ± 0.51%, p = 6.36E−21; 7.03% ± 2.03%, p = 5.68E−07 | 2.70 | 11.18 | 27.16 | 60.49 |
| O14 | OK | 1.11 | 0.41% ± 0.22%, p = 0.863 | 2.73 | 3.80% ± 1.03%, p = 0.009; 18.17% ± 2.1 2%, p = 0.187; 25.64% ± 1.1 9%, p = 3.00E−04 | 7.50 | 2.87 | 3.96 | 4.73 |

TABLE 11-continued (related to Table 5). Cell death-imaging analysis and effects on primary HDF cells for repurchased small molecules. Repurchased small molecules were analyzed first by LC-MS for quality check. Except for three molecules (Gr-6A, O12 and O17 - these molecules also protected human cells from $H_2O_2$ and were included for subsequent analyses), their masses matched with predicted values. Potential pan assay interference compounds are also indicated. Consistent with the results of ATP assay for cell viability, the 38 "core set" small molecules reduced the fraction of propidium iodide-positive cells upon $H_2O_2$ stress treatment (n = 6 for each molecule, Student's t-test, three consecutive time points - 3 hrs, 4 hrs and 5 hrs of $H_2O_2$ treatment). Representative data, normalized fold-changes for ATP measurements and PI-positive fractions, are shown for at least three independent experiments. Small molecules were also analyzed in primary human dermal fibroblasts (HDFs, from multiple donors), along with the WI-38 cells, and found to protect these primary cells from $H_2O_2$.

| Small Molecule ID | A | B | C | D | E | F | G | H | I |
|---|---|---|---|---|---|---|---|---|---|
| O15, enones - PAINS | OK | 0.98 | 3.76% ± 0.68%, p = 5.30E−05 | 1.25 | 4.04% ± 1.09%, p = 0.023; 4.40% ± 0.59%, p = 2.38E−18; 6.06% ± 1.10%, p = 2.12E−12 | 2.92 | 0.57 | 6.45 | 1.77 |
| O17 | | 1.06 | 0.56% ± 0.25%, p = 0.291 | 3.70 | 0.80% ± 0.24%, p = 1.65E−16; 2.83% ± 0.40%, p = 2.33E−21; 10.53% ± 1.6 9%, p = 3.43E−07 | 2.45 | 3.35 | 20.98 | 48.53 |
| O18 | OK | 0.99 | 0.36% ± 0.16%, p = 0.441 | 4.32 | 3.66% ± 1.09%, p = 0.008; 3.06% ± 0.85%, p = 2.35E−14; 4.16% ± 0.70%, p = 5.86E−20 | 1.79 | 72.49 | 26.95 | 1.27 |
| O20 | OK | 1.12 | 0.73% ± 0.25%, p = 0.030 | 3.50 | 3.28% ± 0.50%, p = 1.73E−06; 15.90% ± 2.1 8%, p = 0.376; 22.46% ± 1.4 5%, p = 0.957 | 1.72 | 1.08 | 31.18 | 63.87 |
| O21, rhodanines - PAINS | OK | 0.92 | 1.09% ± 0.39%, p = 0.008 | 1.27 | 2.05% ± 0.42%, p = 2.43E−10; 12.20% ± 4.4 3%, p = 0.051; 17.00% ± 3.0 6%, p = 0.014 | 1.68 | 140.28 | 2.42 | 25.47 |
| O22 | OK | 0.96 | 0.37% ± 0.14%, p = 0.463 | 9.05 | 4.84% ± 0.67%, p = 0.100; 13.83% ± 2.5 2%, p = 0.033; 22.06% ± 1.5 8%, p = 0.571 | 2.35 | 15.30 | 13.59 | 49.57 |
| O23, enones, catechols - PAINS | OK | 0.76 | 2.61% ± 1.37%, p = 0.011 | 3.47 | 5.65% ± 2.49%, p = 0.847; 4.76% ± 1.24%, p = 3.32E−09; 8.00% ± 1.16%, p = 7.76E−09 | 1.77 | 1.68 | 9.30 | 52.37 |
| O27 | Expected mass | 0.75 | 0.50% ± 0.17%, p = 0.442 | 8.45 | 0.55% ±0.25%, p = 6.55E−17; 0.82% ± 0.36%, p = 1.64E−22; 1.07% ± 0.41%, p = 1.25E−24 | 7.68 | 181.60 | 18.20 | 46.06 |

A = Mass match/quality check by LC-MS; B = No H2O2 stress treatment, at 10 uM (fold change); C = Percentage of propidium iodide-positive dead cells (no H2O2 stress treatment), at 10 uM (Negative control: 0.41% ± 0.23%); D = H2O2 stress treatment (3 hrs), at 10 uM (fold change); E = Percentage of propidium iodide-positive dead cells (under H2O2 stress treatment, 3 hrs/4 hrs/5 hrs), at 10 uM (Negative control: 3 hrs, 5.44% ± 0.79%; 4 hrs, 16.81% ± 1.42%; 5 hrs, 22.50% ± 1.53%); F = Experiment 1, WI-38 cells (under H2O2 stress treatment), at 10 uM (fold change); G = Experiment 1, HDF cells (under H2O2 stress treatment), at 10 uM (fold change); H = Experiment 2, WI-38 cells (under H2O2 stress treatment), at 10 uM (fold change); I = Experiment 2, HDF cells (under H2O2 stress treatment), at 10 uM (fold change).

TABLE 12

(related to Table 5). Certain identified small molecules increased the resistance to multiple stressors, including $H_2O_2$, heavy metal $CdCl_2$ and MMS. Repurchased small molecules were analyzed for their ability to protect WI-38 cells from, besides $H_2O_2$, $CdCl_2$ and MMS. Normalized fold-changes for ATP measurements are shown. 21 molecules increased the cellular resistance for both $H_2O_2$ and cadmium only, and another 2 promoted the resistance to all stressors analyzed (at 10 μM final concentration representative data from two independent trials are shown). Fold changes less than 1.5 are highlighted, and asterisks (*) indicate compromised ability of several small molecules to protect cells from $H_2O_2$, which could be due to stability issue of compound assayed.

| Small Molecule ID | $H_2O_2$-resistant | $CdCl_2$-resistant | MMS-resistant | $H_2O_2$- & $CdCl_2$-resistant | Triple resistant |
|---|---|---|---|---|---|
| Group 1: 7 hits (Gr-1A) | YES | YES | NO | YES | NO |
| Gr-1B | YES | YES | NO | YES | NO |
| Gr-1C | YES | YES | NO | YES | NO |
| Gr-1D | YES | YES | NO | YES | NO |
| Gr-1E | YES | YES | NO | YES | NO |
| Gr-1F | YES | YES | NO | YES | NO |
| Gr-1G | YES | YES | NO | YES | NO |
| Group 3: 4 hits (3 available) (Gr-3A) | YES | YES | NO | YES | NO |
| Gr-3B | YES | NO | NO | NO | NO |
| Gr-3C | YES | NO | NO | NO | NO |
| Group 4: 4 hits (chalcones) (Gr-4A) | YES | YES | NO | YES | NO |
| Gr-4B | YES | YES | NO | YES | NO |
| Gr-4C | YES | NO | NO | NO | NO |
| Gr-4D | YES | YES | NO | YES | NO |
| Group 5: 4 hits (3 validated) (Gr-5A) | YES | YES | NO | YES | NO |
| Gr-5B | YES | NO | NO | NO | NO |
| Gr-5D | YES (*) | N/A | N/A | N/A | N/A |
| Group 6: 3 hits (Gr-6A) | YES | YES | YES | YES | YES |
| Gr-6B | YES | YES | NO | YES | NO |
| Gr-6C, rhodanines - PAINS | YES (*) | N/A | N/A | N/A | N/A |
| Group 7: 3 hits (Gr-7A) | YES (*) | NO | NO | NO | NO |
| Gr-7B | YES (*) | NO | NO | NO | NO |
| Gr-7C | YES | NO | NO | NO | NO |
| O1 | YES | YES | NO | YES | NO |
| O6, phenolic mannich PAINS - | YES | YES | NO | YES | NO |
| O10 | YES | YES | NO | YES | NO |
| O11 | YES | YES | NO | YES | NO |
| O12 | YES | YES | NO | YES | NO |
| O13 | YES | NO | NO | NO | NO |
| O14 | YES | YES | NO | YES | NO |
| O15, enones - PAINS | YES (*) | NO | NO | NO | NO |
| O17 | YES | NO | NO | NO | NO |
| O18 | YES | NO | NO | NO | NO |
| O20 | YES | YES | NO | YES | NO |
| O21, rhodanines - PAINS | YES | NO | NO | NO | NO |
| O22 | YES | YES | YES | YES | YES |
| O23, enones, catechols - PAINS | YES (*) | NO | NO | NO | NO |

TABLE 12-continued (related to Table 5). Certain identified small molecules increased the resistance to multiple stressors, including $H_2O_2$, heavy metal $CdCl_2$ and MMS. Repurchased small molecules were analyzed for their ability to protect WI-38 cells from, besides $H_2O_2$, $CdCl_2$ and MMS. Normalized fold-changes for ATP measurements are shown. 21 molecules increased the cellular resistance for both $H_2O_2$ and cadmium only, and another 2 promoted the resistance to all stressors analyzed (at 10 μM final concentration representative data from two independent trials are shown). Fold changes less than 1.5 are highlighted, and asterisks (*) indicate compromised ability of several small molecules to protect cells from $H_2O_2$, which could be due to stability issue of compound assayed.

| O27 | YES | YES | NO | YES | NO |
| --- | --- | --- | --- | --- | --- |

| Small Molecule ID | Exp. 1, under $H_2O_2$ stress treatment, at 10 uM (fold change) | Exp. 1, under $Cd_2Cl_2$ stress treatment, at 10 uM (fold change) | Exp. 1, under MMS stress treatment, at 10 uM (fold change) | Exp. 2, under $H_2O_2$ stress treatment, at 10 uM (fold change) | Exp. 2, under $Cd_2Cl_2$ stress treatment, at 10 uM (fold change) | Exp. 2, under MMS stress treatment, at 10 uM (fold change) |
| --- | --- | --- | --- | --- | --- | --- |
| Group 1: 7 hits (Gr-1A) | 3.36 | 1.46 | 0.72 | 2.36 | 1.45 | 2.42 |
| Gr-1B | 6.98 | 2.01 | 0.70 | 3.07 | 1.72 | 3.03 |
| Gr-1C | 27.32 | 7.90 | 0.73 | 1.90 | 9.86 | 0.39 |
| Gr-1D | 11.24 | 3.14 | 1.16 | 7.36 | 3.84 | 2.31 |
| Gr-1E | 52.76 | 6.69 | 0.72 | 18.85 | 8.82 | 1.21 |
| Gr-1F | 46.70 | 6.65 | 0.74 | 2.44 | 4.80 | 2.07 |
| Gr-1G | 14.33 | 3.81 | 1.32 | 11.12 | 7.21 | 1.89 |
| Group 3: 4 hits (3 available) (Gr-3A) | 2.36 | 1.93 | 1.00 | 1.81 | 1.64 | 0.86 |
| Gr-3B | 4.78 | 2.10 | 1.72 | 3.62 | 2.88 | 1.33 |
| Gr-3C | 19.06 | 0.06 | 1.06 | 1.79 | 0.40 | 0.84 |
| Group 4: 4 hits (chalcones) (Gr-4A) | 2.86 | 1.98 | 0.95 | 2.08 | 1.66 | 1.52 |
| Gr-4B | 2.52 | 2.00 | 1.22 | 2.15 | 1.52 | 1.54 |
| Gr-4C | 2.96 | 1.07 | 1.24 | 2.10 | 1.19 | 1.61 |
| Gr-4D | 4.78 | 2.10 | 1.72 | 3.62 | 2.88 | 1.33 |
| Group 5: 4 hits (3 validated) (Gr-5A) | 2.53 | 4.12 | 0.83 | 2.22 | 2.40 | 1.49 |
| Gr-5B | 1.63 | 1.29 | 1.13 | 2.00 | 1.36 | 1.36 |
| Gr-5D | N/A | N/A | N/A | N/A | N/A | N/A |
| Group 6: 3 hits (Gr-6A) | 2.64 | 2.46 | 2.20 | 2.85 | 2.36 | 7.20 |
| Gr-6B | 27.64 | 5.07 | 2.12 | 1.90 | 2.65 | 1.22 |
| Gr-6C, rhodanines - PAINS | N/A | N/A | N/A | N/A | N/A | N/A |
| Group 7: 3 hits (Gr-7A) | 1.04 | 0.07 | 0.96 | 0.76 | 0.14 | 2.21 |
| Gr-7B | 1.41 | 0.12 | 0.39 | 1.21 | 0.26 | 1.45 |
| Gr-7C | 2.18 | 1.31 | 1.14 | 2.41 | 0.97 | 1.39 |
| O1 | 1.52 | 1.84 | 1.20 | 1.57 | 1.86 | 4.96 |
| O6, phenolic mannich PAINS - | 1.93 | 2.18 | 0.81 | 1.12 | 2.05 | 0.79 |
| O10 | 4.75 | 2.73 | 1.08 | 2.45 | 2.00 | 4.08 |
| O11 | 3.53 | 3.78 | 0.97 | 2.10 | 2.80 | 4.20 |
| O12 | 2.89 | 1.36 | 0.78 | 3.42 | 1.59 | 2.00 |
| O13 | 2.34 | 1.27 | 1.11 | 1.84 | 1.55 | 2.24 |
| O14 | 2.03 | 2.20 | 0.84 | 2.37 | 2.69 | 3.45 |
| O15, enones - PAINS | 1.07 | 0.18 | 0.16 | 0.41 | 0.57 | 0.38 |
| O17 | 2.03 | 0.95 | 0.86 | 1.77 | 1.35 | 5.33 |
| O18 | 2.16 | 1.50 | 1.11 | 1.22 | 1.24 | 1.48 |
| O20 | 3.13 | 6.37 | 2.17 | 1.25 | 4.00 | 1.46 |
| O21, rhodanines - PAINS | 2.87 | 0.03 | 0.74 | 2.39 | 0.04 | 0.94 |

TABLE 12-continued (related to Table 5). Certain identified small molecules increased the resistance to multiple stressors, including $H_2O_2$, heavy metal $CdCl_2$ and MMS. Repurchased small molecules were analyzed for their ability to protect WI-38 cells from, besides $H_2O_2$, $CdCl_2$ and MMS. Normalized fold-changes for ATP measurements are shown. 21 molecules increased the cellular resistance for both $H_2O_2$ and cadmium only, and another 2 promoted the resistance to all stressors analyzed (at 10 µM final concentration representative data from two independent trials are shown). Fold changes less than 1.5 are highlighted, and asterisks (*) indicate compromised ability of several small molecules to protect cells from $H_2O_2$, which could be due to stability issue of compound assayed.

| | | | | | | |
|---|---|---|---|---|---|---|
| O22 | 6.38 | 5.61 | 3.22 | 8.06 | 14.65 | 14.83 |
| O23, enones, catechols - PAINS | 1.10 | 0.69 | 1.04 | 0.95 | 0.64 | 1.28 |
| O27 | 15.17 | 1.68 | 0.74 | 2.10 | 1.89 | 2.45 |

TABLE 13

Long-term effects of small molecules on cell viability. 38 "core set" molecules were analyzed in two batches (31, 2 - confirmed to increase $H_2O_2$-resistance) and assayed for their effects on cell viability upon prolonged incubation (at 10 µM final concentration, n = 6 for each molecule, and mean standard deviation across the whole assay is ~5.9%). Luminescence signals for ATP measurements are shown. Rapamycin, as the control, delayed cell proliferation and significantly reduced ATP levels.

Batch 1: cell viability assay by ATP measurment (day-0, before adding small molecules, luminescence = 320956 ± 24708).

| | day-1 Average | SD | day-2 Average | SD | day-3 Average | SD | day-4 Average | SD | day-5 Average | SD | by day-5 normalized |
|---|---|---|---|---|---|---|---|---|---|---|---|
| DMSO ctrl | 553833 | 34334 | 764391 | 14811 | 954493 | 34053 | 1017995 | 21520 | 1026775 | 41680 | 100.0% |
| H2O ctrl | 567981 | 45301 | 761567 | 19697 | 958965 | 34800 | 1061361 | 45700 | 1035227 | 34100 | 100.8% |
| Rapa ctrl | 454546 | 10444 | 519403 | 23727 | 545026 | 19208 | 552160 | 23811 | 547771 | 22151 | 53.3% |
| Gr-1A | 477461 | 25883 | 610735 | 31005 | 739676 | 11646 | 878508 | 44735 | 943836 | 62968 | 91.9% |
| Gr-1B | 442035 | 31908 | 577575 | 9667 | 726850 | 23498 | 977658 | 20676 | 1021113 | 53459 | 99.4% |
| Gr-1C | 421913 | 16933 | 545683 | 22020 | 662368 | 42724 | 875881 | 107272 | 819655 | 6681 | 79.8% |
| Gr-1D | 396843 | 33850 | 497248 | 29850 | 542643 | 46079 | 797305 | 63893 | 865168 | 40279 | 84.3% |
| Gr-1E | 474558 | 27671 | 698358 | 32177 | 788420 | 36251 | 1038011 | 41115 | 1066135 | 33622 | 103.8% |
| Gr-1F | 383221 | 23666 | 440655 | 18086 | 446240 | 19957 | 534298 | 43515 | 600633 | 71490 | 58.5% |
| Gr-1G | 449436 | 34754 | 530748 | 25386 | 651695 | 36842 | 866631 | 39075 | 955703 | 48363 | 93.1% |
| Gr-4A | 501436 | 29169 | 605711 | 51448 | 772420 | 27038 | 995321 | 40252 | 1019996 | 20027 | 99.3% |
| Gr-4C | 413360 | 43703 | 474171 | 30706 | 485641 | 50895 | 769380 | 37494 | 813018 | 56651 | 79.2% |
| Gr-5A | 527000 | 29829 | 728148 | 13364 | 837593 | 32262 | 1074220 | 51491 | 1082445 | 29904 | 105.4% |
| Gr-5B | 529430 | 25230 | 736318 | 18867 | 867160 | 25365 | 1091073 | 33546 | 1104305 | 32623 | 107.6% |
| Gr-5D | 498641 | 23574 | 763806 | 38700 | 920681 | 14288 | 1052285 | 38352 | 1110868 | 44999 | 108.2% |
| Gr-6A | 581273 | 34435 | 717601 | 25857 | 804970 | 21323 | 1007061 | 22907 | 986943 | 33964 | 96.1% |
| Gr-6B | 467756 | 32079 | 641901 | 31541 | 736245 | 17319 | 969598 | 36524 | 953988 | 43624 | 92.9% |
| Gr-6C | 435273 | 23557 | 542716 | 43049 | 574765 | 66657 | 624471 | 8551 | 548865 | 22967 | 53.5% |
| Gr-7A | 463265 | 58865 | 192116 | 21474 | 67526 | 11693 | 48480 | 5216 | 44670 | 5998 | 4.4% |
| Gr-7B (*) | 311883 | 34714 | 56498 | 4455 | 40001 | 4475 | 44298 | 4451 | 40768 | 4813 | 4.0% |
| Gr-7C | 378655 | 18968 | 140712 | 12554 | 84446 | 10826 | 72490 | 6038 | 127440 | 6576 | 12.4% |
| O1 | 461478 | 20859 | 722566 | 20094 | 824266 | 23259 | 1101026 | 28418 | 977541 | 28798 | 95.2% |
| O10 | 560153 | 21893 | 740923 | 20124 | 847945 | 14630 | 1079863 | 23604 | 1066130 | 38115 | 103.8% |
| O11 | 310373 | 35947 | 412288 | 39063 | 484520 | 86507 | 642267 | 109087 | 633963 | 149645 | 61.7% |
| O12 | 527095 | 11186 | 702483 | 19796 | 876448 | 33125 | 1128385 | 23641 | 1117938 | 25699 | 108.9% |
| O13 | 546070 | 39564 | 704210 | 32246 | 806718 | 30747 | 947030 | 197216 | 992715 | 12546 | 96.7% |
| O14 | 581665 | 47340 | 685103 | 27039 | 819423 | 38948 | 1074238 | 33242 | 1052551 | 29570 | 102.5% |
| O15 | 426828 | 19031 | 601153 | 67550 | 634740 | 79475 | 904970 | 97039 | 761533 | 96306 | 74.2% |
| O17 | 507143 | 33431 | 697351 | 34985 | 849445 | 19518 | 1073975 | 22442 | 1070851 | 24335 | 104.3% |
| O18 | 453443 | 28307 | 639628 | 53472 | 693776 | 20125 | 825623 | 21298 | 760275 | 39450 | 74.0% |
| O20 | 544305 | 47949 | 770055 | 55862 | 888893 | 68909 | 997113 | 18011 | 926888 | 18796 | 90.3% |
| O21 | 460366 | 22372 | 542268 | 22201 | 557236 | 13390 | 677875 | 34086 | 550651 | 28754 | 53.6% |
| O22 | 435891 | 12758 | 566145 | 28030 | 690403 | 24600 | 840178 | 25679 | 805461 | 30549 | 78.4% |
| O23 | 329880 | 22739 | 149226 | 10914 | 52831 | 7565 | 53125 | 7815 | 52771 | 7645 | 5.1% |
| O27 | 431303 | 9431 | 437195 | 14937 | 517210 | 20523 | 634360 | 12988 | 587798 | 51143 | 57.2% |

TABLE 13-continued

Long-term effects of small molecules on cell viability. 38 "core set" molecules were analyzed in two batches (31, 2 - confirmed to increase $H_2O_2$-resistance) and assayed for their effects on cell viability upon prolonged incubation (at 10 μM final concentration, n = 6 for each molecule, and mean standard deviation across the whole assay is ~5.9%). Luminescence signals for ATP measurements are shown. Rapamycin, as the control, delayed cell proliferation and significantly reduced ATP levels.

Batch 2: cell viability assay by ATP measurement (day-0, before adding small molecules, luminescence = 229312 ± 17487).

| | day-1 Average | SD | day-2 Average | SD | day-3 Average | SD |
|---|---|---|---|---|---|---|
| DMSO ctrl | 270512 | 39292 | 341244 | 20901 | 397816 | 29732 |
| H2O ctrl | 273315 | 39976 | 343122 | 23904 | 417519 | 24016 |
| Rapa ctrl | 239521 | 23539 | 221640 | 21615 | 244073 | 21696 |
| Gr-3B | 184710 | 13190 | 110226 | 4689 | 109008 | 4455 |
| Gr-3C | 190045 | 5213 | 194191 | 17252 | 270505 | 25513 |

| | day-4 Average | SD | day-5 Average | SD | by day-5 normalized |
|---|---|---|---|---|---|
| DMSO ctrl | 525030 | 27521 | 555941 | 56223 | 100.0% |
| H2O ctrl | 535928 | 28755 | 579802 | 41697 | 104.3% |
| Rapa ctrl | 276911 | 20239 | 262898 | 12400 | 47.3% |
| Gr-3B | 52193 | 5190 | 63138 | 3531 | 11.4% |
| Gr-3C | 244033 | 21224 | 265285 | 17333 | 47.7% |

TABLE 14

Induction of DNA-damaging markers by certain small molecules. WI-38 cells that had been treated with small molecules (10 μM, 24 hrs) were analyzed in two independent experiments by immuno-staining for two DNA-damaging markers, phosphorylated-γH2A.X and phosphorylated-TP53BP1. Small molecules that induced both markers (in the absence of $H_2O_2$ stress treatment) were scored positive for DNA-damaging. Normalized values for marker-positive fractions are shown (n = 3, Student t-test. In experiment 2, the marker-positive fractions of cells were - γH2A.X-P: DMSO, ~1.7 ± 0.4% (n = 6); $H_2O_2$ ~50.9 ± 4.2% (n = 3); doxorubicin, ~16.9 ± 2.1% (n = 6). TP53BP1-P: DMSO, ~1.0 ± 0.2% (n = 6); $H_2O_2$, ~45.8 ± 5.1% (n = 3); doxorubicin, ~15.1 ± 1.4% (n = 6).

| Small Molecule ID | Experiment 1, H2A.X-P DNA damage foci staining (no $H_2O_2$ stress treatment), at 10 uM | Experiment 2, H2A.X-P DNA damage foci staining (no $H_2O_2$ stress treatment), at 10 uM | Experiment 2, H2A.X-P DNA damage foci staining (under $H_2O_2$ stress treatment), at 10 uM | Experiment 2, TP53BP1-P DNA damage foci staining (no $H_2O_2$ stress treatment), at 10 uM | Experiment 2, TP53BP1-P DNA damage foci staining (under $H_2O_2$ stress treatment), at 10 uM | Potential DNA-damaging-positive (Experiment 1 & 2) |
|---|---|---|---|---|---|---|
| Group 1: 7 hits (Gr-1A) | 196.5%, p = 0.007 | 223.0%, p = 0.018 | 178.8%, p = 3.78E−06 | 410.9%, p = 0.032 | 653.2%, p = 0.085 | YES |
| Gr-1B | 133.9%, p = 0.143 | 95.8%, p = 0.817 | 118.1%, p = 0.174 | 210.8%, p = 0.006 | 136.6%, p = 0.480 | NO |
| Gr-1C | 217.1%, p = 0.0002 | 310.8%, p = 0.0003 | 177.9%, p = 2.64E−05 | 375.1%, p = 0.009 | 552.0%, p = 2.77E−07 | YES |
| Gr-1D | 231.5%, p = 0.006 | 352.7%, p = 0.003 | 163.6%, p = 0.0003 | 352.7%, p = 0.021 | 554.3%, p = 0.0001 | YES |
| Gr-1E | 162.2%, p = 0.030 | 106.7%, p = 0.570 | 150.8%, p = 0.052 | 289.2%, p = 0.007 | 475.1%, p = 1.25E−08 | NO |
| Gr-1F | 219.2%, p = 0.029 | 377.8%, p = 0.005 | 126.7%, p = 0.056 | 459.5%, p = 0.053 | 558.1%, p = 0.0003 | YES |
| Gr-1G | 149.7%, p = 0.080 | 178.8%, p = 0.067 | 63.3%, p = 0.084 | 256.2%, p = 0.047 | N/A | NO |
| Group 3: 4 hits (3 available) (Gr-3A) | 139.3%, p = 0.002 | 338.0%, p = 0.0001 | 143.1%, p = 0.051 | 334.0%, p = 0.028 | 66.1%, p = 0.048 | YES |
| Gr-3B | 81.9%, p = 0.030 | 227.8%, p = 0.001 | 130.4%, p = 0.091 | 243.5%, p = 0.023 | 66.3%, p = 0.152 | NO |
| Gr-3C | 112.6%, p = 0.285 | 403.8%, p = 0.014 | 135.6%, p = 0.001 | 253.9%, p = 0.023 | 390.0%, p = 0.015 | YES |
| Group 4: 4 hits (chalcones) (Gr-4A) | 80.2%, p = 0.115 | 75.0%, p = 0.059 | 105.3%, p = 0.646 | 154.6%, p = 0.042 | 286.8%, p = 0.301 | NO |

TABLE 14-continued

Induction of DNA-damaging markers by certain small molecules. WI-38 cells that had been treated with small molecules (10 µM, 24 hrs) were analyzed in two independent experiments by immuno-staining for two DNA-damaging markers, phosphorylated-γH2A.X and phosphorylated-TP53BP1. Small molecules that induced both markers (in the absence of $H_2O_2$ stress treatment) were scored positive for DNA-damaging. Normalized values for marker-positive fractions are shown (n = 3, Student t-test. In experiment 2, the marker-positive fractions of cells were - γH2A.X-P: DMSO, ~1.7 ± 0.4% (n = 6); $H_2O_2$ ~50.9 ± 4.2% (n = 3); doxorubicin, ~16.9 ± 2.1% (n = 6). TP53BP1-P: DMSO, ~1.0 ± 0.2% (n = 6); $H_2O_2$, ~45.8 ± 5.1% (n = 3); doxorubicin, ~15.1 ± 1.4% (n = 6).

| Small Molecule ID | Experiment 1, H2A.X-P DNA damage foci staining (no $H_2O_2$ stress treatment), at 10 uM | Experiment 2, H2A.X-P DNA damage foci staining (no $H_2O_2$ stress treatment), at 10 uM | Experiment 2, H2A.X-P DNA damage foci staining (under $H_2O_2$ stress treatment), at 10 uM | Experiment 2, TP53BP1-P DNA damage foci staining (no $H_2O_2$ stress treatment), at 10 uM | Experiment 2, TP53BP1-P DNA damage foci staining (under $H_2O_2$ stress treatment), at 10 uM | Potential DNA-damaging-positive (Experiment 1 & 2) |
|---|---|---|---|---|---|---|
| Gr-4B | 116.3%, p = 0.213 | 140.2%, p = 0.340 | 150.5%, p = 0.034 | 117.9%, p = 0.489 | 435.0%, p = 0.014 | NO |
| Gr-4C | 107.7%, p = 0.202 | 135.1%, p = 0.070 | 149.7%, p = 0.042 | 179.3%, p = 0.105 | 443.7%, p = 0.001 | NO |
| Gr-4D | 103.2%, p = 0.737 | 49.6%, p = 0.002 | 123.3%, p = 0.307 | 136.3%, p = 0.139 | 387.5%, p = 0.009 | NO |
| Group 5: 4 hits (3 validated) (Gr-5A) | 104.7%, p = 0.646 | 115.4%, p = 0.723 | 127.4%, p = 0.148 | 147.1%, p = 0.114 | 547.5%, p = 4.85E−05 | NO |
| Gr-5B | 100.3%, p = 0.976 | 127.8%, p = 0.282 | 167.7%, p = 0.0003 | 222.8%, p = 0.015 | 540.3%, p = 7.85E−09 | NO |
| Gr-5D | 94.1%, p = 0.329 | 75.%, p = 0.049 | 111.9%, p = 0.488 | 145.0%, p = 0.195 | 479.8%, p = 0.051 | NO |
| Group 6: 3 hits (Gr-6A) | 116.6%, p = 0.041 | 59.9%, p = 0.014 | 199.7%, p = 4.89E−07 | 137.9%, p = 0.050 | N/A | NO |
| Gr-6B | 93.4%, p = 0.680 | 112.3%, p = 0.295 | 136.5%, p = 0.009 | 175.7%, p = 0.029 | 272.4%, p = 0.071 | NO |
| Gr-6C, rhodanines - PAINS | 181.3%, p = 0.012 | 300.3%, p = 0.002 | 43.0%, p = 6.99E−06 | 289.7%, p = 0.003 | 440.3%, p = 4.87E−05 | YES |
| Group 7: 3 hits (Gr-7A) | 337.3%, p = 0.08 (cells loss during preparation) | 246.0%, p = 0.093 | 112.9%, p = 0.303 | 362.9%, p = 0.290 | 516.4%, p = 6.19E−09 | YES |
| Gr-7B | 694.7%, p = 0.017 (cells loss during prep., many dead) | 348.2%, p = 0.046 | 74.0%, p = 0.005 | 31.3%, p = 0.035 | 4.2%, p = 0.0002 | YES |
| Gr-7C | 132.1%, p = 0.014 | 135.2%, p = 0.136 | 82.9%, p = 0.102 | 196.3%, p = 0.152 | 368.8%, p = 0.0001 | NO |
| O1 | 101.9%, p = 0.757 | 104.4%, p = 0.831 | 216.5%, p = 2.69E−06 | 142.9%, p = 0.051 | 335.6%, p = 0.0002 | NO |
| O6, phenolic mannich - PAINS | 122.4%, N.A. | 87.7%, p = 0.441 | 129.9%, p = 0.246 | 86.3%, p = 0.589 | 537.7%, p = 0.001 | NO |
| O10 | 101.9%, p = 0.875 | 71.5%, p = 0.110 | 153.1%, p = 0.0003 | 134.8%, p = 0.099 | 498.2%, p = 0.0004 | NO |
| O11 | 83.1%, p = 0.208 | 91.2%, p = 0.726 | 151.7%, p = 4.80E−05 | 154.0%, p = 0.011 | 560.5%, p = 4.53E−08 | NO |
| O12 | 106.0%, p = 0.586 | 88.0%, p = 0.509 | 113.4%, p = 0.082 | 141.7%, p = 0.389 | 523.2%, p = 1.51E−06 | NO |
| O13 | 145.2%, p = 0.054 | 98.3%, p = 0.874 | 152.3%, p = 0.003 | 238.3%, p = 0.019 | 672.9%, p = 0.009 | NO |
| O14 | 115.9%, p = 0.315 | 85.3%, p = 0.194 | 221.4%, p = 3.60E−07 | 159.0%, p = 0.289 | 254.4%, p = 0.017 | NO |
| O15, enones - PAINS | 90.0%, p = 0.391 | 183.5%, p = 0.001 | 58.4%, p = 0.0002 | 48.3%, p = 0.029 | 250.9%, p = 0.068 | NO |

TABLE 14-continued

Induction of DNA-damaging markers by certain small molecules. WI-38 cells that had been treated with small molecules (10 μM, 24 hrs) were analyzed in two independent experiments by immuno-staining for two DNA-damaging markers, phosphorylated-γH2A.X and phosphorylated-TP53BP1. Small molecules that induced both markers (in the absence of $H_2O_2$ stress treatment) were scored positive for DNA-damaging. Normalized values for marker-positive fractions are shown (n = 3, Student t-test. In experiment 2, the marker-positive fractions of cells were - γH2A.X-P: DMSO, ~1.7 ± 0.4% (n = 6); $H_2O_2$ ~50.9 ± 4.2% (n = 3); doxorubicin, ~16.9 ± 2.1% (n = 6). TP53BP1-P: DMSO, ~1.0 ± 0.2% (n = 6); $H_2O_2$, ~45.8 ± 5.1% (n = 3); doxorubicin, ~15.1 ± 1.4% (n = 6).

| Small Molecule ID | Experiment 1, H2A.X-P DNA damage foci staining (no $H_2O_2$ stress treatment), at 10 uM | Experiment 2, H2A.X-P DNA damage foci staining (no $H_2O_2$ stress treatment), at 10 uM | Experiment 2, H2A.X-P DNA damage foci staining (under $H_2O_2$ stress treatment), at 10 uM | Experiment 2, TP53BP1-P DNA damage foci staining (no $H_2O_2$ stress treatment), at 10 uM | Experiment 2, TP53BP1-P DNA damage foci staining (under $H_2O_2$ stress treatment), at 10 uM | Potential DNA-damaging-positive (Experiment 1 & 2) |
|---|---|---|---|---|---|---|
| O17 | 96.7%, p = 0.613 | 72.1%, p = 0.055 | 129.0%, p = 0.117 | 147.5%, p = 0.067 | 348.8%, p = 0.033 | NO |
| O18 | 364.1%, p = 0.138 (cells loss during preparation) | 142.7%, p = 0.045 | 137.1%, p = 0.002 | 183.1%, p = 0.069 | 450.0%, p = 1.78E−08 | YES |
| O20 | 115.2%, p = 0.377 | 129.7%, p = 0.085 | 178.5%, p = 0.003 | 107.5%, p = 0.543 | 544.4%, p = 4.26E−05 | NO |
| O21, rhodanines - PAINS | 161.2%, p = 0.001 | 216.4%, p = 0.0001 | 127.4%, p = 0.049 | 196.4%, p = 0.065 | 620.5%, p = 3.27E−06 | YES |
| O22 | 100.9%, p = 0.855 | 120.8%, p = 0.355 | 210.5%, p = 0.0001 | 154.0%, p = 0.017 | 510.2%, p = 0.003 | NO |
| O23, enones, catechols - PAINS | 79.9%, p = 0.033 | 325.5%, p = 0.029 | 33.4%, p = 2.39E−06 | 42.4%, p = 0.021 | 13.2%, p = 0.0001 | NO |
| O27 | 122.2%, p = 0.050 | 337.5%, p = 0.00002 | 26.1%, p = 6.33E−07 | 241.0%, p = 6.22E−06 | 379.2%, p = 0.003 | YES |

Table 15 (related to Table 2 and Table 9). Analysis of small molecule effects on FOXO3- and NRF2-regulated genes, as well as the dependency on FOXO3 or NRF2 for molecules to promote $H_2O_2$-resistance. qPCR analysis of selected, representative FOXO3- and NRF2-regulated genes was performed for WI-38 cells treated with small molecules (at 10 μM, n=4) for 24 hrs. Relative expression levels (normalized by B2M), standard deviations and statistics (Student's t-test) are shown.

Table 15A-15D (Related to Table 6).
Analysis of small molecule effects on FOXO3- and NRF2-regulated genes, as well as the dependency on FOXO3 or NRF2 for molecules to promote $H_2O_2$-resistance. qPCR analysis of selected, representative FOXO3- and NRF2-regulated genes was performed for WI-38 cells treated with small molecules (at 10 μM, n=4) for 24 hrs. Relative expression levels (normalized by B2M), standard deviations and statistics (Student's t-test) are shown.

TABLE 15A

Summary of effects on FOXO3-regulated genes TXNIP, SOD2, and CAT.

| Small Molecule ID | Summary of effects on FOXO3-regulated genes | TXNIP Normalized fold change | TXNIP Normalized SD | TXNIP P value | SOD2 Normalized fold change | SOD2 Normalized SD | SOD2 P value | CAT Normalized fold change | CAT Normalized SD | CAT P value |
|---|---|---|---|---|---|---|---|---|---|---|
| Group 1: 7 hits (Gr-1A) | CAT 1.31, p < 0.01; DDB1 1.36, p < 0.05; SESN1 2.12, p < 0.01 | 1.234 | 0.304 | 0.225 | 1.495 | 0.540 | 0.164 | 1.312 | 0.055 | 0.001 |
| Gr-1B | TXNIP 1.94, p < 0.05; CAT 1.40, p < 0.01; SESN1 1.30, p < 0.01 | 1.938 | 0.523 | 0.034 | 1.211 | 0.392 | 0.362 | 1.397 | 0.058 | 0.000 |

TABLE 15A-continued

Summary of effects on FOXO3-regulated genes TXNIP, SOD2, and CAT.

| Small Molecule ID | Summary of effects on FOXO3-regulated genes | TXNIP Normalized fold change | TXNIP Normalized SD | TXNIP P value | SOD2 Normalized fold change | SOD2 Normalized SD | SOD2 P value | CAT Normalized fold change | CAT Normalized SD | CAT P value |
|---|---|---|---|---|---|---|---|---|---|---|
| Gr-1C | CAT 1.44, p < 0.05 | 1.226 | 0.334 | 0.275 | 1.335 | 0.411 | 0.201 | 1.443 | 0.186 | 0.012 |
| Gr-1D | TXNIP 0.62, p < 0.05; DDB1 1.18, p < 0.05; SESN1 1.73, p < 0.01 | 0.621 | 0.235 | 0.040 | 1.423 | 0.515 | 0.199 | 0.953 | 0.256 | 0.747 |
| Gr-1E | TXNIP 2.02, p > 0.05; CAT 1.45, p < 0.05; SESN1 1.40, p < 0.01 | 2.017 | 0.863 | 0.099 | 1.459 | 0.721 | 0.293 | 1.452 | 0.197 | 0.014 |
| Gr-1F | CAT 1.35, p < 0.05; SESN1 2.00, p < 0.05 | 1.536 | 0.453 | 0.095 | 1.683 | 0.864 | 0.212 | 1.350 | 0.226 | 0.047 |
| Gr-1G | SOD2 0.76, p < 0.05; CAT 1.35, p < 0.05; GADD45A 0.60, p < 0.01 | 1.026 | 0.384 | 0.921 | 0.756 | 0.045 | 0.026 | 1.352 | 0.159 | 0.013 |
| Group 3: 4 hits (3 available) (Gr-3A) | TXNIP 0.75, p < 0.05; CAT 0.87, p < 0.05; SESN1 1.18, p < 0.05 | 0.754 | 0.137 | 0.034 | 1.482 | 0.566 | 0.187 | 0.871 | 0.056 | 0.034 |
| Gr-3B | NO | 1.063 | 0.223 | 0.756 | 1.137 | 0.073 | 0.122 | 1.114 | 0.026 | 0.087 |
| Gr-3C | CAT 0.87, p < 0.05 | 1.026 | 0.213 | 0.839 | 1.199 | 0.259 | 0.223 | 0.868 | 0.065 | 0.036 |
| Group 4: 4 hits (chalcones) (Gr-4A) | CAT 1.26, p < 0.05; DDB1 1.20, p < 0.05 | 0.819 | 0.059 | 0.100 | 0.980 | 0.026 | 0.744 | 1.264 | 0.068 | 0.029 |
| Gr-4B | NO | 0.792 | 0.156 | 0.130 | 1.045 | 0.030 | 0.236 | 1.175 | 0.331 | 0.460 |
| Gr-4C | TXNIP 0.18, p < 0.05; CAT 1.19, p < 0.05; GADD45A 1.23, p < 0.05; DDB1 1.51, p < 0.001; SESN1 1.42, p < 0.05 | 0.179 | 0.012 | 0.013 | 1.039 | 0.055 | 0.600 | 1.189 | 0.038 | 0.022 |
| Gr-4D | RP29: SOD2 1.20, p < 0.05; CAT 1.37, p < 0.01; GADD45A 2.11, p < 0.001; DDB1 1.41, p < 0.01; SESN1 2.16, p < 0.01. RP52: no induction | 1.092 | 0.237 | 0.655 | 1.204 | 0.106 | 0.049 | 1.374 | 0.072 | 0.001 |
| Group 5: 4 hits (3 validated) (Gr-5A) | NO | 1.140 | 0.100 | 0.071 | 1.125 | 0.151 | 0.200 | 1.168 | 0.326 | 0.388 |
| Gr-5B | NO | 1.201 | 0.209 | 0.148 | 1.129 | 0.256 | 0.394 | 1.422 | 0.443 | 0.151 |
| Gr-5D | TXNIP 0.67, p < 0.01 | 0.669 | 0.100 | 0.001 | 1.125 | 0.168 | 0.238 | 1.273 | 0.212 | 0.074 |
| Group 6: 3 hits (Gr-6A) | GADD45A 0.79, p < 0.05 | 1.136 | 0.357 | 0.587 | 0.868 | 0.048 | 0.122 | 1.200 | 0.137 | 0.058 |

TABLE 15A-continued

Summary of effects on FOXO3-regulated genes TXNIP, SOD2, and CAT.

| Small Molecule ID | Summary of effects on FOXO3-regulated genes | TXNIP Normalized fold change | TXNIP Normalized SD | TXNIP P value | SOD2 Normalized fold change | SOD2 Normalized SD | SOD2 P value | CAT Normalized fold change | CAT Normalized SD | CAT P value |
|---|---|---|---|---|---|---|---|---|---|---|
| Gr-6B | DDB1 1.19, $p < 0.05$ | 0.861 | 0.197 | 0.486 | 1.141 | 0.092 | 0.127 | 1.109 | 0.088 | 0.139 |
| Gr-6C, rhodanines - PAINS | TXNIP 0.57, $p < 0.01$; GADD45A 2.17, $p > 0.10$; SESN1 1.42, $p < 0.05$ | 0.568 | 0.115 | 0.001 | 1.008 | 0.187 | 0.943 | 1.126 | 0.329 | 0.509 |
| Group 7: 3 hits (Gr-7A) | TXNIP 0.12, $p < 0.001$; SOD2 1.78, $p < 0.01$; GADD45A 1.91, $p < 0.01$ | 0.120 | 0.034 | 0.000 | 1.778 | 0.226 | 0.004 | 1.145 | 0.213 | 0.282 |
| Gr-7B | TXNIP 0.26, $p < 0.001$; GADD45A 2.07, $p > 0.05$ | 0.262 | 0.079 | 0.000 | 1.331 | 0.515 | 0.290 | 1.134 | 0.178 | 0.249 |
| Gr-7C | TXNIP 0.07, $p < 0.001$; SOD2 2.67, $p < 0.05$; CAT 1.43, $p < 0.01$; GADD45A 10.86, $p < 0.01$; DDB1 1.36, $p < 0.05$ | 0.068 | 0.012 | 0.000 | 2.677 | 0.727 | 0.018 | 1.433 | 0.156 | 0.006 |
| O1 | NO | 1.111 | 0.075 | 0.083 | 1.111 | 0.343 | 0.567 | 1.254 | 0.530 | 0.412 |
| O6, phenolic mannich - PAINS | NO | 1.014 | 0.060 | 0.876 | 0.932 | 0.073 | 0.381 | 0.919 | 0.078 | 0.414 |
| O10 | NO | 0.731 | 0.197 | 0.217 | 0.912 | 0.030 | 0.268 | 0.892 | 0.039 | 0.098 |
| O11 | TXNIP 1.35, $p < 0.05$; CAT 1.41, $p < 0.05$; DDB1 1.31, $p < 0.05$; SESN1 1.77, $p < 0.05$ | 1.346 | 0.199 | 0.034 | 1.143 | 0.107 | 0.125 | 1.410 | 0.230 | 0.028 |
| O12 | SOD2 1.52, $p < 0.05$; CAT 0.80, $p < 0.01$; GADD45A 1.69, $p < 0.05$ | 0.909 | 0.046 | 0.223 | 1.523 | 0.224 | 0.017 | 0.802 | 0.029 | 0.009 |
| O13 | CAT 1.33, $p < 0.05$; GADD45A 1.20, $p < 0.05$; DDB1 1.27, $p < 0.01$ | 0.907 | 0.074 | 0.351 | 1.093 | 0.063 | 0.234 | 1.325 | 0.160 | 0.024 |
| O14 | TXNIP 1.39, $p < 0.05$ | 1.390 | 0.222 | 0.031 | 1.266 | 0.225 | 0.098 | 1.031 | 0.063 | 0.557 |
| O15, enones - PAINS | TXNIP 0.22, $p < 0.001$; CAT 1.28, $p < 0.05$; GADD45A 2.72, $p < 0.01$; SESN1 0.80, $p < 0.05$ | 0.219 | 0.074 | 0.000 | 1.047 | 0.088 | 0.541 | 1.280 | 0.129 | 0.033 |
| O17 | GADD45A 0.85, $p < 0.05$ | 0.801 | 0.081 | 0.070 | 0.997 | 0.045 | 0.965 | 1.107 | 0.059 | 0.274 |
| O18 | TXNIP 0.30, $p < 0.001$ | 0.297 | 0.083 | 0.000 | 1.042 | 0.133 | 0.596 | 1.468 | 0.531 | 0.176 |

TABLE 15A-continued

Summary of effects on FOXO3-regulated genes TXNIP, SOD2, and CAT.

| Small Molecule ID | Summary of effects on FOXO3-regulated genes | TXNIP Normalized fold change | TXNIP Normalized SD | TXNIP P value | SOD2 Normalized fold change | SOD2 Normalized SD | SOD2 P value | CAT Normalized fold change | CAT Normalized SD | CAT P value |
|---|---|---|---|---|---|---|---|---|---|---|
| O20 | CAT 1.35, p < 0.01; DDB1 1.25, p < 0.05; SESN1 1.73, p < 0.05 | 1.121 | 0.315 | 0.614 | 1.086 | 0.069 | 0.297 | 1.348 | 0.105 | 0.003 |
| O21, rhodanines - PAINS | SESN1 1.88, p < 0.05 | 0.900 | 0.097 | 0.164 | 1.121 | 0.192 | 0.302 | 1.305 | 0.329 | 0.160 |
| O22 | GADD45A 1.23, p < 0.01 | 0.742 | 0.232 | 0.235 | 1.017 | 0.102 | 0.845 | 1.045 | 0.056 | 0.452 |
| O23, enones, catechols - PAINS | TXNIP 0.07, p < 0.001; SOD2 2.04 p < 0.01; GADD45 7.22, p < 0.01 | 0.071 | 0.013 | 0.000 | 2.036 | 0.317 | 0.006 | 0.890 | 0.275 | 0.497 |
| O27 | SESN1 1.54, p < 0.05 | 0.882 | 0.168 | 0.352 | 1.147 | 0.119 | 0.133 | 1.133 | 0.171 | 0.305 |

TABLE 15B

Summary of effects on FOXO3-regulated genes GADD45A, DDB1, and SESN1.

| Small Molecule ID | GADD45A Normalized fold change | GADD45A Normalized SD | GADD45A P value | DDB1 Normalized fold change | DDB1 Normalized SD | DDB1 P value | SESN1 Normalized fold change | SESN1 Normalized SD | SESN1 P value |
|---|---|---|---|---|---|---|---|---|---|
| Group 1: 7 hits (Gr-1A) | 1.275 | 0.407 | 0.271 | 1.351 | 0.227 | 0.050 | 2.118 | 0.232 | 0.001 |
| Gr-1B | 0.947 | 0.161 | 0.597 | 1.177 | 0.321 | 0.353 | 1.299 | 0.124 | 0.009 |
| Gr-1C | 0.727 | 0.208 | 0.072 | 1.397 | 0.375 | 0.123 | 1.901 | 0.738 | 0.092 |
| Gr-1D | 1.918 | 0.989 | 0.160 | 1.183 | 0.084 | 0.014 | 1.728 | 0.229 | 0.004 |
| Gr-1E | 0.752 | 0.204 | 0.088 | 1.388 | 0.538 | 0.245 | 1.397 | 0.141 | 0.005 |
| Gr-1F | 1.023 | 0.265 | 0.877 | 1.372 | 0.334 | 0.111 | 2.000 | 0.563 | 0.037 |
| Gr-1G | 0.597 | 0.023 | 0.002 | 1.144 | 0.092 | 0.058 | 1.382 | 0.342 | 0.123 |
| Group 3: 4 hits (3 available) (Gr-3A) | 1.396 | 0.452 | 0.178 | 0.969 | 0.189 | 0.769 | 1.181 | 0.083 | 0.020 |
| Gr-3B | 1.156 | 0.266 | 0.331 | 1.117 | 0.027 | 0.063 | 1.075 | 0.104 | 0.609 |
| Gr-3C | 1.160 | 0.263 | 0.320 | 0.985 | 0.232 | 0.908 | 1.090 | 0.034 | 0.108 |
| Group 4: 4 hits (chalcones) (Gr-4A) | 0.981 | 0.084 | 0.802 | 1.203 | 0.029 | 0.026 | 1.123 | 0.072 | 0.247 |
| Gr-4B | 0.610 | 0.460 | 0.280 | 1.058 | 0.294 | 0.771 | 0.992 | 0.133 | 0.925 |
| Gr-4C | 1.233 | 0.122 | 0.023 | 1.507 | 0.030 | 0.000 | 1.423 | 0.232 | 0.046 |
| Gr-4D | 2.112 | 0.143 | 0.000 | 1.405 | 0.045 | 0.001 | 2.162 | 0.334 | 0.002 |
| Group 5: 4 hits (3 validated) (Gr-5A) | 0.841 | 0.633 | 0.650 | 1.196 | 0.260 | 0.234 | 1.378 | 0.219 | 0.039 |
| Gr-5B | 0.808 | 0.546 | 0.534 | 1.255 | 0.405 | 0.300 | 1.365 | 0.302 | 0.094 |
| Gr-5D | 0.698 | 0.320 | 0.155 | 0.984 | 0.171 | 0.878 | 1.103 | 0.112 | 0.163 |
| Group 6: 3 hits (Gr-6A) | 0.787 | 0.120 | 0.030 | 1.055 | 0.093 | 0.412 | 1.181 | 0.177 | 0.281 |
| Gr-6B | 1.263 | 0.239 | 0.112 | 1.192 | 0.089 | 0.020 | 1.248 | 0.295 | 0.246 |
| Gr-6C, rhodanines - PAINS | 2.167 | 0.864 | 0.144 | 1.215 | 0.398 | 0.363 | 1.418 | 0.240 | 0.038 |
| Group 7: 3 hits (Gr-7A) | 1.913 | 0.149 | 0.001 | 0.979 | 0.141 | 0.817 | 1.143 | 0.109 | 0.071 |

TABLE 15B-continued

Summary of effects on FOXO3-regulated genes GADD45A, DDB1, and SESN1.

| Small Molecule ID | GADD45A | | | DDB1 | | | SESN1 | | |
|---|---|---|---|---|---|---|---|---|---|
| | Normalized fold change | Normalized SD | P value | Normalized fold change | Normalized SD | P value | Normalized fold change | Normalized SD | P value |
| Gr-7B | 2.069 | 1.122 | 0.153 | 1.310 | 0.375 | 0.197 | 0.952 | 0.133 | 0.537 |
| Gr-7C | 10.860 | 3.016 | 0.007 | 1.357 | 0.167 | 0.014 | 1.284 | 0.391 | 0.253 |
| O1 | 0.853 | 0.649 | 0.681 | 1.202 | 0.454 | 0.443 | 1.176 | 0.284 | 0.304 |
| O6, phenolic mannich - PAINS | 0.881 | 0.109 | 0.175 | 0.988 | 0.075 | 0.872 | 1.064 | 0.111 | 0.551 |
| O10 | 1.189 | 0.258 | 0.243 | 0.906 | 0.027 | 0.099 | 0.983 | 0.297 | 0.933 |
| O11 | 1.431 | 0.312 | 0.062 | 1.308 | 0.165 | 0.025 | 1.773 | 0.433 | 0.030 |
| O12 | 1.693 | 0.340 | 0.021 | 1.018 | 0.183 | 0.861 | 1.051 | 0.065 | 0.395 |
| O13 | 1.198 | 0.085 | 0.041 | 1.269 | 0.048 | 0.009 | 1.231 | 0.157 | 0.087 |
| O14 | 1.198 | 0.172 | 0.112 | 1.077 | 0.153 | 0.404 | 1.141 | 0.084 | 0.062 |
| O15, enones - PAINS | 2.715 | 0.554 | 0.007 | 1.168 | 0.087 | 0.065 | 0.679 | 0.120 | 0.018 |
| O17 | 0.846 | 0.036 | 0.046 | 1.039 | 0.081 | 0.621 | 1.115 | 0.073 | 0.262 |
| O18 | 0.861 | 0.593 | 0.671 | 1.330 | 0.393 | 0.191 | 1.057 | 0.217 | 0.640 |
| O20 | 1.039 | 0.041 | 0.456 | 1.253 | 0.121 | 0.017 | 1.728 | 0.432 | 0.035 |
| O21, rhodanines - PAINS | 2.060 | 1.168 | 0.167 | 1.449 | 0.463 | 0.147 | 1.880 | 0.312 | 0.010 |
| O22 | 1.232 | 0.075 | 0.006 | 1.036 | 0.048 | 0.488 | 1.292 | 0.173 | 0.105 |
| O23, enones, catechols - PAINS | 7.216 | 2.072 | 0.009 | 1.261 | 0.351 | 0.236 | 0.799 | 0.195 | 0.129 |
| O27 | 1.460 | 0.362 | 0.078 | 1.055 | 0.078 | 0.503 | 1.538 | 0.245 | 0.012 |

TABLE 15C

Summary of effects on NRF2-regulated genes, HMOX1, GCLC, and NQO1.

| Small Molecule ID | Summary of effects on NRF2-regulated genes | HMOX1 | | | GCLC | | | NQO1 | | |
|---|---|---|---|---|---|---|---|---|---|---|
| | | Normalized fold change | Normalized SD | P value | Normalized fold change | Normalized SD | P value | Normalized fold change | Normalized SD | P value |
| Group 1: 7 hits (Gr-1A) | GCLC 1.61, p < 0.01; NQO1 1.79, p < 0.01; GSTM1 1.45, p < 0.01 | 0.973 | 0.226 | 0.834 | 1.607 | 0.180 | 0.002 | 1.790 | 0.239 | 0.004 |
| Gr-1B | NQO1 1.31, p < 0.05; GSTM1 2.00, p > 0.05 | 1.314 | 0.313 | 0.137 | 1.436 | 0.326 | 0.070 | 1.307 | 0.146 | 0.016 |
| Gr-1C | GCLC 1.82, p < 0.05; NQO1 1.46, p < 0.01 | 1.324 | 0.319 | 0.133 | 1.824 | 0.494 | 0.041 | 1.457 | 0.150 | 0.003 |

TABLE 15C-continued

Summary of effects on NRF2-regulated genes, HMOX1, GCLC, and NQO1.

| Small Molecule ID | Summary of effects on NRF2-regulated genes | HMOX1 Normalized fold change | HMOX1 Normalized SD | HMOX1 P value | GCLC Normalized fold change | GCLC Normalized SD | GCLC P value | NQO1 Normalized fold change | NQO1 Normalized SD | NQO1 P value |
|---|---|---|---|---|---|---|---|---|---|---|
| Gr-1D | RP11: HMOX1 4.68, $p > 0.10$. RP42: HMOX1 5.86, $p > 0.05$; GCLC 0.79, $p < 0.05$. | 4.682 | 3.324 | 0.113 | 1.082 | 0.267 | 0.613 | 0.878 | 0.081 | 0.124 |
| Gr-1E | GSTM1 2.11, $p > 0.10$ | 1.061 | 0.462 | 0.812 | 1.552 | 0.549 | 0.136 | 1.107 | 0.230 | 0.442 |
| Gr-1F | GCLC 1.62, $p < 0.05$ | 1.090 | 0.344 | 0.644 | 1.620 | 0.311 | 0.023 | 1.113 | 0.087 | 0.142 |
| Gr-1G | HMOX1 0.50, $p < 0.05$; GCLC 1.57, $p < 0.05$ | 0.503 | 0.048 | 0.032 | 1.569 | 0.366 | 0.045 | 1.257 | 0.175 | 0.072 |
| Group 3: 4 hits (3 available) (Gr-3A) | HMOX1, 1.41, $p < 0.05$; NQO1 1.37, $p < 0.01$ | 1.413 | 0.231 | 0.031 | 1.008 | 0.120 | 0.927 | 1.369 | 0.092 | 0.002 |
| Gr-3B | NO | 1.041 | 0.201 | 0.818 | 1.097 | 0.135 | 0.491 | 1.071 | 0.135 | 0.518 |
| Gr-3C | NO | 1.116 | 0.297 | 0.500 | 0.991 | 0.143 | 0.928 | 1.185 | 0.148 | 0.089 |
| Group 4: 4 hits (chalcones) (Gr-4A) | HMOX1 5.24, $p < 0.05$; NQO1 2.73, $p < 0.001$; GSTM1 1.24, $p < 0.05$ | 5.239 | 2.485 | 0.042 | 1.183 | 0.180 | 0.234 | 2.731 | 0.262 | 0.000 |
| Gr-4B | HMOX1 4.51, $p > 0.05$; NQO1 2.36, $p < 0.05$ | 4.513 | 2.718 | 0.154 | 1.151 | 0.417 | 0.598 | 2.361 | 0.365 | 0.021 |
| Gr-4C | HMOX1 89.48, $p < 0.01$; GCLC 2.51, $p < 0.001$; NQO1 5.00, $p < 0.001$; GSTM1 1.63, $p < 0.01$ | 89.477 | 12.335 | 0.001 | 2.510 | 0.280 | 0.000 | 5.003 | 0.491 | 0.000 |
| Gr-4D | RP29: HMOX1 4.55, $p < 0.01$; NQO1 2.56, $p < 0.01$; GSTM1 1.52, $p < 0.05$. RP52: HMOX1 2.40, | 4.551 | 1.177 | 0.007 | 0.863 | 0.148 | 0.351 | 2.555 | 0.414 | 0.003 |

TABLE 15C-continued

Summary of effects on NRF2-regulated genes, HMOX1, GCLC, and NQO1.

| Small Molecule ID | Summary of effects on NRF2-regulated genes | HMOX1 Normalized fold change | HMOX1 Normalized SD | HMOX1 P value | GCLC Normalized fold change | GCLC Normalized SD | GCLC P value | NQO1 Normalized fold change | NQO1 Normalized SD | NQO1 P value |
|---|---|---|---|---|---|---|---|---|---|---|
| Group 5: 4 hits (3 validated) (Gr-5A) | $p < 0.01$; NQO1 1.49, $p < 0.01$. HMOX1 2.06, $p < 0.01$; NQO1 1.55, $p < 0.01$ | 2.061 | 0.297 | 0.004 | 0.919 | 0.229 | 0.563 | 1.552 | 0.198 | 0.009 |
| Gr-5B | HMOX1 1.73, $p < 0.05$; NQO1 1.94, $p < 0.01$; GSTM1 1.27, $p < 0.05$ | 1.730 | 0.364 | 0.024 | 1.153 | 0.345 | 0.454 | 1.937 | 0.243 | 0.003 |
| Gr-5D | HMOX1 2.49, $p < 0.01$; NQO1 1.78, $p < 0.001$; TXNIP 0.67, $p < 0.01$ | 2.492 | 0.269 | 0.001 | 0.886 | 0.233 | 0.428 | 1.782 | 0.084 | 0.000 |
| Group 6: 3 hits (Gr-6A) | NO | 1.099 | 0.176 | 0.548 | 1.034 | 0.237 | 0.838 | 1.020 | 0.145 | 0.856 |
| Gr-6B | HMOX1 1.88, $p < 0.05$; NQO1 1.52, $p < 0.01$ | 1.877 | 0.450 | 0.021 | 0.797 | 0.050 | 0.166 | 1.519 | 0.185 | 0.005 |
| Gr-6C, rhodanines - PAINS | HMOX1 2.09, $p < 0.01$; GCLC 0.33, $p < 0.001$ | 2.086 | 0.233 | 0.009 | 0.331 | 0.058 | 0.000 | 0.870 | 0.092 | 0.058 |
| Group 7: 3 hits (Gr-7A) | HMOX1 15.23, $p < 0.01$; GCLC 0.60, $p < 0.001$; NQO1 0.78, $p < 0.05$ | 15.230 | 3.663 | 0.004 | 0.602 | 0.040 | 0.000 | 0.779 | 0.113 | 0.020 |
| Gr-7B | HMOX1 54.15, $p < 0.05$ | 54.153 | 17.901 | 0.010 | 1.804 | 0.649 | 0.087 | 1.411 | 0.437 | 0.156 |
| Gr-7C | HMOX1 28.05, $p < 0.01$; GCLC 2.27, $p < 0.01$; GSTM1 0.78, $p < 0.05$ | 28.048 | 5.297 | 0.002 | 2.272 | 0.506 | 0.009 | 0.811 | 0.211 | 0.197 |
| O1 | NO | 1.255 | 0.318 | 0.208 | 1.209 | 0.558 | 0.514 | 1.082 | 0.243 | 0.553 |
| O6, phenolic mannich - PAINS | HMOX1 3.85, $p < 0.001$; NQO1 1.62, $p < 0.001$ | 3.846 | 0.195 | 0.000 | 1.056 | 0.093 | 0.644 | 1.623 | 0.126 | 0.000 |

TABLE 15C-continued

Summary of effects on NRF2-regulated genes, HMOX1, GCLC, and NQO1.

| Small Molecule ID | Summary of effects on NRF2-regulated genes | HMOX1 Normalized fold change | HMOX1 Normalized SD | HMOX1 P value | GCLC Normalized fold change | GCLC Normalized SD | GCLC P value | NQO1 Normalized fold change | NQO1 Normalized SD | NQO1 P value |
|---|---|---|---|---|---|---|---|---|---|---|
| O10 | NO | 0.755 | 0.096 | 0.166 | 0.933 | 0.083 | 0.598 | 0.937 | 0.120 | 0.549 |
| O11 | NQO1 2.03, $p < 0.01$; GSTM1 1.30, $p < 0.01$ | 1.069 | 0.305 | 0.713 | 1.333 | 0.220 | 0.070 | 2.027 | 0.329 | 0.004 |
| O12 | HMOX1 0.82, $p < 0.05$; GCLC 0.53, $p < 0.01$; NQO1 0.69, $p < 0.01$ | 0.821 | 0.069 | 0.028 | 0.531 | 0.035 | 0.005 | 0.692 | 0.035 | 0.007 |
| O13 | HMOX1 5.52, $p < 0.01$; GCLC 1.99, $p < 0.01$, NQO1 2.95, $p < 0.001$; GSTM1 1.31, $p < 0.01$ | 5.520 | 0.921 | 0.002 | 1.993 | 0.332 | 0.003 | 2.949 | 0.338 | 0.000 |
| O14 | NO | 1.107 | 0.145 | 0.273 | 1.071 | 0.056 | 0.398 | 0.871 | 0.124 | 0.170 |
| O15, enones - PAINS | HMOX1 48.69, $p < 0.001$; NQO1 1.60, $p < 0.05$ | 48.690 | 2.691 | 0.000 | 1.225 | 0.139 | 0.122 | 1.598 | 0.332 | 0.028 |
| O17 | GCLC 1.36, $p < 0.05$; NQO1 1.47, $p < 0.01$ | 1.080 | 0.089 | 0.448 | 1.355 | 0.082 | 0.020 | 1.466 | 0.103 | 0.001 |
| O18 | HMOX1 23.76, $p < 0.05$; GCLC 2.10, $p < 0.05$; NQO1 2.94, $p < 0.01$; GSTM1 1.52, $p < 0.01$ | 23.762 | 9.991 | 0.020 | 2.104 | 0.678 | 0.045 | 2.936 | 0.285 | 0.001 |
| O20 | GCLC 1.76, $p < 0.05$; NQO1 2.49, $p < 0.01$ | 0.937 | 0.222 | 0.730 | 1.764 | 0.394 | 0.022 | 2.486 | 0.541 | 0.009 |
| O21, rhodanines - PAINS | HMOX1 3.02, $p < 0.05$; GCLC 0.51, $p < 0.001$; GSTM1 1.25, $p < 0.01$ | 3.023 | 0.496 | 0.017 | 0.512 | 0.117 | 0.000 | 0.836 | 0.136 | 0.089 |
| O22 | GCLC 0.66, $p < 0.05$ | 0.765 | 0.153 | 0.174 | 0.659 | 0.159 | 0.044 | 0.929 | 0.143 | 0.527 |

TABLE 15C-continued

Summary of effects on NRF2-regulated genes, HMOX1, GCLC, and NQO1.

| Small Molecule ID | Summary of effects on NRF2-regulated genes | HMOX1 Normalized fold change | HMOX1 Normalized SD | HMOX1 P value | GCLC Normalized fold change | GCLC Normalized SD | GCLC P value | NQO1 Normalized fold change | NQO1 Normalized SD | NQO1 P value |
|---|---|---|---|---|---|---|---|---|---|---|
| O23, enones, catechols - PAINS | HMOX1 12.86, $p < 0.05$; GCLC 0.67, $p < 0.01$; NQO1 0.48, $p < 0.001$; GSTM1 0.60, $p < 0.001$ | 12.857 | 4.440 | 0.013 | 0.668 | 0.120 | 0.004 | 0.477 | 0.081 | 0.000 |
| O27 | HMOX1 1.71, $p < 0.05$ | 1.705 | 0.338 | 0.049 | 1.251 | 0.311 | 0.240 | 1.332 | 0.268 | 0.085 |

TABLE 15D

Summary of effects on NRF2-regulated gene GSTM1; and data for gene dependency for $H_2O_2$-resistance.

| Small Molecule ID | GSTM1 Normalized fold change | GSTM1 Normalized SD | GSTM1 P value | FOXO3-dependency for $H_2O_2$-resistance, at 10 uM (experiment 1 & 2) - with $H_2O_2$ | FOXO3-dependency for $H_2O_2$-resistance, at 10 uM (experiment 3) - with & without $H_2O_2$ | NRF2-dependency for $H_2O_2$-resistance, at 10 uM (experiment 1 & 2) - with $H_2O_2$ | NRF2-dependency for $H_2O_2$-resistance, at 10 uM (experiment 3) - with & without $H_2O_2$ |
|---|---|---|---|---|---|---|---|
| Group 1: 7 hits (Gr-1A) | 2.527 | 1.413 | 0.119 | NO | NO | 1st, NO; 2nd, partial. | YES (note: viability of non-stressed cells, reduced by 30%) |
| Gr-1B | 2.003 | 0.779 | 0.081 | NO | N/A | NO | N/A |
| Gr-1C | 1.773 | 0.697 | 0.112 | NO | N/A | NO | N/A |
| Gr-1D | 1.170 | 0.161 | 0.146 | NO | N/A | NO | N/A |
| Gr-1E | 2.106 | 1.092 | 0.135 | NO | N/A | NO | N/A |
| Gr-1F | 1.716 | 0.523 | 0.069 | NO | YES | NO | YES (note: viability of non-stressed cells, reduced by 50%) |
| Gr-1G | 0.948 | 0.188 | 0.671 | NO | N/A | 1st, YES; 2nd, NO. | N/A |
| Group 3: 4 hits (3 available) (Gr-3A) | 1.352 | 0.280 | 0.082 | NO | N/A | NO | N/A |
| Gr-3B | 1.101 | 0.070 | 0.257 | NO | N/A | NO | N/A |
| Gr-3C | 1.451 | 0.441 | 0.131 | NO | N/A | NO | N/A |
| Group 4: 4 hits (chalcones) (Gr-4A) | 1.239 | 0.060 | 0.012 | NO | N/A | NO | N/A |
| Gr-4B | 1.147 | 0.123 | 0.163 | NO | N/A | NO | N/A |
| Gr-4C | 1.631 | 0.231 | 0.006 | NO | N/A | NO | N/A |
| Gr-4D | 1.517 | 0.239 | 0.014 | NO | Partial | NO | Partial |
| Group 5: 4 hits (3 validated) (Gr-5A) | 1.153 | 0.103 | 0.063 | NO | N/A | NO | N/A |

TABLE 15D-continued

Summary of effects on NRF2-regulated gene GSTM1; and data for gene dependency for H₂O₂-resistance.

| Small Molecule ID | GSTM1 Normalized fold change | Normalized SD | P value | FOXO3-dependency for H₂O₂-resistance, at 10 uM (experiment 1 & 2) - with H₂O₂ | FOXO3-dependency for H₂O₂-resistance, at 10 uM (experiment 3) - with & without H₂O₂ | NRF2-dependency for H₂O₂-resistance, at 10 uM (experiment 1 & 2) - with H₂O₂ | NRF2-dependency for H₂O₂-resistance, at 10 uM (experiment 3) - with & without H₂O₂ |
|---|---|---|---|---|---|---|---|
| Gr-5B | 1.269 | 0.140 | 0.020 | NO | N/A | NO | N/A |
| Gr-5D | 1.165 | 0.107 | 0.053 | NO | N/A | NO | N/A |
| Group 6: 3hits (Gr-6A) | 1.091 | 0.171 | 0.440 | NO | N/A | NO | N/A |
| Gr-6B | 1.218 | 0.137 | 0.067 | NO | NO | 1st, NO; 2nd, partial. | YES |
| Gr-6C, rhodanines - PAINS | 0.914 | 0.087 | 0.223 | NO | N/A | 1st, NO; 2nd, partial. | N/A |
| Group 7: 3 hits (Gr-7A) | 1.089 | 0.091 | 0.220 | 1st, partial; 2nd, YES. | YES | 1st, YES; 2nd, YES. | YES (note: viability of non-stressed cells, reduced by 84%) |
| Gr-7B | 0.981 | 0.062 | 0.745 | NO | N/A | 1st, partial; 2nd, partial. | N/A |
| Gr-7C | 0.784 | 0.049 | 0.018 | 1st, YES; 2nd, NO. | Partial | 1st, YES; 2nd, NO. | YES (note: viability of non-stressed cells, reduced by 60%) |
| O1 | 1.087 | 0.212 | 0.495 | NO | N/A | 1st, partial; 2nd, partial. | N/A |
| O6, phenolic mannich - PAINS | 0.965 | 0.092 | 0.662 | NO | N/A | NO | N/A |
| O10 | 1.031 | 0.115 | 0.733 | NO | N/A | NO | N/A |
| O11 | 1.304 | 0.060 | 0.002 | NO | N/A | NO | N/A |
| O12 | 1.208 | 0.136 | 0.063 | NO | N/A | NO | N/A |
| O13 | 1.311 | 0.085 | 0.003 | NO | N/A | NO | N/A |
| O14 | 1.531 | 0.448 | 0.095 | NO | N/A | NO | N/A |
| O15, enones - PAINS | 0.995 | 0.120 | 0.952 | 1st, YES; 2nd, NO. | YES | 1st, YES; 2nd, YES. | YES |
| O17 | 1.122 | 0.089 | 0.143 | NO | N/A | NO | N/A |
| O18 | 1.522 | 0.134 | 0.001 | NO | YES | 1st, NO; 2nd, partial. | YES |
| O20 | 1.364 | 0.281 | 0.075 | 1st, NO; 2nd, YES. | YES | 1st, YES; 2nd, YES. | YES |
| O21, rhodanines - PAINS | 1.250 | 0.092 | 0.005 | NO | YES | 1st, partial; 2nd, NO. | YES |
| O22 | 0.877 | 0.102 | 0.205 | NO | N/A | 1st, partial; 2nd, partial. | N/A |
| O23, enones, catechols - PAINS | 0.595 | 0.079 | 0.000 | NO | YES | 1st, YES; 2nd, YES. | YES (note: yet viability of non-stressed cells, reduced by 40%) |
| O27 | 1.138 | 0.053 | 0.071 | NO | N/A | NO | N/A |

TABLE 16

(related to Table 17). Several small molecules reduced the phosphorylated fraction of RPS6. We examined the effects of our molecules, at multiple doses (n = 4 for each dose), on the phosphorylation status of ribosomal protein S6, a downstream readout of mTOR activity, by In-Cell Western analyses. Rapamycin, as a control, substantially reduced the p-RPS6 fraction (analyzed at 1.25 µM, 2.5 µM, 5.0 µM). For example, in Experiment 3, relative ratios of p-RPS/RPS are: DMSO control (pooled), 0.771 ± 0.111 (average ± standard deviation, n = 12); rapamycin (pooled from three doses), 0.041 ± 0.004. When normalized by the DMSO control, rapamycin treatment resulted in more than 90% reduction of phosphorylated fraction of RPS6. Small molecules that produced more than 40% reduction in p-RPS6 fraction in at least two of three experiments are scored as positive.

| Small Molecule ID | Exp. 1, normalized reduction in p-RPS6/RPS6 ratio, at 1.25 µM, 2.5 µM, 5 µM, 10 µM & 20 µM | Exp. 2, normalized reduction in p-RPS6/RPS6 ratio, at 10 µM | Exp. 3, normalized reduction in p-RPS6/RPS6 ratio, at 5 µM, 10 µM & 20 µM |
|---|---|---|---|
| Group 7: 3 hits (Gr-7A) | ~60% (−), at 10 µM; ~61% (−), at 20 µM | ~75% (−), at 10 µM | ~50% (−), at 5 µM; ~89% (−), at 10 µM; ~92% (−), at 20 µM |
| Gr-7B | ~65% (−), at 10 µM; ~67% (−), at 20 µM | NO | ~48% (−), at 5 µM; ~45% (−), at 10 µM; ~53% (−), at 20 µM |
| Gr-7C | ~80% (−), at 20 µM | NO | ~38% (−), at 5 µM; ~40% (−), at 20 µM |
| O27 | NO | ~30% (−), at 10 µM | ~86% (−), at 20 µM |

TABLE 17

(related to Table 8). Several small molecules induced the LC3A/B autophagy marker. By performing immuno-staining of the LC3A/B autophagic marker for WI-38 cells treated with small molecules, at least 6 small molecules (Gr-1A, Gr-1C, Gr-1D, Gr-1G, O11 and O23) were found to induce LC3A/B puncta. Normalized change of nuclei numbers and LC3A/B puncta intensity are shown and only the molecules that increased fold change by 2-fold or more in two independent experiments were scored positive. Other members of Group 1, including Gr-1B, Gr-1E and Gr-1F, are also shown. Experiment 1: rapamycin control, less cells, 83%, P < 0.05; Up, 174%, P > 0.05 (n = 4).

| Small Molecule ID | Exp. 1, induction of LC3A/B puncta, at 10 µM (10X objective, total intensity, normalized by total number of nuclei in the fields) | Exp. 2, induction of LC3A/B puncta, at 10 µM (20X objective, with lysosomal LAMP co-staining, overlapped signals normalized by total number of nuclei in the fields) | Exp. 2, induction of LC3A/B puncta, at 20 µM (20X objective, with lysosomal LAMP co-staining, overlapped signals normalized by total number of nuclei in the fields) |
|---|---|---|---|
| Group 1: 7 hits (Gr-1A) | Less cells, 55%, p < 0.001; Up, 1876%, p < 0.001 | Less cells, 66%, p < 0.001; Up, 182%, p < 0.001 | Less cells, 57%, p < 0.001; Up, 251%, p < 0.001 |
| Gr-1B | No induction | Up, 136%, p < 0.001 | Up, 139%, p < 0.001 |
| Gr-1C | Less cells, 70%, p < 0.01; Up, 956%, p < 0.01 | Less cells, 58%, p < 0.001; Up, 194%, p < 0.001 | Less cells, 41%, p < 0.001; Up, 205%, p < 0.001 |
| Gr-1D | Less cells, 67%, p < 0.05; Up, 617%, p > 0.05 | Less cells, 67%, p < 0.001; Up, 168%, p < 0.001 | Less cells, 73%, p < 0.001; Up, 198%, p < 0.001 |
| Gr-1E | Up, 260%, p < 0.01 | Less cells, 75%, p < 0.001; Up, 135%, p < 0.01 | Less cells, 58%, p < 0.001; Up, 160%, p < 0.01 |
| Gr-1F | Up, 151%, p < 0.01 | Less cells, 82%, p < 0.01; Up, 181%, p < 0.001 | Less cells, 73%, p < 0.01; Up, 188%, p < 0.001 |
| Gr-1G | Less cells, 41%, p < 0.001; Up, 2006%, p < 0.001 | Less cells, 47%, p < 0.001; Up, 216%, p < 0.001 | Less cells, 67%, p < 0.001; Up, 195%, p < 0.001 |
| O11 | Less cells, 64%, p < 0.01; Up, 315%, p < 0.05 | Less cells, 71%, p < 0.001; Up, 193%, p < 0.001 | Less cells, 69%, p < 0.001; Up, 159%, p < 0.001 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

REFERENCES

Aiken, C. T., Tobin, A. J., and Schweitzer, E. S. (2004). A cell-based screen for drugs to treat Huntington's disease. Neurobiol Dis 16, 546-555.

Alavez, S., Vantipalli, M. C., Zucker, D. J., Klang, I. M., and Lithgow, G. J. (2011). Amyloid-binding compounds maintain protein homeostasis during ageing and extend lifespan. Nature 472, 226-229.

Anselmi, C. V., Malovini, A., Roncarati, R., Novelli, V., Villa, F., Condorelli, G., Bellazzi, R., and Puca, A. A. (2009). Association of the FOXO3A locus with extreme longevity in a southern Italian centenarian study. Rejuvenation Res 12, 95-104.

Apfeld, J., O'Connor, G., McDonagh, T., DiStefano, P. S., and Curtis, R. (2004). The AMP-activated protein kinase AAK-2 links energy levels and insulin-like signals to lifespan in C. elegans. Genes Dev 18, 3004-3009.

Aso, E., and Ferrer, I. (2014). Cannabinoids for treatment of Alzheimer's disease: moving toward the clinic. Front Pharmacol 5, 37.

Bae, S. H., Sung, S. H., Oh, S. Y., Lim, J. M., Lee, S. K., Park, Y. N., Lee, H. E., Kang, D., and Rhee, S. G. (2013). Sestrins activate Nrf2 by promoting p62-dependent autophagic degradation of Keap1 and prevent oxidative liver damage. Cell Metab 17, 73-84.

Baell, J., and Walters, M. A. (2014). Chemistry: Chemical con artists foil drug discovery. Nature 513, 481-483.

Baell, J. B., and Holloway, G. A. (2010). New substructure filters for removal of pan assay interference compounds (PAINS) from screening libraries and for their exclusion in bioassays. J Med Chem 53, 2719-2740.

Bai, P., Canto, C., Oudart, H., Brunyanszki, A., Cen, Y., Thomas, C., Yamamoto, H., Huber, A., Kiss, B., Houtkooper, R. H., et al. (2011). PARP-1 inhibition increases mitochondrial metabolism through SIRT1 activation. Cell Metab 13, 461-468.

Banasik, M., Komura, H., Shimoyama, M., and Ueda, K. (1992). Specific inhibitors of poly(ADP-ribose) synthetase and mono(ADP-ribosyl)transferase. J Biol Chem 267, 1569-1575.

Bartke, A. (2011). Single-gene mutations and healthy ageing in mammals. Philos Trans R Soc Lond B Biol Sci 366, 28-34.

Batovska, D. I., and Todorova, I. T. (2010). Trends in utilization of the pharmacological potential of chalcones. Curr Clin Pharmacol 5, 1-29.

Benjamin, D., Colombi, M., Moroni, C., and Hall, M. N. (2011). Rapamycin passes the torch: a new generation of mTOR inhibitors. Nat Rev Drug Discov 10, 868-880.

Berdichevsky, A., Viswanathan, M., Horvitz, H. R., and Guarente, L. (2006). C. elegans SIR-2.1 interacts with 14-3-3 proteins to activate DAF-16 and extend life span. Cell 125, 1165-1177.

Birse, R. T., Choi, J., Reardon, K., Rodriguez, J., Graham, S., Diop, S., Ocorr, K., Bodmer, R., and Oldham, S. (2010). High-fat-diet-induced obesity and heart dysfunction are regulated by the TOR pathway in Drosophila. Cell Metab 12, 533-544.

Bishop, N. A., and Guarente, L. (2007). Two neurons mediate diet-restriction-induced longevity in C. elegans. Nature 447, 545-549.

Bjedov, I., Toivonen, J. M., Kerr, F., Slack, C., Jacobson, J., Foley, A., and Partridge, L. (2010). Mechanisms of life span extension by rapamycin in the fruit fly Drosophila melanogaster. Cell Metab 11, 35-46.

Booz, G. W. (2011). Cannabidiol as an emergent therapeutic strategy for lessening the impact of inflammation on oxidative stress. Free Radic Biol Med 51, 1054-1061.

Budanov, A. V., and Karin, M. (2008). p53 target genes sestrin1 and sestrin2 connect genotoxic stress and mTOR signaling. Cell 134, 451-460.

Budanov, A. V., Sablina, A. A., Feinstein, E., Koonin, E. V., and Chumakov, P. M. (2004). Regeneration of peroxiredoxins by p53-regulated sestrins, homologs of bacterial AhpD. Science 304, 596-600.

Cabreiro, F., Au, C., Leung, K. Y., Vergara-Irigaray, N., Cocheme, H. M., Noori, T., Weinkove, D., Schuster, E., Greene, N. D., and Gems, D. (2013). Metformin retards aging in C. elegans by altering microbial folate and methionine metabolism. Cell 153, 228-239.

Calamini, B., Silva, M. C., Madoux, F., Hutt, D. M., Khanna, S., Chalfant, M. A., Saldanha, S. A., Hodder, P., Tait, B. D., Garza, D., et al. (2012). Small-molecule proteostasis regulators for protein conformational diseases. Nat Chem Biol 8, 185-196.

Cao, S. Q., Xu, Q. T., Zhou, H. J., Cao, Y. J., Zhu, Y., Yu, F., and Kuai, B. K. (2003). [Screening for lifespan-extension mutants with paraquat in Arabidopsis]. Shi Yan Sheng Wu Xue Bao 36, 233-237.

Caughey, B., and Lansbury, P. T. (2003). Protofibrils, pores, fibrils, and neurodegeneration: separating the responsible protein aggregates from the innocent bystanders. Annu Rev Neurosci 26, 267-298.

Chan, N., Pires, I. M., Bencokova, Z., Coackley, C., Luoto, K. R., Bhogal, N., Lakshman, M., Gottipati, P., Oliver, F. J., Helleday, T., et al. (2010). Contextual synthetic lethality of cancer cell kill based on the tumor microenvironment. Cancer Res 70, 8045-8054.

Chen, L. F., and Greene, W. C. (2004). Shaping the nuclear action of NF-kappaB. Nat Rev Mol Cell Biol 5, 392-401.

Cheng, Z., and White, M. F. (2011). Targeting Forkhead box O1 from the concept to metabolic diseases: lessons from mouse models. Antioxid Redox Signal 14, 649-661.

Cohen, E., Paulsson, J. F., Blinder, P., Burstyn-Cohen, T., Du, D., Estepa, G., Adame, A., Pham, H. M., Holzenberger, M., Kelly, J. W., et al. (2009). Reduced IGF-1 signaling delays age-associated proteotoxicity in mice. Cell 139, 1157-1169.

Costantino, G., Macchiarulo, A., Camaioni, E., and Pellicciari, R. (2001). Modeling of poly(ADP-ribose)polymerase (PARP) inhibitors. Docking of ligands and quantitative structure-activity relationship analysis. J Med Chem 44, 3786-3794.

Dazert, E., and Hall, M. N. (2011). mTOR signaling in disease. Curr Opin Cell Biol 23, 744-755.

de Cabo, R., Carmona-Gutierrez, D., Bernier, M., Hall, M. N., and Madeo, F. (2014). The search for antiaging interventions: from elixirs to fasting regimens. Cell 157, 1515-1526.

de Castro, E., Hegi de Castro, S., and Johnson, T. E. (2004). Isolation of long-lived mutants in *Caenorhabditis elegans* using selection for resistance to juglone. Free Radic Biol Med 37, 139-145.

De Haes, W., Frooninckx, L., Van Assche, R., Smolders, A., Depuydt, G., Billen, J., Braeckman, B. P., Schoofs, L., and Temmerman, L. (2014). Metformin promotes lifespan through mitohormesis via the peroxiredoxin PRDX-2. Proc Natl Acad Sci USA 111, E2501-2509.

Deelen, J., Uh, H. W., Monajemi, R., van Heemst, D., Thijssen, P. E., Bohringer, S., van den Akker, E. B., de Craen, A. J., Rivadeneira, F., Uitterlinden, A. G., et al. (2013). Gene set analysis of GWAS data for human longevity highlights the relevance of the insulin/IGF-1 signaling and telomere maintenance pathways. Age (Dordr) 35, 235-249.

Eijkelenboom, A., and Burgering, B. M. (2013). FOXOs: signalling integrators for homeostasis maintenance. Nat Rev Mol Cell Biol 14, 83-97.

Eisenberg, T., Knauer, H., Schauer, A., Buttner, S., Ruckenstuhl, C., Carmona-Gutierrez, D., Ring, J., Schroeder, S., Magnes, C., Antonacci, L., et al. (2009). Induction of autophagy by spermidine promotes longevity. Nat Cell Biol 11, 1305-1314.

Ekins, S., Nikolsky, Y., Bugrim, A., Kirillov, E., and Nikolskaya, T. (2007). Pathway mapping tools for analysis of high content data. Methods Mol Biol 356, 319-350.

Feng, Y., Yao, Z., and Klionsky, D. J. (2015). How to control self-digestion: transcriptional, post-transcriptional, and post-translational regulation of autophagy. Trends Cell Biol 25, 354-363.

Flachsbart, F., Caliebe, A., Kleindorp, R., Blanche, H., von Eller-Eberstein, H., Nikolaus, S., Schreiber, S., and Nebel, A. (2009). Association of FOXO3A variation with human longevity confirmed in German centenarians. Proc Natl Acad Sci USA 106, 2700-2705.

Fong, P. C., Boss, D. S., Yap, T. A., Tutt, A., Wu, P., Mergui-Roelvink, M., Mortimer, P., Swaisland, H., Lau, A., O'Connor, M. J., et al. (2009). Inhibition of poly (ADP-ribose) polymerase in tumors from BRCA mutation carriers. N Engl J Med 361, 123-134.

Fontana, L., Partridge, L., and Longo, V. D. (2010). Extending healthy life span—from yeast to humans. Science 328, 321-326.

Geiss-Friedlander, R., and Melchior, F. (2007). Concepts in sumoylation: a decade on. Nat Rev Mol Cell Biol 8, 947-956.

Giannakou, M. E., Goss, M., Junger, M. A., Hafen, E., Leevers, S. J., and Partridge, L. (2004). Long-lived *Drosophila* with overexpressed dFOXO in adult fat body. Science 305, 361.

Gomes, A. P., Price, N. L., Ling, A. J., Moslehi, J. J., Montgomery, M. K., Rajman, L., White, J. P., Teodoro, J. S., Wrann, C. D., Hubbard, B. P., et al. (2013). Declining NAD(+) induces a pseudohypoxic state disrupting nuclear-mitochondrial communication during aging. Cell 155, 1624-1638.

Greer, E. L., Dowlatshahi, D., Banko, M. R., Villen, J., Hoang, K., Blanchard, D., Gygi, S. P., and Brunet, A. (2007). An AMPK-FOXO pathway mediates longevity induced by a novel method of dietary restriction in *C. elegans*. Curr Biol 17, 1646-1656.

Guevara-Aguirre, J., Balasubramanian, P., Guevara-Aguirre, M., Wei, M., Madia, F., Cheng, C. W., Hwang, D., Martin-Montalvo, A., Saavedra, J., Ingles, S., et al. (2011). Growth hormone receptor deficiency is associated with a major reduction in pro-aging signaling, cancer, and diabetes in humans. Sci Transl Med 3, 70ra13.

Harel, I., Benayoun, B. A., Machado, B., Singh, P. P., Hu, C. K., Pech, M. F., Valenzano, D. R., Zhang, E., Sharp, S. C., Artandi, S. E., et al. (2015). A platform for rapid exploration of aging and diseases in a naturally short-lived vertebrate. Cell 160, 1013-1026.

Harper, J. M., Salmon, A. B., Leiser, S. F., Galecki, A. T., and Miller, R. A. (2007). Skin-derived fibroblasts from long-lived species are resistant to some, but not all, lethal stresses and to the mitochondrial inhibitor rotenone. Aging Cell 6, 1-13.

Harper, J. M., Wang, M., Galecki, A. T., Ro, J., Williams, J. B., and Miller, R. A. (2011). Fibroblasts from long-lived bird species are resistant to multiple forms of stress. The Journal of experimental biology 214, 1902-1910.

Harrington, S. C., Simari, R. D., and Conover, C. A. (2007). Genetic deletion of pregnancy-associated plasma protein-A is associated with resistance to atherosclerotic lesion development in apolipoprotein E-deficient mice challenged with a high-fat diet. Circ Res 100, 1696-1702.

Harrison, D. E., Strong, R., Sharp, Z. D., Nelson, J. F., Astle, C. M., Flurkey, K., Nadon, N. L., Wilkinson, J. E., Frenkel, K., Carter, C. S., et al. (2009). Rapamycin fed late in life extends lifespan in genetically heterogeneous mice. Nature 460, 392-395.

Hayden, M. S., and Ghosh, S. (2012). NF-kappaB, the first quarter-century: remarkable progress and outstanding questions. Genes Dev 26, 203-234.

Hickey, C. M., Wilson, N. R., and Hochstrasser, M. (2012). Function and regulation of SUMO proteases. Nat Rev Mol Cell Biol 13, 755-766.

Hochmuth, C. E., Biteau, B., Bohmann, D., and Jasper, H. (2011). Redox regulation by Keap1 and Nrf2 controls intestinal stem cell proliferation in *Drosophila*. Cell Stem Cell 8, 188-199.

Hsu, A. L., Murphy, C. T., and Kenyon, C. (2003). Regulation of aging and age-related disease by DAF-16 and heat-shock factor. Science 300, 1142-1145.

Hubbard, B. P., and Sinclair, D. A. (2014). Small molecule SIRT1 activators for the treatment of aging and age-related diseases. Trends Pharmacol Sci 35, 146-154.

Hur, W., and Gray, N. S. (2011). Small molecule modulators of antioxidant response pathway. Curr Opin Chem Biol 15, 162-173.

Hwangbo, D. S., Gershman, B., Tu, M. P., Palmer, M., and Tatar, M. (2004). *Drosophila* dFOXO controls lifespan and regulates insulin signalling in brain and fat body. Nature 429, 562-566.

Hybertson, B. M., Gao, B., Bose, S. K., and McCord, J. M. (2011). Oxidative stress in health and disease: the therapeutic potential of Nrf2 activation. Mol Aspects Med 32, 234-246.

Ikeno, Y., Hubbard, G. B., Lee, S., Cortez, L. A., Lew, C. M., Webb, C. R., Berryman, D. E., List, E. O., Kopchick, J. J., and Bartke, A. (2009). Reduced incidence and delayed occurrence of fatal neoplastic diseases in growth hormone receptor/binding protein knockout mice. J Gerontol A Biol Sci Med Sci 64, 522-529.

Inoki, K., Zhu, T., and Guan, K. L. (2003). TSC2 mediates cellular energy response to control cell growth and survival. Cell 115, 577-590.

Irwin, J. J., Sterling, T., Mysinger, M. M., Bolstad, E. S., and Coleman, R. G. (2012). ZINC: a free tool to discover chemistry for biology. J Chem Inf Model 52, 1757-1768.

Jenny, N. S. (2012). Inflammation in Aging: Cause, Effect, or Both? Discov Med 73, 451-460.

Kalender, A., Selvaraj, A., Kim, S. Y., Gulati, P., Brule, S., Viollet, B., Kemp, B. E., Bardeesy, N., Dennis, P., Schlager, J. J., et al. (2010). Metformin, independent of AMPK, inhibits mTORC1 in a rag GTPase-dependent manner. Cell Metab 11, 390-401.

Kapeta, S., Chondrogianni, N., and Gonos, E. S. (2010). Nuclear erythroid factor 2-mediated proteasome activation delays senescence in human fibroblasts. J Biol Chem 285, 8171-8184.

Keiser, M. J., Roth, B. L., Armbruster, B. N., Ernsberger, P., Irwin, J. J., and Shoichet, B. K. (2007). Relating protein pharmacology by ligand chemistry. Nat Biotechnol 25, 197-206.

Kennedy, B. K., Austriaco, N. R., Jr., Zhang, J., and Guarente, L. (1995). Mutation in the silencing gene SIR4 can delay aging in S. cerevisiae. Cell 80, 485-496.

Kennedy, M. A., Rakoczy, S. G., and Brown-Borg, H. M. (2003). Long-living Ames dwarf mouse hepatocytes readily undergo apoptosis. Exp Gerontol 38, 997-1008.

Kenyon, C. (2010a). A pathway that links reproductive status to lifespan in Caenorhabditis elegans. Ann N Y Acad Sci 1204, 156-162.

Kenyon, C., Chang, J., Gensch, E., Rudner, A., and Tabtiang, R. (1993). A C. elegans mutant that lives twice as long as wild type. Nature 366, 461-464.

Kenyon, C. J. (2010b). The genetics of ageing. In Nature, pp. 504-512.

Kenyon, C. J. (2010c). The genetics of ageing. Nature 464, 504-512.

Kim, Y., and Sun, H. (2007). Functional genomic approach to identify novel genes involved in the regulation of oxidative stress resistance and animal lifespan. Aging Cell 6, 489-503.

Kops, G. J., Dansen, T. B., Polderman, P. E., Saarloos, I., Wirtz, K. W., Coffer, P. J., Huang, T. T., Bos, J. L., Medema, R. H., and Burgering, B. M. (2002). Forkhead transcription factor FOXO3a protects quiescent cells from oxidative stress. Nature 419, 316-321.

Kumar, A., and Zhang, K. Y. (2015). Advances in the development of SUMO specific protease (SENP) inhibitors. Comput Struct Biotechnol J 13, 204-211.

Lawrence, T. (2009). The nuclear factor NF-kappaB pathway in inflammation. Cold Spring Harb Perspect Biol 1, a001651.

Le Couteur, D. G., McLachlan, A. J., Quinn, R. J., Simpson, S. J., and de Cabo, R. (2012). Aging biology and novel targets for drug discovery. J Gerontol A Biol Sci Med Sci 67, 168-174.

Lee, J. H., Budanov, A. V., and Karin, M. (2013). Sestrins orchestrate cellular metabolism to attenuate aging. Cell Metab 18, 792-801.

Lee, J. H., Budanov, A. V., Park, E. J., Birse, R., Kim, T. E., Perkins, G. A., Ocorr, K., Ellisman, M. H., Bodmer, R., Bier, E., et al. (2010). Sestrin as a feedback inhibitor of TOR that prevents age-related pathologies. Science 327, 1223-1228.

Lee, J. H., Budanov, A. V., Talukdar, S., Park, E. J., Park, H. L., Park, H. W., Bandyopadhyay, G., Li, N., Aghajan, M., Jang, I., et al. (2012). Maintenance of metabolic homeostasis by Sestrin2 and Sestrin3. Cell Metab 16, 311-321.

Leiser, S. F., and Miller, R. A. (2010). Nrf2 signaling, a mechanism for cellular stress resistance in long-lived mice. Mol Cell Biol 30, 871-884.

Lerner, C., Bitto, A., Pulliam, D., Nacarelli, T., Konigsberg, M., Van Remmen, H., Torres, C., and Sell, C. (2013). Reduced mammalian target of rapamycin activity facilitates mitochondrial retrograde signaling and increases life span in normal human fibroblasts. Aging Cell 12, 966-977.

Lewis, K. N., Mele, J., Hornsby, P. J., and Buffenstein, R. (2012). Stress resistance in the naked mole-rat: the bare essentials—a mini-review. Gerontology 58, 453-462.

Lewis, K. N., Wason, E., Edrey, Y. H., Kristan, D. M., Nevo, E., and Buffenstein, R. (2015). Regulation of Nrf2 signaling and longevity in naturally long-lived rodents. Proc Natl Acad Sci USA 112, 3722-3727.

Li, C., Wang, L., Kern, T. S., and Zheng, L. (2012). Inhibition of poly(ADP-ribose) polymerase inhibits ischemia/reperfusion induced neurodegeneration in retina via suppression of endoplasmic reticulum stress. Biochem Biophys Res Commun 423, 276-281.

Li, Y., Wang, W. J., Cao, H., Lu, J., Wu, C., Hu, F. Y., Guo, J., Zhao, L., Yang, F., Zhang, Y. X., et al. (2009). Genetic association of FOXO1A and FOXO3A with longevity trait in Han Chinese populations. Hum Mol Genet 18, 4897-4904.

Libina, N., Berman, J. R., and Kenyon, C. (2003). Tissue-specific activities of C. elegans DAF-16 in the regulation of lifespan. Cell 115, 489-502.

Luo, X., and Kraus, W. L. (2012). On PAR with PARP: cellular stress signaling through poly(ADP-ribose) and PARP-1. Genes Dev 26, 417-432.

Madeo, F., Zimmermann, A., Maiuri, M. C., and Kroemer, G. (2015). Essential role for autophagy in life span extension. J Clin Invest 125, 85-93.

Magesh, S., Chen, Y., and Hu, L. (2012). Small molecule modulators of Keap1-Nrf2-ARE pathway as potential preventive and therapeutic agents. Med Res Rev 32, 687-726.

Maiese, K., Chong, Z. Z., Shang, Y. C., and Hou, J. (2009). A "FOXO" in sight: targeting Foxo proteins from conception to cancer. Med Res Rev 29, 395-418.

Marinkovic, D., Zhang, X., Yalcin, S., Luciano, J. P., Brugnara, C., Huber, T., and Ghaffari, S. (2007). Foxo3 is required for the regulation of oxidative stress in erythropoiesis. J Clin Invest 117, 2133-2144.

Martin-Montalvo, A., Mercken, E. M., Mitchell, S. J., Palacios, H. H., Mote, P. L., Scheibye-Knudsen, M., Gomes, A. P., Ward, T. M., Minor, R. K., Blouin, M. J., et al. (2013). Metformin improves healthspan and lifespan in mice. Nat Commun 4, 2192.

Martire, S., Fuso, A., Rotili, D., Tempera, I., Giordano, C., De Zottis, I., Muzi, A., Vernole, P., Graziani, G., Lococo, E., et al. (2013). PARP-1 modulates amyloid beta peptide-induced neuronal damage. PLoS One 8, e72169.

Mason, K. A., Raju, U., Buchholz, T. A., Wang, L., Milas, Z. L., and Milas, L. (2014). Poly (ADP-ribose) polymerase inhibitors in cancer treatment. Am J Clin Oncol 37, 90-100.

Messner, S., Schuermann, D., Altmeyer, M., Kassner, I., Schmidt, D., Schar, P., Muller, S., and Hottiger, M. O. (2009). Sumoylation of poly(ADP-ribose) polymerase 1 inhibits its acetylation and restrains transcriptional coactivator function. FASEB J 23, 3978-3989.

Miller, R. A. (2009). Cell stress and aging: new emphasis on multiplex resistance mechanisms. J Gerontol A Biol Sci Med Sci 64, 179-182.

Morley, J. F., Brignull, H. R., Weyers, J. J., and Morimoto, R. I. (2002). The threshold for polyglutamine-expansion protein aggregation and cellular toxicity is dynamic and influenced by aging in Caenorhabditis elegans. Proc Natl Acad Sci USA 99, 10417-10422.

Morley, J. F., and Morimoto, R. I. (2004). Regulation of longevity in Caenorhabditis elegans by heat shock factor and molecular chaperones. Mol Biol Cell 15, 657-664.

Mouchiroud, L., Houtkooper, R. H., Moullan, N., Katsyuba, E., Ryu, D., Canto, C., Mottis, A., Jo, Y. S., Viswanathan, M., Schoonjans, K., et al. (2013). The NAD(+)/Sirtuin Pathway Modulates Longevity through Activation of Mitochondrial UPR and FOXO Signaling. Cell 154, 430-441.

Murphy, C. T., McCarroll, S. A., Bargmann, C. I., Fraser, A., Kamath, R. S., Ahringer, J., Li, H., and Kenyon, C. (2003). Genes that act downstream of DAF-16 to influence the lifespan of Caenorhabditis elegans. Nature 424, 277-283.

Nemoto, S., and Finkel, T. (2002). Redox regulation of forkhead proteins through a p66shc-dependent signaling pathway. Science 295, 2450-2452.

Nogueira, V., Park, Y., Chen, C. C., Xu, P. Z., Chen, M. L., Tonic, I., Unterman, T., and Hay, N. (2008). Akt determines replicative senescence and oxidative or oncogenic premature senescence and sensitizes cells to oxidative apoptosis. Cancer Cell 14, 458-470.

Ogg, S., Paradis, S., Gottlieb, S., Patterson, G. I., Lee, L., Tissenbaum, H. A., and Ruvkun, G. (1997). The Fork head transcription factor DAF-16 transduces insulin-like metabolic and longevity signals in C. elegans. Nature 389, 994-999.

Ohanna, M., Giuliano, S., Bonet, C., Imbert, V., Hofman, V., Zangari, J., Bille, K., Robert, C., Bressac-de Paillerets, B., Hofman, P., et al. (2011). Senescent cells develop a PARP-1 and nuclear factor-{kappa}B-associated secretome (PNAS). Genes Dev 25, 1245-1261.

Onken, B., and Driscoll, M. (2010). Metformin induces a dietary restriction-like state and the oxidative stress response to extend C. elegans Healthspan via AMPK, LKB 1, and SKN-1. PLoS One 5, e8758.

Orlikova, B., Schnekenburger, M., Zloh, M., Golais, F., Diederich, M., and Tasdemir, D. (2012). Natural chalcones as dual inhibitors of HDACs and NF-kappaB. Oncol Rep 28, 797-805.

Outeiro, T. F., Grammatopoulos, T. N., Altmann, S., Amore, A., Standaert, D. G., Hyman, B. T., and Kazantsev, A. G. (2007). Pharmacological inhibition of PARP-1 reduces alpha-synuclein- and MPP+-induced cytotoxicity in Parkinson's disease in vitro models. Biochem Biophys Res Commun 357, 596-602.

Paik, J. H., Ding, Z., Narurkar, R., Ramkissoon, S., Muller, F., Kamoun, W. S., Chae, S. S., Zheng, H., Ying, H., Mahoney, J., et al. (2009). FoxOs cooperatively regulate diverse pathways governing neural stem cell homeostasis. Cell Stem Cell 5, 540-553.

Panier, S., and Boulton, S. J. (2014). Double-strand break repair: 53BP1 comes into focus. Nat Rev Mol Cell Biol 15, 7-18.

Pawlikowska, L., Hu, D., Huntsman, S., Sung, A., Chu, C., Chen, J., Joyner, A. H., Schork, N.J., Hsueh, W. C., Reiner, A. P., et al. (2009). Association of common genetic variation in the insulin/IGF1 signaling pathway with human longevity. Aging Cell 8, 460-472.

Perez-Cadahia, B., Drobic, B., Khan, P., Shivashankar, C. C., and Davie, J. R. (2010). Current understanding and importance of histone phosphorylation in regulating chromatin biology. Curr Opin Drug Discov Devel 13, 613-622.

Phillips, W., Michell, A., Pruess, H., and Barker, R. A. (2009). Animal models of neurodegenerative diseases. Methods Mol Biol 549, 137-155.

Pirinen, E., Canto, C., Jo, Y. S., Morato, L., Zhang, H., Menzies, K. J., Williams, E. G., Mouchiroud, L., Moullan, N., Hagberg, C., et al. (2014). Pharmacological Inhibition of poly(ADP-ribose) polymerases improves fitness and mitochondrial function in skeletal muscle. Cell Metab 19, 1034-1041.

Renault, V. M., Rafalski, V. A., Morgan, A. A., Salih, D. A., Brett, J. O., Webb, A. E., Villeda, S. A., Thekkat, P. U., Guillerey, C., Denko, N.C., et al. (2009). FoxO3 regulates neural stem cell homeostasis. Cell Stem Cell 5, 527-539.

Rizki, G., Iwata, T. N., Li, J., Riedel, C. G., Picard, C. L., Jan, M., Murphy, C. T., and Lee, S. S. (2011). The evolutionarily conserved longevity determinants HCF-1 and SIR-2.1/SIRT1 collaborate to regulate DAF-16/FOXO. PLoS Genet 7, e1002235.

Robida-Stubbs, S., Glover-Cutter, K., Lamming, D. W., Mizunuma, M., Narasimhan, S. D., Neumann-Haefelin, E., Sabatini, D. M., and Blackwell, T. K. (2012). TOR signaling and rapamycin influence longevity by regulating SKN-1/Nrf and DAF-16/FoxO. Cell Metab 15, 713-724.

Ross, C. A., and Poirier, M. A. (2004). Protein aggregation and neurodegenerative disease. Nat Med 10 Suppl, S10-17.

Rouleau, M., Patel, A., Hendzel, M. J., Kaufmann, S. H., and Poirier, G. G. (2010). PARP inhibition: PARP1 and beyond. Nat Rev Cancer 10, 293-301.

Sahu, N. K., Balbhadra, S. S., Choudhary, J., and Kohli, D. V. (2012). Exploring pharmacological significance of chalcone scaffold: a review. Curr Med Chem 19, 209-225.

Salminen, A., Huuskonen, J., Ojala, J., Kauppinen, A., Kaarniranta, K., and Suuronen, T. (2008). Activation of innate immunity system during aging: NF-kB signaling is the molecular culprit of inflamm-aging. Ageing Res Rev 7, 83-105.

Salmon, A. B., Murakami, S., Bartke, A., Kopchick, J., Yasumura, K., and Miller, R. A. (2005). Fibroblast cell lines from young adult mice of long-lived mutant strains are resistant to multiple forms of stress. Am J Physiol Endocrinol Metab 289, E23-29.

Salmon, A. B., Sadighi Akha, A. A., Buffenstein, R., and Miller, R. A. (2008). Fibroblasts from naked mole-rats are resistant to multiple forms of cell injury, but sensitive to peroxide, ultraviolet light, and endoplasmic reticulum stress. J Gerontol A Biol Sci Med Sci 63, 232-241.

Schlachetzki, J. C., Saliba, S. W., and Oliveira, A. C. (2013). Studying neurodegenerative diseases in culture models. Rev Bras Psiquiatr 35 Suppl 2, S92-100.

Sharma, O. P., and Bhat, T. K. (2009). DPPH antioxidant assay revisited. Food Chem 113, 1202-1205.

Shaw, R. J., Bardeesy, N., Manning, B. D., Lopez, L., Kosmatka, M., DePinho, R. A., and Cantley, L. C. (2004). The LKB 1 tumor suppressor negatively regulates mTOR signaling. Cancer Cell 6, 91-99.

Shimokawa, I., Komatsu, T., Hayashi, N., Kim, S. E., Kawata, T., Park, S., Hayashi, H., Yamaza, H., Chiba, T., and Mori, R. (2015). The life-extending effect of dietary restriction requires Foxo3 in mice. Aging Cell.

Shin, B. Y., Jin, S. H., Cho, I. J., and Ki, S. H. (2012). Nrf2-ARE pathway regulates induction of Sestrin-2 expression. Free Radic Biol Med 53, 834-841.

Singh, S. P., Niemczyk, M., Saini, D., Sadovov, V., Zimniak, L., and Zimniak, P. (2010). Disruption of the mGsta4 gene increases life span of C57BL mice. J Gerontol A Biol Sci Med Sci 65, 14-23.

Slack, C., Giannakou, M. E., Foley, A., Goss, M., and Partridge, L. (2011). dFOXO-independent effects of reduced insulin-like signaling in *Drosophila*. Aging Cell 10, 735-748.

Smith-Vikos, T., and Slack, F. J. (2012). MicroRNAs and their roles in aging. J Cell Sci 125, 7-17.

Soerensen, M., Dato, S., Christensen, K., McGue, M., Stevnsner, T., Bohr, V. A., and Christiansen, L. (2010). Replication of an association of variation in the FOXO3A gene with human longevity using both case-control and longitudinal data. Aging Cell 9, 1010-1017.

Solis, G. M., and Petrascheck, M. (2011). Measuring *Caenorhabditis elegans* life span in 96 well microtiter plates. J Vis Exp.

Solomon, V. R., and Lee, H. (2012). Anti-breast cancer activity of heteroaryl chalcone derivatives. Biomed Pharmacother 66, 213-220.

Steinbaugh, M. J., Sun, L. Y., Bartke, A., and Miller, R. A. (2012). Activation of genes involved in xenobiotic metabolism is a shared signature of mouse models with extended lifespan. Am J Physiol Endocrinol Metab 303, E488-495.

Suzuki, T., Motohashi, H., and Yamamoto, M. (2013). Toward clinical application of the Keap1-Nrf2 pathway. Trends Pharmacol Sci 34, 340-346.

Sykiotis, G. P., and Bohmann, D. (2008). Keap1/Nrf2 signaling regulates oxidative stress tolerance and lifespan in *Drosophila*. Dev Cell 14, 76-85.

Tazearslan, C., Huang, J., Barzilai, N., and Suh, Y. (2011). Impaired IGF1R signaling in cells expressing longevity-associated human IGF1R alleles. Aging Cell 10, 551-554.

Thorne, N., Auld, D. S., and Inglese, J. (2010). Apparent activity in high-throughput screening: origins of compound-dependent assay interference. Curr Opin Chem Biol 14, 315-324.

Tothova, Z., Kollipara, R., Huntly, B. J., Lee, B. H., Castrillon, D. H., Cullen, D. E., McDowell, E. P., Lazo-Kallanian, S., Williams, I. R., Sears, C., et al. (2007). FoxOs are critical mediators of hematopoietic stem cell resistance to physiologic oxidative stress. Cell 128, 325-339.

Tran, H., Brunet, A., Griffith, E. C., and Greenberg, M. E. (2003). The many forks in FOXO's road. Sci STKE 2003, RE5.

Tullet, J. M., Hertweck, M., An, J. H., Baker, J., Hwang, J. Y., Liu, S., Oliveira, R. P., Baumeister, R., and Blackwell, T. K. (2008). Direct inhibition of the longevity-promoting factor SKN-1 by insulin-like signaling in *C. elegans*. Cell 132, 1025-1038.

Valenzano, D. R., Terzibasi, E., Genade, T., Cattaneo, A., Domenici, L., and Cellerino, A. (2006). Resveratrol prolongs lifespan and retards the onset of age-related markers in a short-lived vertebrate. Curr Biol 16, 296-300.

Walters, W. P., and Namchuk, M. (2003). Designing screens: how to make your hits a hit. Nat Rev Drug Discov 2, 259-266.

Wang, G., Han, T., Nijhawan, D., Theodoropoulos, P., Naidoo, J., Yadavalli, S., Mirzaei, H., Pieper, A. A., Ready, J. M., and McKnight, S. L. (2014a). P7C3 neuroprotective chemicals function by activating the rate-limiting enzyme in NAD salvage. Cell 158, 1324-1334.

Wang, L., Karpac, J., and Jasper, H. (2014b). Promoting longevity by maintaining metabolic and proliferative homeostasis. The Journal of experimental biology 217, 109-118.

Wang, T. T., Zeng, G. C., Li, X. C., and Zeng, H. P. (2010). In vitro studies on the antioxidant and protective effect of 2-substituted-8-hydroxyquinoline derivatives against $H(2)O(2)$-induced oxidative stress in BMSCs. Chem Biol Drug Des 75, 214-222.

Weaver, A. N., and Yang, E. S. (2013). Beyond DNA Repair: Additional Functions of PARP-1 in Cancer. Front Oncol 3, 290.

Wessells, R. J., Fitzgerald, E., Cypser, J. R., Tatar, M., and Bodmer, R. (2004). Insulin regulation of heart function in aging fruit flies. Nat Genet 36, 1275-1281.

Wilkinson, J. E., Burmeister, L., Brooks, S. V., Chan, C. C., Friedline, S., Harrison, D. E., Hejtmancik, J. F., Nadon, N., Strong, R., Wood, L. K., et al. (2012). Rapamycin slows aging in mice. Aging Cell 11, 675-682.

Willcox, B. J., Donlon, T. A., He, Q., Chen, R., Grove, J. S., Yano, K., Masaki, K. H., Willcox, D. C., Rodriguez, B., and Curb, J. D. (2008). FOXO3A genotype is strongly associated with human longevity. Proc Natl Acad Sci USA 105, 13987-13992.

Yadav, V. R., Prasad, S., Sung, B., and Aggarwal, B. B. (2011). The role of chalcones in suppression of NF-kappaB-mediated inflammation and cancer. Int Immunopharmacol 11, 295-309.

Yalcin, S., Zhang, X., Luciano, J. P., Mungamuri, S. K., Marinkovic, D., Vercherat, C., Sarkar, A., Grisotto, M., Taneja, R., and Ghaffari, S. (2008). Foxo3 is essential for the regulation of ataxia telangiectasia mutated and oxidative stress-mediated homeostasis of hematopoietic stem cells. J Biol Chem 283, 25692-25705.

Yang, Y. L., Loh, K. S., Liou, B. Y., Chu, I. H., Kuo, C. J., Chen, H. D., and Chen, C. S. (2013). SESN-1 is a positive regulator of lifespan in *Caenorhabditis elegans*. Exp Gerontol 48, 371-379.

Ye, X., Linton, J. M., Schork, N.J., Buck, L. B., and Petrascheck, M. (2014). A pharmacological network for lifespan extension in *Caenorhabditis elegans*. Aging Cell 13, 206-215.

Yeh, E. T. (2009). SUMOylation and De-SUMOylation: wrestling with life's processes. J Biol Chem 284, 8223-8227.

Zhang, G., Li, J., Purkayastha, S., Tang, Y., Zhang, H., Yin, Y., Li, B., Liu, G., and Cai, D. (2013). Hypothalamic programming of systemic ageing involving IKK-beta, NF-kappaB and GnRH. Nature 497, 211-216.

Zhang, S., Lin, Y., Kim, Y. S., Hande, M. P., Liu, Z. G., and Shen, H. M. (2007). c-Jun N-terminal kinase mediates hydrogen peroxide-induced cell death via sustained poly (ADP-ribose) polymerase-1 activation. Cell Death Differ 14, 1001-1010.

Zhao, S., Lin, L., Kan, G., Xu, C., Tang, Q., Yu, C., Sun, W., Cai, L., Xu, C., and Cui, S. (2014). High autophagy in the naked mole rat may play a significant role in maintaining good health. Cell Physiol Biochem 33, 321-332.

Zhou, W., Ryan, J. J., and Zhou, H. (2004). Global analyses of sumoylated proteins in *Saccharomyces cerevisiae*. Induction of protein sumoylation by cellular stresses. J Biol Chem 279, 32262-32268.

Zoncu, R., Efeyan, A., and Sabatini, D. M. (2011). mTOR: from growth signal integration to cancer, diabetes and ageing. Nat Rev Mol Cell Biol 12, 21-35.

What is claimed is:

1. A method of treating lung cancer in a subject in need thereof, the method comprising administering to the subject an effective amount of a compound of Formula (Ia) or a pharmaceutically acceptable salt thereof:

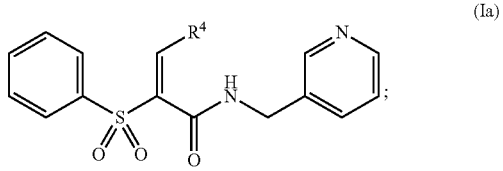

wherein:

R⁴ is R²⁹-substituted or unsubstituted phenyl or R²⁹-substituted or unsubstituted 5 or 6 membered heteroaryl;

R²⁹ is halogen, —CF₃, —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)—OH, —NHOH, —OCF₃, —OCHF₂, phenoxy, R³⁰-substituted or unsubstituted C₁-C₆ alkyl, R³⁰-substituted or unsubstituted 2 to 6 membered heteroalkyl, R³⁰-substituted or unsubstituted C₃-C₆ cycloalkyl, R³⁰-substituted or unsubstituted 3 to 6 membered heterocycloalkyl, R³⁰-substituted or unsubstituted phenyl, or R³⁰-substituted or unsubstituted 5 to 6 membered heteroaryl;

R³⁰ is halogen, —CF₃, —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)—OH, —NHOH, —OCF₃, —OCHF₂, R³¹-substituted or unsubstituted C₁-C₆ alkyl, R³¹-substituted or unsubstituted 2 to 6 membered heteroalkyl, R³¹-substituted or unsubstituted C₃-C₆ cycloalkyl, R³¹-substituted or unsubstituted 3 to 6 membered heterocycloalkyl, R³¹-substituted or unsubstituted phenyl, or R³¹-substituted or unsubstituted 5 to 6 membered heteroaryl;

R³¹ is halogen, oxo, —CF₃, —CCl₃, —CN, —S(O)CH₃, —OH, —NH₂, —COOH, —CONH₂, —NO₂, —C(O)CH₃, —CH₂CH₂OH, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)OH, —NHOH, —OCH₃, —OCF₃, —OCHF₂ unsubstituted C₁-C₆ alkyl, unsubstituted 2 to 6 membered heteroalkyl, unsubstituted C₃-C₆ cycloalkyl, unsubstituted 3 to 6 membered heterocycloalkyl, unsubstituted phenyl, or unsubstituted 5 to 6 membered heteroaryl.

2. The method of claim 1, wherein the compound of Formula (Ia) is:

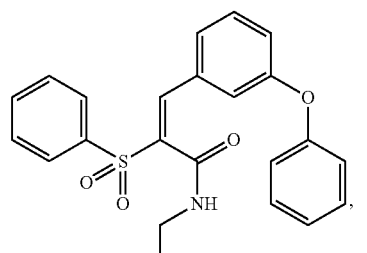

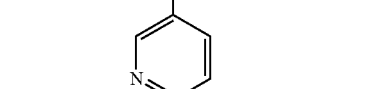

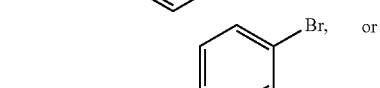

3. The method of claim 1, wherein the lung cancer is non-small cell lung cancer.

4. A method of inhibiting proliferation of lung cancer cells or inhibiting survival of lung cancer cells, the method comprising contacting the lung cancer cells with a compound of formula (Ia) or a pharmaceutically acceptable salt thereof;

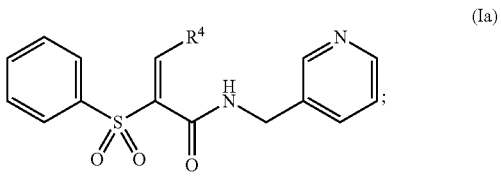

wherein:

R⁴ is R²⁹-substituted or unsubstituted phenyl or R²⁹-substituted or unsubstituted 5 or 6 membered heteroaryl;

R²⁹ is halogen, —CF₃, —CN, —OH, —NH₂, —COOH, —CONH₂, —NO₂, —SH, —SO₃H, —SO₄H, —SO₂NH₂, —NHNH₂, —ONH₂, —NHC═(O)NHNH₂, —NHC═(O)NH₂, —NHSO₂H, —NHC═(O)H, —NHC(O)—OH, —NHOH, —OCF₃, —OCHF₂, phenoxy, R³⁰-substituted or unsubstituted C₁-C₆ alkyl, R³⁰-substituted or unsubstituted 2 to 6 membered heteroalkyl, R³⁰-substituted or unsubstituted C₃-C₆ cycloalkyl, R³⁰-substituted or unsubstituted 3 to 6 membered heterocycloalkyl, R³⁰-substituted or unsubstituted phenyl, or R³⁰-substituted or unsubstituted 5 to 6 membered heteroaryl;

R³⁰ is halogen, —CF₃, —CN, —OH, —NH₂, —COOH, —CONH₂, —NO₂, —SH, —SO₃H, —SO₄H, —SO₂NH₂, —NHNH₂, —ONH₂, —NHC═(O)NHNH₂, —NHC═(O)NH₂, —NHSO₂H, —NHC═(O)H, —NHC(O)—OH, —NHOH, —OCF₃, —OCHF₂, R³¹-substituted or unsubstituted C₁-C₆ alkyl, R³¹-substituted or unsubstituted 2 to 6 membered heteroalkyl, R³¹-substituted or unsubstituted C₃-C₆ cycloalkyl, R³¹-substituted or unsubstituted 3 to 6 membered heterocycloalkyl, R³¹-substituted or unsubstituted phenyl, or R³¹-substituted or unsubstituted 5 to 6 membered heteroaryl;

R³¹ is halogen, oxo, —CF, —CCl₃, —CN, —S(O)CH₃, —OH, —NH, —COOH, —CONH₂, —NO₂, —C(O)CH₃, —CH₂CH₂OH, —SH, —SO₃H, —SO₄H, —SO₂NH₂, —NHNH₂, —ONH₂, —NHC═(O)NHNH₂, —NHC═(O)NH₂, —NHSO₂H, —NHC═(O)H, —NHC(O)OH, —NHOH, —OCH, —OCF₃, —OCHF₂, unsubstituted C₁-C₆ alkyl, unsubstituted 2 to 6 membered heteroalkyl, unsubstituted C₃-C₆ cycloalkyl, unsubstituted 3 to 6 membered heterocycloalkyl, unsubstituted phenyl, or unsubstituted 5 to 6 membered heteroaryl.

5. The method of claim 4, wherein the compound of Formula (Ia) is:

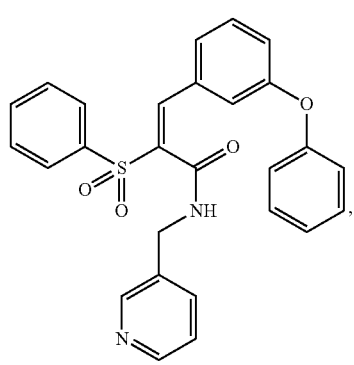

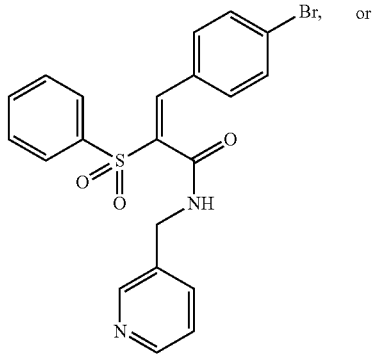

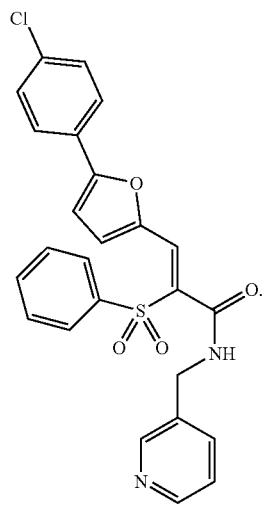

6. The method of claim 4, wherein the lung cancer cells are non-small cell lung cancer cells.

7. The method of claim 2, wherein the compound of Formula (Ia) is:

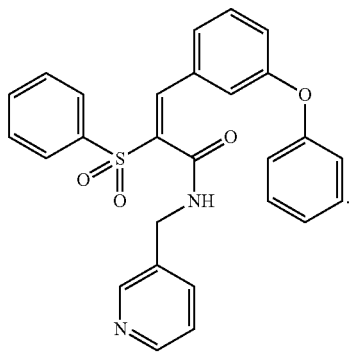 [SMILES: O=C(NCc1cccnc1)/C(=C\c1cccc(Oc2ccccc2)c1)S(=O)(=O)c1ccccc1]

8. The method of claim 2, wherein the compound of Formula (Ia) is:
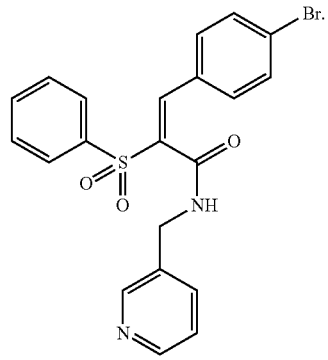 [SMILES: O=C(NCc1cccnc1)/C(=C\c1ccc(Br)cc1)S(=O)(=O)c1ccccc1]
9. The method of claim 2, wherein the compound of Formula (Ia) is:
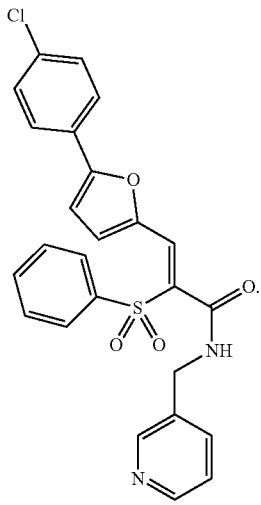
* * * * *